United States Patent
Okada et al.

(10) Patent No.: US 9,365,553 B2
(45) Date of Patent: Jun. 14, 2016

(54) HETEROCYCLIC COMPOUND AND H1 RECEPTOR ANTAGONIST

(75) Inventors: Makoto Okada, Kawasaki (JP); Koichi Hasumi, Kawasaki (JP); Takahiro Nishimoto, Hamura (JP); Miwa Yoshida, Hamura (JP); Kouki Ishitani, Hamura (JP); Tomoji Aotsuka, Hamura (JP); Hashime Kanazawa, Hamura (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/699,892

(22) PCT Filed: May 23, 2011

(86) PCT No.: PCT/JP2011/061734
§ 371 (c)(1),
(2), (4) Date: Nov. 26, 2012

(87) PCT Pub. No.: WO2011/148888
PCT Pub. Date: Dec. 1, 2011

(65) Prior Publication Data
US 2013/0085127 A1   Apr. 4, 2013

(30) Foreign Application Priority Data

May 27, 2010   (JP) ................................. 2010-122125
Jul. 22, 2010   (JP) ................................. 2010-165134

(51) Int. Cl.
| C07D 401/06 | (2006.01) |
| C07D 211/46 | (2006.01) |
| C07D 405/06 | (2006.01) |
| C07D 213/79 | (2006.01) |
| C07D 333/40 | (2006.01) |
| C07D 407/08 | (2006.01) |
| C07D 409/06 | (2006.01) |
| C07D 413/06 | (2006.01) |
| C07D 417/06 | (2006.01) |

(52) U.S. Cl.
CPC ............ C07D 405/06 (2013.01); C07D 211/46 (2013.01); C07D 213/79 (2013.01); C07D 333/40 (2013.01); C07D 401/06 (2013.01); C07D 407/08 (2013.01); C07D 409/06 (2013.01); C07D 413/06 (2013.01); C07D 417/06 (2013.01)

(58) Field of Classification Search
CPC ... C07D 401/06; C07D 405/06; C07D 211/46
USPC ................. 514/253.13, 210.2, 318, 326, 218; 544/365; 546/194, 214, 216, 218, 546/268.1; 540/575
See application file for complete search history.

(56) References Cited

U.S. PATENT DOCUMENTS 4,002,629 A   1/1977   Delarge et al. ................ 544/360
4,994,456 A * 2/1991   Miura ................... C07D 213/81
                                                    514/218
5,025,012 A * 6/1991   Miura ................... C07D 213/80
                                                    514/211.15
6,387,910 B1* 5/2002   Hara ..................... A61K 31/495
                                                    514/255.04

FOREIGN PATENT DOCUMENTS

| EP | 0 204 309 | 12/1986 |
| JP | 61-282359 | 12/1986 |
| JP | 5-345765 | 12/1993 |
| JP | 7-224038 | 8/1995 |
| JP | 2002-504149 | 2/2002 |
| JP | 2003-518107 | 6/2003 |
| JP | 2004-051600 | 2/2004 |
| JP | 2006-516281 | 6/2006 |
| JP | 2007-534696 | 11/2007 |
| JP | 2009-504637 | 2/2009 |
| WO | 01/46166 | 6/2001 |
| WO | 03/057223 | 7/2003 |

(Continued)

OTHER PUBLICATIONS

PCT-237 (2011).*
Kumazawa et al. "Preparation of tricycle . . . " CA126:212158(1997).*
Miura et al. "Preparation and formulation . . . " CA114:102055 (1991).*
Miura et al. "Preparation and formulation of 6-. . . . " CAl14:122412 (1991).*
Olson et al. "Prepartion of heterocycle . . . " CA119:271161 (1993).*
Tegele et al. "1,2,4-oxadiazol . . . " CA104:207280 (1986).*
Tegeler et al. "Isoxazol . . . " CA104:224887 (1986).*

(Continued)

*Primary Examiner* — Celia Chang
(74) *Attorney, Agent, or Firm* — Wenderoth, Lind & Ponack, L.L.P.

(57) ABSTRACT

A heterocyclic compound useful as an antiallergic agent is provided.
A compound represented by the following formula (1) or a salt thereof:

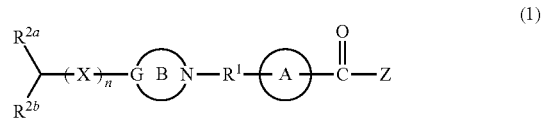

(1)

wherein the ring A is a homocyclic or heterocyclic ring; the ring B is a heterocyclic ring which contains G and nitrogen atom N as constituent atoms thereof, wherein G is CH or N; $R^1$ is a carbonyl group or an alkylene group; $R^{2a}$ and $R^{2b}$ are an alkyl group, a cycloalkyl group, an aryl group, or a heterocyclic group; X is an oxygen atom or a sulfur atom; Z is a hydroxyl group, an alkoxy group, a cycloalkyloxy group, an aryloxy group, an aralkyloxy group, an amino group, or an N-substituted amino group; and n is 0 or 1; with the proviso that when the ring A is a benzene ring or when the ring B is a piperazine ring, $R^1$ is an alkylene group which may have a substituent.

11 Claims, 5 Drawing Sheets

(56) References Cited

FOREIGN PATENT DOCUMENTS

| WO | 2004/060321 | 7/2004 |
|---|---|---|
| WO | 2005/103041 | 11/2005 |
| WO | 2007/018459 | 2/2007 |

OTHER PUBLICATIONS

Improper Markush Fed. Reg. v.76, p. 7162-75, slides 1, 64-67 (2011).*
Supplementary European Search Report issued Dec. 17, 2013 in European Application No. 11 78 6587.
International Search Report issued Jul. 19, 2011 in International (PCT) Application No. PCT/JP2011/061734.
E. Carceller et al., [(3-Pyridylalkyl)piperidylidene]benzocycloheptapyridine Derivatives as Dual Antagonists of PAF and Histamine, American Chemical Society, J. Med. Chem., vol. 37, pp. 2697-2703, 1994.
English translation of International Preliminary Report on Patentability and Written Opinion issued Dec. 4, 2012 in International (PCT) Application No. PCT/JP2011/061734.
Japanese Office Action dated Feb. 10, 2015 issued in corresponding Japanese Patent Application No. 2012-517249 (with English translation).

* cited by examiner

HETEROCYCLIC COMPOUND AND H1 RECEPTOR ANTAGONIST

TECHNICAL FIELD

The present invention relates to heterocyclic compounds (or pharmacologically active compounds), antiallergic agents (or $H_1$ receptor antagonists), and pharmaceutical compositions.

BACKGROUND ART

As a compound having a pharmacological activity, various heterocyclic compounds are known. Japanese Patent Application Laid-Open Publication No. 2007-534696 (JP-2007-534696A, Patent Document 1) discloses a modified antihistamine compound represented by the formula [AH]-A (wherein AH represents an antihistamine moiety, A represents a linker molecule comprising SP and Z, wherein SP is a spacer molecule and Z is a drug modulating moiety). This document also discloses a pheniramine-like compound and a diphenhydramine-like compound.

WO 03/057223 (Patent Document 2) discloses a δ opioid receptor agonist represented by the following formula:

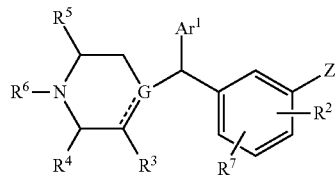

wherein $Ar^1$ is a 5- or 6-membered carbocyclic or aromatic heterocyclic ring which may have a substituent; Z is a hydrogen, a carboxyl group or an ester group thereof, or the like; G is a carbon or a nitrogen; $R^2$ is a hydrogen, a $C_{1-4}$alkyl group, or the like; $R^3$ and $R^4$ are a hydrogen or a $C_{1-6}$alkyl group, $R^4$ may form a C=O group; $R^5$ is a hydrogen, an alkoxy group, or the like; $R^6$ is a phenyl, a halogen, or the like; and $R^7$ is a hydrogen, a $C_{1-8}$alkyl group, or the like.

WO 01/046166 (Japanese Patent Application Laid-Open Publication No. 2003-518107, Patent Document 3) discloses compounds represented by the following formulae (piperazine derivatives having benzhydril and a 6-membered heterocyclic moiety) for treating conditions associated with aberrant N-type calcium channel activity. This document also discloses that the compounds are also useful for treating stroke, migraine, chronic neuropathic and acute pain, hypertension, cardiac arrhythmia, and other diseases.

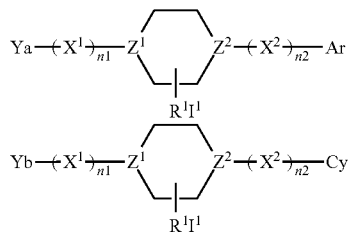

In the formulae, $Z^1$ and $Z^2$ are N or CH, one of $Z^1$ and $Z^2$ is N; n1 is 1, n2 is 0 or 1; $X^1$ and $X^2$ are a straight chain linker; Ar is an aromatic monocyclic ring or an aromatic heterocyclic monocyclic ring, Cy is an alicyclic monocyclic ring or a heterocyclic monocyclic ring, or the like; Ya and Yb are an aromatic monocyclic ring or an aromatic heterocyclic monocyclic ring, an alicyclic monocyclic ring or a heterocyclic monocyclic ring, or the like; $l^1$ is 0 or 1; and $R^1$ is a $C_{1-6}$alkyl, a $C_{6-10}$aryl, a $C_{7-16}$arylalkyl, or the like.

Patent Document 3 specifically discloses compounds in which $Z^1$ and $Z^2$ are N, $X^1$ is a $C_{2-6}$alkylene group or a $C_{1-5}$alkylene-CO—, $X^2$ is a methylene group, an ethylene group, or an alkenylene group, Ya is a cyclohexyl group and a phenyl group, and Ar is a phenyl group.

Japanese Patent Application Laid-Open Publication No. 2004-51600 (JP-2004-51600A, Patent Document 4) discloses a hematopoietic organ-type prostaglandin D2 synthetic enzyme inhibitor represented by the following formula and also discloses that the inhibitor has an antiallergic effect (or action), an anti-allergic-inflammation, and/or an antiasthmatic effect.

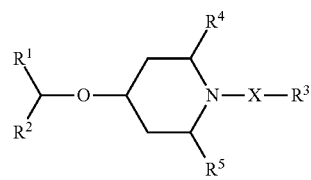

In the formula, X is a single bond, a $C_{1-6}$alkylene group, or the like; $R^1$ is a $C_{6-10}$aryl group; $R^2$ is a hydrogen atom, a $C_{1-6}$alkyl group, or a $C_{6-10}$aryl group; $R^3$ is an acyl group or a 4- to 10-membered cyclic group; and $R^4$ and $R^5$ is a hydrogen atom, or $R^4$ and $R^5$ bond together to form a $C_{1-4}$alkylene group.

This document also discloses a compound represented by the formula in which X is carbonyl group, $R^1$ and $R^2$ are phenyl group, and $R^3$ is 4-methoxycarbonylphenyl group (Compound Number 27).

Japanese Patent Application Laid-Open Publication No. 2009-504637 (JP-2009-504637A, Patent Document 5) discloses apiperazine compound represented by the following formula useful for the treatment of obesity, psychiatric and neurological disorders.

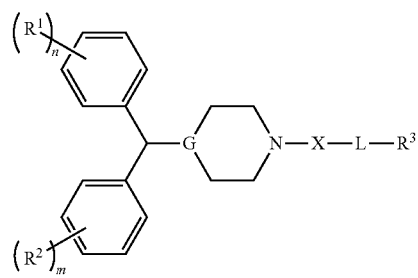

In the formula, G is selected from the group consisting of CH and N; $R^1$ and $R^2$ are independently a hydrogen atom or the like; m and n are independently selected from 1 to 5; X is a bond, —C(=O)—, or the like; L is a bond, —$(CH_2)_p$—, or the like; p is selected from 0, 1 and 2; $R_3$ is, for example, a $C_{6-10}$aryl group substituted by a substituent such as a $C_{1-6}$alkoxy or —$CO_2R^5$ (wherein $R^5$ is a hydrogen, a $C_{1-6}$alkyl, or the like); at least one of X and L is not a bond.

Patent Document 5 specifically discloses a compound represented by the formula in which G is N and X is carbonyl group.

RELATED ART DOCUMENTS

Patent Documents

[Patent Document 1] JP-2007-534696A (Claims, Paragraphs [0462] [0463])
[Patent Document 2] WO 03/057223 (Claims)
[Patent Document 3] WO 01/046166 (Claims, Paragraphs [0010] [0077])
[Patent Document 4] JP-2004-51600A (Claims, Paragraph [0034] Table 2)
[Patent Document 5] JP-2009-504637A (Claims, Examples)

SUMMARY OF THE INVENTION

Problems to be Solved by the Invention

It is therefore an object of the present invention to provide a novel heterocyclic compound, a novel antiallergic agent (or antihistaminic agent, $H_1$ receptor antagonist, or the like), and a novel pharmaceutical composition containing such a component.

Another object of the present invention is to provide a novel heterocyclic compound, a novel antiallergic agent having an $H_1$ antagonistic effect (or $H_1$ receptor antagonist), and a novel pharmaceutical composition containing such a component, which have not only a wide safety margin but also no toxicity (cardiotoxicity, carcinogenicity).

It is still another object of the present invention to provide a novel heterocyclic compound, a novel antiallergic agent having an $H_1$ antagonistic effect (or $H_1$ receptor antagonist), and a novel pharmaceutical composition containing such a component, which have a high antiinflammatory effect and a low central nervous system effect.

It is a further object of the present invention to provide a novel heterocyclic compound, a novel antiallergic agent, and a novel pharmaceutical composition containing such a component, which have an effect on a late phase.

It is a still further object of the present invention to provide a process for producing the heterocyclic compound.

Means to Solve the Problems

The inventors of the present invention made intensive studies to achieve the above objects and finally found that a heterocyclic compound having a skeleton in which an aromatic homocyclic (carbocyclic) or heterocyclic ring having a carboxyl group is linked (or coupled) to a nitrogen atom of a heterocyclic ring through an alkylene group shows a high pharmacological activity (e.g., an antiallergic effect) and has not only a wide safety margin but also a low toxicity (such as cardiotoxicity or carcinogenicity). The present invention was accomplished by further studies based on the above findings.

That is, the present invention includes a heterocyclic compound represented by the following formula (1) or a salt thereof.

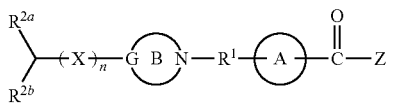

(1)

In the formula, the ring A represents a carbocyclic or heterocyclic ring which may have a substituent;

the ring B represents a heterocyclic ring which contains G and nitrogen atom N as constituent atoms thereof and which may have a substituent, wherein G represents CH or N (nitrogen atom);

$R^1$ represents a carbonyl group, or an alkylene group which may have a substituent;

$R^{2a}$ and $R^{2b}$ are the same or different and each represent an alkyl group which may have a substituent, a carbocyclic ring (or hydrocarbon ring) which may have a substituent (a carbocyclic group such as a cycloalkyl group which may have a substituent or an aryl group which may have a substituent), or a heterocyclic group which may have a substituent (a heterocycle group which may have a substituent), wherein the substituent on the ring (the carbocyclic group or the heterocyclic group) as $R^{2a}$ may bond to the substituent on the ring as $R^{2b}$ to form a ring (a carbocyclic ring or a heterocyclic ring) which may have a substituent;

X represents an oxygen atom or a sulfur atom;

Z represents a hydroxyl group, an alkoxy group, a cycloalkyloxy group, an aryloxy group, an aralkyloxy group, an amino group, or an N-substituted amino group; and n denotes 0 or 1;

with the proviso that when the ring A is a benzene ring or when the ring B is a piperazine ring, $R^1$ is an alkylene group which may have a substituent.

In the compound, the ring A may be an aromatic ring which may have at least one substituent selected from the group consisting of a halogen atom, an alkyl group, a haloalkyl group, an alkoxy group, and a haloalkoxy group. The ring A may be an aromatic carbocylic ring or an arene ring (e.g., benzene ring) or an aromatic heterocyclic ring (e.g., a 5- or 6-membered heterocyclic ring). The ring A may also be an aromatic heterocyclic ring containing at least one hetero atom selected from the group consisting of a nitrogen atom, an oxygen atom, and a sulfur atom, for example, a pyridine ring.

The ring B may be either an aliphatic ring or an aromatic heterocyclic ring, for example, an aliphatic 4- to 10-membered heterocyclic ring (e.g., an aliphatic 5- or 6-membered heterocyclic ring such as a piperidine ring or a piperazine ring).

$R^1$ may be a straight chain or branched chain alkylene group which may have a halogen atom (for example, a straight chain or branched chain $C_{1-4}$alkylene group). $R^1$ may also be a straight chain or branched chain $C_{1-3}$alkylene group (e.g., a $C_{1-2}$alkylene group such as methylene group).

$R^{2a}$ and $R^{2b}$ may be the same or different and each may be a $C_{6-10}$arene ring (for example, a benzene ring) or an aromatic 5- or 6-membered heterocyclic ring, wherein each ring may have at least one substituent selected from the group consisting of a halogen atom, an alkyl group (e.g., a $C_{1-6}$alkyl group), a haloalkyl group (e.g., a haloC$_{1-6}$alkyl group), an alkoxy group (e.g., a $C_{1-6}$alkoxy group) and a haloalkoxy group (e.g., a haloC$_{1-6}$alkoxy group); or $R^{2a}$ and $R^{2b}$ may form a tricyclic group represented by the following formula (2):

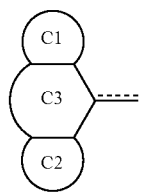

(2)

wherein the ring C1 and the ring C2 are the same of different and each represent a $C_{6-10}$arene ring or an aromatic 5- or 6-membered heterocyclic ring, wherein each ring may have at least one substituent selected from the group consisting of a halogen atom, an alkyl group, a haloalkyl group, an alkoxy group and a haloalkoxy group;

the ring C3 represents a 4- to 10-membered carbocyclic or heterocyclic ring which may have at least one substituent selected from the group consisting of a halogen atom, an alkyl group, a haloalkyl group, a hydroxyl group, an alkoxy group, a haloalkoxy group, a carboxyl group, an alkoxycarbonyl group, an acyl group and a carbonyl group;

the bond represented by the following formula (3):

$$----- \quad (3)$$

represents a single bond or a double bond; and
when n is 0 and G is CH, the bond represents a double bond.

Moreover, $R^{2a}$ and $R^{2b}$ may be the same or different and each may be a benzene ring which may have at least one substituent selected from the group consisting of a fluorine atom, a chlorine atom, a $C_{1-3}$alkyl group, a halo$C_{1-3}$alkyl group (e.g., a fluoro$C_{1-3}$alkyl group), a $C_{1-3}$alkoxy group and a halo$C_{1-3}$alkoxy group (e.g., a fluoro$C_{1-3}$alkoxy group).

Further, Z may be a hydroxyl group; a $C_{1-6}$alkoxy group (e.g., a $C_{1-4}$alkoxy group); an amino group; or an N-substituted amino group in which the nitrogen atom has at least one substituent selected from the group consisting of a $C_{1-6}$alkyl group (e.g., a $C_{1-4}$alkyl group) and a $C_{1-6}$alkyl-carbonyl group (e.g., a $C_{1-4}$alkyl-carbonyl group); or Z may be a hydroxyl group; a $C_{1-4}$alkoxy group (e.g., a $C_{1-2}$alkoxy group); an amino group; or an N-substituted amino group in which the nitrogen atom has at least one substituent selected from the group consisting of a $C_{1-3}$alkyl group (e.g., a $C_{1-2}$alkyl group) and a $C_{1-3}$alkyl-carbonyl group (e.g., a $C_{1-2}$alkyl-carbonyl group).

When G is CH, n is practically 1. When G is N, n is practically 0. Moreover, when G is CH, X is practically an oxygen atom.

Representative compounds represented by the formula (1) include, for example, a (4-benzhydryloxypiperidin-1-ylmethyl)pyridinecarboxylic acid, a {4-[(halophenyl)phenylmethoxy]piperidin-1-ylmethyl}pyridinecarboxylic acid, a {4-[(C$_{1-4}$alkylphenyl)phenylmethoxy]piperidin-1-ylmethyl}pyridinecarboxylic acid, a {4-[(fluoroC$_{1-4}$alkylphenyl)phenylmethoxy]piperidin-1-ylmethyl}pyridinecarboxylic acid, a {4-[(C$_{1-4}$alkoxyphenyl)phenylmethoxy]piperidin-1-ylmethyl}pyridinecarboxylic acid, a {4-[(fluoroC$_{1-4}$alkoxyphenyl)phenylmethoxy]piperidin-1-ylmethyl}pyridinecarboxylic acid, a {4-[bis(halophenyl)methoxy]piperidin-1-ylmethyl}pyridinecarboxylic acid, a {4-[bis(halophenyl)methyl]piperazin-1-ylmethyl}pyridinecarboxylic acid, a (3-benzhydryloxypyrrolidin-1-ylmethyl)pyridinecarboxylic acid, a [4-(10,11-dihydrodibenzo[a,d]cyclohepten-5-ylidene)piperidin-1-ylmethyl]pyridinecarboxylic acid, and a [4-(6H-dibenzo[b,e]oxepin-11-ylidene)piperidin-1-ylmethyl]pyridinecarboxylic acid. These compounds may form a salt, a pro-drug, or an active metabolite.

The present invention also includes a process for producing a heterocyclic compound represented by the above formula (1); the process comprises one of reaction steps according to the following reaction schemes:

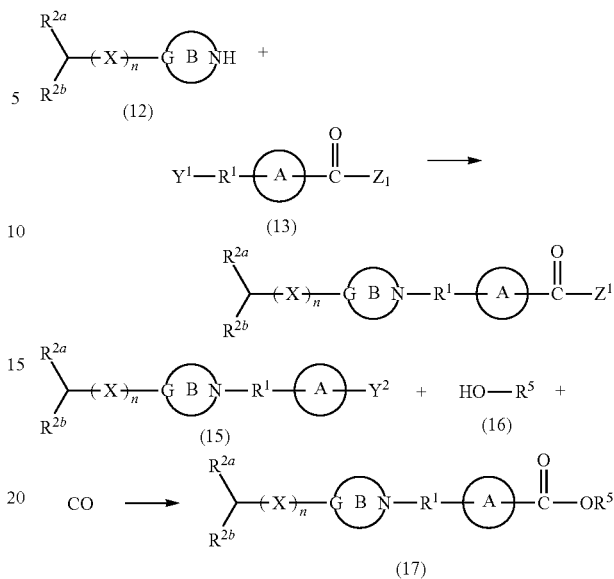

wherein $Y^1$ represents a halogen atom; $Z^1$ represents an alkoxy group, a cycloalkyloxy group, an aryloxy group, or an aralkyloxy group; $Y^2$ represents a halogen atom; $R^5$ represents an alkyl group, a cycloalkyl group, an aryl group, or an aralkyl group; the ring A, the ring B, $R^1$, G, X, n, $R^{2a}$, and $R^{2b}$ have the same meanings as defined above, for obtaining a heterocyclic compound represented by the formula (1) wherein Z is an alkoxy group, a cycloalkyloxy group, an aryloxy group, or an aralkyloxy group;

the process may further comprise a step for subjecting the heterocyclic compound represented by the formula (1) wherein Z is an alkoxy group, a cycloalkyloxy group, an aryloxy group, or an aralkyloxy group to hydrolysis or amide bond formation reaction for obtaining a heterocyclic compound represented by the formula (1) wherein Z is a hydroxyl group, an amino group, or an N-substituted amino group; or the process furthermore comprise a step for subjecting the heterocyclic compound represented by the formula (1) wherein Z is an amino group to alkylation or acylation reaction for obtaining a heterocyclic compound represented by the formula (1) wherein Z is an N-alkylamino group or an N-acylamino group.

The compound or the salt thereof of the present invention shows a pharmacological activity (e.g., an antiallergic effect, a histamine H1 antagonistic effect, and an anti inflammatory effect). In addition, the compound or the salt thereof has not only a wide safety margin but also no toxicity (a genotoxicity such as cardiotoxicity or carcinogenicity) and thus has an excellent safety. Further, the compound or the salt thereof has a low central nervous system effect and does not cause awakening or sleepiness. The present invention therefore also includes an antiallergic agent, an antihistaminic agent (or $H_1$ receptor antagonist) and an antiinflammatory agent each of which contains the compound or the salt thereof (pharmaceutically acceptable salt). Moreover, the present invention includes an agent for preventing and/or treating an allergic disease (or an allergosis), comprising the compound or the salt thereof (pharmaceutically acceptable salt); the allergic disease may include, for example, allergic symptom, bronchial asthma, rhinitis, nasal blockage, atopic dermatitis, urticaria, eczema, pruritus cutaneous, prurigo, psoriasis vulgaris accompanied by pruritus, allergic conjunctivitis, hypereosinophilic syndrome, systemic lupus erythematosus, chronic rheumatism and/or inflammation. Further, the pharmaceutical composition of the present invention contains the compound or the pharmaceutically acceptable salt thereof and a carrier.

In this description, the compound or the salt thereof (or pharmaceutically acceptable salt) also includes a pro-drug and an active metabolite.

Effects of the Invention

The heterocyclic compound of the present invention show a high pharmacological activity (e.g., an antiallergic effect, a histamine H1 antagonistic effect, and an antiinflammatory effect) and has not only a wide safety margin but also no toxicity (a genotoxicity such as cardiotoxicity or carcinogenicity) and thus has an excellent safety. Further, the heterocyclic compound has a low central nervous system effect and does not cause awakening or sleepiness. Thus, the heterocyclic compound is useful as a medicine (or a pharmaceutical) such as an antiallergic agent.

DESCRIPTION OF EMBODIMENTS

Figure 1:
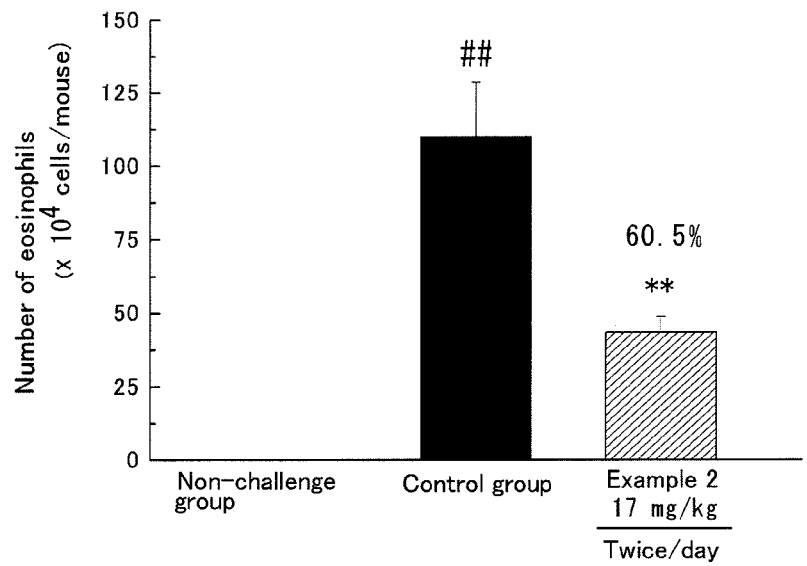
FIG. 1 is a graph showing results of the compound of Example 2 in Test Example 6.

In the formula (1), the ring A represents a homocyclic (carbocyclic) ring or a heterocyclic ring and is usually a 4- to 12-membered ring (preferably a 5- to 10-membered ring, and more preferably a 5- or 6-membered ring). The ring A may be a condensed ring (e.g., a condensed ring of a homocyclic ring and a heterocyclic ring) and is usually a monocyclic ring. The ring A may be an aliphatic ring. In order to increase a pharmacological activity, the ring A is preferably an aromatic ring. The aromatic ring may be an aromatic homocyclic ring or an arene ring or an aromatic heterocyclic ring (such as a 5- or 6-membered heterocyclic ring). Further, the ring A is usually a heterocyclic ring (e.g., an aromatic heterocyclic ring containing at least one hetero atom selected from the group consisting of a nitrogen atom, an oxygen atom, and a sulfur atom) in practical cases. The heterocyclic ring may contain a plurality of hetero atoms which may be the same or different from each other (for example, two nitrogen atoms, and a nitrogen atom and an oxygen atom and/or a sulfur atom).

Examples of the ring A may include an aliphatic carbocyclic (or hydrocarbon) ring (e.g., a $C_{4-10}$cycloalkane ring such as cyclopentane ring or cyclohexane ring), an aromatic carbocyclic ring (e.g., a $C_{6-10}$arene ring such as benzene ring or naphthalene ring), an aliphatic heterocyclic ring (a 5- or 6-membered ring containing an oxygen atom as a hetero atom, e.g., pyran; a condensed ring of a 5- or 6-membered ring containing an oxygen atom as a hetero atom and a carbocyclic ring, e.g., isochroman and chroman; a 5- or 6-membered ring containing a nitrogen atom as a hetero atom, e.g., pyrrolidine, pyrroline, imidazolidine, imidazoline, pyrazolidine, pyrazoline, piperidine, and piperazine), and an aromatic heterocyclic ring [a 5- or 6-membered ring containing a sulfur atom as a hetero atom, e.g., thiophene; a condensed ring of a 5- or 6-membered ring containing a sulfur atom as a hetero atom and a carbocyclic ring (such as benzene ring); a 5- or 6-membered ring containing an oxygen atom as a hetero atom, e.g., furan; a condensed ring of a 5- or 6-membered ring containing an oxygen atom as a hetero atom and a carbocyclic ring (such as benzene ring), e.g., isobenzofuran and chromene; a 5- or 6-membered ring containing a nitrogen atom as a hetero atom, e.g., pyrrole, imidazole, pyrazole, pyridine, pyrazine, pyrimidine, and pyridazine; a condensed ring of a 5- or 6-membered ring containing a nitrogen atom as a hetero atom and a carbocyclic ring (such as benzene ring), e.g., indole, isoindole, isoquinoline, and quinoline; a condensed ring of a 5- or 6-membered ring containing a nitrogen atom as a hetero atom and a 5- or 6-membered heterocyclic ring, e.g., purine and naphthyridine; a 5- or 6-membered ring containing a nitrogen atom and a sulfur atom as hetero atoms, e.g., thiazole and isothiazole; and a 5- or 6-membered ring containing a nitrogen atom and an oxygen atom as hetero atoms, e.g., oxazole and isoxazole].

The preferred ring A may include, for example, a benzene ring, a heterocyclic ring (a 5-membered ring such as thiophene, furan, pyrrole, pyrazole, thiazole, or oxazole; a 6-membered ring such as pyridine, pyrazine, pyrimidine, or pyridazine), particularly an aromatic heterocyclic ring containing at least a nitrogen atom as a hetero atom (such as pyridine or pyrazine).

The ring A may have a substituent. The substituent may include, for example, a halogen atom (a fluorine atom, a chlorine atom, a bromine atom, an iodine atom), an alkyl group (e.g., a straight chain or branched chain $C_{1-10}$alkyl group such as methyl, ethyl, propyl, isopropyl, butyl, s-butyl, isobutyl, t-butyl, pentyl, isopentyl, neopentyl, or hexyl group), a haloalkyl group [a halo$C_{1-6}$alkyl group such as a fluoromethyl group (such as trifluoromethyl group), a fluoroethyl group (such as 2,2,2-trifluoroethyl group or perfluoroethyl group), 3,3,3,2,2-pentafluoropropyl group, or perfluoropropyl group), and chloroalkyl groups corresponding to these fluoroalkyl groups], an alkoxy group (e.g., a straight chain or branched chain $C_{1-10}$alkoxy group such as methoxy, ethoxy, propoxy, isopropoxy, butoxy, s-butoxy, isobutoxy, t-butoxy, pentyloxy, or hexyloxy group), a haloalkoxy group [a halo$C_{1-6}$alkoxy group such as a fluoromethoxy group (such as trifluoromethoxy group), a fluoroethoxy group (such as 2,2,2-trifluoroethoxy group or perfluoroethoxy group), 3,3,3,2,2-pentafluoropropoxy group, perfluoropropoxy group), or chloroalkoxy groups corresponding to these fluoroalkoxy groups], an acyl group (e.g., formyl group, a straight chain or branched chain $C_{1-6}$alkyl-carbonyl group such as acetyl, propionyl or butylyl group, a $C_{3-10}$cycloalkyl-carbonyl group such as cyclohexylcarbonyl group, a $C_{6-10}$aryl-carbonyl group such as benzoyl group, and a $C_{6-10}$aryl-$C_{1-4}$alkyl-carbonyl group such as benzylcarbonyl group), an acyloxy group (e.g., a straight chain or branched chain $C_{2-6}$acyloxy group such as acetoxy group, propionyloxy group, or butylyloxy group), a carboxyl group, an alkoxycarbonyl group [e.g., a straight chain or branched chain $C_{1-6}$alkoxy-carbonyl group such as methoxycarbonyl group, ethoxycarbonyl group, n-propoxycarbonyl group, isopropoxycarbonyl group, n-butoxycarbonyl group, isobutoxycarbonyl group, s-butoxycarbonyl group, or t-butoxycarbonyl group], a carbamoyl group, an N-substituted carbamoyl group [e.g., an N-mono$C_{1-6}$alkylcarbamoyl group, an N—$C_{1-6}$acyl-carbamoyl group, an N,N-di$C_{1-6}$alkylcarbamoyl group, and an N,N-di$C_{1-6}$acyl-carbamoyl group], a sulfonyl group, a sulfoamide group, an amino group, an N-substituted amino group [e.g., an N—$C_{1-4}$alkylamino group, an N,N-di$C_{1-4}$alkylamino group such as N,N-dimethylamino group or N,N-diethylamino group; an N—$C_{1-4}$alkyl-carbonylamino group, an N,N-di$C_{1-4}$alkyl-carbonylamino group such as N-acetylamino group], a cyano group, and a nitro group. The ring A may have one or more substituents as described above.

Among these substituents, the preferred one may include a halogen atom (such as a fluorine atom or a chlorine atom), a straight chain or branched chain $C_{1-6}$alkyl group (preferably a $C_{1-4}$alkyl group, and more preferably a $C_{1-2}$alkyl group), a straight chain or branched chain haloalkyl group [e.g., a fluoro$C_{1-6}$alkyl group (preferably a fluoro$C_{1-4}$alkyl group, and more preferably a fluoro$C_{1-3}$alkyl group) such as trifluoromethyl group, 2,2,2-trifluoroethyl group, or perfluoroethyl group, and chloroalkyl groups corresponding to these fluoroalkyl groups], a straight chain or branched chain $C_{1-6}$alkoxy group (e.g., preferably a $C_{1-4}$alkoxy group, more preferably a $C_{1-3}$alkoxy group, and particularly a $C_{1-2}$alkoxy group), and a straight chain or branched chain haloalkoxy group [a fluoro$C_{1-6}$alkoxy group (preferably a fluoro$C_{1-4}$alkoxy group, and more preferably a fluoro$C_{1-3}$alkoxy group) such as trifluoromethoxy group, 2,2,2-trifluoroethoxy group, or 3,3,3,2,2-pentafluoropropoxy group, chloroalkoxy groups corresponding to these fluoroalkoxy groups].

There is no particular limitation as to the position of the substituent in the ring A. For a homocyclic ring as the ring A, based on the bond position of $R^1$, the substituent may be located on 2-, 3-, 4-, or 5-position in a homocyclic ring as the ring A. For a heterocyclic ring as the ring A, depending on the position of a hetero atom thereof, the substituent may be located on 2-, 3-, 4-, or 5-position in the heterocyclic ring. Moreover, a hetero atom (a nitrogen atom) of the heterocyclic ring may have the substituent; usually a carbon atom thereof has the substituent in practical cases.

The position of the group —C(O)—Z in the ring A may also be 2-, 3-, 4-, or 5-position of the ring A based on the bond position of $R^1$. For example, in the case of benzene ring as the ring A, the group —C(O)—Z may be located on o-, m-, or p-position to the group $R^1$; in the case of pyridine ring as the ring A, the group —C(O)—Z may be located on 2-, 3-, or 4-position to a nitrogen atom constituting the ring.

The ring B represents a heterocyclic ring containing G and nitrogen atom N as constituent atoms of the ring as shown the formula (1), wherein G of the ring B represents CH or N. The ring B may usually be a 4- to 12-membered ring (for example, a 4- to 10-membered ring, preferably a 5- to 10-membered ring, and more preferably a 5- to 8-membered ring (e.g., a 5- or 6-membered ring)).

The ring B may be either an aliphatic heterocyclic ring or an aromatic heterocyclic ring. The aliphatic heterocyclic ring may include, for example, a 4- to 8-membered ring (e.g., a 5- or 6-membered ring) containing at least one nitrogen atom as a hetero atom, e.g., azetidine, pyrrolidine, pyrroline, imidazolidine, imidazoline, pyrazolidine, pyrazoline, piperidine, piperazine, and 1,4-diazepane. The aromatic heterocyclic ring may include, for example, a 5-, 6- or 7-membered ring containing at least one nitrogen atom as a hetero atom, e.g., pyrrole, imidazole, and pyrazole; a condensed ring of a 5- or 6-membered ring containing a nitrogen atom as a hetero atom and a carbocyclic ring (such as benzene ring), e.g., indole, carbazole, indoline, and isoindoline; a condensed ring of a 5- or 6-membered ring containing a nitrogen atom as a hetero atom and a 5- or 6-membered heterocyclic ring of the same as or different kind from the 5- or 6-membered ring, e.g., purine; and a 5- or 6-membered ring containing a nitrogen atom and an oxygen atom as hetero atoms, e.g., morpholine. The preferred ring B may include an aliphatic 5- or 6-membered heterocyclic ring, for example, piperidine ring and piperazine ring.

The ring B may have a substituent, for example, the same substituent (e.g., a halogen atom, an alkyl group, and an alkoxy group) as that of the ring A.

The group $R^1$ represents a carbonyl group or an alkylene group. The alkylene group may have a substituent. Examples of the alkylene group may include a straight chain or branched chain $C_{1-10}$alkylene group such as methylene, ethylene, ethane-1,1-diyl, trimethylene, propylene, propane-2,2-diyl, tetramethylene, pentamethylene, or hexamethylene group. The preferred alkylene group may include a $C_{1-6}$alkylene group, for example, a straight chain or branched chain $C_{1-4}$alkylene group, particularly a straight chain or branched chain $C_{1-3}$alkylene group (e.g., a $C_{1-2}$alkylene group such as methylene group), and specifically methylene group.

The substituent of the alkylene group may be the same substituent as that of the ring A; the substituent may include, for example, a halogen atom, a haloalkyl group, an alkoxy group, a haloalkoxy group, an acyl group, an acyloxy group, a carboxyl group, an alkoxycarbonyl group, a carbamoyl group, an N-substituted carbamoyl group, an amino group, an N-substituted amino group, a cyano group, and a nitro group. The preferred substituent may for example be a halogen atom (a fluorine atom, a chlorine atom, a bromine atom, an iodine atom), a haloalkyl group [e.g., a halo$C_{1-4}$alkyl group such as trifluoromethyl group or trichloromethyl group], an alkoxy group (e.g., a $C_{1-4}$alkoxy group such as methoxy, ethoxy, propoxy, isopropoxy, or butoxy group), and a haloalkoxy group [e.g., a halo$C_{1-4}$alkoxy group such as trifluoromethoxy group]. The alkylene group usually has no substituent or has a halogen atom (such as a fluorine atom or a chlorine atom) as a substituent in practical cases.

Compared with the compound in which $R^1$ is a carbonyl group, the compound in which $R^1$ is an alkylene group having a substituent or having no substituent shows a high pharmacological activity. Thus, it is preferable that the group $R^1$ be an alkylene group having a substituent or having no substituent (e.g., a short-chain alkylene group having no substituent, such as methylene group).

The groups $R^{2a}$ and $R^{2b}$ are the same or different and each represent an alkyl group, a homocyclic ring or carbocyclic ring group [a carbocyclic group [a cycloalkyl group (an aliphatic homocyclic group), an aryl group (an aromatic homocyclic group)]], or a heterocyclic group (an aliphatic or aromatic heterocyclic group). Examples of the alkyl group may include a straight chain or branched chain $C_{1-10}$alkyl group such as methyl, ethyl, propyl, isopropyl, butyl, s-butyl, isobutyl, t-butyl, pentyl, isopentyl, neopentyl, or hexyl group. The cycloalkyl group (aliphatic homocyclic group) among the carbocyclic ring may include a $C_{4-10}$cycloalkyl group such as cyclobutyl, cyclopentyl, cyclohexyl, cycloheptyl, or cyclooctyl group, and other groups. Examples of the aryl group (aromatic homocyclic group) may include a $C_{6-10}$aryl group such as phenyl group or naphthyl group. As the heterocyclic group, for example, there may be mentioned a group corresponding to the heterocyclic ring exemplified as the ring A [e.g., a 5- or 6-membered heterocyclic ring containing at least one hetero atom selected from the group consisting of a nitrogen atom, an oxygen atom, and a sulfur atom; and a condensed ring of the heterocyclic ring and a carbocyclic ring (such as benzene ring)]. The heterocyclic group may be an aliphatic heterocyclic group or may be an aromatic heterocyclic group.

The preferred $R^{2a}$ and $R^{2b}$ each are an aromatic ring, for example, a $C_{6-10}$arene ring (e.g., benzene ring) or an aromatic 5- or 6-membered heterocyclic ring containing at least one hetero atom selected from the group consisting of a nitrogen atom, an oxygen atom, a sulfur atom (for example, an aromatic heterocyclic ring containing a nitrogen atom as a hetero atom, e.g., pyridine ring). In particular, a benzene ring is preferred. As a combination of $R^{2a}$ and $R^{2b}$, it is preferable that at least one of $R^{2a}$ and $R^{2b}$ be a benzene ring. The preferred combination includes a combination in which both $R^{2a}$ and $R^{2b}$ are a benzene ring; and a combination in which one of $R^{2a}$ and $R^{2b}$ is a benzene ring and the other is a cycloalkane ring (e.g., a $C_{5-7}$cycloalkane ring such as cyclohexane ring) or an aromatic 5- or 6-membered heterocyclic ring containing at least one hetero atom selected from the group consisting of a nitrogen atom, an oxygen atom, and a sulfur atom (for example, an aromatic heterocyclic ring containing a nitrogen atom as a hetero atom, e.g., pyrrole, pyrazole, imidazole, pyridine, oxazole, and thiazole).

The groups $R^{2a}$ and $R^{2b}$ may have the same or different substituent. The substituents of $R^{2a}$ and $R^{2b}$ may include, for example, a halogen atom, an alkyl group (e.g., a straight chain or branched chain $C_{1-6}$alkyl group), a cycloalkyl group (e.g., a $C_{4-10}$cycloalkyl group), an aryl group (e.g., a $C_{6-10}$aryl group), a haloalkyl group (e.g., a straight chain or branched chain halo$C_{1-6}$alkyl group), an alkoxy group (e.g., a straight chain or branched chain $C_{1-6}$alkoxy group), a haloalkoxy group (e.g., a straight chain or branched chain halo$C_{1-6}$alkoxy group), an acyl group (e.g., a straight chain or branched chain $C_{1-6}$alkyl-carbonyl group), an acyloxy group (e.g., a straight chain or branched chain $C_{2-6}$acyloxy group), a carboxyl group, an alkoxycarbonyl group (e.g., a straight chain or branched chain $C_{1-6}$alkoxy-carbonyl group), a carbamoyl group, an N-substituted carbamoyl group (e.g., a $C_{1-6}$alkyl-carbamoyl group and a $C_{1-6}$acyl-carbamoyl group), an amino group, an N-substituted amino group (e.g., N,N-di$C_{1-4}$alkylamino group and an N,N-di$C_{1-4}$alkyl-carbonylamino group), an oxo group, a cyano group, and a nitro group. According to the species of the substituent, if necessary, these substituents may further have a substituent (such as a halogen atom such as a fluorine atom, a straight chain or branched chain $C_{1-4}$alkyl group, a straight chain or branched chain $C_{1-4}$alkoxy group, a straight chain or branched chain halo$C_{1-4}$alkyl group, a straight chain or branched chain halo$C_{1-4}$alkoxy group, a straight chain or branched chain $C_{1-4}$alkyl-carbonyl group, a carboxyl group, or a straight chain or branched chain $C_{1-6}$alkoxy-carbonyl group) to form an alkoxyalkyl group, an alkoxyalkoxy group, a carboxyalkyl group, or other groups.

The preferred substituents of $R^{2a}$ and $R^{2b}$ may include, for example, a halogen atom (e.g., a fluorine atom and a chlorine atom), a straight chain or branched chain $C_{1-3}$alkyl group, a straight chain or branched chain halo$C_{1-3}$alkyl group (e.g., a fluoro$C_{1-3}$alkyl group), a straight chain or branched chain $C_{1-3}$alkoxy group, and a straight chain or branched chain halo$C_{1-3}$alkoxy group (e.g., a fluoro$C_{1-3}$alkoxy group).

The substituents of $R^{2a}$ and $R^{2b}$ may be the same or different in species from each other. Each of $R^{2a}$ and $R^{2b}$ may have a single or a plurality of substituents. Further, the position of the substituent in $R^{2a}$ may be different from that in $R^{2b}$. For example, $R^{2a}$ and $R^{2b}$ may have the same substituent (such as a halogen atom, an alkyl group, a haloalkyl group, an alkoxy group, or a haloalkoxy group) on the same position (e.g., 2-, 3-, or 4-position in benzene ring); or $R^{2a}$ may have a halogen atom, an alkyl group, a haloalkyl group, an alkoxy group, or a haloalkoxy group as the substituent and $R^{2b}$ may have no substituent.

More specifically, when each of $R^{2a}$ and $R^{2b}$ is benzene ring, the substituent may be located on 2-, 3-, or 4-position; one benzene ring may have a substituent on one of 2-, 3-, and 4-positions thereof (for example, one benzene ring has one or a plurality of substituents on at least one position selected from the group consisting of 2-, 3-, and 4-positions thereof), and the other benzene ring may have no substituent. Moreover, the substituent of one benzene ring and that of the other benzene ring may be different in the substituent position from each other (for example, one benzene ring may have a substituent on 2- or 3-position thereof and the other benzene ring may have a substituent on 4-position thereof).

Further, the substituents on these rings represented by $R^{2a}$ and $R^{2b}$ [the homocyclic rings (carbocyclic rings) or the heterocyclic rings] may bond together to form a carbocyclic ring or a heterocyclic ring. The carbocyclic ring or heterocyclic ring to be formed may have a substituent. More specifically, $R^{2a}$ and $R^{2b}$ may form a tricyclic group represented by the following formula (2).

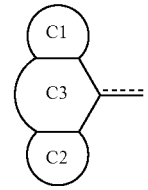

(2)

In the formula (2), the ring C1 and the ring C2 are the same or different and each represent an arene ring (e.g., a $C_{6-10}$arene ring such as benzene ring) or a heterocyclic ring (e.g., an aliphatic or aromatic heterocyclic ring such as an aromatic 5- or 6-membered heterocyclic ring). The ring C1 and the ring C2 each may have the same or different substituent, for example, at least one substituent selected from the group consisting of a halogen atom (such as a fluorine atom or a chlorine atom), an alkyl group (such as a straight chain or branched chain $C_{1-6}$alkyl group), a haloalkyl group (e.g., a straight chain or branched chain halo$C_{1-6}$alkyl group such as trifluoromethyl group), an alkoxy group (such as a straight chain or branched chain $C_{1-6}$alkoxy group), and a haloalkoxy group (e.g., a straight chain or branched chain halo$C_{1-6}$alkoxy group such as trifluoromethoxy group). Each of the ring C1 and the ring C2 may have one or a plurality of substituents. The position of the substituent is not particularly limited to a specific one. For example, the position of the substituent may be 1- to 4-position (for example, 2-position or 3-position) from the bond site between the ring C3 and the ring C1 or C2 (from the left bond site (or on the left side) in the formula (2)).

The ring C3 is usually a 4- to 10-membered ring (preferably a 5- to 8-membered ring, and particularly a 6- to 8-membered ring). Each of the carbocyclic ring and the heterocyclic ring as the ring C3 may be an aliphatic or aromatic ring, and is usually an aliphatic ring in practical cases. The carbocyclic ring may be an aliphatic carbocyclic ring, for example, a cycloalkane ring (e.g., a $C_{4-10}$cycloalkane ring such as cyclohexane ring, cycloheptane ring, or cyclooctane ring), a cycloalkene ring (e.g., a $C_{4-10}$cycloalkene ring such as cyclohexene ring, cycloheptene ring, or cyclooctene ring), and a $C_{4-10}$cycloalkadiene ring (e.g., cyclooctadiene ring) or may be an aromatic carbocyclic ring (e.g., a $C_{6-10}$arene ring such as benzene ring). The heterocyclic ring contains at least one hetero atom selected from the group consisting of a nitrogen atom, an oxygen atom, and a sulfur atom, as a constituent atom thereof. The heterocyclic ring may be a ring containing an oxygen atom as a hetero atom (for example, a 6- to 8-membered heterocyclic ring such as oxepin ring). The hetero atom of the ring C3 may be positioned at 1-position to 3-position (for example, 1-position or 2-position) from the bond site between the ring C3 and the ring C1 or C2 (from the left bond site (or on the left side) in the formula (2)) depending on the number of members of the ring C3.

The ring C3 may have a substituent which is the same as the substituent of the groups $R^{2a}$ and $R^{2b}$. The substituent may for example be at least one substituent selected from the group consisting of a halogen atom (such as a fluorine atom or a chlorine atom), an alkyl group (e.g., a straight chain or branched chain $C_{1-6}$alkyl group), a haloalkyl group (e.g., a straight chain or branched chain halo$C_{1-6}$alkyl group), a hydroxyl group, an alkoxy group (e.g., a straight chain or branched chain $C_{1-6}$alkoxy group), a haloalkoxy group (e.g., a straight chain or branched chain halo$C_{1-6}$alkoxy group), a carboxyl group, an alkoxycarbonyl group (e.g., a straight chain or branched chain $C_{1-6}$alkoxy-carbonyl group), an acyl group (e.g., a straight chain or branched chain $C_{1-6}$alkyl-carbonyl group), and a carbonyl group (or oxo group). Specifically, the ring C3 may have one or a plurality of substituents. The position of the substituent is not particularly limited to a specific one. For example, the position of the substituent may be 1-position to 3-position (for example, 2-position or 3-position) from the bond site between the ring C3 and the ring C1 or C2 (from the left bond site (or on the left side) in the formula (2)).

In the formula (2), the bond represented by the following formula (3) represents a single bond or a double bond; when n is 0 and G is CH, the bond represents a double bond.

$$\text{-----} \quad (3)$$

The atom X represents an oxygen atom or a sulfur atom, usually an oxygen atom.

In the formula (1), the introduction of the substituent —C(O)—Z into the ring A can significantly improve the pharmacological activity. The alkoxy group represented by Z may include the same alkoxy group as the substituent of the ring A. The preferred alkoxy group includes a straight chain or branched chain $C_{1-6}$alkoxy group (e.g., a $C_{1-4}$alkoxy group).

As the cycloalkyloxy group, for example, there may be mentioned a $C_{4-10}$cycloalkyloxy group such as cyclobutyloxy, cyclopentyloxy, cyclohexyloxy, cycloheptyloxy, or cyclooctyloxy group. The aryloxy group may include a $C_{6-10}$aryloxy group such as phenoxy group or naphthoxy group, and other groups. Examples of the aralkyloxy group may include a $C_{6-10}$aryl-$C_{1-4}$alkyloxy group such as benzyloxy or phenethyloxy group. The N-substituted amino group may include the same N-substituted amino group as the substituent of the ring A. As the preferred N-substituted amino group, for example, there may be mentioned an N,N-di$C_{1-6}$ alkylamino group such as N,N-dimethylamino group or N,N-diethylamino group; an N—$C_{1-6}$alkyl-carbonylamino group such as N-acetylamino group, an N,N-di$C_{1-6}$alkyl-carbonylamino group; and other groups.

The preferred Z includes a hydroxyl group; a $C_{1-3}$alkoxy group (for example, a $C_{1-2}$alkoxy group); an amino group; or an N-substituted amino group (mono- or di-substituted amino group) in which a $C_{1-3}$alkyl group (e.g., a $C_{1-2}$alkyl group) or a $C_{1-3}$alkyl-carbonyl group (e.g., a $C_{1-2}$alkyl-carbonyl group) as a substituent is attached to the nitrogen atom.

The group Z may form a pro-drug which produces an active compound in a living body, or may form an active metabolite.

The coefficient n denotes 0 or 1. When G is CH, n is often 1; When G is N, n is practically 0. Moreover, when G is CH, X is practically oxygen atom.

Further, when the ring A is a benzene ring or when the ring B is a piperazine ring, $R^1$ is an alkylene group which may have a substituent. When $R^1$ is a carbonyl group, the ring A is not a benzene ring but a heterocyclic ring.

Among these compounds, representative compounds can be represented by the following formula (1a), in particular (1b):

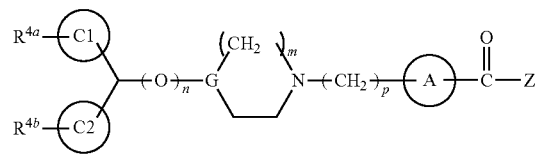

(1a)

wherein p is an integer of 1 to 4;
m is an integer of 1 to 5;
n is 1 when G is CH; n is 0 when G is N;
the ring C1 and the ring C2 are the same or different and each represent a $C_{6-10}$arene ring (e.g., benzene ring) or an aromatic 5- or 6-membered heterocyclic ring; and
$R^{4a}$ and $R^{4b}$ are the same or different and each represent a substituent selected from the group consisting of a hydrogen atom, a halogen atom (such as a fluorine atom or a chlorine atom), a straight chain or branched chain $C_{1-4}$alkyl group, a straight chain or branched chain halo$C_{1-4}$alkyl group, a straight chain or branched chain $C_{1-4}$alkoxy group, and a straight chain or branched chain halo$C_{1-4}$alkoxy group;
in the ring C1 and the ring C2, $R^{4a}$ and $R^{4b}$ may be the same or different in species from each other;
$R^{4a}$ and $R^{4b}$ may bond together to form the ring C3 (e.g., a 4- to 10-membered carbocyclic ring, or a heterocyclic ring containing an oxygen atom as a hetero atom), wherein the ring C3 may have a substituent such as the above-mentioned halogen atom;

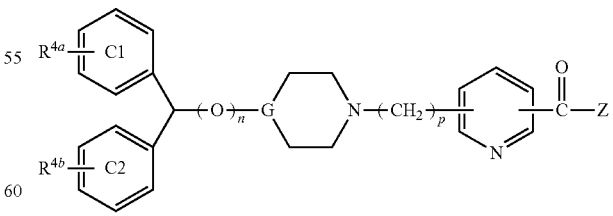

(1b)

wherein p is 1 or 2;
n is 1 when G is CH; n is 0 when G is N;
$R^{4a}$ and $R^{2b}$ have the same meanings as defined above; and
in the ring C1 and the ring C2, $R^{4a}$ and $R^{4b}$ may be the same or different in species from each other.

Examples of concrete compounds represented by the formula (1a) or (1b) may include the following compounds:

a (4-benzhydryloxypiperidin-1-ylmethyl)pyridinecarboxylic acid [e.g., 6-(4-benzhydryloxypiperidin-1-ylmethyl)pyridine-2-carboxylic acid], or an ester or a salt thereof;

a {4-[(halophenyl)phenylmethoxy]piperidin-1-ylmethyl} pyridinecarboxylic acid [e.g., 2-{4-[(4-fluorophenyl)phenylmethoxy]piperidin-1-ylmethyl}isonicotinic acid], or an ester or a salt thereof (a pro-drug, an active metabolite);

a {4-[($C_{1-4}$alkylphenyl)phenylmethoxy]piperidin-1-ylmethyl} pyridinecarboxylic acid [e.g., 6-{4-[phenyl-p-tolylmethoxy]piperidin-1-ylmethyl}pyridine-2-carboxylic acid], or an ester or a salt thereof (a pro-drug, an active metabolite);

a {4-[(fluoro$C_{1-4}$alkylphenyl)phenylmethoxy]piperidin-1-ylmethyl}pyridinecarboxylic acid [e.g., 6-{4-[phenyl(3-trifluoromethylphenyl)methoxy]piperidin-1-ylmethyl}pyridine-2-carboxylic acid], or an ester or a salt thereof (a pro-drug, an active metabolite);

a {4-[($C_{1-4}$alkoxyphenyl)phenylmethoxy]piperidin-1-ylmethyl}pyridinecarboxylic acid [e.g., 2-{4-[(4-methoxyphenyl)phenylmethoxy]piperidin-1-ylmethyl}isonicotinic acid], or an ester or a salt thereof (a pro-drug, an active metabolite);

a {4-[(fluoro$C_{1-4}$alkoxyphenyl)phenylmethoxy]piperidin-1-ylmethyl}pyridinecarboxylic acid [e.g., 6-{4-[phenyl(4-trifluoromethoxyphenyl)methoxy]piperidin-1-ylmethyl}pyridine-2-carboxylic acid], or an ester or a salt thereof (a pro-drug, an active metabolite);

a {4-[bis(halophenyl)methoxy]piperidin-1-ylmethyl} pyridinecarboxylic acid [e.g., 2-{4-[bis(4-fluorophenyl)methoxy]piperidin-1-ylmethyl}isonicotinic acid], or an ester or a salt thereof (a pro-drug, an active metabolite);

a {4-[bis(halophenyl)methyl]piperazin-1-ylmethyl} pyridinecarboxylic acid [e.g., 6-{4-[bis(4-fluorophenyl)methyl]piperazin-1-ylmethyl}pyridine-2-carboxylic acid], or an ester or a salt thereof (a pro-drug, an active metabolite);

a (3-benzhydryloxypyrrolidin-1-ylmethyl)pyridinecarboxylic acid [e.g., 6-(3-benzhydryloxypyrrolidin-1-ylmethyl)pyridine-2-carboxylic acid], or an ester or a salt thereof (a pro-drug, an active metabolite);

a [4-(10,11-dihydrodibenzo[a,d]cyclohepten-5-ylidene)piperidin-1-ylmethyl]pyridinecarboxylic acid [e.g., 6-[4-(10,11-dihydrodibenzo[a,d]cyclohepten-5-ylidene)piperidin-1-ylmethyl]pyridine-2-carboxylic acid], or an ester or a salt thereof (a pro-drug, an active metabolite); and a [4-(6H-dibenzo[b,e]oxepin-11-ylidene)piperidin-1-ylmethyl]pyridinecarboxylic acid [e.g., 6-[4-(6H-dibenzo[b,e]oxepin-11-ylidene)piperidin-1-ylmethyl]pyridine-2-carboxylic acid], or an ester or a salt thereof (a pro-drug, an active metabolite).

The heterocyclic compound also includes a salt (a salt with a pharmacologically acceptable acid or base) of the compound of the formula (1). The acid for forming such a salt may include an inorganic acid (e.g., hydrochloric acid, hydrobromic acid, sulfuric acid, nitric acid, and phosphoric acid) and an organic acid (e.g., an organic carboxylic acid such as acetic acid, propionic acid, trichloroacetic acid, trifluoroacetic acid, oxalic acid, succinic acid, fumaric acid, or maleic acid; an hydroxycarboxylic acid such as lactic acid, malic acid, tartaric acid, or citric acid; and a sulfonic acid such as methanesulfonic acid or toluenesulfonic acid). As the base, there may be mentioned, for example, an inorganic base (such as ammonia; an alkali metal hydroxide such as sodium hydroxide or potassium hydroxide; an alkali metal carbonate; an alkaline earth metal hydroxide such as calcium hydroxide or magnesium hydroxide; and an alkaline earth metal carbonate such as calcium carbonate) and an organic base (e.g., an alkylamine such as triethylamine; an alkanolamine such as ethanolamine; and a polyamine such as an alkylenediamine). These acids or bases may be used alone or in combination.

The heterocyclic compound or the salt thereof may be an anhydride or a hydrate or may be a solvate (e.g., a solvate of an organic solvent such as ethanol). Moreover, the heterocyclic compound or the salt thereof also includes a hydrate or solvate of the compound of the formula (1) or the salt thereof, and in addition, an isolated crystal (e.g., a polymorphic crystalline substance). Moreover, the heterocyclic compound or the salt thereof according to the present invention also includes a tautomer, optically active substance having an asymmetric carbon atom (such as (R)-body, (S)-body, diastereomer), or racemic body of the compound of the formula (1) or the salt thereof, or a mixture of these compounds. In particular, the compound in which X is oxygen atom or sulfur atom may be an optically active substance due to an asymmetric carbon atom thereof. Further, the group —C(O)—Z, the heterocyclic group as the ring A, or other groups of the heterocyclic compound or the salt thereof may be modified for forming a pro-drug which expresses an activity in a living body (or an active metabolite). The pro-drug may include, for example, a compound which expresses an activity by metabolism such as hydrolysis, oxidation, reduction, or transesterification (for example, an esterbody, etherbody, alcohol body, or amide body of the compound of the formula (1)).

[Production Process]

The heterocyclic compound represented by the formula (1) or the salt thereof can be produced by a conventional manner, for example, according to the following reaction scheme:

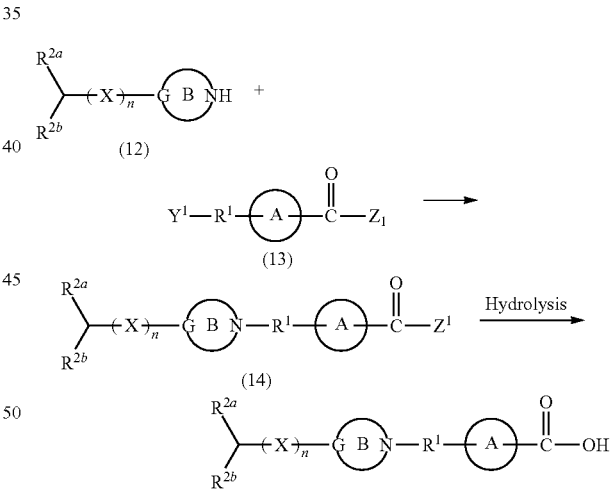

wherein $Y^1$ represents a halogen atom; $Z^1$ represents an alkoxy group, a cycloalkyloxy group, an aryloxy group, or an aralkyloxy group; the ring A, the ring B, $R^1$, G, X, n, $R^{2a}$, and $R^{2b}$ have the same meanings as defined above.

The halogen atom represented by $Y^1$ is a fluorine atom, a chlorine atom, a bromine atom, or an iodine atom, and is usually a chlorine atom or a bromine atom. The alkoxy group represented by $Z^1$ may include the same alkoxy group as the group Z and is usually a straight chain or branched chain $C_{1-6}$alkoxy group (preferably a $C_{1-4}$alkoxy group, and more preferably a $C_{1-2}$alkoxy group). As the cycloalkyloxy group, for example, there may be mentioned a $C_{4-10}$cycloalkyloxy group such as cyclohexyloxy group. Examples of the aryloxy group may include a $C_{6-10}$aryloxy group such as phenoxy group. The aralkyloxy group may include a $C_{6-10}$aryl-$C_{1-4}$alkyloxy group such as benzyloxy group or phenethyloxy group, and other groups. The group $Z^1$ is usually an alkoxy group or an aralkyloxy group.

The reaction of the compound represented by the formula (12) and the compound represented by the formula (13) can produce a compound represented by the formula (14). The reaction can usually be carried out in a solvent inactive to the reaction in the presence of a base. The amount of the compound (13) relative to 1 mol of the compound (12) is about 0.8 to 5 mol, preferably about 1 to 3 mol, and more preferably about 1.1 to 2 mol.

The solvent may include, for example, a hydrocarbon (an aliphatic hydrocarbon such as hexane; an alicyclic hydrocarbon such as cyclohexane; and an aromatic hydrocarbon such as toluene), an ester (such as ethyl acetate), a ketone (such as acetone or methyl ethyl ketone), an ether (a chain ether such as diethyl ether or diisopropyl ether; and a cyclic ether such as dioxane or tetrahydrofuran), a nitrile (such as acetonitrile, propionitrile, or benzonitrile), an amide (such as N,N-dimethylformamide or N,N-dimethylacetamide), a sulfoxide (such as dimethylsulfoxide), a sulfolane, and an alcohol (such as ethanol or isopropanol). These solvents may be used alone or as a mixed solvent in combination. As the base, for example, there may be mentioned an inorganic base (e.g., an alkali metal hydroxide such as sodium hydroxide or potassium hydroxide; an alkali metal carbonate; an alkaline earth metal hydroxide such as calcium hydroxide or magnesium hydroxide; and an alkaline earth metal carbonate), an organic base (e.g., an amine such as trimethylamine, triethylamine, triethanolamine, or dimethylaminoethanol), or the like. These bases may be used alone or in combination. The amount to be used of the base may be equivalent to 1 mol of the compound (2) or in excess of that of the compound (2) (for example, about 1 to 10 equivalents, and preferably about 1.1 to 5 equivalents).

The reaction can for example be carried out at a temperature of about 0 to 150° C. [preferably about 10 to 100° C., and more preferably a room temperature (about 20 to 25° C.) to 50° C.]. Moreover, the reaction can be conducted in air or under an inactive (or inert) gas atmosphere (such as nitrogen, helium, or argon gas). The reaction may be carried out under an applied pressure and is usually carried out under an atmospheric pressure.

After the completion of the reaction, the produced compound (14) may be separated or purified by a conventional separation or purification (or isolation) method, for example, filtration, distillation, solvent removal, precipitation, crystallization, recrystallization, decantation, extraction, drying, washing, chromatography, and a combination thereof.

The compound (4) can be hydrolyzed to obtain a compound represented by the formula (1) in which Z is hydroxyl group. The hydrolysis can be carried out by a conventional method, for example, in a solvent in the presence of a hydrolysis catalyst (e.g., an inorganic base such as sodium hydroxide, potassium hydroxide, sodium carbonate, potassium carbonate, potassium hydrogen carbonate). As the solvent, for example, various solvents as exemplified above (e.g., an alcohol) can be used. To the reaction system, water may be added.

The hydrolysis can be carried out at a proper temperature, for example, at 30 to 150° C. or under reflux. The hydrolysis reaction may be conducted continuously after the reaction of the compound (12) and the compound (13) without isolation or purification of the produced compound (14).

After the completion of the reaction, the reaction product can be separated or purified (or isolated) in the same manner as above.

The compound represented by the formula (12) in which G is N is known. The compound represented by the formula (12) in which G is CH can be prepared by a conventional method, for example, by a dehydration condensation of a compound represented by the following formula (12a) and a compound represented by the formula (12b) in the presence of an acid catalyst.

As the acid catalyst, for example, an inorganic acid (such as sulfuric acid) and an organic acid (such as p-toluenesulfonic acid) may be mentioned. Lewis acid may also be used as the acid catalyst. The reaction is usually conducted in a solvent. As the solvent, for the dehydration condensation of these compounds, a hydrophobic solvent, e.g., a hydrocarbon (such as hexane or toluene) and an ether may be used. The reaction can be carried out, for example, at a temperature of about 50 to 200° C. (e.g., about 75 to 150° C.) or can be carried out under a reflux of the solvent.

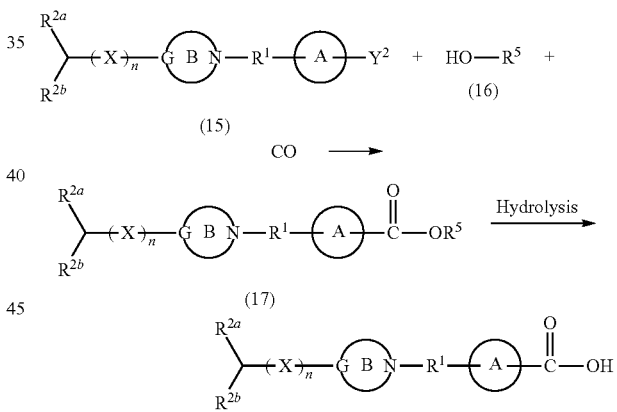

In the formulae, $Y^2$ represents a halogen atom; $R^5$ represents an alkyl group, a cycloalkyl group, an aryl group, or an aralkyl group; the ring A, the ring B, $R^1$, G, X, n, $R^{2a}$, and $R^{2b}$ have the same meanings as defined above.

The halogen atom represented by $Y^2$ represents a fluorine atom, a chlorine atom, a bromine atom, or an iodine atom and is usually a chlorine atom or a bromine atom.

The alkyl group represented by $R^5$ may include an alkyl group corresponding to the same alkoxy group as the group Z and is usually a straight chain or branched chain $C_{1-6}$alkyl group (preferably a $C_{1-4}$alkyl group). The cycloalkyl group, aryl group, and aralkyl group represented by $R^5$ may include the same $C_{4-10}$cycloalkyl group, $C_{6-10}$aryl group, and $C_{6-10}$aryl-$C_{1-4}$alkyl group, respectively, as described above.

The reaction (carbonylation reaction) of the compound represented by the formula (15), the compound represented by the formula (16), and carbon monoxide in the presence of a catalyst allows the compound represented by the formula (17) to be produced. The reaction is usually conducted in a solvent and in the presence of a base. The amount to be used of the compound (16) may be equivalent or more to 1 mol of the compound (15) (usually, excessive mol, for example, about 1.5 to 1000 mol, preferably about 2 to 500 mol, more preferably about 5 to 200 mol, and particularly about 10 to 100 mol). Moreover, the amount to be used of the carbon monoxide is also in excess of 1 mol of the compound (15) (for example, 2 to 1000 mol, and preferably 5 to 500 mol). The reaction can usually be carried out in carbon monoxide atmosphere or carbon monoxide flow or by blowing of carbon monoxide into the reaction system.

Examples of the catalyst may include a carbonylation catalyst, for example, a palladium catalyst (such as palladium acetate, palladium sulfate, or a palladium complex) and a rhodium catalyst. The amount of the catalyst may for example be about 0.1 to 50 mol %, preferably about 0.5 to 20 mol %, and more preferably about 1 to 10 mol % (e.g., about 3 to 7 mol %) relative to the amount of the compound represented by the formula (15).

Further, as a co-catalyst, a phosphine (for example, 1,3-bis(diphenylphosphino)propane, triphenylphosphine) may be used. The amount of the co-catalyst may for example be about 0.1 to 50 mol %, preferably about 0.5 to 20 mol %, and more preferably about 1 to 10 mol % (e.g., about 3 to 7 mol %) relative to the amount of the compound represented by the formula (15).

The species and amount of the base are the same as those in the reaction of the compound (12) and the compound (13). The solvent may include a hydrocarbon (an aliphatic hydrocarbon such as hexane; an alicyclic hydrocarbon such as cyclohexane; an aromatic hydrocarbon such as toluene), a halogenated hydrocarbon (such as chloroform, dichloromethane, or trichloroethane), an ester (such as ethyl acetate), a ketone (such as acetone or methyl ethyl ketone), an ether (a chain ether such as diethyl ether or diisopropyl ether; a cyclic ether such as dioxane or tetrahydrofuran), a nitrile (such as acetonitrile, propionitrile, or benzonitrile), an amide (such as N,N-dimethylformamide or N,N-dimethylacetamide), a sulfoxide (such as dimethyl sulfoxide), a sulfolane, and an alcohol (such as ethanol or isopropanol).

The reaction can for example be carried out at a temperature of about 20 to 150° C. (preferably about 50 to 120° C., more preferably about 50 to 100° C.). Moreover, the reaction can be conducted in air or under an inactive (or inert) atmosphere (such as nitrogen, helium, or argon gas). The reaction may be carried out under an atmospheric pressure or an applied pressure.

After the completion of the reaction, the produced compound (17) may be separated or purified by the same conventional separation or purification (or isolation) method as described above.

The compound (17) may be hydrolyzed to obtain a compound represented by the formula (1) in which Z is a hydroxyl group. The hydrolysis can be carried out by the same manner as the hydrolysis of the compound (14). Moreover, after the completion of the reaction, the reaction product can be separated or purified (or isolated) in the same manner as the above-mentioned method.

The compound (15) can be prepared by a conventional method, for example, a reaction of a compound represented by the following formula (15a) and a compound represented by the formula (15b):

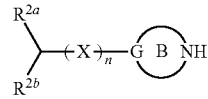

(15a)

(15b)

wherein the ring A, the ring B, $R^1$, $Y^1$, $Y^2$, G, X, n, $R^{2a}$, and $R^{2b}$ have the same meanings as defined above.

The reaction of the compound (15a) and the compound (15b) can be carried out in the same manner as the reaction of the compound (12) and the compound (13). When $Y^1$ and $Y^2$ are the same halogen atom, $Y^1$ is preferentially allowed to react with NH of the ring B of the compound (15a). The preferred $Y^1$ may be a halogen atom having a higher leaving-group ability than that of $Y^2$ (for example, when $Y^2$ is a chlorine atom, $Y^1$ may be a bromine atom).

The compound (1) containing a basic group (such as amino group, imino group, or a basic nitrogen atom of a heterocyclic ring) can easily form a salt (for example, a pharmaceutically acceptable salt) thereof with the above-exemplified acid (an organic acid and/or an inorganic acid); the compound (1) containing an acidic group (such as carboxyl group or sulfonyl group) can easily form a salt (for example, a pharmaceutically acceptable salt) thereof with the above-exemplified base (an organic base and/or an inorganic base).

Further, the amino group and N-alkylamino group (forming carbamoyl group and an N-alkylcarbamoyl group, respectively, as the group —C(O)—Z) represented by Z can be obtained by a conventional amide bond formation method, for example, allowing the compound in which Z is a hydroxyl group, an alkoxy group, a cycloalkyloxy group, an aryloxy group, or an aralkyloxy group (forming carboxyl group or an alkoxycarbonyl group or the like as the group —C(O)—Z) to react with ammonia and an amine (a primary amine such as ethylamine; a secondary amine such as dimethylamine), respectively. Moreover, the N-alkylamino group or N-acylamino group represented by Z can be formed by subjecting the heterocyclic compound in which Z is an amino group to alkylation or acylation reaction. For example, the compound in which Z is an amino group can be allowed to react with an alkyl halide (e.g., a $C_{1-6}$alkyl halide such as methyl chloride or ethyl chloride) or an acylation agent (e.g., a $C_{1-4}$acyl chloride such as acetyl chloride; a $C_{1-3}$alkanecarboxylic anhydride such as acetic anhydride; and a $C_{6-10}$aryl-$C_{1-4}$alkyl chloride such as benzyl chloride) to obtain the compound in which Z is an N-alkylamino group or an N-acylamino group.

[Use and Pharmaceutical Composition]

The heterocyclic compound represented by the formula (1) or the salt thereof shows a high pharmacological activity, for example, an antiallergic effect, an antihistaminic effect (including a histamine $H_1$ antagonistic effect), an antiinflammatory effect, antipruritic effect, and other effects. The heterocyclic compound or the salt thereof is thus useful as an antiallergic agent for an allergic disease, an antihistaminic agent (e.g., a histamine $H_1$ receptor antagonist), an antiinflammatory agent, an antipruritic agent, and other agents. Moreover, the heterocyclic compound or the salt thereof is useful as an agent for preventing and/or treating an allergic disease. The allergic disease may include, for example, allergic rhinitis, nasal blockage, allergic dermatitis (such as atopic dermatitis), allergic inflammation, asthma (bronchial asthma), urticaria, eczema, pruritus cutaneous, prurigo, psoriasis vulgaris accompanied by pruritus, allergic conjunctivitis, hypereosinophilic syndrome, systemic lupus erythematosus, and chronic rheumatism inflammation.

Further, the heterocyclic compound represented by the formula (1) or the salt thereof has a wide safety margin and a low toxicity. Furthermore, the heterocyclic compound represented by the formula (1) or the salt thereof has a low central nervous system effect or hypnotic effect (such as sleepiness or malaise).

The heterocyclic compound may be used as a medicine alone, or the heterocyclic compound may be used in combination with a carrier (e.g., a pharmacologically or physiologically acceptable carrier) to provide a pharmaceutical composition (or preparation). With respect to the pharmaceutical composition of the present invention, the carrier may be selected depending on the form of the pharmaceutical composition or preparation (or the dosage form), the route of administration, the application (or use), and others. The dosage form is not particularly limited to a specific one and may be a solid preparation (for example, powdered preparations, powders, granulated preparations (e.g., granules and microfine granules or the like), spherical or spheroidal preparations, pills, tablets, capsules, dry syrups, and suppositories), a semisolid preparation (for example, creams, ointments, gels, gumdrop-like preparations, and film-like preparations, sheet-like preparations), a liquid preparation (for example, solutions, suspensions, emulsions, syrup, elixir, lotions, and injectable solutions (or injections)), and others. Moreover, sprays or aerosols of the powdered preparations and/or the liquid preparation may be also included. Incidentally, the capsules may be a capsule filled with a liquid or a capsule filled with a solid preparation (such as granules). Moreover, the preparation may be a lyophilized preparation. Further, the preparation of the present invention may be a preparation releasing the active ingredient(s) at a controlled rate (a sustained release preparation or a rapid-release preparation). In aerosols utilized for an inhalant agent and others, a method for generating an aerosol is not particularly limited to a specific one. For example, a medically effective ingredient and a propellant (e.g., an alternative for chlorofluorocarbon) may be filled in a single hermetic container and sprayed. Moreover, a medically effective ingredient and a compressed gas (such as carbon dioxide or nitrogen gas) may be filled in separate containers and sprayed in the form of a nebulizer or an atomizer. Further, the preparation may be a preparation for oral administration or a preparation for parenteral administration (for example, a nosal preparation (or a collunarium), an inhalant preparation, and a preparation for transdermal administration). Furthermore, the preparation may be a preparation for topical administration (for example, solutions such as injectable solutions (e.g., aqueous injectable solutions and nonaqueous injectable solutions), suspensions, ointments, plasters and pressure sensitive adhesives, and cataplasms). The preparation of the present invention is practically a solid preparation (particularly, a preparation for oral administration).

The carrier may for example be selected depending on the administration route and the application of preparation, from components (e.g., an excipient, a binder, a disintegrant, a lubricant, and a coating agent) listed in Japanese Pharmacopoeia, (1) Handbook of Pharmaceutical Excipients (Maruzen Company, ltd., (1989)), (2) Japanese Pharmaceutical Excipients Dictionary 2007 (Yakuji Nippo Ltd., issued July, 2007), (3) Pharmaceutics, revised fifth edition (Nankodo, Co., Ltd. (1997)), and (4) Japanese Pharmaceutical Excipients 2003 (Yakuji Nippo Ltd., issued August, 2003). For example, the carrier for a solid preparation is practically at least one member selected from the group consisting of an excipient, a binder, and a disintegrant. Moreover, the pharmaceutical composition may contain a lipid.

The excipient may include a saccharide or a sugar alcohol such as lactose, white sugar or refined sugar, glucose, sucrose, mannitol, sorbitol, or xylitol; a starch such as a corn starch; a polysaccharide such as a crystalline cellulose (including a microcrystalline cellulose); silicon dioxide or a silicate such as a light silicic anhydride or a synthetic aluminum silicate; and others. The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, or a sodium chondroitin sulfate; a synthetic polymer such as a polyvinylpyrrolidone (PVP), a polyvinyl alcohol (PVA), a carboxyvinyl polymer, a polyacrylic polymer, a polylactic acid, or a polyethylene glycol; a cellulose ether such as a methyl cellulose (MC), an ethyl cellulose (EC), a carboxymethyl cellulose (CMC), a carboxymethyl cellulose sodium, a hydroxyethyl cellulose (HEC), a hydroxypropyl cellulose (HPC), or a hydroxypropylmethyl cellulose (HPMC); and others. The disintegrant may include calcium carbonate, a sodium carboxymethyl starch, a carboxymethyl cellulose or a salt thereof (e.g., a carmellose, a carmellose sodium, a carmellose calcium, and a croscarmellose sodium), a crosslinked polyvinylpyrrolidone (crospovidone), a low-substituted hydroxypropyl cellulose, and others. These carriers may be used alone or in combination.

For example, there may be used, as the coating agent, a saccharide or a sugar, a cellulose derivative such as an ethyl cellulose or a hydroxymethyl cellulose, a polyoxyethylene glycol), a cellulose acetate phthalate, a hydroxypropylmethyl cellulose phthalate, a methyl methacrylate-(meth)acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer containing a basic component such as a dialkylaminoalkyl(meth)acrylate (e.g., eudragit). Moreover, the preparation may be a capsule having such an enteric component or gastric soluble component as a capsule shell.

In the carrier of the liquid preparation, an oil-based carrier may include an oil derived from plants or animals (e.g., an oil derived from vegetables such as a jojoba oil, an olive oil, a palm oil, or a cotton seed oil; and an oil derived from animals such as squalene), a mineral oil (e.g., a liquid petrolatum and a silicone oil), and others. An aqueous carrier may include water (e.g., a purified water or a sterile water, a distilled water for injection), a physiological saline, a Ringer's solution, a glucose solution, a water-soluble organic solvent [for example, a lower aliphatic alcohol such as ethanol or isopropanol; a (poly)alkylene glycol (e.g., ethylene glycol and a polyethylene glycol); and glycerin], dimethyl isosorbide, dimethylacetamide, and others. Moreover, the carrier of the semisolid preparation may be selected from the carrier of the solid preparation and/or that of the liquid preparation. Further, the carrier of the semisolid preparation may contain a lipid.

The lipid may include a wax (e.g., a bees wax, a carnauba wax, a lanolin, a paraffin, and a petrolatum), a higher (or long chain) fatty acid ester [e.g., an alkyl ester of a saturated or unsaturated fatty acid, and an ester of a fatty acid with a polyvalent alcohol (such as a polyC$_{2-4}$alkylene glycol, glycerin, or a polyglycerin) (e.g., a glyceride)], a hardened (or hydrogenated) oil, a higher alcohol (e.g., a saturated aliphatic alcohol such as stearyl alcohol and an unsaturated aliphatic alcohol such as oleyl alcohol), a higher fatty acid (e.g., linoleic acid, linoleic acid, stearic acid and oleic acid), a metallic soap (e.g., a metal salt of a fatty acid, such as a sodium salt of palm oil fatty acid or calcium stearate), and others.

In the preparation, known additives can be suitably used depending on an administration route, a dosage form, and others. Such an additive may include, for example, a lubricant (e.g., a talc, magnesium stearate, and a polyethylene glycol 6000), a disintegrant aid, an antioxidation agent or an antioxidant, an emulsifier (e.g., a variety of surfactants such as a nonionic surfactant), a dispersing agent, a suspending agent, a dissolving agent, a dissolution aid, a thickener (e.g., a water-soluble polymer such as a carboxyvinyl polymer, a polyvinyl alcohol, a carrageen, or a gelatin; and a cellulose ether such as a carboxymethyl cellulose), a pH adjusting agent or a buffer (e.g., a citric acid-sodium citrate buffer), a stabilizer, an antiseptic agent or a preservative (e.g., a paraben such as methyl paraben or butyl paraben), a fungicide or antibacterial agent (e.g., a benzoic acid compound such as sodium benzoate), an antistatic agent, a corrigent or a masking agent (e.g., sweetening agent), a coloring agent (e.g., a dye and a pigment such as colcothar), a deodorant or a perfume (e.g., an aromatic substance), an algefacient, an antifoaming agent, an isotonizing agent, and a soothing agent. These additives may be used singly or in combination.

For example, in the injectable solution, usually, the dissolving agent, the dissolution aid, the suspending agent, the buffer, the stabilizer, the preservative, and others may be used as the additive in practical cases. Incidentally, to powders for an injection, which are dissolved or suspended before administration, may be added conventional additive(s) used for powders for an injection.

Moreover, in a topically administering preparation such as an inhalant preparation or a transdermal absorption preparation, as the additive, usually, the dissolution aid, the stabilizer, the buffer, the suspending agent, the emulsifier, the preservative, and others may be practically used.

The pharmaceutical composition of the present invention may be prepared by using a carrier component in addition to an effective ingredient, and if necessary, an additive and the like, with a conventional preparation manner (for example, a production process described in Japanese Pharmacopoeia 15$^{th}$ edition or a process in accordance with the production process).

The heterocyclic compound or the salt thereof (including the antiallergic agent, the prophylactic and/or therapeutic agent, and the pharmaceutical composition) of the present invention is safely administered to human beings and non-humans, usually mammals (e.g., human beings, mice, rats, rabbits, dogs, cats, bovines, horses, pigs, and monkeys). The amount to be administered (or dose) of the heterocyclic compound or the salt thereof of the present invention may be selected according to the subject of administration, the age, body weight, sex, and condition (e.g., a performance status, a condition of a disease, and a presence of a complication) of the subject, the time (or period or schedule) of administration, the dosage form, the method (or route) of administration, and others.

The amount to be administered (or dose) to human beings is, for example, in an oral administration, usually about 0.01 to 1,000 mg a day, preferably about 0.1 to 700 mg a day, and more preferably about 0.2 to 500 mg a day, in a free form of the heterocyclic compound or the salt thereof. Moreover, in an injection, the amount to be administered to human beings is usually about 0.01 to 200 mg a day, preferably about 0.05 to 100 mg a day, and more preferably about 0.1 to 80 mg a day, in a free form of the heterocyclic compound or the salt thereof. Further, in a topically administering agent, the amount to be administered to human beings is usually about 0.01 to 200 mg a day, preferably about 0.05 to 100 mg a day, and more preferably about 0.1 to 80 mg a day, in a free form of the heterocyclic compound or the salt thereof.

EXAMPLES

The following examples are intended to describe this invention in further detail and should by no means be interpreted as defining the scope of the invention.

In the following Production Examples and Examples, abbreviated words have conventional interpretations. For example, the meanings of the following abbreviated words are as follows.

NMR: nuclear magnetic resonance spectrum

MS: mass spectroscopy

EIMS: electron impact mass spectroscopy

HPLC: high-performance liquid chromatography

TFA: trifluoroacetic acid p-TLC: preparative thin-layer chromatography

In the following Examples, the compounds represented by the formula (1) wherein Z is a hydroxyl group are described in Examples. Accordingly, the compound of the present invention (for example, the compounds represented by the formula (1) wherein Z is an alkoxy group) is sometimes described in Production Examples.

Production Example 1

4-Benzhydryloxypiperidine

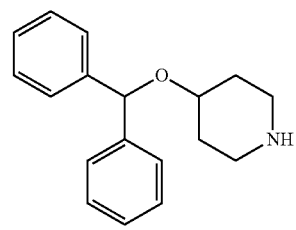 [SMILES: c1ccc(C(OC2CCNCC2)c2ccccc2)cc1]

Molecular sieves, benzhydrol (1.1 g, 5.5 mmol), and p-toluenesulfonic acid monohydrate (1.0 g, 5.5 mmol) were added to a suspension of 4-hydroxypiperidine (505 mg, 5 mmol) in toluene, and the mixture was refluxed for 3 hours while removing water using a Dean-Stark condenser. After the completion of the reaction was confirmed by HPLC, the reaction mixture was allowed to cool down to a room temperature. From the reaction mixture, the insoluble matter was removed, and then the solvent was distilled off. The resulting residue was dissolved in ethyl acetate and washed with a 2-N sodium hydroxide solution 3 times. The organic layer was dried over magnesium sulfate, and then the solvent was distilled off. Thus the title compound (676 mg, 50.6%) was obtained as an oily substance.

$^1$H-NMR (CDCl$_3$, δ): 1.2-1.5 (2H, m), 1.8-1.9 (2H, m), 2.3-2.5 (2H, m), 2.8-3.0 (2H, m), 3.2-3.4 (1H, m), 5.64 (1H, s), 7.1-7.4 (10H, m)

Production Example 2

Methyl 5-(4-benzhydryloxypiperidin-1-ylmethyl)furan-2-carboxylate

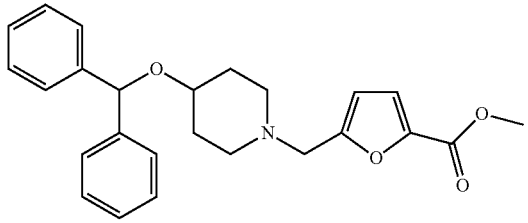 [SMILES: COC(=O)c1ccc(CN2CCC(OC(c3ccccc3)c3ccccc3)CC2)o1]

A mixture of 401 mg of 4-benzhydryloxypiperidine synthesized in Production Example 1, 288 mg of methyl 5-chloromethylfuran-2-carboxylate, 352 mg of potassium carbonate, and 3.5 mL of acetonitrile was stirred for 18 hours. The reaction solution was diluted with ethyl acetate and then thrown into water, and the organic layer was collected by separation. The organic layer was washed with a saturated saline solution and then dried over magnesium sulfate. The solvent was distilled off. The resulting product was subjected to a silica gel column chromatography (chloroform/acetone (volume ratio)=20:1 to 10:1) to give the title compound (475 mg).

$^1$H-NMR (CDCl$_3$, δ): 1.6-2.0 (4H, m), 2.1-2.4 (2H, m), 2.6-2.9 (2H, m), 3.3-3.5 (1H, m), 3.59 (2H, s), 3.87 (3H, s), 5.49 (1H, s), 6.31 (1H, d, J=3.5 Hz), 7.11 (1H, d, J=3.5 Hz), 7.1-7.4 (10H, m)

MS (m/z): 404 (M$^+$-1)

Example 1

5-(4-Benzhydryloxypiperidin-1-ylmethyl)furan-2-carboxylic acid

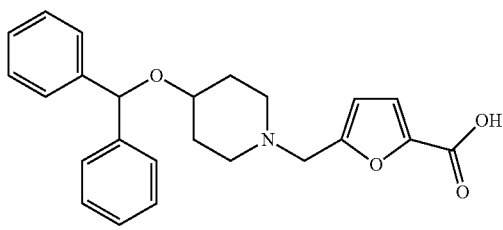 [SMILES: O=C(O)c1ccc(CN2CCC(OC(c3ccccc3)c3ccccc3)CC2)o1]

A mixture of 465 mg of methyl 5-(4-benzhydryloxypiperidin-1-ylmethyl)furan-2-carboxylate synthesized in Production Example 2, 1.7 mL of ethanol, and 3.4 mL of a 1-N sodium hydroxide aqueous solution was heated under reflux for 40 minutes. To the mixture were added 10 mL of water and 3.4 mL of 1-N hydrochloric acid, and the resulting mixture was stirred. The precipitated crystal was separated by filtration and washed with water. The resulting product was dried to give the title compound (316 mg).

$^1$H-NMR (d$_6$-DMSO, δ): 1.4-2.3 (6H, m), 2.6-2.8 (2H, m), 3.2-3.4 (1H, m), 3.53 (2H, s), 5.61 (1H, s), 6.44 (1H, d, J=3.5 Hz), 7.12 (1H, d, J=3.5 Hz), 7.1-7.5 (10H, m)

MS (m/z): 391 (M$^+$)

Production Examples 3 to 12, 14, 15, 17 to 21, 23, 25 to 28, 30, 32, 34 to 35, 50, 52 to 61, 63, 65, 67 to 70, 74, 76 to 79, 81 to 83, 91, 112, 113, 116 to 119, 121 to 124, 127, 128, 131, 133 to 135, 138, 139, 141, 142, 144, 145, 147, 148, 150, 151, 153, 155, 156, 158, 159, 161, 162, 189, 190, 194, 197, 198, 201, 202, 204, 206, 207, and Examples 2 to 27, 36, 38 to 54, 56 to 62, 66, 83, 84, 86 to 93, 96, 97, 100 to 103, 105 to 121, 140 to 149

Ester compounds (compound (14)) shown in Tables 1 to 50 were obtained in the same manner as in Production Example 2 except that anyone of the compounds synthesized in Production Examples 16, 22, 24, 29, 31, 33, 62, 64, 66, 80, 115, 120, 132, 137, 140, 143, 146, 149, 152, 154, 157, 160, 188, 193, 200, 203 and 205 or a known compound was used instead of 4-benzhydryloxypiperidine as the compound (12), and/or that the compound synthesized in Production Example 13 or a known compound was used instead of methyl 5-chloromethylfuran-2-carboxylate as the compound (13). Moreover, carboxylic acids shown in Tables 1 to 50 were obtained in the same manner as in Example 1 except that any one of these ester compounds was used.

TABLE 1

| Compound (12) | Compound (13) | Ester compound/Caboxylic acid Chemical formula |
|---|---|---|
| Production Example 1 | | Production Example 3 |

TABLE 1-continued

| | | Ester compound/Caboxylic acid | |
|---|---|---|---|
| Compound (12) | Compound (13) | ¹H-NMR | MS (m/z) |
| Production Example 1 | | (CDCl₃, δ): 1.42 (3H, t, J = 7.1 Hz), 1.6-2.0 (4H, m), 2.1-2.4 (2H, m), 2.7-2.9 (2H, m), 3.3-3.6 (1H, m), 3.75 (2H, s), 4.46 (2H, q, J = 7.2 Hz), 5.52 (1H, s), 7.1-7.4 (10H, m), 7.70 (1H, d, J = 7.7 Hz), 7.78 (1H, t, J = 7.7 Hz), 7.96 (1H, d, J = 7.7 Hz) | 430 (M⁺) |
| | | (d₆-DMSO, δ): 1.4-2.4 (6H, m), 2.5-2.9 (2H, m), 3.2-3.8 (3H, m), 5.63 (1H, s), 7.1-7.7 (11H, m), 7.8-8.0 (2H, m) | 403 (M⁺ + 1) |
| Production Example 1 | | (CDCl₃, δ): 1.6-2.0 (4H, m), 2.2-2.4 (2H, m), 2.7-2.9 (2H, m), 3.73 (2H, s), 3.90 (3H, s), 5.48 (1H, s), 7.1-7.4 (10H, m), 8.21 (1H, s) | 407 (M⁺ + 1) |
| | | (d₆-DMSO, δ): 1.5-1.9 (4H, m), 2.1-2.4 (2H, m), 2.6-2.9 (2H, m), 3.6-3.8 (2H, m), 5.61 (1H, s), 7.1-7.5 (10H, m), 8.68 (1H, s) | 392 (M⁺) |

TABLE 1-continued

| Production Example 1 | | (CDCl$_3$, δ) 1.29 (3H, t, J = 7.1 Hz), 1.5-1.7 (2H, m), 1.8-2.0 (2H, m), 2.2-2.4 (2H, m), 2.7-2.9 (2H, m), 3.3-3.5 (1H, m), 3.79 (2H, s), 4.28 (2H, q, J = 7.1 Hz), 5.64 (1H, s), 7.1-7.5 (10H, m), 8.44 (1H, s) | 437 (M$^+$ + 1) |
|---|---|---|---|

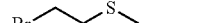

TABLE 2

| Compound (12) | Compound (13) | Ester compound/Caboxylic acid Chemical formula |
|---|---|---|
| Production Example 1 | | Example 4 |
| Production Example 1 | | Production Example 6 |
| | | Example 5 |
| Production Example 1 | | Production Example 7 |
| | | Example 6 |

| Compound (12) | Compound (13) | Ester compound/Caboxylic acid | |
|---|---|---|---|
| | | $^1$H-NMR | MS (m/z) |
| | | (d$_6$-DMSO, δ): 1.5-1.7 (2H, m), 1.8-2.0 (2H, m), 2.2-2.4 (2H, m), 2.7-2.9 (2H, m), 3.3-3.5 (1H, m), 3.79 (2H, s), 5.64 (1H, s), 7.1-7.5 (10H, m), 8.36 (1H, s) | 409 (M$^+$ + 1) |

TABLE 2-continued

| | | | |
|---|---|---|---|
| Production Example 1 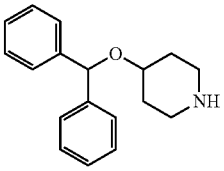 | 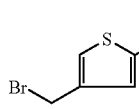 | (CDCl$_3$, δ): 1.6-2.3 (6H, m), 2.6-2.8 (2H, m), 3.3-3.6 (3H, m), 3.86 (3H, m), 5.49 (1H, s), 7.1-7.4 (11H, m), 7.71 (1H, d, J = 1.5 Hz) | 422 (M$^+$ + 1) |
| | | (d$_6$-DMSO, δ): 1.5-2.0 (4H, m), 2.1-2.3 (2H, m), 2.6-2.8 (2H, m), 3.3-3.5 (1H, m), 3.56 (2H, s), 5.62 (1H, s), 7.1-7.7 (12H, m) | 406 (M$^+$ − 1) |
| Production Example 1 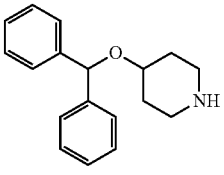 | 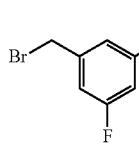 | (CDCl$_3$, δ): 1.6-2.3 (6H, m), 2.6-2.8 (2H, m), 3.3-3.6 (1H, m), 3.49 (2H, s), 3.91 (3H, s), 5.50 (1H, s), 7.1-7.5 (11H, m), 7.58 (1H, d, J = 8.9 Hz), 7.74 (1H, s) | 432 (M$^+$ − 1) |
| | | (d$_6$-DMSO, δ): 1.6-2.0 (4H, m), 2.8-3.1 (2H, m), 3.4-3.6 (1H, m), 3.7-4.2 (2H, m), 5.63 (1H, s), 7.1-8.0 (13H, m) | 418 (M$^+$ − 1) |

TABLE 3

| Compound (12) | Compound (13) | Ester compound/Caboxylic acid Chemical formula |
|---|---|---|
| Production Example 1 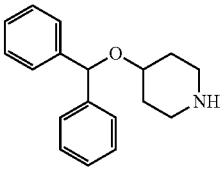 | 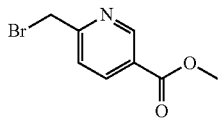 | Production Example 8 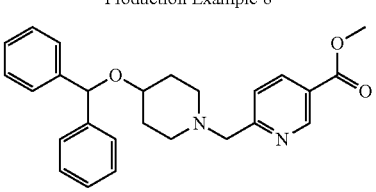 |
| | | Example 7 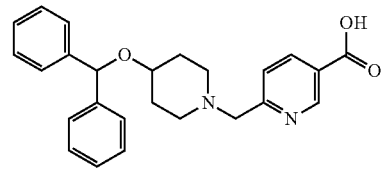 |
| Production Example 1 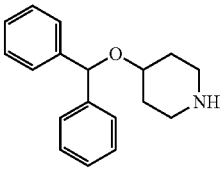 | 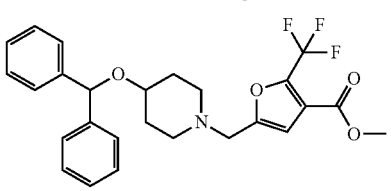 | Production Example 9 |

TABLE 3-continued
Example 8
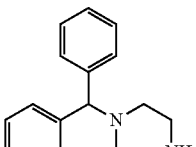
Production Example 10
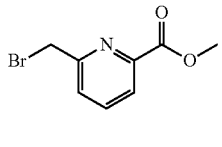
| Compound (12) | Compound (13) | Ester compound/Caboxylic acid | |
|---|---|---|---|
| | | ¹H-NMR | MS (m/z) |
| Production Example 1 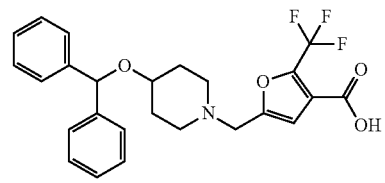 | 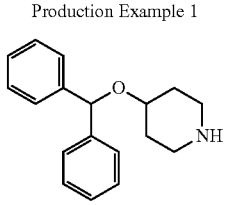 [SMILES: c1ccc(C(OC2CCNCC2)c2ccccc2)cc1] | (CDCl₃, δ): 1.6-2.0 (4H, m), 2.1-2.3 (2H, m), 2.6-2.9 (2H, m), 3.3-3.6 (1H, m), 3.68 (2H, s), 3.93 (3H, s), 5.59 (1H, s), 7.1-7.4 (10H, m), 7.53 (1H, d, J = 8.5 Hz), 8.24 (1H, dd, J = 2.1, 8.8 Hz), 9.13 (1H, d, J = 1.9 Hz) | 415 (M⁺ + 1) |
| | | (d₆-DMSO, δ): 1.5-1.7 (2H, m), 1.8-2.0 (2H, m), 2.1-2.3 (2H, m), 2.6-2.8 (2H, m), 3.65 (2H, s), 5.63 (1H, s), 7.1-7.4 (10H, m), 7.56 (1H, d, J = 8.1 Hz), 8.23 (1H, dd, J = 2.3, 8.1 Hz), 8.9-9.1 (1H, m) | 403 (M⁺ + 1) |
| Production Example 1 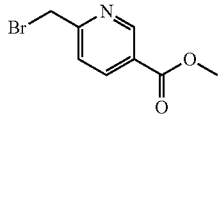 | 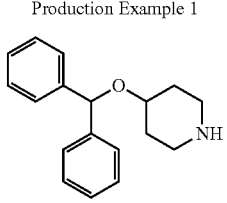 [SMILES: c1ccc(C(OC2CCNCC2)c2ccccc2)cc1] | (CDCl₃, δ): 1.6-2.0 (4H, m), 2.1-2.3 (2H, m), 2.6-2.8 (2H, m), 3.3-3.5 (1H, m), 3.56 (2H, s), 3.87 (3H, s), 5.49 (1H, s), 6.64 (1H, s), 7.1-7.4 (10H, m) | 474 (M⁺ + 1) |
| | | (d₆-DMSO, δ): 1.5-1.9 (4H, m), 2.1-2.3 (2H, m), 2.6-2.8 (2H, m), 3.59 (2H, s), 5.61 (1H, s), 6.77 (1H, s), 7.1-7.4 (10H, m) | 440 (M⁺ − 19) |
| 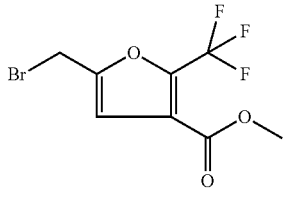 | 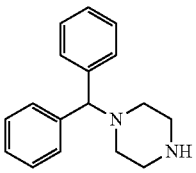 [SMILES: c1ccc(C(c2ccccc2)N2CCNCC2)cc1] | (CDCl₃, δ): 2.2-2.8 (8H, m), 3.79 (2H, s), 3.98 (3H, s), 4.23 (1H, s), 7.1-7.5 (10H, m), 7.68 (1H, d, J = 6.9 Hz), 7.77 (1H, t, J = 7.7 Hz), 7.98 (1H, d, J = 7.3 Hz) | 401 (M⁺) |

TABLE 4

| Compound (12) | Compound (13) | Ester compound/Caboxylic acid Chemical formula |
|---|---|---|
| | | Example 9 |
| | | (diphenylmethyl-piperazine-CH2-pyridine-COOH structure) |
| | | Production Example 11 |
| (bis(4-fluorophenyl)methoxy-piperidine NH) | (Br-CH2-pyridine-COOCH3) | (bis(4-fluorophenyl)methoxy-piperidine-CH2-pyridine-COOCH3) |
| | | Example 10 |
| | | (bis(4-fluorophenyl)methoxy-piperidine-CH2-pyridine-COOCH3) |
| | | Production Example 12 |
| (bis(4-fluorophenyl)methyl-piperazine NH) | (Br-CH2-pyridine-COOCH3) | (bis(4-fluorophenyl)methyl-piperazine-CH2-pyridine-COOCH3) |

| Compound (12) | Compound (13) | Ester compound/Caboxylic acid | |
|---|---|---|---|
| | | $^1$H-NMR | MS (m/z) |
| | | (d$_6$-DMSO, δ): 2.1-2.9 (8H, m), 3.79 (2H, brs), 4.32 (1H, s), 7.1-7.5 (10H, m), 7.65 (1H, dd, J = 1.9, 6.9 Hz), 7.8-8.0 (2H, m) | 387 (M$^+$) |
| (bis(4-fluorophenyl)methoxy-piperidine NH) | (Br-CH2-pyridine-COOCH3) | (CDCl$_3$, δ): 1.6-2.0 (4H, m), 2.1-2.3 (2H, m), 2.7-2.9 (2H, m), 3.3-3.5 (1H, m), 3.75 (2H, s), 3.98 (3H, s), 5.46 (1H, s), 6.9-7.1 (4H, m), 7.2-7.4 (4H, m), 7.71 (1H, dd, J = 1.0, 7.9 Hz), 7.80 (1H, t, J = 7.7 Hz), 7.99 (1H, dd, J = 1.0, 7.5 Hz) | 452 (M$^+$ + 1) |
| | | (d$_6$-DMSO, δ): 1.5-2.0 (4H, m), 2.1-2.5 (2H, m), 2.6-2.9 (2H, m), 3.3-3.5 (1H, m), 3.6-3.9 (2H, m), 5.68 (1H, s), 7.0-7.5 (8H, m), 7.6-8.1 (3H, m) | 437 (M$^+$ − 1) |

TABLE 4-continued

| Structure | Reagent | ¹H-NMR | MS |
|---|---|---|---|
| bis(4-fluorophenyl)methyl-piperazine | methyl 6-(bromomethyl)picolinate | (CDCl₃, δ): 2.1-2.8 (8H, m), 3.78 (2H, s), 3.98 (3H, s), 4.22 (1H, s), 6.8-7.1 (4H, m), 7.2-7.4 (4H, m), 7.67 (1H, d, J = 7.7 Hz), 7.77 (1H, t, J = 7.9 Hz), 7.98 (1H, d, J = 7.7 Hz) | 437 (M⁺) |

TABLE 5

| Compound (12) | Compound (13) | Ester compound/Caboxylic acid Chemical formula |
|---|---|---|

Example 11

(structure: 4-fluorophenyl-piperazine-methyl-pyridine-carboxylic acid)

| Production Example 1 | Production Example 13 | Production Example 14 |
|---|---|---|
| (diphenylmethoxy-piperidine NH) | (ethyl 2-(bromomethyl)nicotinate) | (diphenylmethoxy-piperidine-N-CH₂-pyridine-CO₂Et) |

Example 12

(diphenylmethoxy-piperidine-N-CH₂-pyridine-CO₂H)

| Production Example 1 | Compound (13) | Production Example 15 |
|---|---|---|
| (diphenylmethoxy-piperidine NH) | (ethyl bromomethyl-pyrazine-carboxylate) | (diphenylmethoxy-piperidine-N-CH₂-pyrazine-CO₂Et) |

| Compound (12) | Compound (13) | Ester compound/Caboxylic acid ¹H-NMR | MS (m/z) |
|---|---|---|---|
| | | (d₆-DMSO, δ): 2.1-2.9 (8H, m), 3.79 (2H, brs), 4.41 (1H, s), 7.12 (4H, t, d = 8.9 Hz), 7.43 (4H, dd, J = 5.8, 8.5 Hz), 7.64 (1H, dd, J = 3.0, 6.9 Hz), 7.8-8.0 (2H, m) | 423 (M⁺) |

TABLE 5-continued

| Production Example 1 | Production Example 13 | (CDCl₃, δ): 1.39 (3H, t, J = 7.3 Hz), 1.5-1.7 (2H, m), 2.0-2.2 (2H, m), 2.6-2.7 (2H, m), 3.3-3.5 (1H, m), 3.86 (2H, s), 4.35 (2H, q, J = 7.0 Hz), 5.49 (1H, s), 7.2-7.4 (11H, m), 7.91 (1H, dd, J = 1.6, 7.6 Hz), 8.58 (1H, dd, J = 2.2, 5.1 Hz) | — |
|---|---|---|---|
| | | (CDCl₃, δ): 1.9-2.1 (4H, m), 3.1-3.3 (4H, m), 3.7-3.9 (1H, m), 4.35 (2H, s), 5.44 (1H, s), 7.2-7.5 (11H, m), 8.47 (1H, dd, J = 1.6, 7.8 Hz), 8.60 (1H, dd, J = 1.4, 4.3 Hz) | 403.2 (M⁺) |
| Production Example 1 | | (CDCl₃, δ): 1.43 (3H, t, J = 7.1 Hz), 1.6-2.0 (4H, m), 2.1-2.4 (2H, m), 2.7-2.9 (2H, m), 3.4-3.6 (1H, m), 3.79 (2H, s), 4.49 (2H, q, J = 7.2 Hz), 5.51 (1H, s), 7.1-7.4 (10H, m), 8.94 (1H, s), 9.14 (1H, s) | 432 (M⁺ + 1) | ns/tables in this page contain chemical structures which cannot be faithfully reproduced as text. Below is the textual data from TABLE 6.

TABLE 6

| Compound (12) | Compound (13) | Ester compound/Carboxylic acid | | |
|---|---|---|---|---|
| | | Chemical formula | ¹H-NMR | MS (m/z) |
| Production Example 16 (piperidine with bis(2-fluorophenyl)methoxy group) | methyl 6-(bromomethyl)picolinate | Example 13 (carboxylic acid derivative with diphenylmethoxy piperidine and pyrazine carboxylic acid) | (d₆-DMSO, δ): 1.5-1.9 (4H, m), 2.0-2.3 (2H, m), 2.6-2.8 (2H, m), 3.61 (2H, s), 5.63 (1H, s), 7.1-7.4 (10H, m), 8.52 (1H, s), 8.86 (1H, s) | 265 (M⁺ − 138) |
| | | Production Example 17 (methyl ester with bis(2-fluorophenyl)methoxy piperidine and picolinate) | (CDCl₃, δ): 1.6-2.0 (4H, m), 2.1-2.3 (2H, m), 2.6-2.9 (2H, m), 3.4-3.6 (1H, m), 3.48 (1H, s), 3.74 (2H, s), 3.98 (3H, s), 6.16 (1H, s), 6.9-7.5 (8H, m), 7.71 (1H, d, J = 8.1 Hz), 7.79 (1H, t, J = 7.7 Hz), 7.9-8.1 (1H, m) | 452 (M⁺) |
| | | Example 14 (carboxylic acid with bis(2-fluorophenyl)methoxy piperidine and picolinate) | (d₆-DMSO, δ): 1.5-2.4 (6H, m), 2.6-2.9 (2H, m), 3.3-3.6 (1H, m), 3.70 (2H, brs), 6.10 (1H, s), 7.1-7.6 (8H, m), 7.65 (1H, d, J = 6.9 Hz), 7.8-8.0 (2H, m) | 437 (M⁺ − 1) |
| Production Example 16 (piperidine with (4-chlorophenyl)(pyridin-2-yl)methoxy group) | methyl 6-(bromomethyl)picolinate | Production Example 18 (methyl ester with (4-chlorophenyl)(pyridin-2-yl)methoxy piperidine and picolinate) | (CDCl₃, δ): 1.63 (3H, m), 1.6-2.0 (4H, m), 2.1-2.4 (2H, m), 2.6-2.9 (2H, m), 3.4-3.6 (1H, m), 3.74 (2H, s), 3.98 (3H, s), 5.59 (1H, s), 7.15 (1H, ddd, J = 1.2, 5.0, 7.3 Hz), 7.2-7.8 (8H, m), 7.80 (1H, t, J = 7.7 Hz), 7.99 (1H, d, J = 7.7 Hz), 7.4-7.6 (1H, m) | 451 (M⁺) |

TABLE 7

| Compound (12) | Compound (13) | Ester compound/Caboxylic acid | | |
|---|---|---|---|---|
| | | Chemical formula | ¹H-NMR | MS (m/z) |
| | | Example 15 | (d₆-DMSO, δ): 1.4-2.4 (6H, m), 2.5-2.8 (2H, m), 3.2-3.8 (3H, m), 5.65 (1H, s), 7.2-7.5 (5H, m), 7.55 (1H, d, J = 7.7 Hz), 7.5-7.7 (1H, m), 7.81 (1H, dt, J = 1.5, 7.7 Hz), 7.8-8.0 (2H, m), 8.4-8.5 (1H, m) | 437 (M⁺) |
| | | Production Example 19 | (d₆-DMSO, δ): 1.6-2.3 (6H, m), 2.6-2.8 (2H, m), 3.4-3.6 (1H, m), 3.50 (2H, brs), 3.90 (3H, s), 5.58 (1H, s), 7.1-7.6 (8H, m), 7.65 (1H, dt, J = 1.8, 7.6 Hz), 7.91 (1H, dd, J = 1.5, 7.7 Hz), 7.94 (1H, s), 7.4-7.6 (1H, m) | 450 (M⁺) |
| | | Example 16 | (CDCl₃, δ): 1.4-2.2 (6H, m), 2.5-2.8 (2H, m), 3.48 (2H, s), 5.65 (1H, s), 7.2-7.6 (7H, m), 7.54 (1H, d, J = 7.7 Hz), 7.7-7.9 (3H, m), 8.4-8.6 (1H, m) | 436 (M⁺) |
| | | Production Example 20 | (CDCl₃, δ): 1.42 (t, J = 6.9 Hz, 3H), 1.6-2.3 (m, 6H), 2.7-2.9 (m, 2H), 3.3-3.5 (m, 1H), 3.76 (s, 2H), 3.78 (s, 3H), 4.46 (q, J = 6.9 Hz, 2H), 5.48 (s, 1H), 6.85 (d, J = 8.8 Hz, 2H), 7.4-7.2 (m, 7H), 7.71 (d, J = 7.3 Hz, 1H), 7.79 (t, J = 7.7 Hz, 1H), 7.97 (d, J = 7.7 Hz, 1H) | 460 (M⁺), 197 (base peak) |

TABLE 8
| Compound (12) | Compound (13) | Chemical formula | ¹H-NMR | MS (m/z) |
|---|---|---|---|---|
| 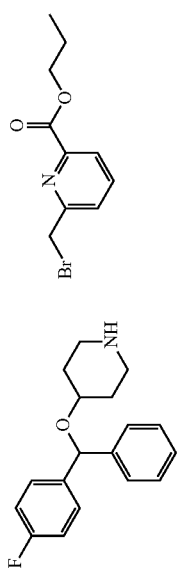 | 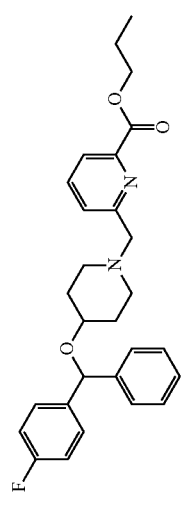 | Example 17 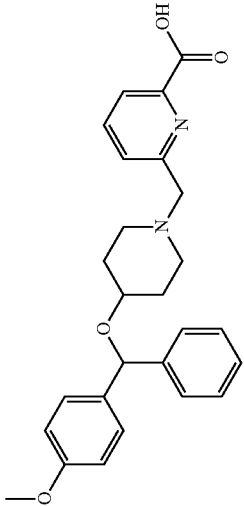 | (CDCl₃, δ): 1.7-2.2 (m, 4H), 2.4-2.7 (m, 2H), 2.8-3.0 (m, 2H), 3.5-3.7 (m, 1H), 3.78 (s, 3H), 3.90 (s, 2H), 5.45 (s, 1H), 6.85 (d, J = 8.9 Hz, 2H), 7.1-7.3 (m, 3H), 7.31 (d, J = 4.6 Hz, 4H), 7.70 (d, J = 7.7 Hz, 1H), 7.87 (t, J = 7.7 Hz, 1H), 8.10 (d, J = 7.7 Hz, 1H) | 432 (M⁺), 197 (base peak) |
| | | Production Example 21 | (CDCl₃, δ): 1.01 (3H, t, J = 7.3 Hz), 1.5-2.0 (6H, m), 2.1-2.3 (2H, m), 2.7-2.9 (2H, m), 3.3-3.5 (1H, m), 3.75 (2H, s), 4.35 (2H, t, J = 6.9 Hz), 5.49 (1H, s), 6.9-7.4 (9H, m), 7.69 (1H, d, J = 7.3 Hz), 7.78 (1H, t, J = 7.7 Hz), 7.95 (1H, d, J = 7.7 Hz) | 463 (M⁺ + 1) |
| | | Example 18 | (d₆-DMSO, δ): 1.4-2.3 (6H, m), 2.6-2.8 (2H, m), 3.2-3.8 (3H, m), 5.64 (1H, s), 7.0-7.7 (10H, m), 7.8-8.0 (2H, m) | 419 (M⁺ − 1) |

TABLE 8-continued

| Compound (12) | Compound (13) | Ester compound/Caboxylic acid | | |
|---|---|---|---|---|
| | | Chemical formula | ¹H-NMR | MS (m/z) |
| Production Example 22 | Production Example 23 | (CDCl₃, δ): 1.01 (3H, t, J = 7.3 Hz), 1.5-2.0 (6H, m), 2.1-2.4 (2H, m), 2.7-2.9 (2H, m), 3.3-3.6 (1H, m), 3.75 (2H, s), 4.35 (2H, t, J = 6.9 Hz), 5.51 (1H, s), 7.0-7.5 (9H, m), 7.68 (1H, d, J = 7.7 Hz), 7.78 (1H, t, J = 7.7 Hz), 7.9-8.0 (1H, m) | 529 (M⁺ + 1) | |

TABLE 9

| | | Ester compound/Caboxylic acid | | |
|---|---|---|---|---|
| Compound (12) | Compound (13) | Chemical formula | $^1$H-NMR | MS (m/z) |
| | | Example 19 | (d$_6$-DMSO, δ): 1.3-2.3 (6H, m), 2.4-2.9 (2H, m), 3.2-3.8 (3H, m), 5.69 (1H, br s), 7.1-7.7 (10H, m), 7.8-8.0 (2H, m) | 486 (M$^+$) |
| Production Example 24 | | Production Example 25 | (CDCl$_3$, δ): 1.01 (3H, t, J = 7.3 Hz), 1.6-2.0 (6H, m), 2.1-2.3 (2H, m), 2.7-2.9 (2H, m), 3.3-3.6 (1H, m), 3.75 (2H, s), 4.35 (2H, t, J = 6.9 Hz), 5.88 (1H, s), 6.9-7.5 (9H, m), 7.69 (1H, d, J = 8.1 Hz), 7.78 (1H, t, J = 7.7 Hz), 7.95 (1H, d, J = 7.3 Hz) | 462 (M$^+$) |
| | | Example 20 | (d$_6$-DMSO, δ): 1.6-2.0 (4H, m), 2.1-2.4 (2H, m), 2.6-2.9 (2H, m), 3.3-3.9 (3H, m), 5.86 (1H, s), 7.1-7.7 (10H, m), 7.8-8.0 (2H, m) | 284 (M$^+$ − 136) |

TABLE 9-continued
|  |  | Ester compound/Caboxylic acid | | |
|---|---|---|---|---|
| Compound (12) | Compound (13) | Chemical formula | ¹H-NMR | MS (m/z) |
| 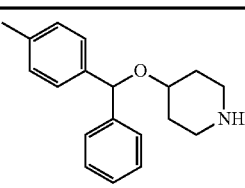 | 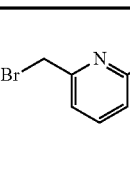 | Production Example 26 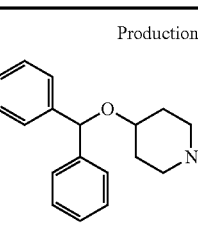 | (CDCl$_3$, δ): 1.01 (3H, t, J = 7.3 Hz), 1.5-2.0 (6H, m), 2.1-2.3 (2H, m), 2.31 (3H, s), 2.7-2.9 (2H, m), 3.3-3.5 (1H, m), 3.75 (2H, s), 4.35 (2H, t, J = 6.9 Hz), 5.48 (1H, s), 7.0-7.4 (9H, m), 7.69 (1H, d, J = 7.7 Hz), 7.78 (1H, t, J = 7.7 Hz), 7.95 (1H, d, J = 7.3 Hz) | 459 (M$^+$ + 1) |

TABLE 10

| Compound (12) | Compound (13) | Ester compound/Caboxylic acid | | MS (m/z) |
|---|---|---|---|---|
| | | Chemical formula | ¹H-NMR | |
| | | Example 21 | (d₆-DMSO, δ): 1.4-2.4 (6H, m), 2.26 (3H, s), 2.5-2.9 (2H, m), 3.2-3.8 (3H, m), 5.51 (1H, s), 7.0-7.4 (9H, m), 7.5-7.7 (1H, m), 7.8-8.0 (2H, m) | 415 (M⁺ − 1) |
| | | Production Example 27 | (CDCl₃, δ): 1.01 (3H, t, J = 7.3 Hz), 1.5-2.0 (6H, m), 2.1-2.3 (2H, m), 2.7-2.9 (2H, m), 3.3-3.5 (1H, m), 3.75 (2H, s), 4.35 (2H, t, J = 6.8 Hz), 5.47 (1H, s), 7.1-7.4 (9H, m), 7.69 (1H, d, J = 7.3 Hz), 7.78 (1H, t, J = 7.7 Hz), 7.95 (1H, d, J = 7.3 Hz) | 478 (M⁺) |
| | | Example 22 | (d₆-DMSO, δ): 1.3-2.4 (6H, m), 2.5-2.9 (2H, m), 3.2-3.8 (3H, m), 5.64 (1H, br s), 7.1-7.7 (10H, m), 7.8-8.0 (2H, m) | 435 (M⁺ − 1) |

TABLE 10-continued

| Compound (12) | Compound (13) | Ester compound/Caboxylic acid | |
|---|---|---|---|
| | | Chemical formula | ¹H-NMR | MS (m/z) |
| | | Production Example 28 | (CDCl₃, δ): 1.01 (3H, t, J = 7.5 Hz), 1.7-1.9 (2H, m), 2.2-2.8 (8H, m), 3.79 (2H, s) 4.22 (1H, s), 4.35 (2H, t, J = 6.9 Hz), 7.1-7.4 (9H, m), 7.65 (1H, d, J = 7.3 Hz), 7.76 (1H, t, J = 7.7 Hz), 7.94 (1H, d, J = 7.7 Hz) | 463 (M⁺) |

TABLE 11

| | | Ester compound/Caboxylic acid | | |
|---|---|---|---|---|
| Compound (12) | Compound (13) | Chemical formula | ¹H-NMR | MS (m/z) |
| | | Example 23 | (d$_6$-DMSO, δ): 1.9-2.7 (8H, m), 3.4-3.8 (2H, m), 4.1-4.4 (1H, m), 7.1-7.7 (10H, m), 7.8-8.1 (2H, m) | 421 (M⁺) |
| Production Example 29 | | Production Example 30 | (CDCl$_3$, δ): 1.01 (3H, t, J = 7.3 Hz), 1.7-2.2 (4H, m), 2.5-2.9 (4H, m), 3.91 (2H, q, J = 15.3 Hz), 4.1-4.3 (1H, m), 4.35 (2H, t, J = 6.9 Hz), 5.36 (1H, s), 7.1-7.4 (10H, m), 7.65 (1H, d, J = 7.7 Hz), 7.76 (1H, t, J = 7.7 Hz), 7.95 (1H, d, J = 7.7 Hz) | 431 (M⁺ + 1) |
| | | Example 24 | (d$_6$-DMSO, δ): 1.7-2.1 (2H, m), 2.4-2.8 (4H, m), 3.7-3.9 (2H, m), 4.0-4.1 (1H, m), 5.48 (1H, s), 7.2-7.4 (10H, m), 7.5-7.7 (1H, m), 7.8-8.0 (2H, m) | 388 (M⁺) |

TABLE 11-continued
| Ester compound/Caboxylic acid | | | | |
|---|---|---|---|---|
| Compound (12) | Compound (13) | Chemical formula | $^1$H-NMR | MS (m/z) |
| Production Example 31 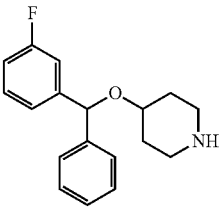 | 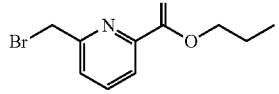 | Production Example 32 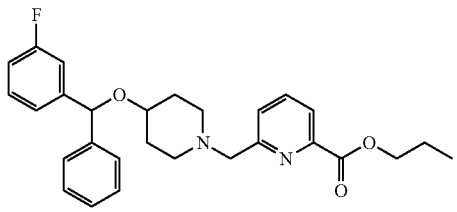 | (CDCl$_3$, δ): 1.01 (3H, t, J = 7.3 Hz), 1.5-2.0 (6H, m), 2.1-2.3 (2H, m), 2.7-2.9 (2H, m), 3.3-3.5 (1H, m), 3.75 (2H, s), 4.35 (2H, t, J = 6.9 Hz), 5.49 (1H, s), 6.8-7.4 (9H, m), 7.69 (1H, d, J = 7.7 Hz), 7.82 (1H, t, J = 7.7 Hz), 7.95 (1H, dd, J = 1.0, 7.5 Hz) | 462 (M$^+$) |
TABLE 12
| Ester compound/Caboxylic acid | | | | |
|---|---|---|---|---|
| Compound (12) | Compound (13) | Chemical formula | $^1$H-NMR | MS (m/z) |
| | | Example 25 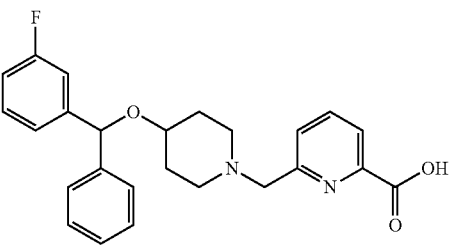 | (d$_6$-DMSO, δ): 1.4-2.3 (6H, m), 2.5-2.9 (2H, m), 3.2-3.8 (3H, m), 5.67 (1H, s), 7.0-7.7 (10H, m), 7.8-8.0 (2H, m) | 419 (M$^+$ − 1) |

TABLE 12-continued

|  | | Ester compound/Caboxylic acid | | |
|---|---|---|---|---|
| Compound (12) | Compound (13) | Chemical formula | $^1$H-NMR | MS (m/z) |
| Production Example 33 | Production Example 34 | | (CDCl$_3$, δ): 1.01 (3H, t, J = 7.3 Hz), 1.5-2.0 (6H, m), 2.1-2.4 (2H, m), 2.7-2.9 (2H, m), 3.3-3.6 (1H, m), 3.76 (2H, s), 4.35 (2H, t, J = 6.9 Hz), 5.54 (1H, s), 7.2-7.6 (8H, m), 7.62 (1H, s), 7.69 (1H, d, J = 7.7 Hz), 7.82 (1H, t, J = 7.7 Hz), 7.95 (1H, d, J = 7.7 Hz) | 512 (M$^+$) |
| | | Example 26 | (d$_6$-DMSO, δ): 5.76 (1H, br s), 7.2-8.0 (12H, m) | 469 (M$^+$ − 1) |

TABLE 12-continued

| Compound (12) | Compound (13) | Ester compound/Caboxylic acid | | |
|---|---|---|---|---|
| | | Chemical formula | $^1$H-NMR | MS (m/z) |
| Production Example 1 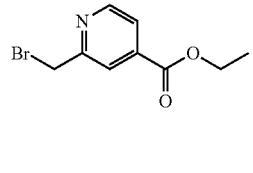 | 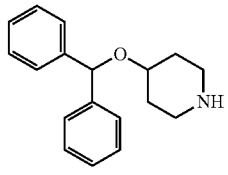 | Production Example 35 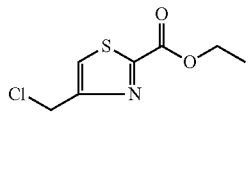 | (CDCl$_3$, δ): 1.41 (t, J = 7.3 Hz, 3H), 1.7-2.0 (m, 4H), 2.1-2.4 (m, 2H), 2.7-2.9 (m, 2H), 3.4-3.6 (m, 1H), 3.69 (s, 2H), 4.41 (q, J = 7.3 Hz, 2H), 5.51 (s, 1H), 7.1-7.4 (m, 10H), 7.71 (dd, J = 5.0, 1.5 Hz, 1H), 7.94 (s, 1H), 8.69 (d, J = 5.0 Hz, 1H) | 429 (M$^+$− 1), 167 (base peak) |

TABLE 13

| Compound (12) | Compound (13) | Ester compound/Caboxylic acid | | |
|---|---|---|---|---|
| | | Chemical formula | $^1$H-NMR | MS (m/z) |
| | | Example 27 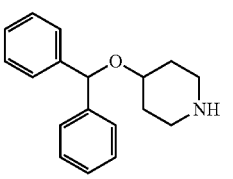 | (CDCl$_3$, δ): 1.9-2.1 (m, 2H), 2.3-2.6 (m, 2H), 3.20-3.5 (m, 4H), 3.7-3.9 (m, 1H), 4.16 (s, 2H), 5.45 (s, 1H), 7.32 (d, J = 4.2 Hz, 10H), 7.88 (dd, J = 5.0, 1.5 Hz, 1H), 8.44 (br s, 1H), 8.62 (d, J = 5.0 Hz, 1H) | 401 (M$^+$ − 1), 167 (base peak) |
| Production Example 1 | | Production Example 50 | (CDCl$_3$, δ): 1.42 (3H, t, J = 7.3 Hz), 1.7-2.0 (4H, m), 2.1-2.4 (2H, m), 2.7-2.9 (2H, m), 3.3-3.5 (1H, m), 3.75 (2H, s), 4.46 (2H, q, J = 7.3 Hz), 5.50 (1H, s), 7.1-7.4 (10H, m), 7.47 (1H, s) | 437 (M$^+$ + 1), 167 (base peak) |

TABLE 13-continued
| Compound (12) | Compound (13) | Chemical formula | $^1$H-NMR | MS (m/z) |
|---|---|---|---|---|
| | | Example 36 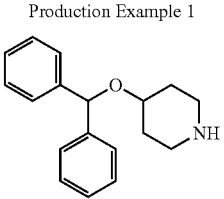 [SMILES: c1ccc(C(OC2CCNCC2)c2ccccc2)cc1] | (d$_6$-DMSO, δ: 1.4-1.9 (4H, m), 2.0-2.2 (2H, m), 2.6-2.8 (2H, m), 3.52 (2H, s), 5.62 (1H, s), 7.1-7.5 (11H, m) | 266 (M$^+$ − 142), 167 (base peak) |
| Production Example 1 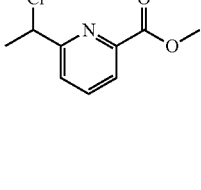 | 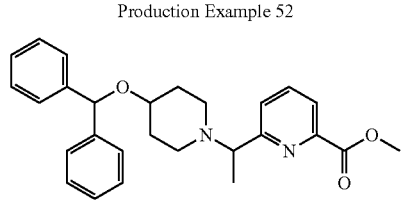 [SMILES: COC(=O)c1cccc(C(C)N2CCC(OC(c3ccccc3)c3ccccc3)CC2)n1] | Production Example 52 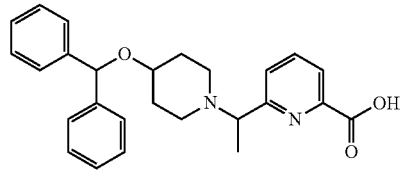 | (CDCl$_3$, δ): 1.36 (d, J = 6.5 Hz, 3H), 2.3-1.5 (m, 5H), 2.5-2.7 (m, 2H), 3.0-3.2 (m, 1H), 3.3-3.5 (m, 1H), 3.6-3.8 (m, 1H), 3.98 (s, 3H), 5.50 (s, 1H), 7.1-7.4 (m, 10H), 7.71 (d, J = 1.2 Hz, 1H), 7.78 (t, J = 7.7 Hz, 1H), 7.98 (d, J = 7.3, 1.2 Hz, 1H) | 431 (M$^+$ + 1), 165 (base peak) |
| | | Example 52 | (CDCl$_3$, δ): 5.47 (s, 1H), 7.1-7.4 (m, 10H), 7.64 (d, J = 7.3 Hz, 1H), 7.84 (t, J = 7.3 Hz, 1H), 8.09 (d, J = 6.9 Hz, 1H) | 417 (M$^+$ + 1), 167 (base peak) |

TABLE 14
| Compound (12) | Compound (13) | Ester compound/Caboxylic acid | | |
|---|---|---|---|---|
| | | Chemical formula | ¹H-NMR | MS (m/z) |
| 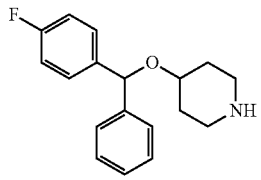 [SMILES: Fc1ccc(C(OC2CCNCC2)c2ccccc2)cc1] | 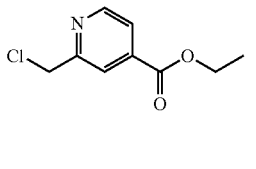 | Production Example 53 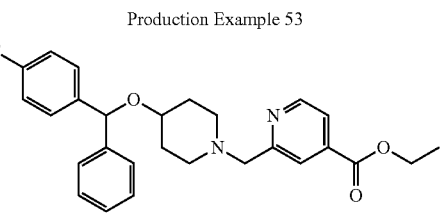 | (CDCl₃, δ): 1.40 (3H, t, J = 7.3 Hz), 1.6-2.0 (4H, m), 2.1-2.4 (2H, m), 2.6-2.9 (2H, m), 3.3-3.5 (1H, m), 3.69 (2H, s), 4.40 (2H, q, J = 6.9 Hz), 5.48 (1H, s), 6.97 (2H, dd, J = 1.9, 8.9 Hz), 7.2-7.4 (8H, m), 7.70 (1H, d, J = 4.6 Hz), 7.93 (1H, s), 8.68 (1H, d, J = 5.0 Hz) | 449 (M⁺ + 1), 185 (base peak) |
| | | Example 39 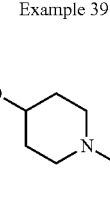 | (d₆-DMSO, δ): 1.5-2.0 (4H, m), 2.1-2.4 (2H, m), 2.7-2.8 (2H, m), 3.3-3.5 (1H, m), 3.72 (2H, s), 5.65 (1H, s), 7.0-7.5 (9H, m), 7.67 (1H, dd, J = 1.5, 5.0 Hz), 7.88 (1H, s), 8.64 (1H, d, J = 5.0 Hz) | 419 (M⁺ − 1), 185 (base peak) |

TABLE 14-continued
|  |  | Ester compound/Caboxylic acid | | |
|---|---|---|---|---|
| Compound (12) | Compound (13) | Chemical formula | ¹H-NMR | MS (m/z) |
| Production Example 31 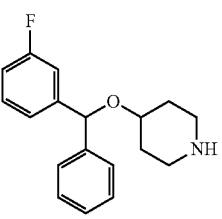 | 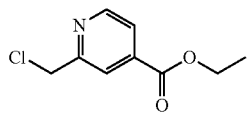 | Production Example 54 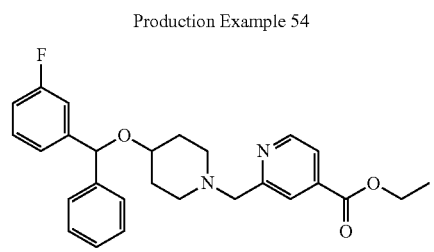 [SMILES: CCOC(=O)c1ccnc(CN2CCC(OC(c3ccccc3)c3cccc(F)c3)CC2)c1] | (CDCl$_3$, δ): 1.41 (3H, t, J = 7.1 Hz), 1.6-2.0 (4H, m), 2.1-2.4 (2H, m), 2.6-2.9 (2H, m), 3.4-3.5 (1H, m), 3.69 (2H, s), 4.40 (2H, q, J = 6.9 Hz), 5.48 (1H, s), 6.8-7.4 (9H, m), 7.70 (1H, d, J = 3.9 Hz), 7.93 (1H, s), 8.68 (1H, d, J = 5.0 Hz) | 449 (M$^+$ + 1), 185 (base peak) |
|  |  | Example 40 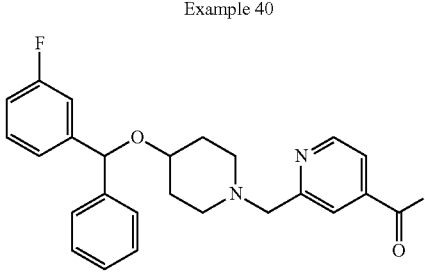 | (d$_6$-DMSO, δ): 1.6-1.7 (2H, m), 1.8-2.0 (2H, m), 2.2-2.4 (2H, m), 2.7-2.9 (2H, m), 3.3-3.5 (1H, m), 3.76 (2H, s), 5.67 (1H, s), 7.0-7.5 (9H, m), 7.68 (1H, dd, J = 1.5, 5.0 Hz), 7.88 (1H, s), 8.66 (1H, d, J = 5.0 Hz) | 419 (M$^+$ − 1), 185 (base peak) |

TABLE 15
| Compound (12) | Compound (13) | Ester compound/Caboxylic acid | | |
|---|---|---|---|---|
| | | Chemical formula | ¹H-NMR | MS (m/z) |
| 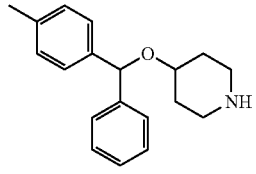 [SMILES: Cc1ccc(C(OC2CCNCC2)c2ccccc2)cc1] | 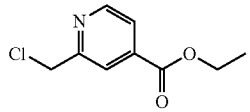 | Production Example 55 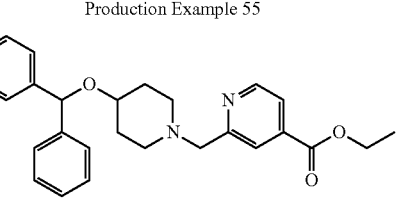 | (CDCl$_3$, δ): 1.41 (3H, t, J = 6.9 Hz), 1.6-2.0 (4H, m), 2.1-2.4 (2H, m), 2.31 (3H, s), 2.6-2.9 (2H, m), 3.3-3.6 (1H, m), 3.68 (2H, s), 4.40 (2H, q, J = 6.9 Hz), 5.48 (1H, s), 7.11 (2H, d, J = 8.1 Hz), 7.1-7.4 (7H, m), 7.70 (1H, dd, J = 1, 2, 5.0 Hz), 7.93 (1H, s), 8.68 (1H, d, J = 5.0 Hz) | 445 (M⁺ + 1), 181 (base peak) |
| | | Example 41 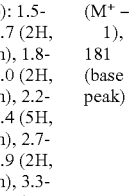 | (CDCl$_3$, δ): 1.5-1.7 (2H, m), 1.8-2.0 (2H, m), 2.2-2.4 (5H, m), 2.7-2.9 (2H, m), 3.3-3.5 (1H, m), 3.72 (3H, s), 5.58 (1H, s), 7.11 (2H, d, J = 8.1 Hz), 7.1-7.4 (7H, m), 7.67 (1H, dd, J = 1.5, 5.0 Hz), 7.88 (1H, s), 8.68 (1H, d, J = 5.0 Hz) | 415 (M⁺ − 1), 181 (base peak) |

TABLE 15-continued
| Compound (12) | Compound (13) | Ester compound/Caboxylic acid | | |
|---|---|---|---|---|
| | | Chemical formula | $^1$H-NMR | MS (m/z) |
| 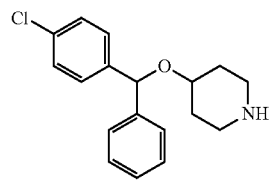 | 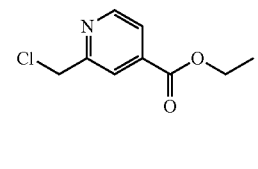 | Production Example 56<br>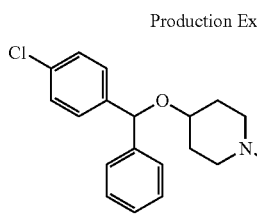 | (CDCl$_3$, δ): 1.40 (3H, t, J = 7.1 Hz), 1.6-2.0 (4H, m), 2.1-2.4 (2H, m), 2.6-2.9 (2H, m), 3.3-3.5 (1H, m), 3.69 (3H, s), 4.40 (2H, q, J = 7.3 Hz), 5.47 (1H, s), 7.1-7.4 (9H, m), 7.70 (1H, d, J = 4.2 Hz), 7.93 (1H, s), 8.68 (1H, d, J = 5.0 Hz) | 463 (M$^+$ − 1), 165 (base peak) |
| | | Example 42<br>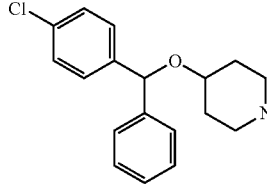 | (d$_6$-DMSO, δ): 1.5-1.7 (2H, m), 1.8-2.0 (2H, m), 2.1-2.4 (2H, m), 2.6-2.9 (2H, m), 3.3-3.5 (1H, m), 3.72 (2H, s), 5.66 (1H, s), 7.2-7.5 (9H, m), 7.67 (1H, dd, J = 3.5, 5.0 Hz), 7.88 (1H, s), 8.64 (1H, d, J = 5.0 Hz) | 435 (M$^+$ − 1), 137 (base peak) |

TABLE 16
| Ester compound/Caboxylic acid | | | | |
|---|---|---|---|---|
| Compound (12) | Compound (13) | Chemical formula | ¹H-NMR | MS (m/z) |
| 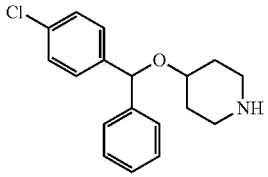 [SMILES: Clc1ccc(C(OC2CCNCC2)c2ccccc2)cc1] | 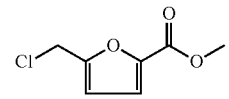 | Production Example 57 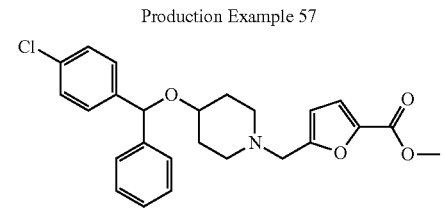 [SMILES: COC(=O)c1ccc(CN2CCC(OC(c3ccccc3)c3ccc(Cl)cc3)CC2)o1] | (CDCl$_3$, δ): 1.6-1.9 (4H, m), 2.1-2.3 (2H, m), 2.6-2.8 (2H, m), 3.3-3.5 (1H, m), 3.59 (2H, s), 3.87 (3H, s), 5.45 (1H, s), 6.31 (1H, d, J = 3.1 Hz), 7.11 (1H, d, J = 3.5 Hz), 7.1-7.4 (9H, m) | 439 (M$^+$), 139 (base peak) |
| | | Example 43 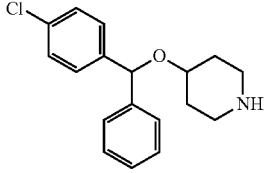 | (d$_6$-DMSO, δ): 1.4-1.9 (4H, m), 2.0-2.2 (2H, m), 2.6-2.8 (2H, m), 3.2-3.4 (1H, m), 3.52 (2H, s), 5.64 (1H, s), 6.43 (1H, d, J = 3.5 Hz), 7.11 (1H, d, J = 3.5 Hz), 7.2-7.5 (9H, m) | 425 (M$^+$), 125 (base peak) |
| 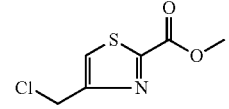 | 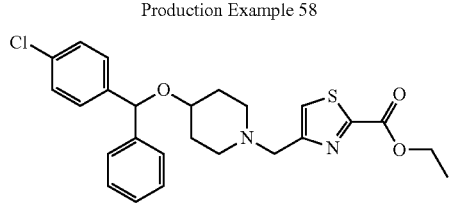 [SMILES: CCOC(=O)c1nc(CN2CCC(OC(c3ccccc3)c3ccc(Cl)cc3)CC2)cs1] | Production Example 58 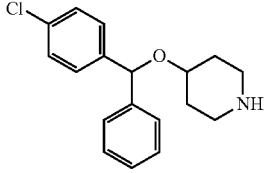 | (CDCl$_3$, δ): 1.42 (3H, t, J = 7.1 Hz), 1.6-2.0 (4H, m), 2.1-2.4 (2H, m), 2.7-2.9 (2H, m), 3.3-3.5 (1H, m), 3.76 (2H, s), 4.46 (2H, q, J = 7.1 Hz), 5.46 (1H, s), 7.1-7.4 (9H, m), 7.47 (1H, br s) | 470 (M$^+$), 201 (base peak) |
| | | Example 44 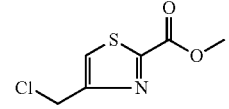 | (CDCl$_3$, δ): 1.3-2.2 (6H, m), 3.2-3.4 (1H, m), 3.42 (2H, br s), 5.61 (1H, s), 7.2-7.5 (10H, m) | 397 (M$^+$ − 45), 201 (base peak) |

TABLE 17

| | | Ester compound/Caboxylic acid | | |
|---|---|---|---|---|
| Compound (12) | Compound (13) | Chemical formula | ¹H-NMR | MS (m/z) |
| Production Example 1 | | Production Example 59 | (CDCl$_3$, δ): 1.7-1.8 (2H, m), 1.90 (2H, d, J = 9.2 Hz), 2.22 (2H, t, J = 9.4 Hz), 2.79 (2H, t, d = 5.7 Hz), 3.65 (3H, s), 3.7-3.9 (3H, m), 4.45 (3H, q, J = 7.3 Hz), 5.73 (1H, s), 7.2-7.4 (10H, m), 7.78 (1H, t, J = 7.7 Hz), 7.96 (1H, d, J = 7.7 Hz) | 447 (M$^+$ + 1), 167 (base peak) |
| | | Example 45 | (CDCl$_3$, δ): 1.6-2.4 (4H, m), 2.6-2.8 (2H, m), 3.2-3.7 (3H, m), 3.80 (2H, s), 3.89 (3H, s), 5.63 (1H, s), 7.1-7.6 (10H, m), 7.73 (1H, t, J = 7.7 Hz), 7.94 (1H, d, J = 7.7 Hz) | 433 (M$^+$ + 1), 167 (base peak) |
| | | Production Example 60 | (CDCl$_3$, δ): 1.6-2.0 (4H, m), 2.1-2.3 (2H, m), 2.31 (3H, s), 2.6-2.9 (2H, m), 3.3-3.5 (1H, m), 3.59 (2H, s), 3.87 (3H, s), 5.46 (1H, s), 6.31 (1H, d, J = 3.5), 7.1-7.4 (10H, m) | 420 (M$^+$ + 1), 138 (base peak) |
| | | Example 46 | (d$_6$-DMSO, δ): 1.4-1.9 (4H, m), 2.0-2.2 (2H, m), 2.25 (3H, s), 2.6-2.8 (2H, m), 3.2-3.4 (1H, m), 3.52 (2H, s), 5.56 (1H, s), 6.44 (1H, d, J = 3.5 Hz), 7.0-7.4 (10H, m) | 404 (M$^+$ − 1), 224 (base peak) |

TABLE 18
| | | Ester compound/Caboxylic acid | | |
|---|---|---|---|---|
| Compound (12) | Compound (13) | Chemical formula | ¹H-NMR | MS (m/z) |
| 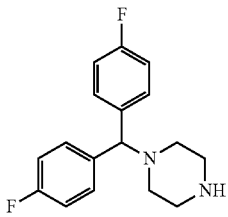 [SMILES: Fc1ccc(C(c2ccc(F)cc2)N2CCNCC2)cc1] | 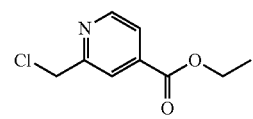 | Production Example 61<br>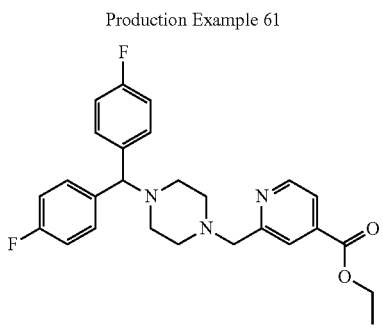 [SMILES: CCOC(=O)c1ccnc(CN2CCN(C(c3ccc(F)cc3)c3ccc(F)cc3)CC2)c1] | (CDCl₃, δ): 1.40 (3H, t, J = 7.1 Hz), 2.1-2.8 (8H, m), 3.72 (2H, s) 4.22 (1H, s), 4.39 (2H, q, J = 7.3 Hz), 6.8-7.0 (4H, m), 7.2-7.4 (4H, m), 7.69 (1H, dd, J = 1.5, 5.0 Hz), 7.90 (1H, s), 8.68 (1H, d, J = 5.0 Hz) | 451 (M⁺), 203 (base peak) |
| | | Example 47<br>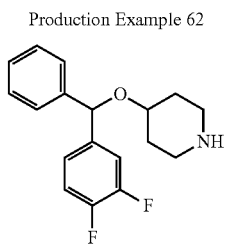 [SMILES: Fc1ccc(C(OC2CCNCC2)c2ccccc2)cc1F] | (d₆-DMSO, δ): 2.2-2.7 (8H, m), 3.71 (2H, s), 4.39 (1H, s), 7.0-7.2 (4H, m), 7.3-7.5 (4H, m), 7.67 (1H, dd, J = 1.5, 5.0 Hz), 7.84 (1H, s), 8.66 (1H, d, J = 5.0 Hz) | 423 (M⁺), 203 (base peak) |
| Production Example 62<br>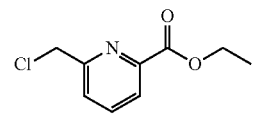 | 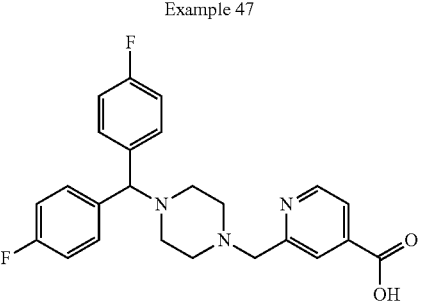 | Production Example 63<br>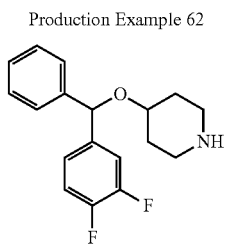 [SMILES: Fc1ccc(C(OC2CCNCC2)c2ccccc2)cc1F] | (CDCl₃, δ): 1.42 (3H, t, J = 7.3 Hz), 1.6-2.0 (4H, m), 2.1-2.4 (2H, m), 2.7-2.9 (2H, m), 3.3-3.5 (1H, m), 3.76 (2H, s), 4.46 (2H, q, J = 6.9 Hz), 5.44 (1H, s), 6.9-7.4 (8H, m), 7.69 (1H, d, J = 7.7 Hz), 7.78 (1H, t, J = 7.7 Hz), 7.97 (1H, d, J = 7.7 Hz) | 467 (M⁺ + 1), 165 (base peak) |

TABLE 19

| Compound (12) | Compound (13) | Chemical formula | ¹H-NMR | MS (m/z) |
|---|---|---|---|---|
| | | Example 48 | (CDCl₃, δ): 1.7-2.2 (4H, m), 2.4-2.8 (4H, m), 3.4-3.6 (1H, m), 3.8-4.1 (2H, m), 5.43 (1H, s), 6.9-7.4 (8H, m), 7.69 (1H, d, J = 6.9 Hz), 7.87 (1H, t, J = 7.7 Hz), 8.09 (1H, d, J = 7.7 Hz) | 439 (M⁺ + 1), 203 (base peak) |
| Production Example 64 | | Production Example 65 | (CDCl₃, δ): 1.41 (3H, t, J = 7.1 Hz), 1.6-2.1 (4H, m), 2.2-2.4 (2H, m), 2.78 (2H, d, J = 5.0 Hz), 3.3-3.5 (1H, m), 3.76 (2H, s), 4.46 (2H, q, J = 7.3 Hz), 5.46 (1H, s), 6.9-7.4 (8H, m), 7.69 (1H, d, J = 7.7 Hz), 7.78 (1H, t, J = 7.7 Hz), 7.96 (1H, d, J = 7.3 Hz) | 467 (M⁺ + 1), 203 (base peak) |
| | | Example 49 | (CDCl₃, δ): 1.6-2.0 (4H, m), 2.6-3.0 (4H, m), 3.7-3.9 (3H, m), 5.40 (1H, s), 6.8-7.1 (8H, m), 7.65 (1H, d, J = 6.9 Hz), 7.86 (1H, t, J = 7.7 Hz), 8.00 (1H, d, J = 7.7 Hz) | 439 (M⁺ + 1), 203 (base peak) |

TABLE 19-continued

| | | Ester compound/Caboxylic acid | | |
|---|---|---|---|---|
| Compound (12) | Compound (13) | Chemical formula | ¹H-NMR | MS (m/z) |
| Production Example 66 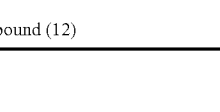 | 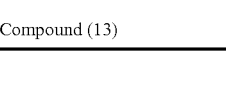 | Production Example 67 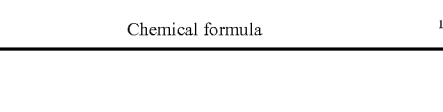 | (CDCl$_3$, δ): 1.01 (3H, t, J = 7.1 Hz), 1.6-1.9 (2H, m), 2.2-2.4 (2H, m), 2.6-2.9 (2H, m), 3.5-3.7 (3H, m), 3.88 (2H, s), 4.25 (2H, q, J = 7.1 Hz), 5.49 (1H, s), 7.4-8.6 (11H, m) | 431 (M$^+$ − 1), 269 (base peak) |

TABLE 20

| | | Ester compound/Caboxylic acid | | |
|---|---|---|---|---|
| Compound (12) | Compound (13) | Chemical formula | ¹H-NMR | MS (m/z) |
| | | Example 50 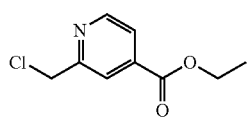 | (CDCl$_3$, δ): 1.5-2.0 (4H, m), 2.22 (2H, t, J = 8.5 Hz), 3.3-3.5 (2H, m), 3.7-4.0 (3H, m), 5.50 (1H, s), 7.5-8.2 (11H, m) | 404 (M$^+$), 269 (base peak) |
| Production Example 62 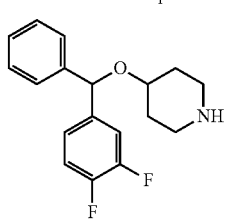 | | Production Example 68 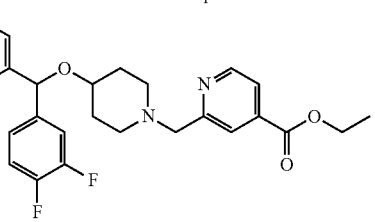 | (CDCl$_3$, δ): 1.40 (3H, t, J = 7.1 Hz), 1.5-2.1 (4H, m), 2.2-2.4 (2H, m), 2.79 (2H, d, J = 5.8 Hz), 3.4-3.6 (1H, m), 3.76 (2H, s), 4.44 (2H, q, J = 7.3 Hz), 5.44 (1H, s), 6.9-7.4 (8H, m), 7.69 (1H, d, J = 7.7 Hz), 7.78 (1H, t, J = 7.7 Hz), 7.96 (1H, d, J = 7.7 Hz) | 467 (M$^+$ + 1), 165 (base peak) |

TABLE 20-continued

| | | Ester compound/Caboxylic acid | | |
|---|---|---|---|---|
| Compound (12) | Compound (13) | Chemical formula | ¹H-NMR | MS (m/z) |
| | | Example 51 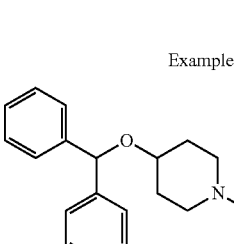 | (CDCl₃, δ): 1.8-2.2 (4H, m), 2.3-2.6 (2H, m), 3.0-3.5 (2H, m), 3.7-3.9 (1H, m), 4.13 (2H, s), 5.39 (1H, s), 6.9-7.4 (8H, m), 7.86 (1H, d, J = 4.6 Hz), 8.44 (1H, s), 5 (1H, d, J = 5.0 Hz) | 439 (M⁺ + 1), 203 (base peak) |
|  |  | Production Example 69 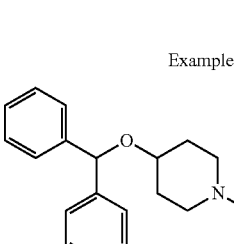 | (CDCl₃, δ): 1.40 (3H, t, J = 7.1 Hz), 1.7-2.0 (4H, m), 2.23 (2H, d, J = 9.9 Hz), 2.76 (2H, t, J = 4.6 Hz), 3.4-3.6 (1H, m), 3.69 (2H, s), 4.37 (2H, q, J = 7.3 Hz), 5.46 (1H, s), 6.9-7.3 (8H, m), 7.70 (1H, t, J = 5.0 Hz), 7.93 (1H, s), 8.69 (1H, d, J = 1.0 Hz) | 467 (M⁺ + 1), 203 (base peak) |

TABLE 21

| | | Ester compound/Caboxylic acid | | |
|---|---|---|---|---|
| Compound (12) | Compound (13) | Chemical formula | ¹H-NMR | MS (m/z) |
| | | Example 52 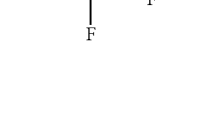 | (CDCl₃, δ): 1.9-2.2 (4H, m), 2.4-2.6 (2H, m), 3.1-3.5 (4H, m), 3.8-3.9 (1H, m), 5.45 (1H, s), 6.9-7.1 (3H, m), 7.2-7.3 (5H, m), 7.86 (1H, d, J = 3.9 Hz), 8.45 (1H, s), 8.60 (1H, d, J = 4.6 Hz) | 439 (M⁺ + 1), 203 (base peak) |

TABLE 21-continued

| | | Ester compound/Caboxylic acid | | |
|---|---|---|---|---|
| Compound (12) | Compound (13) | Chemical formula | ¹H-NMR | MS (m/z) |
| Production Example 62 | Production Example 70 | Production Example 70 | (CDCl$_3$, δ): 1.7-2.0 (2H, m), 1.90 (2H, d, J = 9.4 Hz), 2.22 (2H, t, J = 9.4 Hz), 2.79 (2H, t, J = 5.7 Hz), 3.4-3.7 (1H, m), 3.76 (3H, s), 3.82 (2H, s), 3.91 (3H, s), 5.73 (1H, s), 7.1-7.4 (8H, m), 7.78 (1H, t, J = 7.7 Hz), 7.96 (1H, d, J = 7.7 Hz) | 483 (M$^+$ + 1), 203 (base peak) |
| | | Example 53 | (CDCl$_3$, δ): 1.7-1.8 (2H, m), 1.90 (2H, d, J = 9.4 Hz), 2.22 (2H, t, J = 9.4 Hz), 2.79 (2H, t, J = 5.0 Hz), 3.4-3.7 (1H, m), 3.76 (3H, s), 3.86 (2H, s), 5.80 (1H, s), 7.2-7.5 (8H, m), 7.80 (1H, t, J = 7.7 Hz), 7.93 (1H, d, J = 7.7 Hz) | 467 (M$^+$ − 1), 203 (base peak) |
| Production Example 1 | Production Example 73 | Production Example 74 | (CDCl$_3$, δ): 1.36 (3H, t, J = 7.0 Hz), 1.6-1.9 (4H, m), 2.1-2.3 (2H, m), 2.7-2.8 (2H, m), 3.4-3.5 (1H, m), 3.68 (2H, s), 4.32 (2H, q, J = 7.0 Hz), 5.51 (1H, s), 6.87 (1H, d, J = 3.8 Hz), 7.2-7.4 (10H, m), 7.64 (1H, d, J = 3.8 Hz) | — |

TABLE 22

| Compound (12) | Compound (13) | Ester compound/Caboxylic acid | | |
|---|---|---|---|---|
| | | Chemical formula | ¹H-NMR | MS (m/z) |
| | | Example 54 | (d₆-DMSO, δ): 1.5-1.9 (4H, m), 2.1-2.3 (2H, m), 2.6-2.8 (2H, m), 3.70 (2H, s), 5.63 (1H, s), 7.00 (1H, d, J = 3.8 Hz), 7.2-7.4 (10H, m), 7.56 (1H, d, J = 3.5 Hz) | 408.1 (M⁺) |
| | | Production Example 76 | (CDCl₃, δ): 1.41 (3H, t, J = 7.3 Hz), 2.3-2.7 (8H, m), 3.73 (2H, s), 4.24 (1H, s), 4.40 (2H, q, J = 7.0 Hz), 7.1-7.5 (9H, m), 7.70 (1H, dd, J = 1.6, 4.9 Hz), 7.91 (1H, s), 8.69 (1H, dd, J = 0.8, 5.1 Hz) | — |
| | | Example 56 | (d₆-DMSO, δ): 3.3-3.4 (8H, m), 4.45 (2H, s), 4.51 (1H, s), 7.1-7.5 (10H, m), 7.85 (1H, d, J = 4.1 Hz), 8.00 (1H, s), 8.82 (1H, d, J = 4.3 Hz) | 388.3 (M⁺) |
| | Production Example 73 | Production Example 77 | (CDCl₃, δ): 1.36 (3H, t, J = 7.0 Hz), 2.1-2.6 (8H, m), 3.71 (2H, s), 4.22 (1H, s), 4.32 (2H, q, J = 7.0 Hz), 6.88 (1H, d, J = 3.8 Hz), 6.9-7.0 (5H, m), 7.2-7.4 (5H, m), 7.63 (1H, d, J = 3.5 Hz) | — |

TABLE 23
| Compound (12) | Compound (13) | Ester compound/Carboxylic acid | | |
|---|---|---|---|---|
| | | Chemical formula | ¹H-NMR | MS (m/z) |
| 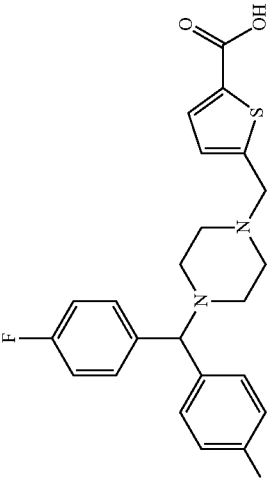 | 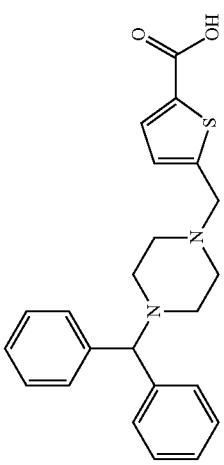 Production Example 73 | Example 57 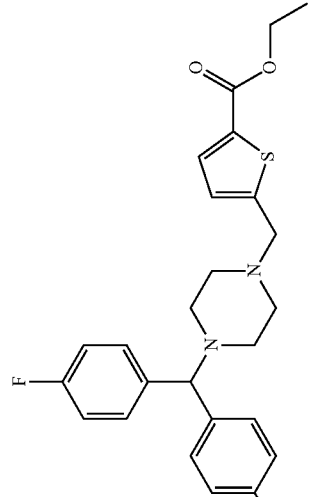 | (d₆-DMSO, δ): 2.2-2.4 (2H, m), 2.7-2.9 (2H, m), 3.0-3.4 (4H, m), 4.55 (2H, s), 4.61 (1H, s), 7.1-7.5 (10H, m), 7.70 (1H, d, J = 3.0 Hz), 7.92 (1H, br), 10.80 (1H, br) | 393.1 (M⁺) |
| | | Production Example 78 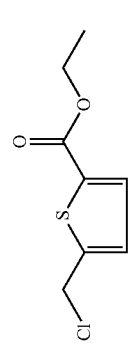 | (CDCl₃, δ): 1.36 (3H, t, J = 7.3 Hz), 2.1-2.6 (8H, m), 3.71 (2H, s), 4.23 (1H, s), 4.32(2H, q, J = 7.0 Hz), 6.88 (1H, d, J = 3.8 Hz), 7.0-7.5 (8H, m), 7.63 (1H, d, J = 3.5 Hz) | — |
| | | Example 58 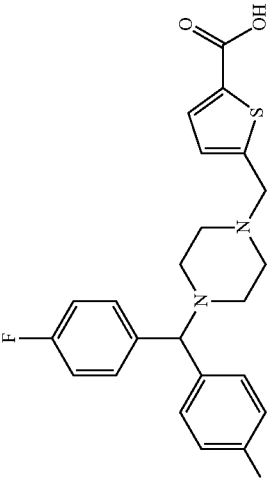 | (d₆-DMSO, δ): 2.2-2.4 (2H, m), 2.7-2.9 (2H, m), 3.0-3.1 (2H, m), 3.2-3.4 (2H, m), 4.5-4.6 (3H, m), 7.1-7.5 (9H, m), 7.69-7.70 (1H, br) | 429.2 (M⁺) |

TABLE 23-continued
| Ester compound/Caboxylic acid | | | |
|---|---|---|---|
| Compound (12) | Compound (13) | Chemical formula | $^1$H-NMR | MS (m/z) |
| 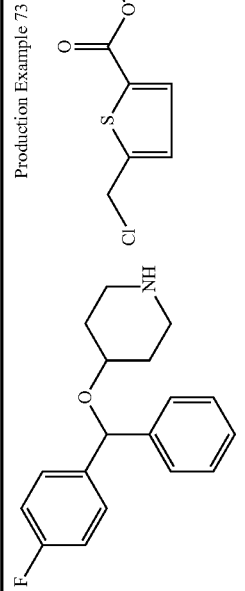 | Production Example 73<br>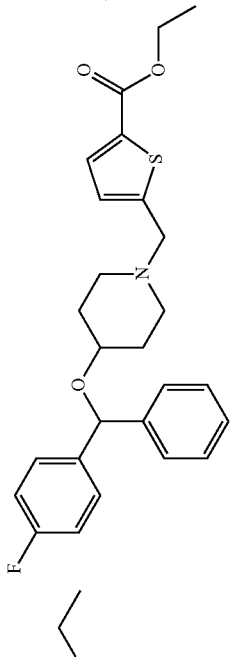 | Production Example 79 | (CDCl$_3$, δ): 1.36 (3H, t, J = 7.0 Hz), 1.6-2.0 (4H, m), 2.1-2.3 (2H, m), 2.7-2.9 (2H, m), 3.3-3.6 (1H, m), 3.68 (2H, s), 4.33 (2H, q, J = 7.0 Hz), 5.48 (1H, s), 6.87 (1H, d, J = 3.8 Hz), 6.9-7.1 (2H, m), 7.2-7.4 (7H, m), 7.64 (1H, d, J = 3.5 Hz) | — |

TABLE 24

| Compound (12) | Compound (13) | Ester compound/Carboxylic acid | | |
|---|---|---|---|---|
| | | Chemical formula | ¹H-NMR | MS (m/z) |
| Production Example 80: [structure of 4-[(2,4-difluorophenyl)(phenyl)methoxy]piperidine] | Production Example 79: [structure of ethyl 6-(chloromethyl)picolinate] | Example 59: [structure with thiophene-2-carboxylic acid, piperidine, and (4-fluorophenyl)(phenyl)methoxy group] | (d₆-DMSO, δ): 1.5-1.7 (2H, m), 1.8-1.9 (2H, m), 2.1-2.2 (2H, m), 2.6-2.8 (2H, m), 3.66 (2H, s), 5.65 (1H, s), 6.97 (1H, d, J = 3.2 Hz) 7.1-7.4 (9H, m), 7.53 (1H, d, J = 3.5 Hz) | 426.2 (M⁺) |
| | | Production Example 81: [ethyl ester of pyridine-2-carboxylate with piperidine and (2,4-difluorophenyl)(phenyl)methoxy group] | (CDCl₃, δ): 1.42 (3H, t, J = 7.3 Hz), 1.6-1.9 (4H, m), 2.1-2.4 (2H, m), 2.7-2.8 (2H, m), 3.4-3.5 (1H, m), 3.75 (2H, s), 4.46 (2H, q, J = 7.0 Hz), 5.82 (1H, s), 6.7-6.9 (2H, m), 7.2-7.5 (6H, m), 7.6-7.8 (1H, m), 7.79 (1H, t, J = 7.6 Hz), 7.98 (1H, d, J = 7.0 Hz) | — |
| | | Example 60: [pyridine-2-carboxylic acid with piperidine and (2,4-difluorophenyl)(phenyl)methoxy group] | (d₆-DMSO, δ): 1.5-1.6 (2H, m), 1.8-1.9 (2H, m), 2.1-2.3 (2H, m), 2.6-2.8 (2H, m), 3.3-3.5 (1H, m), 3.63 (2H, m), 5.83 (1H, s), 7.0-7.6 (8H, m), 7.64 (1H, dd, J = 2.4, 6.8 Hz), 7.8-8.0 (2H, m) | 439.1 (M⁺) |

TABLE 24-continued
| Ester compound/Caboxylic acid | | |
|---|---|---|
| Compound (12) | Compound (13) | |
| | Chemical formula | $^1$H-NMR | MS (m/z) |
| Production Example 80 | Production Example 82 | (CDCl$_3$, δ): 1.41 (3H, t, J = 7.3 Hz), 1.7-2.0 (4H, m), 2.1-2.3 (2H, m), 2.7-2.8 (2H, m), 3.45 (1H, sep, J = 4.3 Hz), 3.69 (2H, s), 4.41 (2H, q, J = 7.0 Hz), 5.82 (1H, s), 6.7-6.9 (2H, m), 7.2-7.5 (6H, m), 7.71 (1H, dd, J = 1.6, 5.1 Hz), 7.93 (1H, s), 8.69 (1H, d, J = 5.7 Hz) | — |
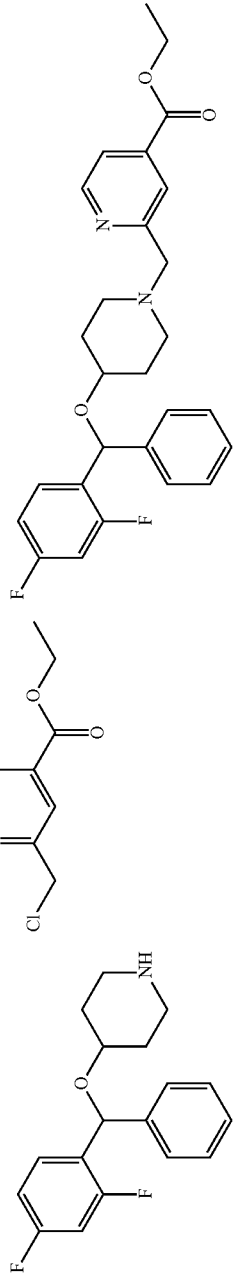

TABLE 25

| | Ester compound/Caboxylic acid | | | |
|---|---|---|---|---|
| Compound (12) | Compound (13) | Chemical formula | $^1$H-NMR | MS (m/z) |
| | | Example 61 (structure: 2,4-difluorophenyl-phenylmethyl ether linked to piperidine-N-CH$_2$-pyridine-COOH) | (d$_6$-DMSO, δ): 1.5-1.7 (2H, m), 1.8-2.0 (2H, m), 2.2-2.3 (2H, m), 2.7-2.8 (2H, m), 3.3-3.5 (1H, m), 3.70 (2H, s), 5.83 (1H, s), 7.1-7.7 (9H, m), 7.86 (1H, s), 8.64 (1H, d, J = 4.9 Hz) | 439.1 (M$^+$) |
| (structure: 4-fluorophenyl-phenylmethyl-piperazine-NH) | (structure: ethyl 2-(chloromethyl)pyridine-4-carboxylate) | Production Example 83 (structure: 4-fluorophenyl-phenylmethyl-piperazine-CH$_2$-pyridine-COOEt) | (CDCl$_3$, δ): 1.39 (3H, t, J = 7.1 Hz), 2.4-2.6 (8H, m), 3.72 (2H, s), 4.23 (1H, s), 4.39 (2H, q, J = 7.1 Hz), 6.9-7.0 (2H, m), 7.1-7.4 (7H, m), 7.68 (1H, dd, J = 3.5, 5.0 Hz), 7.90 (1H, s), 8.68 (1H, d, J = 5.0 Hz) | 433 (M$^+$), 185 (base peak) |

TABLE 25-continued
| Compound (12) | Compound (13) | Ester compound/Caboxylic acid | | |
|---|---|---|---|---|
| | | Chemical formula | ¹H-NMR | MS (m/z) |
| | | Example 62 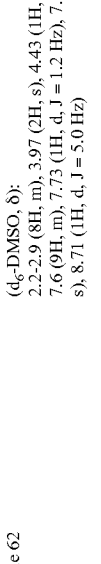 | (d₆-DMSO, δ): 2.2-2.9 (8H, m), 3.97 (2H, s), 4.43 (1H, s), 7.0-7.6 (9H, m), 7.73 (1H, d, J = 1.2 Hz), 7.91 (1H, s), 8.71 (1H, d, J = 5.0 Hz) | 405 (M⁺), 185 (base peak) |
| Production Example 90 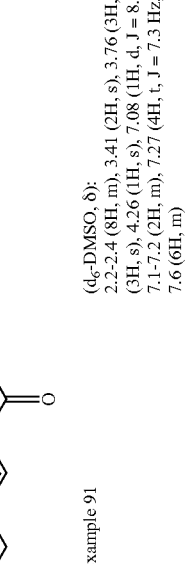 |  | Production Example 91  | (d₆-DMSO, δ): 2.2-2.4 (8H, m), 3.41 (2H, s), 3.76 (3H, s), 3.79 (3H, s), 4.26 (1H, s), 7.08 (1H, d, J = 8.4 Hz), 7.1-7.2 (2H, m), 7.27 (4H, t, J = 7.3 Hz, 7.3-7.6 (6H, m) | — |

TABLE 26

| Compound (12) | Compound (13) | Ester compound/Carboxylic acid | | |
|---|---|---|---|---|
| | | Chemical formula | ¹H-NMR | MS (m/z) |
| | | Example 66 | (CDCl₃, δ): 2.8-3.0 (6H, m), 3.2-3.4 (2H, m), 4.0-4.2 (5H, m), 5.30 (1H, s), 7.1-7.3 (4H, m), 7.3-7.4 (7H, m), 8.4-8.5 (1H, m), 8.09 (1H, s) | 417.2 (M⁺) |
| | Production Example 13 | Production Example 112 | (CDCl₃, δ): 1.39 (3H, t, J = 7.3 Hz), 1.5-1.6 (2H, m), 1.6-1.7 (2H, m), 2.1-2.2 (2H, m), 2.6-2.7 (2H, m), 3.3-3.4 (1H, m), 3.86 (2H, s), 4.35 (2H, q, J = 7.0 Hz), 5.46 (1H, s), 6.9-7.0 (2H, m), 7.2-7.3 (6H, m), 7.8-7.9 (1H, m), 8.5-8.6 (1H, m) | — |
| | | Example 83 | (CDCl₃, δ): 1.8-2.0 (4H, m), 2.9-3.1 (4H, m), 3.7-3.9 (1H, m), 4.17 (2H, s), 5.41 (1H, s), 7.02 (2H, t, J = 8.4 Hz), 7.3-7.4 (8H, m), 8.49 (1H, dd, J = 1.4, 7.6 Hz), 8.57 (1H, dd, J = 1.9 Hz, 4.9 Hz) | 421.2 (M⁺) |

TABLE 26-continued

| Compound (12) | Compound (13) | Ester compound/Caboxylic acid | | |
|---|---|---|---|---|
| | | Chemical formula | ¹H-NMR | MS (m/z) |
| Production Example 1 | | Production Example 113 | (CDCl₃, δ): 1.6-1.8 (2H, m), 1.8-1.9 (2H, m), 2.2-2.4 (2H, m), 2.8-2.9 (2H, m), 3.3-3.4 (1H, m), 3.82 (3H, s), 4.92 (2H, s), 5.46 (1H, s), 7.2-7.3 (10H, m), 7.90 (2H, s) | — |

TABLE 27

| Compound (12) | Compound (13) | Ester compound/Carboxylic acid | | |
|---|---|---|---|---|
| | | Chemical formula | ¹H-NMR | MS (m/z) |
| Production Example 115 | Production Example 115 | Example 84 | (CDCl₃, δ): 1.6-1.7 (2H, m), 1.8-2.0 (4H, m), 2.1-2.2 (2H, m), 2.83 (2H, s), 2.93 (1H, s), 3.4-3.5 (1H, m), 5.52 (1H, s), 7.2-7.5 (12H, m) | — |
| | | Production Example 116 | (CDCl₃, δ): 1.42 (3H, t, J = 7.3 Hz), 1.7-1.9 (4H, m), 2.2-2.3 (2H, m), 2.7-2.8 (2H, m), 3.4-3.5 (1H, m), 3.78 (2H, s), 4.46 (2H, q, J = 7.0 Hz), 5.85 (1H, s), 7.0-7.5 (8H, m), 7.7-7.8(2H, m), 7.98 (1H, d, J = 7.6 Hz) | — |
| | | Example 86 | (CDCl₃, δ): 1.8-1.9 (2H, m), 2.1-2.2 (2H, m), 2.8-3.0 (4H,m), 3.3-3.5 (1H, m), 3.63 (1H, brs), 4.05 (2H, s), 5.81 (1H, s), 7.0-7.4 (8H, m), 7.72 (1H, d, J = 7.6 Hz), 7.89 (1H, t, J = 7.8 Hz), 8.12 (1H, d, J = 7.6 Hz) | 439.2 (M⁺) |

TABLE 27-continued

| Compound (12) | Compound (13) | Ester compound/Carboxylic acid | | |
|---|---|---|---|---|
| | | Chemical formula | ¹H-NMR | MS (m/z) |
| Production Example 115 | | Production Example 117 | (CDCl₃, δ): 1.41 (3H, t, J = 7.3 Hz), 1.7-1.9 (4H, m), 2.2-2.3 (2H, m), 2.7-2.8 (2H, m), 3.4-3.5 (1H, m), 3.69 (2H, s), 4.41 (2H, q, J = 7.0 Hz), 5.85 (1H, s), 7.0-7.5 (8H, m), 7.71 (1H, dd, J = 1.6 Hz, 4.9 Hz), 7.93 (1H, s), 8.69 (1H, dd, J = 1.1 Hz, 5.4 Hz) | — |

TABLE 28

| Compound (12) | Compound (13) | Ester compound/Carboxylic acid | | |
|---|---|---|---|---|
| | | Chemical formula | ¹H-NMR | MS (m/z) |
| | | Example 87 | (CDCl₃, δ): 2.0-2.1 (2H, m), 2.4-2.5 (2H, m), 3.2-3.3 (4H, m), 3.7-3.8 (1H, m), 4.20 (2H, s), 5.78 (1H, s), 7.02 (3H, t, J = 8.6 Hz), 7.1-7.4 (5H, m), 7.88 (1H, d, J = 5.1 Hz), 8.43 (1H, s), 8.63 (1H, d, J = 5.4 Hz) | 439.2 (M⁺) |
| | | Production Example 118 | (CDCl₃, δ): 1.7-1.8 (4H, m), 2.1-2.2 (2H, m), 2.6-2.7 (2H, m), 3.4-3.5 (1H, m), 3.95 (2H, s), 5.48 (1H, s), 6.9-7.0 (2H, m), 7.2-7.3 (7H, m), 8.24 (1H, t, J = 1.9 Hz), 8.69 (1H, d, J = 2.2 Hz), 9.10 (1H, d, J = 2.2 Hz) | — |
| | | Example 88 | (CDCl₃, δ): 1.9-2.1 (2H, m), 2.4-2.5 (2H, m), 3.0-3.2 (4H, m), 3.8-3.9 (1H, m), 3.94 (2H, s), 5.46 (1H, s), 7.0 (2H, t, J = 8.6 Hz), 7.3-7.4 (7H, m), 8.52 (1H, d, J = 1.6 Hz), 8.85 (1H, s), 9.24 (1H, d, J = 1.4 Hz) | 421.3 (M⁺) |

TABLE 28-continued

| Ester compound/Caboxylic acid | | | |
|---|---|---|---|
| Compound (12) | Compound (13) | Chemical formula | $^1$H-NMR | MS (m/z) |
| [structure: 4-fluorophenyl-phenyl-methoxy-piperidine-NH with thiophene-CH2Br methyl ester] | | Production Example 119 [structure: 4-fluorophenyl-phenyl-methoxy-piperidine-N-CH2-thiophene methyl ester] | (CDCl$_3$, δ): 1.6-1.9 (4H, m), 2.0-2.2 (2H, m), 2.7-2.8 (2H, m), 3.3-3.4 (1H, m), 3.47 (2H, s), 3.87 (3H, s), 5.48 (1H, s), 6.99 (2H, t, J = 8.4 Hz), 7.2-7.4 (8H, m), 7.72 (1H, d, J = 1.4 Hz) | — |

TABLE 29

| Compound (12) | Compound (13) | Ester compound/Carboxylic acid | | |
|---|---|---|---|---|
| | | Chemical formula | ¹H-NMR | MS (m/z) |
| Production Example 120 (structure: 4-(trifluoromethyl)phenyl-phenylmethyl ether of 4-hydroxypiperidine) | Compound (13) (structure: ethyl 6-(chloromethyl)picolinate) | Example 89 (4-fluorophenyl-phenylmethyl ether of 1-((thiophen-2-yl-5-carboxylic acid)methyl)piperidin-4-ol) | (d₆-DMSO, δ): 1.6-1.7 (2H, m), 1.8-1.9 (2H, m), 2.2-2.3 (2H, m), 2.7-2.8 (2H, m), 3.3-3.4 (1H, m), 3.64 (2H, s), 5.64 (1H, s), 7.1-7.4 (9H, m), 7.65 (1H, d, J = 1.6 Hz), 7.68 (1H, s) | 426.2 (M⁺) |
| | | Production Example 121 (ethyl ester of pyridine-2-carboxylic acid derivative with 4-(trifluoromethyl)phenyl-phenylmethyl piperidine) | (CDCl₃, δ): 1.42 (3H, t, J = 7.3 Hz), 1.7-1.9 (4H, m), 2.2-2.3 (2H, m), 2.7-2.8 (2H, m), 3.4-3.5 (1H, m), 3.76 (2H, s), 4.46 (2H, q, J = 7.0 Hz), 5.55 (1H, s), 7.3-7.4 (5H, m), 7.47 (2H, d, J = 8.4 Hz), 7.57 (2H, d, J = 8.6 Hz), 7.70 (1H, d, J = 7.3 Hz), 7.80 (1H, t, J = 0.7,6 Hz), 7.98 (1H, d, J = 0.8 Hz, 7.6 Hz) | — |
| | | Example 90 (carboxylic acid of above) | (CDCl₃, δ): 1.6-2.0 (4H, m), 2.47 (2H, brs), 2.86 (2H, brs), 3.54 (1H, brs), 3.84 (2H, s), 5.54 (1H, s), 7.3-7.4 (6H, m), 7.47 (2H, d, J = 8.4 Hz), 7.57 (2H, d, J = 8.6 Hz), 7.68 (1H, d, J = 8.1 Hz), 7.87 (1H, t, J = 7.6 Hz), 8.10 (1H, d, J = 7.3 Hz) | 471.2 (M⁺) |

TABLE 29-continued
| Compound (12) | Compound (13) | Ester compound/Caboxylic acid | | |
|---|---|---|---|---|
| | | Chemical formula | ¹H-NMR | MS (m/z) |
| Production Example 120 | | Production Example 122 | (CDCl₃, δ): 1.41 (3H, t, J = 7.3 Hz), 1.8-1.9 (4H, m), 2.2-2.3 (2H, m), 2.7-2.8 (2H, m), 3.4-3.5 (1H, m), 3.70 (2H, s), 4.41 (2H, q, J = 7.3 Hz), 5.55 (1H, s), 7.3-7.4 (5H, m), 7.47 (2H, d, J = 8.6 Hz), 7.57 (2H, d, J = 8.6 Hz), 7.71 (1H, d, J = 4.9 Hz), 7.94 (1H, s), 8.69 (1H, d, J = 5.1 Hz) | — |
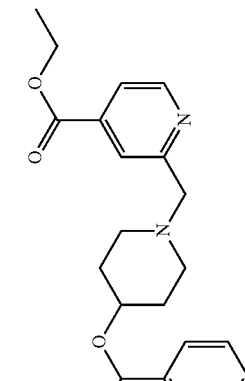

TABLE 30

| Compound (12) | Compound (13) | Ester compound/Carboxylic acid | | |
|---|---|---|---|---|
| | | Chemical formula | ¹H-NMR | MS (m/z) |
| | | Example 91 | (CDCl₃, δ): 1.9-2.1 (2H, m), 2.46 (2H, brs), 3.25 (4H, br s), 3.82 (1H, brs), 4.16 (2H, s), 5.50 (1H, s), 7.3-7.4 (5H, m), 7.47 (2H, d, J = 8.1 Hz), 7.59 (2H, d, J = 8.4 Hz), 7.88 (1H, d, J = 3.8 Hz), 8.45 (1H, s), 8.62 (1H, d, J = 5.1 Hz) | 471.1 (M⁺) |
| | | Production Example 123 | (CDCl₃, δ): 2.3-2.5 (8H, m), 3.50 (2H, s), 3.87 (3H, s), 4.21 (1H, s), 6.9-7.0 (4H, m), 7.3-7.4 (5H, m), 7.71 (1H, d, J = 1.6 Hz) | — |
| | | Example 92 | (d₆-DMSO, δ): 2.3-2.4 (4H, m), 2.5-2.7 (4H, m), 3.70 (2H, s), 4.41 (1H, s), 7.12 (4H, t, J = 8.6 Hz), 7.3-7.4 (4H, m), 7.64 (1H, dd, J = 3.0, 6.9 Hz), 7.66 (1H, s), 7.73 (1H, s) | 429.1 (M⁺) |

TABLE 31
| Compound (12) | Compound (13) | Ester compound/Caboxylic acid | | |
|---|---|---|---|---|
| | | Chemical formula | ¹H-NMR | MS (m/z) |
| 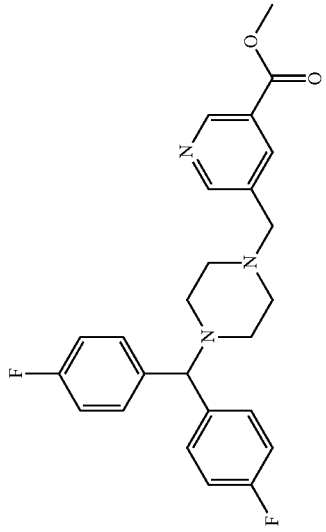 | 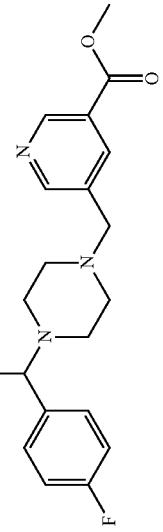 | Production Example 124<br>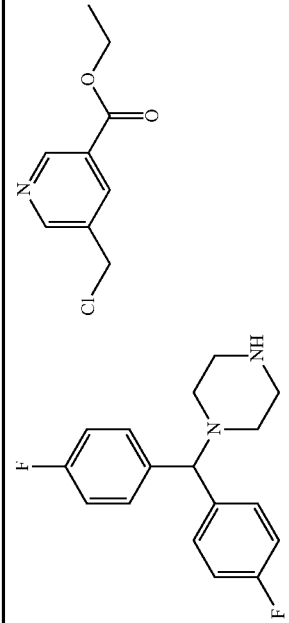 | (CDCl₃, δ):<br>2.3-2.5 (8H, m), 3.57 (2H, s), 3.95 (3H, s), 4.27 (1H, s), 6.9-7.0 (4H, m), 7.3-7.4 (4H, m), 8.23 (1H, t, J = 2.2 Hz), 8.69 (1H, d, J = 2.4 Hz), 9.10 (1H, d, J = 1.9 Hz) | — |
| | | Example 9<br>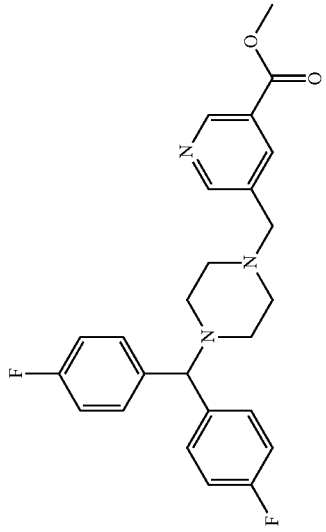 | (d₆-DMSO, δ):<br>2.2-2.4 (8H, m), 3.57 (2H, s), 4.36 (1H, s), 7.11 (4H, t, J = 8.6 Hz), 7.3-7.4 (4H, m), 8.13 (1H, s), 8.63 (1H, s), 8.93 (1H, s) | 424.2 (M⁺) |

TABLE 31-continued
| Compound (12) | Compound (13) | Ester compound/Caboxylic acid | | |
| --- | --- | --- | --- | --- |
| | | Chemical formula | ¹H-NMR | MS (m/z) |
| 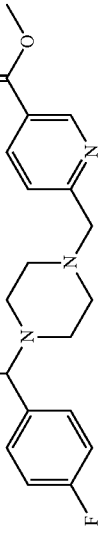 | 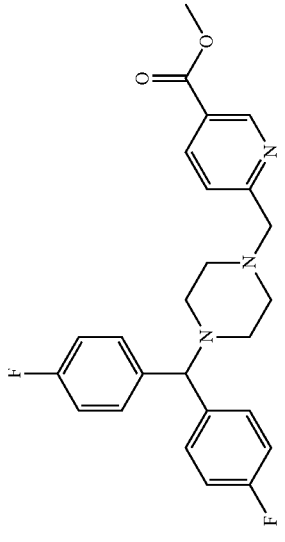 | Production Example 127<br>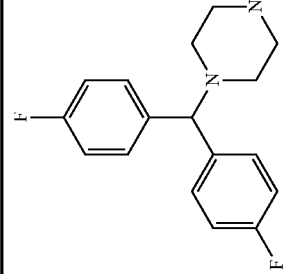 | (CDCl$_3$, δ):<br>2.4-2.6 (8H, m), 3.72 (2H, s), 3.94 (3H, s), 4.23 (1H, s), 6.9-7.0 (4H, m), 7.3-7.4 (4H, m), 7.49 (1H, d, J = 8.1 Hz), 8.23 (1H, dd, J = 2.2 Hz, 8.1 Hz) 9.14 (1H, d, J = 1.4 Hz) | — |

TABLE 32

| Compound (12) | Compound (13) | Ester compound/Caboxylic acid | | MS (m/z) |
|---|---|---|---|---|
| | | Chemical formula | ¹H-NMR | |
| | | Example 96 | (d₆-DMSO, δ): 2.3-2.4 (4H, m), 2.7-2.8 (4H, m), 3.63 (2H, s), 4.37 (1H, s), 7.11 (4H, t, J = 8.6 Hz), 7.4-7.5 (5H, m), 8.15 (1H, dd, J = 2.2 Hz, 8.4 Hz), 8.92 (1H, d, J = 2.2 Hz) | 424.2 (M⁺) |
| | | Production Example 128 | (CDCl₃, δ): 1.36 (3H, t, J = 7.3 Hz), 2.2-2.4 (8H, m), 3.91 (2H, s), 4.18 (1H, s), 4.54 (2H, q, J = 7.3 Hz), 6.9-7.0 (4H, m), 7.2-7.3 (5H, m), 7.91 (1H, dd, J = 1.6 Hz, 7.7 Hz), 8.57 (1H, dd, J = 1.6 Hz, 4.9 Hz) | — |
| | Production Example 13 | | | |

TABLE 32-continued
| Compound (12) | Compound (13) | Ester compound/Caboxylic acid | | |
|---|---|---|---|---|
| | | Chemical formula | ¹H-NMR | MS (m/z) |
| | | Example 97<br>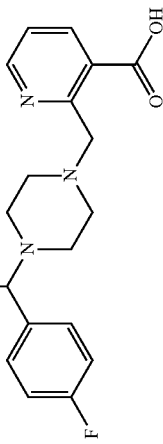 | (CDCl$_3$, δ):<br>2.1-2.3 (2H, m), 2.7-3.0 (6H, m), 4.11 (2H, s), 4.27 (1H, s), 6.9-7.0 (4H, m), 7.3-7.4 (5H, m), 8.45 (1H, dd, J = 1.9 Hz, 8.1 Hz), 8.58 (1H, dd, J = 1.9 Hz, 4.6 Hz) | 424.1 (M⁺) |

TABLE 33
| Compound (12) | Compound (13) | Ester compound/Caboxylic acid | | |
|---|---|---|---|---|
| | | Chemical formula | ¹H-NMR | MS (m/z) |
| 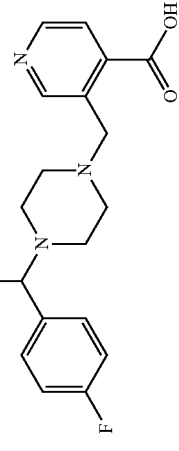 | 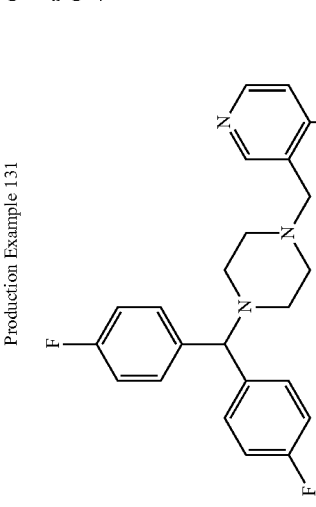 | Production Example 131<br />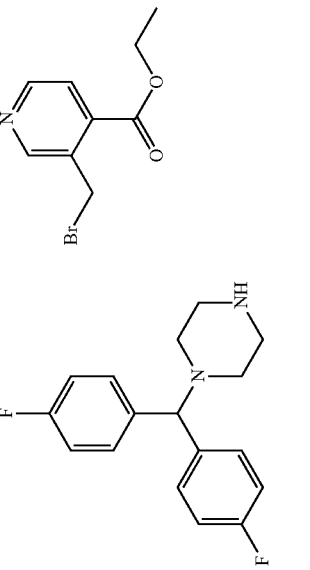 | (CDCl₃, δ):<br />1.36 (3H, t, J = 7.3 Hz), 2.2-2.4 (8H, m), 3.73 (2H, s), 4.19 (1H, s), 4.33 (2H, q, J = 7.3 Hz), 6.95 (4H, t, J = 8.6 Hz), 7.3-7.4 (4H, m), 7.46 (1H, d, J = 5.1 Hz), 8.58 (1H, d, J = 5.1 Hz), 8.61 (1H, s) | — |
| | | Example 100<br />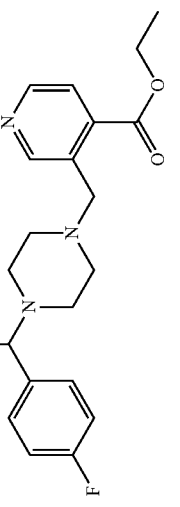 | (CDCl₃, δ):<br />2.1-2.3 (2H, m), 2.6-3.0 (6H, m), 3.90 (2H, s), 4.27 (1H, s), 6.9-7.0 (4H, m), 7.3-7.4 (4H, m), 7.97 (1H, d, J = 4.9 Hz), 8.49 (1H, s), 8.73 (1H, d, J = 4.9 Hz) | 424.1 (M⁺) |

TABLE 33-continued

| Compound (12) | Compound (13) | Ester compound/Caboxylic acid | | |
|---|---|---|---|---|
| | | Chemical formula | ¹H-NMR | MS (m/z) |
| Production Example 132 | | Production Example 133 | (CDCl$_3$, δ): 2.3-2.5 (8H, m), 3.59 (2H, s), 3.95 (3H, s), 4.22 (1H, s), 6.9-7.0 (2H, m), 7.2-7.4 (7H, m), 8.23 (1H, t, J = 2.2 Hz), 8.69 (1H, d, J = 2.2 Hz), 9.09 (1H, d, J = 2.2 Hz) | — |

TABLE 34

| Compound (12) | Compound (13) | Ester compound/Carboxylic acid | | |
|---|---|---|---|---|
| | | Chemical formula | ¹H-NMR | MS (m/z) |
| | | Example 101 | (CDCl₃, δ): 2.6-3.0 (8H, m), 3.84 (2H, s), 4.29 (1H, s), 6.94 (2H, t, J = 8.6 Hz), 7.2-7.3 (7H, m), 8.5-8.6 (2H, m), 9.22 (1H, s) | 406.2 (M⁺) |
| Production Example 132 | Production Example 134 | | (CDCl₃, δ): 1.41 (3H, t, J = 7.3 Hz), 2.3-2.4 (8H, m), 3.74 (2H, s), 4.21 (1H, s), 4.41 (2H, q, J = 7.3 Hz), 6.9-7.0 (2H, m), 7.1-7.4 (8H, m), 7.80 (1H, dd, J = 1.6 Hz, 8.1 Hz), 8.54 (1H, dd, J = 1.6 Hz, 5.1 Hz) | — |

TABLE 34-continued

| Compound (12) | Compound (13) | Ester compound/Caboxylic acid | | |
|---|---|---|---|---|
| | | Chemical formula | ¹H-NMR | MS (m/z) |
| | | Example 102 | (CDCl$_3$, δ): 2.51 (4H, brs), 2.75 (4H, brs), 3.87 (2H, s), 4.26 (1H, s), 6.9-7.0 (2H, m), 7.2-7.4 (8H, m), 7.65 (1H, d, J = 6.8 Hz), 8.75 (1H, d, J = 3.2 Hz) | 406.4 (M$^+$) |

TABLE 35

| Compound (12) | Compound (13) | Ester compound/Carboxylic acid | | |
|---|---|---|---|---|
| | | Chemical formula | ¹H-NMR | MS (m/z) |
| Production Example 132 (4-fluorobenzhydryl piperazine) | Production Example 135 (methyl 6-(bromomethyl)nicotinate) | Production Example 135 (methyl ester product) | (CDCl$_3$, δ): 2.4-2.5 (8H, m), 3.72 (2H, s), 3.94 (3H, s), 4.23 (1H, s), 6.9-7.0 (2H, m), 7.2-7.4 (7H, m), 7.49 (1H, d, J = 7.8 Hz), 8.23 (1H, dd, J = 1.9 Hz, 7.8 Hz), 9.1-9.2 (1H, m) | — |
| | | Example 103 (carboxylic acid) | (CDCl$_3$, δ): 2.60 (4H, brs), 3.01 (4H, brs), 4.07 (2H, s), 4.26 (1H, s), 6.94 (2H, t, J = 8.9 Hz), 7.1-7.4 (7H, m), 7.54 (1H, d, J = 7.8 Hz), 8.18 (1H, dd, J = 1.9 Hz, 7.8 Hz), 9.14 (1H, d, J = 1.4 Hz) | 406.4 (M$^+$) |
| Production Example 137 (3-chlorobenzhydryl piperazine) | Production Example 137 (ethyl 6-(chloromethyl)picolinate) | Production Example 138 (ethyl ester product) | (CDCl$_3$, δ): 1.43 (3H, t, J = 7.3 Hz), 2.4-2.6 (8H, m), 3.80 (2H, s), 4.21 (3H, s), 4.46 (2H, q, J = 7.3 Hz), 7.1-7.4 (9H, m), 7.6-7.7 (1H, m), 7.77 (1H, t, J = 7.8 Hz), 7.97 (1H, dd, J = 1.1 Hz, 7.6 Hz) | — |

TABLE 35-continued
| Compound (12) | Compound (13) | Ester compound/Caboxylic acid | | |
|---|---|---|---|---|
| | | Chemical formula | ¹H-NMR | MS (m/z) |
| | | Example 105 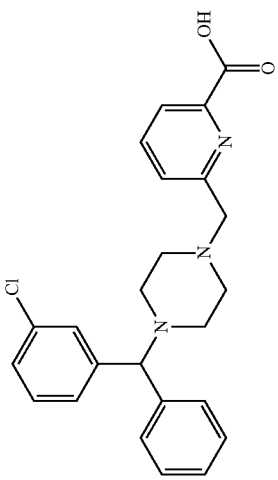 | (CDCl$_3$, δ): 2.0-3.0 (8H, m), 3.8-4.2 (3H, m), 7.1-7.4 (10H, m), 7.73 (1H, brs), 8.07 (1H, brs) | 422.2 (M⁺) |

TABLE 36

| Compound (12) | Compound (13) | Ester compound/Caboxylic acid | | |
|---|---|---|---|---|
| | | Chemical formula | ¹H-NMR | MS (m/z) |
| Production Example 137 | | Production Example 139 | (CDCl$_3$, δ): 1.41 (3H, t, J = 7.3 Hz), 2.4-2.6 (8H, m), 3.73 (2H, s), 4.21 (1H, s), 4.41 (2H, q, J = 7.3 Hz), 7.1-7.4 (9H, m), 7.70 (1H, dd, J = 1.9 Hz, 5.4 Hz), 7.91 (1H, s), 8.70 (1H, dd, J = 0.8 Hz, 5.4 Hz) | — |
| | | Example 106 | (CDCl$_3$, δ): 2.8-3.2 (8H, m), 4.13 (2H, s), 4.31 (1H, s), 7.1-7.4 (9H, m), 7.64 (1H, d, J = 4.9 Hz), 8.25 (1H, s), 8.61 (1H, d, J = 4.9 Hz) | 422.2 (M$^+$) |
| Production Example 140 | | Production Example 141 | (CDCl$_3$, δ): 1.43 (3H, t, J = 7.0 Hz), 2.44 (4H, brs), 2.57 (4H, brs), 3.80 (2H, s), 4.24 (1H, s), 4.47(2H, q, J = 7.0 Hz), 6.8-6.9 (2H, m), 7.1-7.3 (6H, m), 7.65 (1H, dd, J = 1.1 Hz, 7.6 Hz), 7.77 (1H, t, J = 7.6 Hz), 7.97(1H, dd, J = 1.4 Hz, 7.6 Hz) | — |

TABLE 36-continued
| Compound (12) | Compound (13) | Ester compound/Caboxylic acid | | |
|---|---|---|---|---|
| | | Chemical formula | ¹H-NMR | MS (m/z) |
| | | Example 107 | (CDCl$_3$, δ): 2.50 (4H, brs), 2.65 (4H, brs), 3.82 (2H, s), 4.27 (1H, s), 6.8-7.0 (2H, m), 7.1-7.3 (6H, m), 7.69 (1H, d, J = 7.8 Hz), 7.89 (1H, t, J = 7.6 Hz), 8.11 (1H, d, J = 7.6 Hz) | 424.1 (M⁺) |

TABLE 37

| Compound (12) | Compound (13) | Ester compound/Caboxylic acid | | |
|---|---|---|---|---|
| | | Chemical formula | ¹H-NMR | MS (m/z) |
| Production Example 140 | Production Example 142 | | (CDCl₃, δ): 1.41 (3H, t, J = 7.3 Hz), 2.45 (4H, brs), 2.56 (4H, brs), 3.74 (2H, s), 4.24 (1H, s), 4.41 (2H, q, J = 7.3 Hz), 6.8-6.9 (2H, m) 7.1-7.3 (6H, m), 7.71 (1H, dd, J = 1.6 Hz, 5.1 Hz), 7.91(1H, s), 8.70 (1H, dd, J = 0.5 Hz, 5.4 Hz) | — |
| | Example 108 | | (d₆-DMSO, δ): 2.50 (4H, brs), 3.34 (4H, brs), 4.5-4.6 (3H, m), 7.0-7.1 (2H, m), 7.3-7.4 (6H, m) 7.86 (2H, d, J = 4.9 Hz), 8.03 (1H, s), 8.83 (1H, d, J = 4.3 Hz) | 424.1 (M⁺) |
| Production Example 143 | Production Example 144 | | (CDCl₃, δ): 1.42 (3H, t, J = 7.0 Hz), 2.4-2.6 (8H, m), 3.80 (2H, s), 4.46 (2H, q, J = 7.0 Hz), 5.09(1H, s), 6.9-7.2 (6H, m), 7.5-7.6 (2H, m), 7.69 (1H, d, J = 7.8 Hz), 7.78 (1H, t, J = 7.6 Hz), 7.97 (1H, d, J = 7.6 Hz) | — |

TABLE 38

| Compound (12) | Compound (13) | Ester compound/Caboxylic acid Chemical formula |
|---|---|---|
| | | Example 109 |
| Production Example 143 | | Production Example 145 |
| Production Example 146 | | Production Example 147 |
| | | Example 110 |

| Ester compound/Carboxylic acid | |
|---|---|
| ¹H-NMR | MS m/z |
| (CDCl₃, δ): 2.52 (8H, brs), 3.86 (2H, brs), 5.08 (1H, s), 6.9-7.2 (7H, m), 7.54 (2H, brs), 7.79 (1H, brs), 8.13 (1H, brs) | 424.1 (M⁺) |

TABLE 38-continued
(CDCl₃, δ):
1.41 (3H, t, J = 7.3Hz),
2.54 (8H, brs), 3.73 (2
H, s), 4.41 (2H, q, J =
7.3Hz), 5.09 (1H, s), 6.9-
7.2 (6H, m), 7.5-7.6 (2H, m),
7.70 (1H, dd, J = 1.4Hz,
4.9Hz), 7.92 (1H, s),
8.69 (1H, d, J = 4.9Hz)
—
(CDCl₃, δ):
2.82 (4H, brs), 3.19 (4H,
brs), 4.11 (2H, s), 5.16
(1H, s), 6.9-7.0 (2H, m),
7.1-7.2 (4H, m), 7.5-
7.6 (2H, m), 7.86 (1H,
dd, J = 1.4Hz, 5.1Hz),
8.19 (1H, s), 8.61 (1H,
d, J = 5.1Hz)
424.1 (M⁺)
(CDCl₃, δ):
1.43 (3H, t, J = 7.3Hz),
2.44 (4H, brs), 2.57 (4
H, brs), 3.80 (2H, s), 4.24
(1H, s), 4.47 (2H, q,
J = 7.3Hz), 6.8-6.9 (1H,
m), 7.2-7.3 (6H, m), 7.38
(2H, d, J = 7.0Hz), 7.66
(1H, d, J = 7.6Hz), 7.77
(1H, t, J = 7.8Hz), 7.97 (1H,
d, J = 7.3Hz)
—
TABLE 39
| Compound (12) | Compound (13) | Ester compound/Carboxylic acid Chemical formula |
|---|---|---|
Example 111
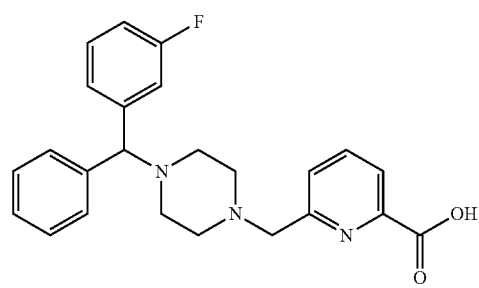 [SMILES: O=C(O)c1cccc(CN2CCN(C(c3ccccc3)c3cccc(Cl)c3)CC2)n1]
Production Example 146
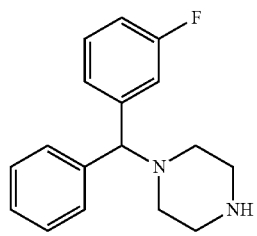 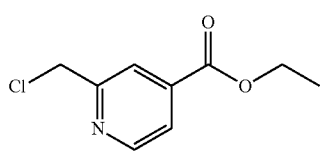
Production Example 148
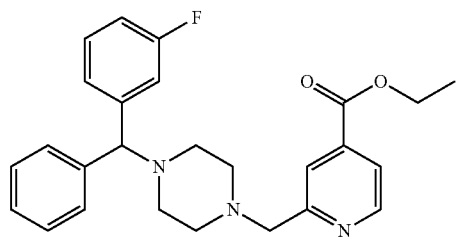 [SMILES: CCOC(=O)c1ccnc(CN2CCN(C(c3ccccc3)c3cccc(Cl)c3)CC2)c1]

TABLE 39-continued
Example 112
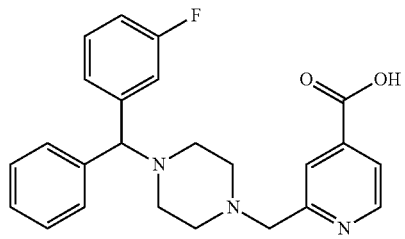 [SMILES: O=C(O)c1ccnc(CN2CCN(C(c3ccccc3)c3cccc(F)c3)CC2)c1]
Production Example 149
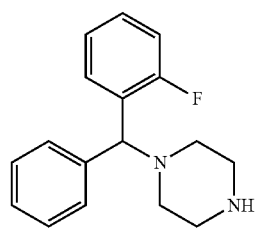 [SMILES: Fc1ccccc1C(c1ccccc1)N1CCNCC1]
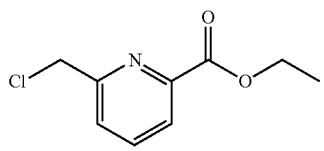
Production Example 150
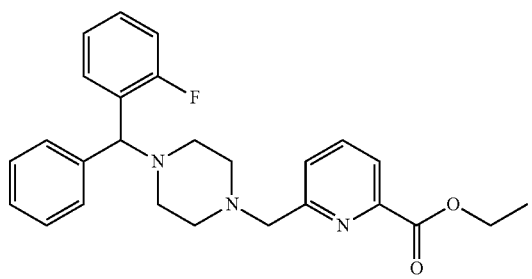 [SMILES: CCOC(=O)c1cccc(CN2CCN(C(c3ccccc3)c3ccccc3F)CC2)n1]
| | Ester compound/Carboxylic acid | |
|---|---|---|
| | $^1$H-NMR | MS m/z |
| | (CDCl$_3$, δ): 2.59 (4H, brs), 2.81 (4H, brs), 3.98 (2H, s), 4.29 (1H, s), 6.8-6.9 (1H, m), 7.1-7.4 (8H, m), 7.64 (1H, dd, J = 1.1Hz, 8.0Hz), 7.89 (1H, t, J = 8.1 Hz), 8.1 (1H, dd, J = 0.5Hz, 7.6Hz) | 406.1 (M$^+$) |
| | (CDCl$_3$, δ): 1.41 (3H, t, J = 7.3Hz), 2.45 (4H, brs), 2.56 (4H, brs), 3.73 (2H, s), 4.23 (1H, s), 4.39 (2H, q, J = 7.0Hz), 6.8-6.9 (1H, m), 7.2-7.4 (8H, m), 7.70 (1H, dd, J = 1.4Hz, 5.1Hz), 7.91 (1H, s), 8.70 1H, d, J = 5.1Hz) | — |
| | (d$_6$-DMSO, δ): 3.36 (8H, brs), 4.53 (3H, brs), 7.0-7.1 (1H, m), 7.2-7.4 (8H, m), 7.87 (1H, d, J = 4.6Hz), 8.1 (1H, s), 8.84 (1H, d, J = 4.6Hz) | 406.1 (M$^+$) |
| | (CDCl$_3$, δ): 1.43 (3H, t, J = 7.0Hz), 2.48 (4H, brs), 2.57 (4H, brs), 3.80 (2H, s), 4.46 (2H, q, J = 7.3Hz), 4.70 (1H, s), 6.9-7.0 (1H, m), 7.1-7.3 (5H, m), 7.43 (2H, d, J = 3.8Hz), 7.6-7.7 (2H, m), 7.77 (1H, t, J = 7.8Hz), 7.97 (1H, d, J = 7.6Hz) | — |

TABLE 40

| Compound (12) | Compound (13) | Ester compound/Carboxylic acid Chemical formula |
|---|---|---|
| Production Example 149 | Production Example 151 | Example 113<br><br>Example 114 |

| | Ester compound/Carboxylic acid | |
|---|---|---|
| | $^1$H-NMR | MS m/z |
| | (CDCl$_3$, δ): 2.5-2.8 (6H, m), 3.30 (2H, brs), 3.90 (2H, s), 4.74 (1H, s), 6.9-7.3 (5H, m), 7.42 (3H, d, J = 7.6Hz), 7.5-7.6 (2H, m), 7.83 (1H, brs), 8.09 (1H, brs) | 406.2 (M$^+$) |
| | (CDCl$_3$, δ): 1.41 (3H, t, J = 7.3Hz), 2.49 (4H, brs), 2.56 (4H, brs), 3.73 (2H, s), 4.46 (2H, q, J = 7.0Hz), 4.71 (1H, s), 6.9-7.0 (1H, m), 7.1-7.3 (5H, m), 7.61 (1H, dt, J = 2.4Hz, 7.0Hz), 7.70 (1H, dd, J = 1.6Hz, 4.9Hz), 7.92 (1H, s), 8.69 (1H, dd, J = 0.8Hz, 5.1Hz) | — |
| | (CDCl$_3$, δ): 2.84 (4H, brs), 3.24 (4H, brs), 4.19 (2H, s), 4.79 (1H, s), 6.9-7.3 (6H, m), 7.41 (2H, d, J = 7.3Hz), 7.63 (1H, brs), 7.87 (1H, dd, J = 1.4Hz, 5.1Hz), 8.24 (1H, s), 8.64 (1H, d, J = 4.9Hz) | 406.1 (M$^+$) |

TABLE 41

| Compound (12) | Compound (13) | Ester compound/Carboxylic acid Chemical formula |
|---|---|---|
| Production Example 152 | | Production Example 153 |

Example 115

| Production Example 154 | | Production Example 155 |

| Ester compound/Carboxylic acid | |
|---|---|
| ¹H-NMR | MS m/z |
| (CDCl₃, δ): 2.43 (4H, brs), 2.57 (4H, brs), 3.80 (2H, s), 4.21 (1H, s), 4.46 (2H, q, J = 7.3Hz), 7.1-7.4 (8H, m), 7.66 (1H, d, J = 7.8Hz), 7.77 (1H, t, J = 7.6Hz), 8.02 (1H, d, J = 7.8Hz) | — |
| (CDCl₃, δ): 2.51 (4H, brs), 2.68 (4H, brs), 3.85 (2H, s), 4.25 (1H, s), 7.0-7.4 (8H, m), 7.68 (1H, d, J = 7.6Hz), 7.90 (1H, t, J = 7.6Hz), 8.11 (1H, d, J = 7.6Hz) | 424.2 (M⁺) |

TABLE 41-continued
(CDCl$_3$, δ):
1.43 (3H, t, J = 7.0Hz),
1.7-1.9 (4H, m), 2.2-2.3
(2H, m), 2.7-2.8 (2H,
m), 3.4-3.5 (1H, m), 3.76
(2H, s), 4.46 (2H, q,
J = 7.0Hz), 5.48 (1H, s),
7.2-7.4 (9H, m), 7.70 (1H,
d, J = 6.8Hz), 7.80 (1
H, t, J = 7.6Hz), 7.98 (1H
d, J = 7.3Hz)
—
TABLE 42
| Compound (12) | Compound (13) | Ester compound/Carboxylic acid Chemical formula |
|---|---|---|
| | | Example 116 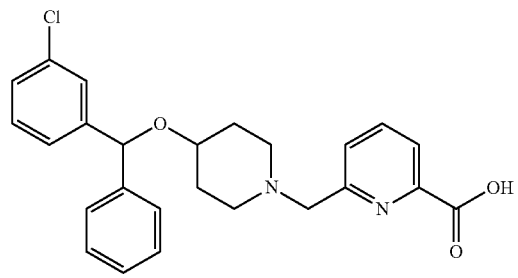 [SMILES: O=C(O)c1cccc(CN2CCC(OC(c3ccccc3)c3cccc(Cl)c3)CC2)n1] |
| Production Example 154 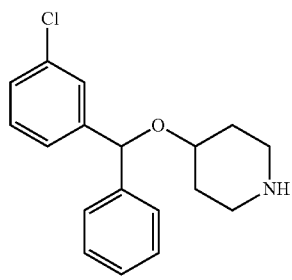 | 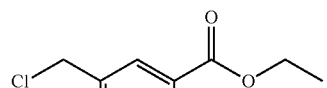 | Production Example 156 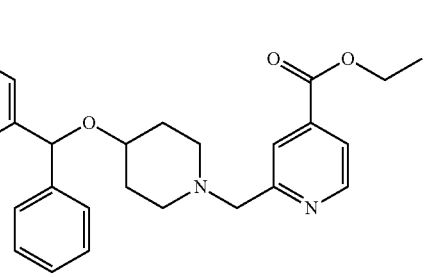 |
| | | Example 117 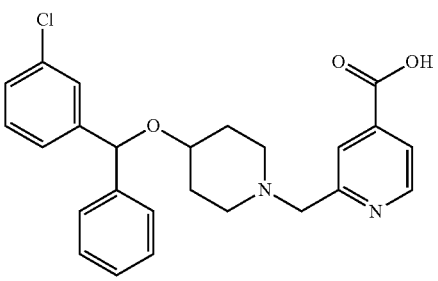 [SMILES: O=C(O)c1ccnc(CN2CCC(OC(c3ccccc3)c3cccc(Cl)c3)CC2)c1] |

TABLE 42-continued
| | Ester compound/Carboxylic acid | |
|---|---|---|
| | ¹H-NMR | MS m/z |
| | (CDCl₃, δ): 1.8-1.9 (2H, m), 2.0-2.2 (2H, m), 2.7-2.8 (2H, m), 2.9-3.0 (2H, m) 3.6-3.7 (1H, m), 4.03 (2H, s), 5.45 (1H, s), 7.2-7.3 (9H, m), 7.69 (1H, d, J = 7.3Hz), 7.87 (1H, t, J = 7.6Hz), 8.10 (1H, d, J = 7.6Hz) | 437.2 (M⁺) |
| | (CDCl₃, δ): 1.42 (3H, t, J = 7.3Hz), 1.7-1.9 (4H, m), 2.2-2.3 (2H, m), 2.7-2.8 (2H, m), 3.4-3.5 (1H, m), 3.70 (2H, s), 4.41 (2H, q, J = 7.3Hz), 5.47 (1H, s), 7.2-7.4 (9H, m), 7.71 (1H, dd, J = 1.9Hz, 5.4Hz), 7.94 (1H, s), 8.70 (1H, d, J = 5.4Hz) | — |
| | (CDCl₃, δ): 1.9-2.1 (2H, m), 2.3-2.4 (2H, m), 3.33 (4H, brs), 3.80 (1H, brs), 4.29 (2H, s), 5.40 (1H, s), 7.1-7.3 (9H, m), 7.88 (1H, dd, J = 1.4Hz, 5.1Hz), 8.40 (1H, s), 8.67 (1H, d, J = 4.9Hz) | 437.2 (M⁺) |
TABLE 43
| Compoun (12) | Compound (13) | Ester compound/Carboxylic acid Chemical formula |
|---|---|---|
| Production Example 157 | | Production Example 158 |
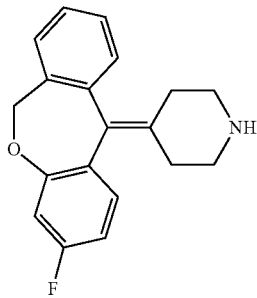 [SMILES: Clc1ccc2c(c1)OCc1ccccc1C2=C1CCNCC1]
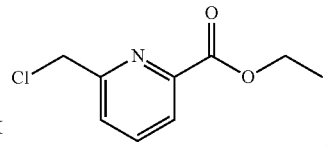
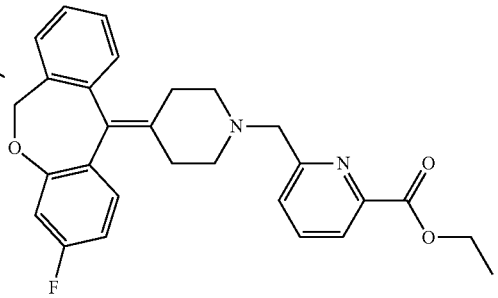
Example 118
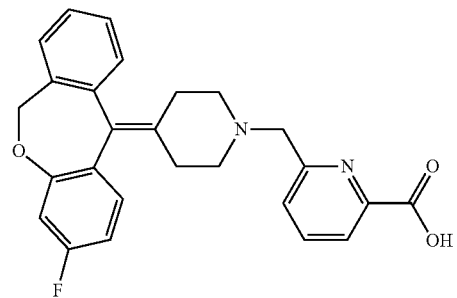 [SMILES: O=C(O)c1cccc(CN2CCC(=C3c4ccccc4COc4cc(Cl)ccc43)CC2)n1]

TABLE 43-continued
Production Example 157
Production Example 159
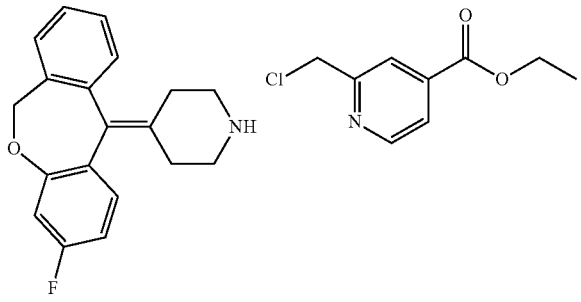
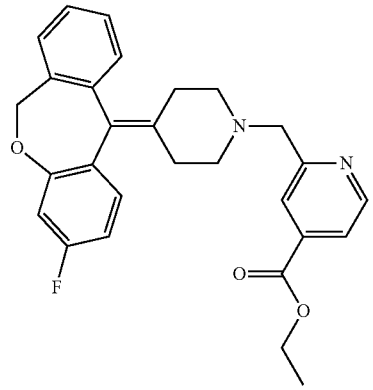
| | Ester compound/Carboxylic acid | |
|---|---|---|
| | ¹H-NMR | MS m/z |
| | (CDCl₃, δ): 1.42 (3H, t, J = 7.3Hz), 2.5-3.5 (10H, m), 4.4-4.5 (2H, m), 4.7-4.8 (1H, m), 5.62 (1H, d, J = 12.7Hz), 6.4-6.5 (2H, m), 6.8-6.9 (1H, m), 7.0-7.1 (1H, m), 7.3-7.4 (4H, m), 7.9-8.1 (2H, m) | — |
| | (CDCl₃, δ): 2.0-2.9 (10H, m), 4.75 (1H, brs), 5.65 (1H, brs), 6.4-6.5 (3H, m), 6.8-7.1 (4H, m), 7.3-7.4 (2H, m), 7.65 (1H, brs) | 431.2 (M⁺) |
| | (CDCl₃, δ): 1.43 (3H, t, J = 7.0Hz), 2.2-3.6 (8H, m), 4.20 (2H, brs), 4.38 (2H, q, J = 7.0Hz), 4.78 (1H, d, J = 1.2, 2Hz), 5.59 (1H, d, J = 12.4Hz), 6.5-6.6 (2H, m), 6.8-6.9 (1H, m), 7.1-7.2 (1H, m), 7.3-7.4 (3H, m), 7.7-7.9 (1H, m), 8.03 (1H, s), 8.7-8.8 (1H, m) | — |
TABLE 44
| Compound (12) | Compound (13) | Ester compound/Carboxylic acid Chemical formula |
|---|---|---|
| | | Example 119 |
| | | 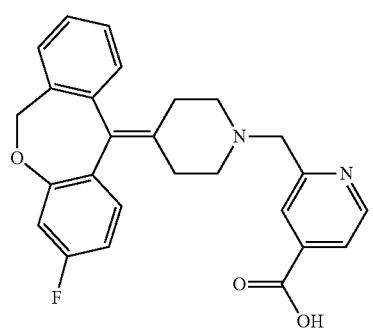 [SMILES: O=C(O)c1ccnc(CN2CCC(=C3c4ccccc4COc4cc(Cl)ccc43)CC2)c1] |

TABLE 44-continued
Production Example 160
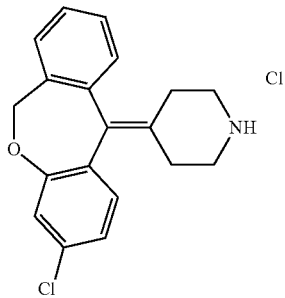
Production Example 161
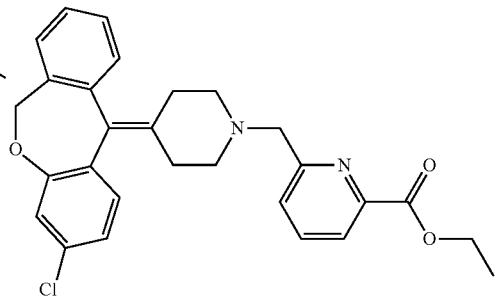
Example 120
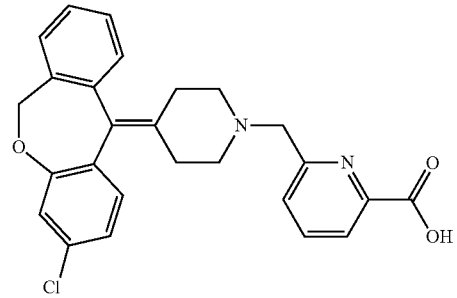
| | Ester compound/Carboxylic acid | |
|---|---|---|
| | ¹H-NMR | MS (m/z) |
| | (d₆-DMSO, δ): 2.3-2.6 (4H, m), 2.8-2.9 (2H, m), 3.2-3.5 (2H, m), 3.84 (2H, s), 4.91 (1H, d, J = 11.9Hz), 5.63 (1H, d, J = 11.9Hz), 6.5-6.7 (2H, m), 7.0-7.1 (1H, m), 7.16 (1H, d, J = 6.8Hz), 7.3-7.4 (2H, m), 7.49 (1H, d, J = 7.0Hz), 7.71 (1H, d, J = 4.6Hz), 7.94 (1H, s), 8.69 (1H, d, J = 4.9Hz) | 431.3 (M⁺) |
| | (CDCl₃, δ): 1.43 (3H, t, J = 7.3Hz), 2.2-2.8 (8H, m), 3.78 (2H, s), 4.46 (2H, q, J = 7.3Hz), 4.78 (1H, d, J = 12.2Hz), 5.70 (1H, d, J = 11.9Hz), 6.7-6.8 (2H, m), 6.92 (1H, d, J = 8.9Hz), 7.1-7.2 (1H, m), 7.2-7.4 (3H, m), 7.73 (1H, dd, J = 1.4Hz, 7.8Hz), 7.81 (1H, t, J = 7.6Hz), 7.99 (1H, dd, J = 0.8Hz, 7.6Hz) | — |
| | (CDCl₃, δ): 2.3-3.0 (8H, m), 3.93 (2H, s), 4.78 (1H, d, J = 11.9Hz), 5.67 (1H, d, J = 12.1 Hz), 6.7-6.8 (2H, m), 6.89 (1H, d, J = 6.9Hz), 7.1-7.2 (1H, m), 7.2-7.4 (3H, m), 7.5-7.6 (1H, m), 7.80 (1H, t, J = 7.6Hz), 8.09 (1H, d, J = 7.6Hz) | 447.3 (M⁺) |

TABLE 45

| Compoun (12) | Compoun (13) | Ester compound/Carboxylic acid Chemical formula |
|---|---|---|
| Production Example 160 | | Production Example 162 |
| Production Example 188 | | Production Example 189 |

| Ester compound/Carboxylic acid | |
|---|---|
| ¹H-NMR | MS m/z |
| (CDCl₃, δ): 1.42 (3H, t, J = 7.3Hz), 2.2-2.8 (8H, m), 3.72 (2 H, s), 4.42 (2H, q, J = 7.3Hz), 4.77 (1H, d, J = 12.2Hz), 5.71 (1H, d, J = 12.2Hz), 6.7-6.8 (2H, m), 6.92 (1H, d, J = 8.6Hz), 7.1-7.2 (1H, m) 7.3-7.4 (4H, m), 7.72 (2H, dd, J = 1.6Hz, 4.9Hz), 7.95 (1 H, s), 8.71 (1H, dd, J = 0.8Hz, 5.1Hz) | — |

TABLE 45-continued
(d₆-DMSO, δ):
2.2-2.8 (8H, m), 3.73 (2H,
s), 4.91 (1H, d, J =
1.9Hz), 5.62 (1H, d, J =
12.2Hz), 6.79 (1H, s),
6.89 (1H, d, J = 8.1Hz),
7.03 (1H, d, J = 8.1Hz),
7.17 (1H, d, J = 6.2Hz),
7.3-7.4 (1H, m), 7.49 (1
H, d, J = 6.2Hz), 7.7-
7.8 (1H, m), 7.92 (1H, s),
8.66 (1H, d, J = 4.1Hz)
447.3 (M⁺)
(CDCl₃, δ):
1.41 (3H, t, J = 7.0Hz),
1.6-1.8 (2H, m), 1.8-2.0
(2H, m), 2.1-2.3 (2H,
m), 2.6-2.9 (2H, m), 3.3-
3.6 (1H, m), 3.75 (1H, s),
4.46 (2H, q, J = 7.0Hz),
5.83 (1H, s), 7.00 (1H,
t, J = 8.0Hz), 7.11 (1
H, t, J = 7.0Hz), 7.2-7.4
(6H, m), 7.4-7.5 (1H,
m), 7.69 (1H, d, J = 8.0Hz),
7.7-7.9 (1H, m), 7.96
(1H, d, J = 8.0Hz)
483 (M⁺)
TABLE 46
| Compound (12) | Compound (13) | Ester compound/Carboxylic acid Chemical formula |
|---|---|---|
Example 140
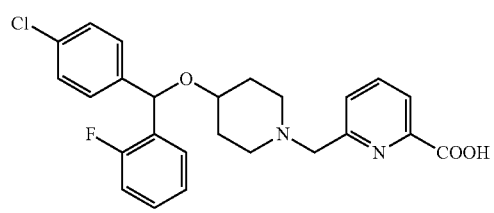 [SMILES: O=C(O)c1cccc(CN2CCC(OC(c3ccc(Cl)cc3)c3ccccc3F)CC2)n1]
Production Example 188
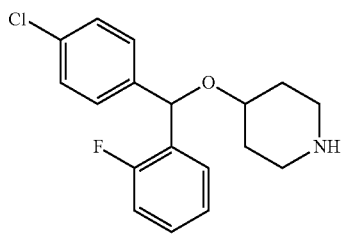 [SMILES: Fc1ccccc1C(OC1CCNCC1)c1ccc(Cl)cc1]
Production Example 190
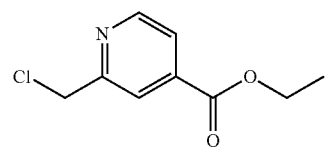
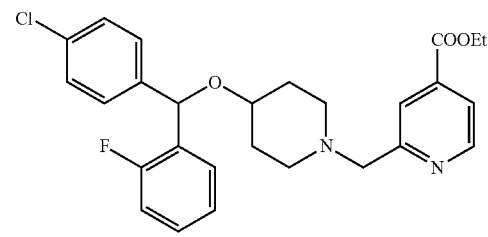 [SMILES: CCOC(=O)c1ccnc(CN2CCC(OC(c3ccc(Cl)cc3)c3ccccc3F)CC2)c1]
Example 141
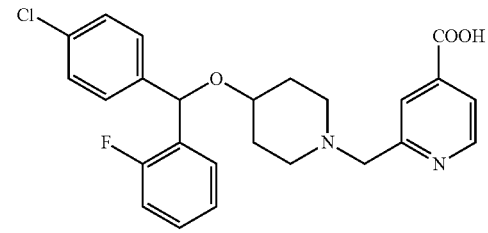 [SMILES: O=C(O)c1ccnc(CN2CCC(OC(c3ccc(Cl)cc3)c3ccccc3F)CC2)c1]

TABLE 46-continued

Production Example 193

Production Example 194

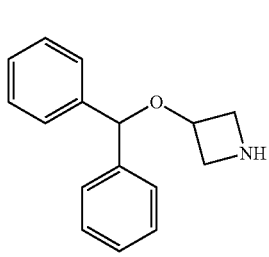 [SMILES: c1ccc(C(OC2CNC2)c2ccccc2)cc1]
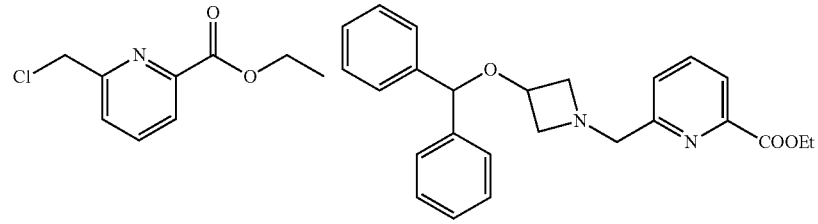

| | Ester compound/Carboxylic acid | |
|---|---|---|
| | $^1$H-NMR | MS m/z |
| | (CDCl$_3$, δ): 1.41 (3H, t, J = 7.0Hz), 1.6-1.8 (2H, m), 1.8-2.0 (2H, m), 2.1-2.3 (2H, m), 2.6-2.9 (2H, m), 3.3-3.6 (1H, m), 3.75 (1H, s), 4.46 (2H, q, J = 7.0Hz), 5.83 (1H, s), 7.00 (1H, t, J = 8.0Hz), 7.11 (1H, t, J = 7.0Hz), 7.2-7.4 (2H, m), 7.4-7.5 (1H, m), 7.69 (1H, d, J = 8.0Hz), 7.7-7.9 (1H, m), 7.96 (1H, d, J = 8.0Hz) | 455 (M$^+$) |
| | (CDCl$_3$, δ): 1.40 (3H, t, J = 7.0Hz), 1.6-2.0 (4H, m), 2.1-2.3 (2H, m), 2.6-2.9 (2H, m), 3.3-3.6 (1H, m), 3.68 (2H, s), 4.41 (2H, q, J = 7.0Hz), 5.83 (1H, s), 6.9-7.2 (2H, m), 7.2-7.4 (5H, m), 7.4-7.6 (1H, m), 7.70 (1H, dd, J = 1.5Hz, 5.0Hz), 7.92 (1H, s), 8.68 (1H, d, J = 5.0Hz) | 483 (M$^+$) |
| | (CDCl$_3$, δ): 1.9-2.2 (2H, m), 2.3-2.6 (2H, m), 3.0-3.4 (4H, m), 2.6-2.9 (2H, m), 3.7-4.0 (1H, m), 4.11 (2H, s), 5.83 (1H, s), 6.9-7.1 (1H, m), 7.1-7.2 (1H, m), 7.2-7.5 (5H, m), 7.88 (1H, dd, J = 1.2Hz, 3.9 Hz), 8.39 (1H, s), 8.60 (1H, d, J = 5.0Hz) | 455 (M$^+$) |
| | (CDCl$_3$, δ): 1.40 (3H, q, J = 2.0Hz), 3.0-3.2 (2H, m), 3.5-3.7 (2H, m), 3.88 (2H, s), 4.1-4.3 (1H, m), 4.45 (2H, q, J = 7.3Hz), 5.32 (1H, s), 7.1-7.4 (10H, m), 7.49 (1H, d, J = 7.3Hz), 7.75 (1H, t, J = 7.7Hz), 7.94 (1H, d, J = 7.7Hz) | 403 (M$^+$) |

TABLE 47

| Compound (12) | Compound (13) | Ester compound/Carboxylic acid Chemical formula |
|---|---|---|
| | | Example 142 |
| Production Example 132 | Production Example 197 | |
| | | Example 143 |
| Production Example 132 | Production Example 198 | |

| Ester compound/Carboxylic acid | |
|---|---|
| ¹H-NMR | MS m/z |
| (CDCl₃, δ): 3.1-3.4 (2H, m), 3.7-3.9 (2H, m), 3.9-4.1 (2H, m), 4.3-4.5 (1H, m), 5.34 (1H, s), 7.1-7.4 (10 H, m), 7.50 (1H, d, J = 7.7Hz), 7.82 (1H, t, J = 7.7 Hz), 8.07 (1H, d, J = 7.7Hz) | 331 (M⁺ − 43) |

TABLE 47-continued

| | |
|---|---|
| (CDCl$_3$, δ): 1.40 (3H, t, J = 7.0Hz), 2.2-2.7 (8H, m), 3.72 (2H, s), 4.23 (1H, s), 4.39 (2H, q, J = 7.0Hz), 6.8-7.0 (2H, m), 7.1-7.5 (7H, m), 7.6-7.7 (1H, m), 7.90 (1H, s), 8.68 (1H, d, J = 5.0Hz) | 433 (M$^+$) |
| (CDCl$_3$, δ): 2.2-2.6 (8H, m), 3.60 (2H, s), 4.21 (1H, s), 6.8-7.0 (2H, m), 7.1-7.5 (7H, m), 7.6-7.8 (1H, m), 7.90 (1H, s), 8.61 (1H, d, J = 5.0Hz) | 405 (M$^+$) |
| (CDCl$_3$, δ): 1.41 (3H, t, J = 7.1Hz), 2.2-2.8 (8H, m), 3.80 (2H, s), 4.21 (1H, s), 4.38 (2H, q, J = 6.9Hz), 6.88 (2H, t, J = 8.6Hz), 7.1-7.5 (4H, m), 7.68 (1H, d, J = 7.7Hz), 7.83 (1H, t, J = 7.7Hz), 8.03 (1H, d, J = 1.3Hz) | 433 (M$^+$) |

TABLE 48

| Compound (12) | Compound (13) | Ester compound/Carboxylic acid Chemical formula |
|---|---|---|
| | | Example 144 |
| Production Example 200 | Production Example 201 | |
| | | Example 145 |

TABLE 48-continued

Production Example 200

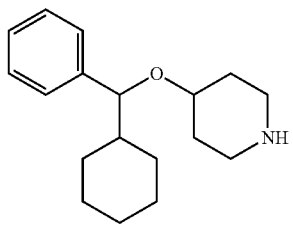 [SMILES: c1ccc(C(OC2CCNCC2)C2CCCCC2)cc1]

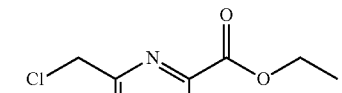

Production Example 202

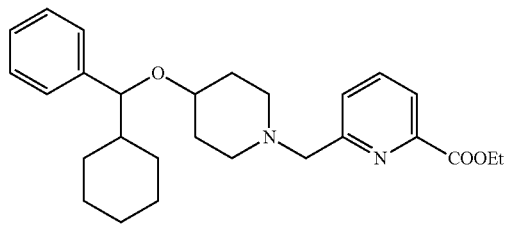 [SMILES: CCOC(=O)c1cccc(CN2CCC(OC(c3ccccc3)C3CCCCC3)CC2)n1]

| | Ester compound/Carboxylic acid | |
|---|---|---|
| | ¹H-NMR | MS m/z |
| | (CDCl₃, δ): 2.2-2.8 (8H, m), 3.7-3.9 (2H, m), 4.21 (2H, s), 6.88 (1H, t, J = 8.5Hz), 7.1-7.5 (7H, m), 7.5-7.7 (1H, m), 7.7-7.9 (1H, m), 8.0-8.2 (1H, m) | 405 (M⁺) |
| | (CDCl₃, δ): 0.8-1.3 (3H, m), 1.40 (3H, t, J = 7.0Hz), 1.5-1.9 (8H, m), 2.0-2.3 (3H, m), 2.6-2.9 (2H, m), 3.1-3.3 (1H, m), 3.66 (2H, s), 3.98 (2H, d, J = 7.0Hz), 7.1-7.4 (5H, m), 7.69 (1H, dd, J = 1.2Hz, 1.5 Hz), 7.92 (1H, s), 8.67 (1H, d, J = 5.0Hz) | 437 (M⁺) |
| | (CDCl₃, δ): 0.7-1.4 (7H, m), 1.4-2.5 (10H, m), 2.9-3.7 (3H, m), 3.93 (2H, d, J = 7.3Hz), 4.0-4.3 (2H, m), 7.1-7.4 (5H, m), 7.7-8.0 (1H, m), 8.3-8.7 (2H, m) | 409 (M⁺) |
| | (CDCl₃, δ): 0.8-1.3 (6H, m), 1.41 (3H, t, J = 7.0Hz), 1.5-1.8 (8H, m), 2.0-2.3 (4H, m), 2.6-2.9 (2H, m), 3.1-3.3 (1H, m), 3.73 (2H, s), 4.4-4.6 (2H, m), 7.1-7.4 (5H, m), 7.68 (1H, d, J = 7.7Hz), 7.8 (1H, t, J = 7.7Hz), 7.95 (1H, d, J = 7.7Hz) | 437 (M⁺) |

TABLE 49

| Compoun (12) | Compound (13) | Ester compound/Carboxylic acid Chemical formula |
|---|---|---|
| | | Example 146 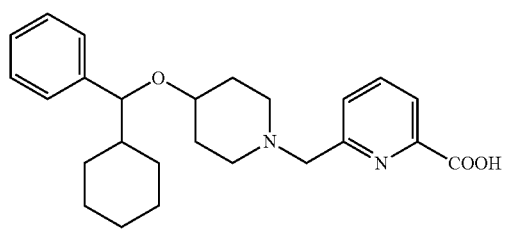 [SMILES: O=C(O)c1cccc(CN2CCC(OC(c3ccccc3)C3CCCCC3)CC2)n1] |

TABLE 49-continued
Production Example 203
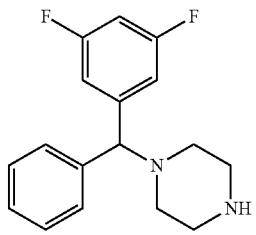 [SMILES: Fc1cc(F)cc(C(c2ccccc2)N2CCNCC2)c1]
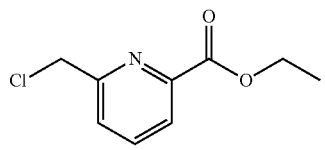
Production Example 204
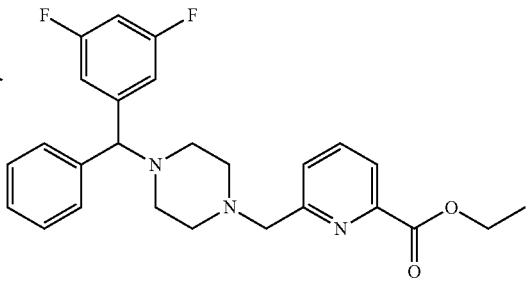
Example 147
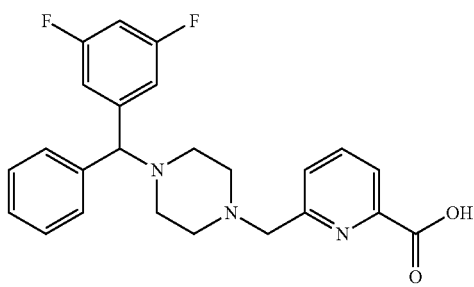 [SMILES: O=C(O)c1cccc(CN2CCN(C(c3ccccc3)c3cc(F)cc(F)c3)CC2)n1]
Production Example 205
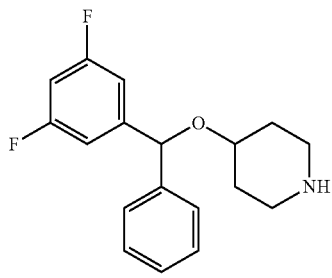
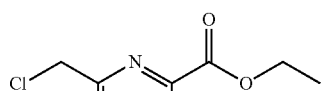
Production Example 206
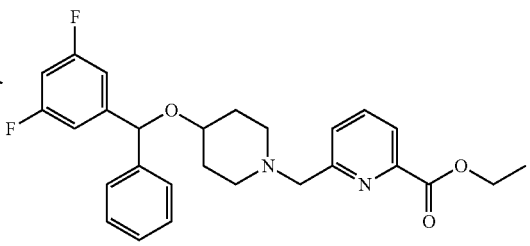
| | Ester compound/Carboxylic acid | |
|---|---|---|
| | $^1$H-NMR | MS m/z |
| | (CDCl$_3$, δ): 0.7-1.4 (7H, m), 1.4-2.2 (10H, m), 2.4-3.1 (3H, m), 3.8-4.2 (3H, m), 5.35 (1H, brs) 7.1-7.4 (5H, m), 7.5-7.8 (2H, m), 7.9-8.2 (1H, m) | 407 (M$^+$ − 1) |
| | (CDCl$_3$, δ): 1.42 (3H, t, J = 7.3Hz), 2.4-2.6 (8H, m), 3.80 (2H, s), 4.21 (1H, s), 4.46 (2H, q, J = 7.0Hz), 6.5-6.7 (1H, m), 6.9-7.0 (2H, m), 7.2-7.4 (5H, m), 7.66 (1H, d, J = 7.6Hz), 7.77 (1H, t, J = 7.6Hz), 7.97 (1H, d, J = 6.8Hz) | — |
| | (d$_6$-DMSO, δ): 2.5-2.8 (4H, m), 3.44 (4H, brs), 4.5-4.6 (3H, m), 7.1-7.5 (8H, m), 7.87 (1H, dd, J = 1.4Hz, 7.0 Hz), 8.1-8.2 (2H, m) | 424.5 (M$^+$) |

TABLE 49-continued
(CDCl₃, δ):
1.43 (3H, t, J = 7.3Hz),
1.7-1.9 (4H, m), 2.2-2.3
(2H, m), 2.8-2.9 (2H, m),
3.4-3.5 (1H, m), 3.76
(2H, s), 4.47 (2H, q, J =
7.3Hz), 5.45 (1H, s),
6.6-6.7 (1H, m), 6.8-6.9
(2H, m), 7.2-7.4 (5H,
m), 7.70 (1H, d, J = 7.0Hz),
7.80 (1H, t, J = 7.6Hz),
7.98 (1H, d, J = 7.6Hz)
TABLE 50
| Compound (12) | Compound (13) | Ester compound/Carboxylic acid Chemical formula |
|---|---|---|
| | | Example 148 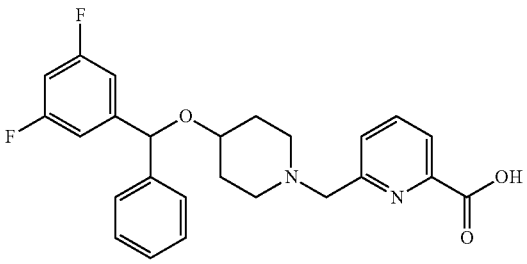 [SMILES: O=C(O)c1cccc(CN2CCC(OC(c3ccccc3)c3cc(F)cc(F)c3)CC2)n1] |
| Production Example 205 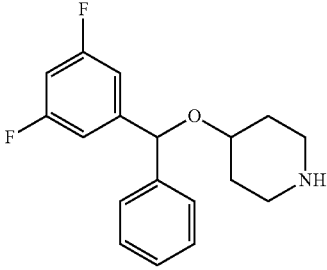 [SMILES: Fc1cc(F)cc(C(OC2CCNCC2)c2ccccc2)c1] | Production Example 207 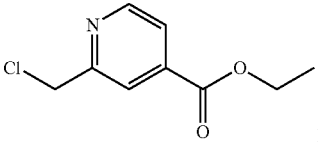 | Example 149 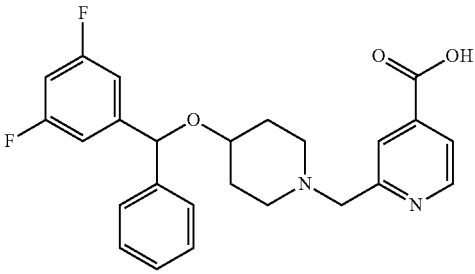 [SMILES: O=C(O)c1ccnc(CN2CCC(OC(c3ccccc3)c3cc(F)cc(F)c3)CC2)c1] |

TABLE 50-continued

| Ester compound/Carboxylic acid | |
|---|---|
| ¹H-NMR | MS m/z |
| (CDCl₃, δ): 1.8-2.2 (4H, m), 2.5-2.7 (2H, m), 2.9-3.0 (2H, m), 3.4-3.6 (1H, m), 3.93 (2H, s), 5.43 (1H, s), 6.6-6.7 (1H, m), 6.8-6.9 (2H, m), 7.3-7.4 (5H, m), 7.68 (1H, d, J = 7.6Hz), 7.87 (1H, t, J = 7.6Hz), 8.10 (1H, d, J = 7.6Hz) | 439.3 (M⁺) |
| (CDCl₃, δ): 1.42 (3H, t, J = 7.3Hz), 1.7-1.9 (4H, m), 2.2-2.3 (2H, m), 2.7-2.8 (2H, m), 3.4-3.5 (1H, m), 3.70 (2H, s), 4.42 (2H, q, J = 7.3Hz), 5.45 (1H, s), 6.6-6.7 (1H, m), 6.8-6.9 (2H, m), 7.3-7.4 (5H, m), 7.71 (1H, dd, J = 1.6Hz, 5.4Hz), 7.94 (1H, s), 8.70 (1H, d, J = 4.9Hz) | — |
| (d₆-DMSO, δ): 1.5-1.7 (2H,m), 1.8-1.9 (2H, m), 2.2-2.3 (2H, m), 2.7-2.8 (2H, m), 3.3-3.4 (1H, m), 3.72 (2H, s), 5.69 (1H, s), 7.0-7.1 (3H, m), 7.3-7.4 (5H, m), 7.67 (1H, d, J = 4.6Hz), 7.87 (1H, s), 8.65 (1 H, d, J = 5.4Hz) | 439.5 (M⁺) |

Production Example 13

Ethyl 2-bromomethylnicotinate

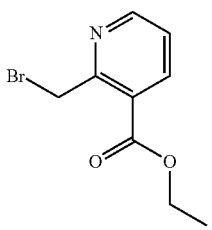

Under a nitrogen atmosphere, ethyl 2-methylnicotinate (1.65 g, 10 mmol) was dissolved in carbon tetrachloride, and N-bromosuccinimide (2.31 g, 13 mmol) and azoisobutyronitrile (164 mg, 1 mmol) were added thereto. The mixture was refluxed for 8 hours. After the completion of the reaction was confirmed by HPLC, the reaction mixture was allowed to cool down to a room temperature. The organic layer was washed with water 3 times and then with a saturated saline solution, and dried over magnesium sulfate. After the solvent was distilled off, the resulting residue was purified by flash column chromatography (Yamazen, Hi-Flash column, silica gel, hexane/ethyl acetate (volume ratio)=10:1) to give the title compound (1.45 g, 59.4%) as an oily substance.

¹¹-NMR (CDCl₃, δ): 1.39 (3H, t, J=7.3 Hz), 4.42 (2H, q, J=7.3 Hz), 5.04 (2H, s), 7.34 (1H, app-dd, J=4.6, 7.8 Hz), 8.29 (1H, dd, J=1.9, 8.1 Hz), 8.71 (1H, dd, J=1.6, 4.6 Hz)

Production Examples 16, 22, 24, 29, 31, 33, 62, 64, 66, 115, 120, 154, 168, 170, 188, 214, 217

Compounds (12) shown in Tables 51 to 53 were obtained according to the same procedure as in Production Example 1 except that another known compound was used instead of benzhydrol as the compound (12a) and/or that another known compound was used instead of 4-hydroxypiperidine as the compound (12b).

TABLE 51

| Compound (12a) | Compound (12b) | Compound (12) Chemical formula | ¹H-NMR (CDCl₃, δ) | MS m/z |
|---|---|---|---|---|
| | | Production Example 16 | 1.3-1.7 (2H, m), 1.8-2.1 (2H, m), 2.4-2.7 (2H, m), 3.0-3.2 (2H, m), 3.4-3.6 (1H, m), 6.20 (1H, s), 6.9-7.6 (8H, m) | 303 (M⁺) |
| | | Production Example 22 | 1.3-1.7 (2H, m), 1.8-2.0 (2H, m), 2.4-2.7 (2H, m), 3.0-3.2 (2H, m), 3.3-3.6 (1H, m), 5.54 (1H, s), 7.0-7.5 (9H, m) | 351 (M⁺) |
| | | Production Example 24 | 1.3-1.7 (2H, m), 1.8-2.1 (2H, m), 2.4-2.7 (2H, m), 3.4-3.6 (1H, m), 5.91 (1H, s), 6.9-7.6 (9H, m) | 286 (M⁺ + 1) |
| | | Production Example 29 | 1.7-2.0 (2H, m), 2.7-2.9 (2H, m), 3.0-3.2 (2H, m), 4.0-4.2 (1H, m), 5.39 (1H, s), 7.1-7.5 (10H, m) | 254 (M⁺ + 1) |
| | | Production Example 31 | 1.4-1.7 (2H, m), 1.8-2.0 (2H, m), 2.4-2.7 (2H, m), 3.0-3.2 (2H, m), 3.4-3.6 (1H, m), 5.52 (1H, s), 6.8-7.4 (9H, m) | 285 (M⁺) |

TABLE 51-continued

| Compound (12a) | Compound (12b) | Compound (12) Chemical formula | $^1$H-NMR (CDCl$_3$, δ) | MS m/z |
|---|---|---|---|---|
| Production Example 33 | | | | |
| 3-(trifluoromethyl)phenyl-phenyl-methanol | 4-hydroxypiperidine | 4-((3-(trifluoromethyl)phenyl)(phenyl)methoxy)piperidine | 1.5-2.1 (4H, m), 2.6-2.8 (2H, m), 3.0-3.2 (2H, m), 3.4-3.6 (1H, m), 5.55 (1H, s), 7.1-7.7 (9H, m) | 334 (M$^+$ − 1) |

TABLE 52

| Compound (12a) | Compound (12b) | Compound (12) Chemical formula | $^1$H-NMR (CDCl$_3$, δ) | MS m/z |
|---|---|---|---|---|
| Production Example 62 | | | | |
| (3,4-difluorophenyl)(phenyl)methanol | 4-hydroxypiperidine | 4-((3,4-difluorophenyl)(phenyl)methoxy)piperidine | 1.7-2.1 (4H, m), 2.2-2.4 (2H, m), 2.7-2.9 (2H, m), 3.4-3.6 (1H, m), 5.41 (1H, s), 6.9-7.6 (8H, m) | — |
| Production Example 64 | | | | |
| (4-fluorophenyl)(3-fluorophenyl)methanol | 4-hydroxypiperidine | 4-((4-fluorophenyl)(3-fluorophenyl)methoxy)piperidine | 1.4-1.6 (2H, m), 1.8-2.0 (2H, m), 2.5-2.6 (2H, m), 3.0-3.2 (2H, m), 3.4-3.5 (1H, m), 5.51 (1H, s), 6.9-7.4 (8H, m) | — |
| Production Example 66 | | | | |
| di(pyridin-2-yl)methanol | 4-hydroxypiperidine | 4-(di(pyridin-2-yl)methoxy)piperidine | 1.7-1.8 (2H, m), 2.2-2.3 (2H, m), 2.6-2.8 (2H, m), 3.2-3.4 (2H, m), 3.6-3.8 (1H, m), 5.50 (1H, s), 7.1-7.2 (2H, m), 7.5-7.7 (4H, m), 8.5-8.6 (2H, m) | 268 (M$^+$ − 1), 108 (base peak) |

TABLE 52-continued

| Compound (12a) | Compound (12b) | Compound (12) Chemical formula | ¹H-NMR (CDCl₃, δ) | MS m/z |
|---|---|---|---|---|
| | | Production Example 115 | 1.5-1.6 (3H, m), 1.9-2.0 (2H, m), 2.5-2.6 (2H, m), 3.0-3.1 (2H, m), 3.4-3.5 (1H, m), 5.89 (1H, s), 7.0-7.5 (8H, m) | — |
| | | Production Example 120 | 1.5-1.6 (3H, m), 1.90 (2H, m), 2.5-2.6 (2H, m), 3.0-3.1 (2H, m), 3.4-3.5 (1H, m), 5.59 (1H, s), 7.2-7.3 (5H, m), 7.48 (2H, d, J = 8.6Hz), 7.57 (2H, d, J = 8.1Hz) | — |
| | | Production Example 154 | 1.5-1.7 (3H, m), 1.9-2.10 (2H, m), 2.5-2.6 (2H, m), 3.1-3.2 (2H, m), 3.4-3.5 (1H, m), 5.51 (1H, s), 7.2-7.4 (9H, m) | — |

TABLE 53

| Compound (12a) | Compound (12b) | Compound (12) Chemical formula | ¹H-NMR (CDCl₃, δ) | MS (m/z) |
|---|---|---|---|---|
| | | Production Example 168 | 1.6-2.0 (2H, m), 2.7-2.9 (2H, m), 3.0-3.2 (2H, m) 4.0-4.2 (1H, m), 5.39 (1H, s), 7.1-7.5 (10H, m) | 252 (M⁺ − 1) |

TABLE 53-continued

| Compound (12a) | Compound (12b) | Compound (12) Chemical formula | ¹H-NMR (CDCl₃, δ) | MS (m/z) |
|---|---|---|---|---|
| (diphenylmethanol) | (3-hydroxypyrrolidine) | Production Example 170 | 1.6-2.0 (2H, m), 2.7-2.9 (2H, m), 3.0-3.2 (2H, m) 4.0-4.2 (1H, m), 5.39 (1H, s), 7.1-7.5 (10H, m) | 252 (M⁺ − 1) |
| (4-chloro-2-fluoro-diphenylmethanol) | (4-hydroxypiperidine) | Production Example 188 | 1.4-1.6 (3H, m), 1.9-2.1 (2H, m), 2.5-2.7 (2H, m), 2.9-3.2 (2H, m), 3.4-3.6 (1H, m), 5.89 (1H, s), 7.0-7.5 (8H, m) | 319 (M⁺) |
| (bis(4-fluorophenyl)methanol) | (3-hydroxypyrrolidine) | Production Example 214 | 1.7-2.0 (2H, m), 2.7-2.9 (2H, m), 3.0-3.2 (2H, m), 3.9-4.1 (1H, m), 5.35 (1H, s), 6.8-7.4 (8H, m) | 290 (M⁺ + 1) |
| (bis(4-fluorophenyl)methanol) | ((R)-3-hydroxypyrrolidine) | Production Example 217 | 1.7-2.0 (2H, m), 2.7-2.9 (2H, m), 3.0-3.2 (2H, m), 3.9-4.1 (1H, m), 5.35 (1H, s), 6.8-7.4 (8H, m) | — |

Production Example 36

5-(4-Benzhydryloxypiperidin-1-ylmethyl)-2-chloro-pyridine

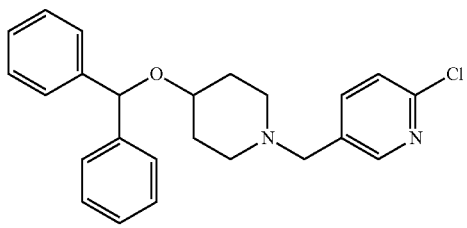 [SMILES: Clc1ccc(CN2CCC(OC(c3ccccc3)c3ccccc3)CC2)cn1]

The title compound was obtained according to the same procedure as in Production Example 2 except that 2-chloro-5-chloromethylpyridine was used instead of methyl 5-chloromethylfuran-2-carboxylate.

¹H-NMR (CDCl₃, δ): 1.6-2.3 (6H, m), 2.6-2.8 (2H, m), 3.4-3.6 (3H, m), 5.50 (1H, s), 7.1-7.4 (11H, m), 7.63 (1H, dd, J=2.3, 8.1 Hz), 8.27 (1H, d, J=2.3 Hz)
MS (m/z): 393 (M⁺+1)

Production Example 37

Propyl 5-(4-benzhydryloxypiperidin-1-ylmethyl)pyridine-2-carboxylate

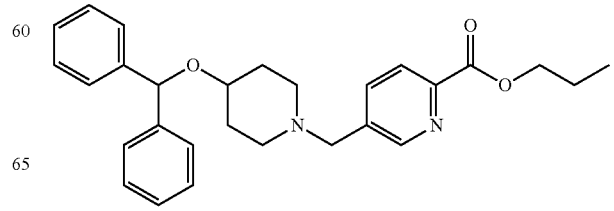

A mixture of 721 mg of 5-(4-benzhydryloxypiperidin-1-ylmethyl)-2-chloropyridine synthesized in Production Example 36, 21 mg of palladium acetate, 41 mg of 1,3-bis(diphenylphosphino)propane, 380 mg of potassium carbonate, 7.0 mL of n-propanol, and 3.5 mL of N,N-dimethylformamide was stirred under a carbon monoxide atmosphere at an external temperature of 90° C. for 7 hours. After the solvent was distilled off, the mixture was diluted with ethyl acetate. The resulting mixture was thrown into water, and the organic layer was collected by separation. The organic layer was washed with a saturated saline solution and then dried over magnesium sulfate. After the solvent was distilled off, the resulting product was subjected to a p-TLC to give the title compound (569 mg).

$^1$H-NMR (CDCl$_3$, δ): 1.02 (3H, t, J=7.7 Hz), 1.6-2.0 (6H, m), 2.0-2.3 (2H, m), 2.6-2.8 (2H, m), 3.3-3.7 (3H, m), 4.36 (2H, t, J=6.9 Hz), 5.50 (1H, s), 7.1-7.4 (10H, m), 7.79 (1H, d, J=7.7 Hz), 8.06 (1H, d, J=7.7 Hz), 8.66 (1H, d, J=1.5 Hz)

MS (m/z): 443 (M$^+$−1), 262 (base peak)

Example 28

5-(4-Benzhydryloxypiperidin-1-ylmethyl)pyridine-2-carboxylic acid

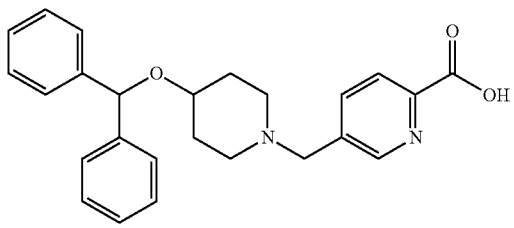 [SMILES: O=C(O)c1ccc(CN2CCC(OC(c3ccccc3)c3ccccc3)CC2)cn1]

The title compound was obtained according to the same procedure as in Example 1 except that propyl 5-(4-benzhydryloxypiperidin-1-ylmethyl)pyridine-2-carboxylate synthesized in Production Example 37 was used instead of the compound synthesized in Production Example 2.

$^1$H-NMR (d$_6$-DMSO, δ): 1.5-1.7 (2H, m), 1.8-1.9 (2H, m), 2.0-2.2 (2H, m), 2.5-2.8 (2H, m), 3.2-3.5 (1H, m), 3.56 (2H, s), 5.62 (2H, s), 7.1-7.5 (10H, m), 7.86 (2H, dd, J=1.9, 8.1 Hz), 7.99 (1H, d, J=7.7 Hz), 8.59 (1H, d, J=7.7 Hz)

MS (m/z): 401 (M$^+$−1), 220 (base peak)

Production Example 38

4-(4-Benzhydryloxypiperidin-1-ylmethyl)-2-bromopyridine

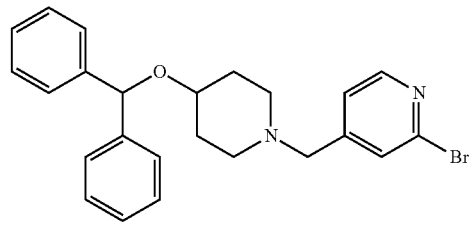 [SMILES: Brc1cc(CN2CCC(OC(c3ccccc3)c3ccccc3)CC2)ccn1]

A mixture of 904 mg of 4-benzhydryloxypiperidine synthesized in Production Example 1, 6.4 mL of dichloromethane, and 629 mg of 2-bromo-4-pyridinecarbaldehyde was stirred for 50 minutes. Sodium triacetoxyborohydride (1.075 g) was added thereto little by little, and the resulting mixture was stirred for 14 hours. The resulting mixture was diluted with ethyl acetate, and the diluted mixture was thrown into sodium bicarbonate water. The organic layer was collected by separation and washed with a saturated saline solution. The washed organic layer was dried over magnesium sulfate, and the solvent was distilled off. The resulting product was subjected to a silica gel column chromatography (hexane/ethyl acetate (volume ratio)=2:1 to 1:1) to give the title compound (1.027 g).

$^1$H-NMR (CDCl$_3$, δ): 1.6-2.3 (6H, m), 2.6-2.8 (2H, m), 3.3-3.6 (3H, m), 5.51 (1H, s), 7.1-7.4 (11H, m), 7.46 (1H, s), 8.27 (1H, d, J=5.0 Hz)

MS (m/z): 437 (M$^+$)

Production Examples 39, 41, 44, 46, 48, and Examples 29 to 30, 32 to 34

Ester compounds (compound (17)) shown in Tables 54 to 56 were obtained in the same manner as in Production Example 37 except that any one of the compounds synthesized in Production Examples 38, 40, 43, 45 and 47 was used instead of the compound synthesized in Production Example 36 as the compound (15). Moreover, carboxylic acids shown in Tables 54 to 56 were obtained in the same manner as in Example 1 except that any one of these ester compounds was used.

TABLE 54

| Ester compound/Caboxylic acid | | | |
|---|---|---|---|
| Compound (15) | Chemical formula | $^1$H-NMR | MS (m/z) |
| Production Example 38 | Production Example 39 | (CDCl$_3$, δ): 1.01 (3H, t, J = 7.7 Hz), 1.6-2.0 (6H, m), 2.1-2.3 (2H, m), 2.6-2.8 (2H, m), 3.4-3.6 (1H, m), 3.53 (2H, s), 4.37 (2H, t, J = 6.9 Hz), 5.50 (1H, s), 7.1-7.4 (10H, m), 7.45 (1H, d, J = 4.2 Hz), 8.05 (1H, s), 8.67 (1H, d, J = 5.0 Hz) | 443 (M$^+$−1), 277 (base peak) |

TABLE 54-continued

Ester compound/Caboxylic acid

| Compound (15) | Chemical formula | ¹H-NMR | MS (m/z) |
|---|---|---|---|
| | Example 29 | (d$_6$-DMSO, δ): 1.5-1.7 (2H, m), 1.7-2.0 (2H, m), 2.0-2.2 (2H, m), 2.5-2.8 (2H, m), 3.2-3.5 (1H, m), 3.56 (2H, s), 5.63 (1H, s), 7.1-7.5 (10H, m), 7.51 (1H, d, J = 5.0 Hz), 7.97 (1H, s), 8.61 (1H, d, J = 4.6 Hz) | 402 (M$^+$), 235 (base peak) |
| Production Example 40 | Production Example 41 | (CDCl$_3$, δ): 1.03 (3H, t, J = 7.3 Hz), 1.6-2.3 (8H, m), 2.6-2.8 (2H, m), 3.3-3.6 (1H, m), 3.53 (2H, s), 4.30 (2H, t, J = 6.6 Hz), 5.50 (1H, s), 7.1-7.4 (10H, m), 8.22 (1H, s), 8.69 (1H, s), 9.10 (1H, s) | 445 (M$^+$ + 1), 262 (base peak) |
| | Example 30 | (d$_6$-DMSO, δ): 1.5-2.3 (6H, m), 2.6-2.8 (2H, m), 3.2-3.5 (1H, m), 3.58 (2H, s,), 5.62 (1H, s), 7.1-7.4 (10H, m), 8.17 (1H, t, J = 1.9 Hz), 8.66 (1H, d, J = 1.9 Hz), 8.95 (1H, d, J = 2.3 Hz) | 385 (M$^+$ − 17), 235 (base peak) |

TABLE 55

Ester compound/Caboxylic acid

| Compound (15) | Chemical formula | ¹H-NMR | MS (m/z) |
|---|---|---|---|
| Production Example 43 | Production Example 44 | (d$_6$-DMSO, δ): 1.00 (3H, t, J = 7.5 Hz), 1.6-1.9 (6H, m), 2.0-2.3 (2H, m), 2.5-2.8 (2H, m), 3.3-3.5 (1H, m), 3.68 (2H, s,), 4.32 (2H, t, J = 6.9 Hz), 5.49 (1H, s), 7.1-7.5 (11H, m), 7.81 (1H, d, J = 7.7 Hz), 8.54 (1H, d, J = 5.0 Hz) | 444 (M$^+$), 167 (base peak) |
| | Example 32 | (d$_6$-DMSO, δ): 1.5-2.2 (4H, m), 5.66 (1H, s), 7.2-7.7 (11H, m), 7.9-8.6 (2H, m) | 402 (M$^+$), 167 (base peak) |

TABLE 55-continued

| Compound (15) | Ester compound/Caboxylic acid | | |
|---|---|---|---|
| | Chemical formula | ¹H-NMR | MS (m/z) |
| Production Example 45 | Production Example 46 | (CDCl₃, δ): 1.02 (3H, t, J = 7.3 Hz), 1.6-2.0 (6H, m), 2.1-2.3 (2H, m), 2.6-2.8 (2H, m), 3.4-3.6 (1H, m), 3.78 (2H, s), 4.26 (2H, t, J = 6.9 Hz), 5.51 (1H, s), 7.1-7.4 (10H, m), 7.54 (1H, d, J = 5.0 Hz), 8.61 (1H, d, J = 5.0 Hz), 8.95 (1H, s) | 444 (M⁺), 167 (base peak) |
| | Example 33 | (d₆-DMSO, δ): 1.6-2.0 (4H, m), 2.6-3.1 (4H, m), 3.5-3.7 (1H, m), 4.08 (1H, s), 5.65 (1H, s), 7.2-7.5 (11H, m), 8.60 (1H, d, J = 5.0 Hz), 8.95 (1H, s) | 402 (M⁺), 235 (base peak) |

TABLE 56

| Compound (15) | Ester compound/Caboxylic acid | | |
|---|---|---|---|
| | Chemical formula | ¹H-NMR | MS (m/z) |
| Production Example 47 | Production Example 48 | (CDCl₃, δ): 1.01 (3H, t, J = 7.3 Hz), 1.5-1.9 (6H, m), 2.0-2.3 (2H, m), 2.5-2.8 (2H, m), 3.3-3.5 (1H, m), 3.68 (1H, s), 4.25 (2H, t, J = 6.9 Hz), 5.49 (1H, s), 7.1-7.4 (10H, m), 7.46 (1H, d, J = 4.6 Hz), 8.59 (1H, d, J = 5.0 Hz), 8.62 (1H, s) | 444 (M⁺), 167 (base peak) |
| | Example 34 | (CDCl₃, δ): 1.6-2.1 (4H, m), 2.7-3.2 (4H, m), 3.5-3.7 (1H, m), 4.19 (2H, s), 5.66 (1H, s), 7.2-7.5 (10H, s), 7.69 (1H, d, J = 5.0 Hz), 8.54 (1H, s), 8.63 (1H, d, J = 5.0 Hz) | 402 (M⁺), 167 (base peak) |

Production Examples 40, 43, 45, 47

Compounds (15) shown in Table 57 were obtained according to the same procedure as in Production Example 38 except that another known compound was used instead of 2-bromo-4-pyridinecarbaldehyde as the carbaldehyde compound.

TABLE 57

| Carbaldehyde compound | Compound (15) | | |
|---|---|---|---|
| | Chemical formula | $^1$H-NMR (CDCl$_3$, δ) | MS (m/z) |
| 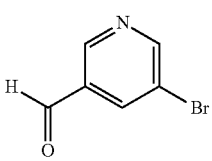 | Production Example 40 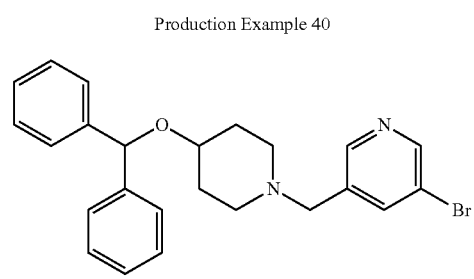 | 1.6-2.3 (6H, m), 2.6-2.8 (2H, m), 3.3-3.5 (3H, m), 5.50 (1H, s), 7.1-7.4 (10H, m), 7.8-7.9 (1H, m), 8.41 (1H, d, J = 1.5 Hz), 8.54 (1H, d, J = 1.9 Hz) | 437 (M$^+$) |
| 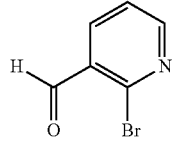 | Production Example 43 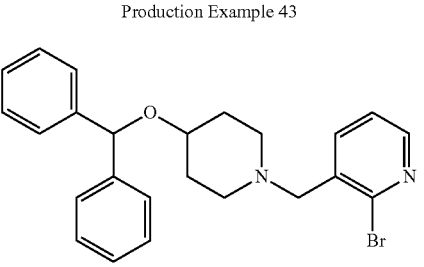 | 1.6-2.0 (4H, m), 2.1-2.4 (2H, m), 2.6-2.9 (2H, m), 3.4-3.6 (3H, m), 5.52 (1H, s), 7.1-7.4 (11H, m), 7.80 (1H, d, J = 6.2 Hz), 8.23 (1H, dd, J = 1.9, 4.6 Hz) | 437 (M$^+$) |
| 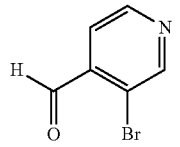 | Production Example 45 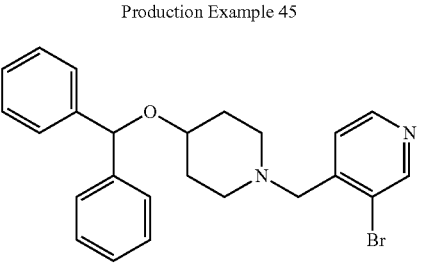 | 1.6-2.0 (4H, m), 2.1-2.4 (2H, m), 2.6-2.9 (2H, m), 3.4-3.6 (3H, m), 5.52 (1H, s), 7.2-7.4 (10H, m), 7.47 (1H, d, J = 4.6 Hz), 8.45 (1H, d, J = 5.0 Hz), 8.63 (1H, s) | 437 (M$^+$) |
| 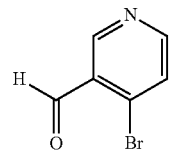 | Production Example 47 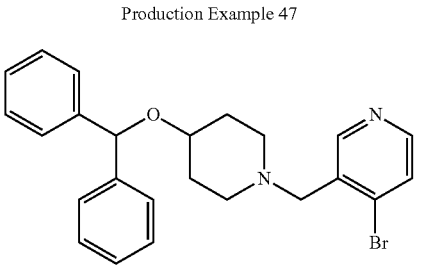 | 1.6-2.0 (4H, m), 2.1-2.4 (2H, m), 2.6-2.9 (2H, m), 3.3-3.6 (1H, m), 3.57 (2H, s), 5.51 (1H, s), 7.1-7.5 (10H, m), 7.46 (1H, d, J = 5.4 Hz), 8.26 (1H, d, J = 5.4 Hz), 8.58 (1H, s) | 437 (M$^+$) |

Production Example 42

Methyl 6-(4-benzhydryloxypiperidine-1-carbonyl)pyridine-2-carboxylate

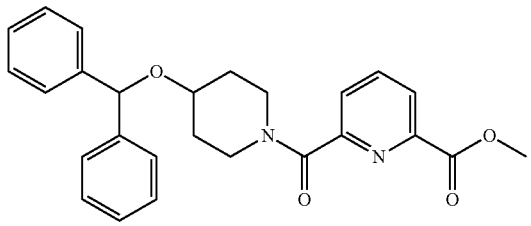 [SMILES: COC(=O)c1cccc(C(=O)N2CCC(OC(c3ccccc3)c3ccccc3)CC2)n1]

Into a 100-mL three-neck flask, 4.0 g (15 mmol) of 4-benzhydryloxypiperidine synthesized in Production Example 1 and 25 mL of tetrahydrofuran were fed, and the internal temperature was cooled to −10° C. Thereinto, 11 mL (17 mmol, 1.1 eq.) of 1.6-M n-butyl lithium (hexane solution) was dropped at an internal temperature of not higher than −5° C., and the mixture was stirred for 30 minutes at the same temperature.

A separately prepared suspension of 2.9 g (15 mmol) of dimethyl 2,6-pyridinecarboxylate in tetrahydrofuran was cooled to −20° C., and the above-mentioned reaction mixture was added dropwise to the suspension at a temperature of not higher than −10° C. After the dropping was completed, the resulting mixture was aged at the same temperature for 5 minutes, then heated gradually to a room temperature and stirred overnight.

After the completion of the reaction was confirmed, the contents were concentrated, and ethyl acetate and water were added to the residue, and the resulting solution was subjected to separatory extraction. The organic layer was washed with water and a saturated saline solution in order and then dried over sodium sulfate, and the solvent was distilled off. The resulting residue was purified by column chromatography (chloroform:ethyl acetate (volume ratio)=10:1) to give the title compound (3.1 g (66%)).

$^1$H-NMR (CDCl$_3$, δ): 1.7-2.0 (4H, m), 3.3-3.5 (1H, m), 3.6-3.9 (4H, m), 3.98 (3H, s) 5.52 (1H, s), 7.2-7.4 (10H, m), 7.83 (1H, dd, J=1.2, 7.3 Hz), 7.9-8.0 (1H, m), 8.1-8.2 (1H, m)

MS (m/z): 430 (M$^+$), 166 (base peak)

Example 31

6-(4-Benzhydryloxypiperidine-1-carbonyl)pyridine-2-carboxylic acid

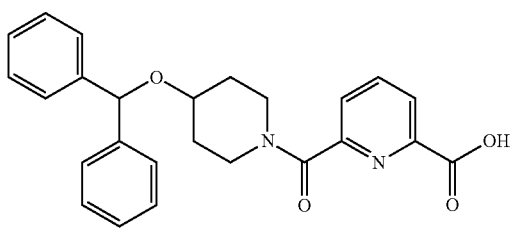 [SMILES: O=C(O)c1cccc(C(=O)N2CCC(OC(c3ccccc3)c3ccccc3)CC2)n1]

Into a 50-mL recovery flask (eggplant flask), 250 mg (0.58 mmol) of methyl 6-(4-benzhydryloxypiperidine-1-carbonyl)pyridine-2-carboxylate synthesized in Production Example 42 was fed, and the compound was dissolved in 10 mL of ethanol. To the flask, 0.9 mL of 1-N sodium hydroxide was added, and the reaction was conducted at a room temperature. After the completion of the reaction was confirmed, the contents in the system were concentrated, and the residue was diluted with water. The diluted residue was neutralized with 1-N hydrochloric acid, and the resulting white crystal was filtered by suction, and the separated product was dried under a reduced pressure to give the title compound (200 mg (83%)).

$^1$H-NMR (d$_6$-DMSO, δ): 1.41 (2H, m), 1.9-2.1 (2H, m), 3.3-3.8 (5H, m), 5.58 (1H, s), 7.2-7.4 (10H, m), 7.9 (1H, d, J=7.1 Hz), 8.0 (1H, d, J=5.0 Hz), 8.12 (1H, d, J=5.0 Hz)

MS (m/z): 416 (M$^+$), 167 (base peak)

Production Example 49

5-(4-Benzhydryloxypiperidin-1-ylmethyl)pyrrole-1,2-dicarboxylic acid 1-tert-butyl ester 2-methyl ester

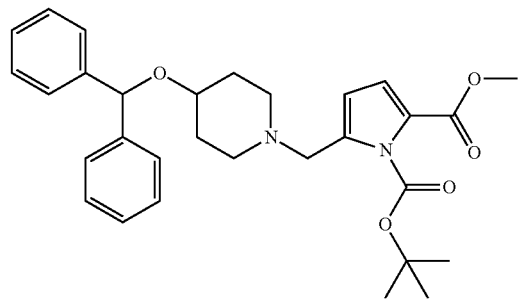 [SMILES: COC(=O)c1ccc(CN2CCC(OC(c3ccccc3)c3ccccc3)CC2)n1C(=O)OC(C)(C)C]

Into a 100-mL three-neck flask, 1.1 g (4.0 mmol) of 4-benzhydryloxypiperidine synthesized in Production Example 1, 1.0 g (4.0 mmol) of methyl N-tert-butoxycarbonyl-5-formylpyrrole-2-carboxylate, and 20 mL of dichloromethane were fed under an argon atmosphere, and the internal temperature was cooled to 0° C. Thereinto, 1.3 g (6.1 mmol, 1.5 eq.) of sodium triacetoxyborohydride was added at an internal temperature of not higher than −5° C., and the mixture was stirred for 5 minutes at the same temperature. Then, the mixture was heated to a room temperature and stirred overnight.

After the completion of the reaction was confirmed, the reaction mixture was quenched with a 5% sodium hydrogen carbonate aqueous solution and washed with water.

The organic layer was washed with water again and then dried over sodium sulfate, and the solvent was concentrated. Thus yellow oil was obtained. The yellow oil was then purified by column chromatography (hexane/ethyl acetate (volume ratio)=10:1) to give the title compound (1.0 g (52%)).

$^1$H-NMR (CDCl$_3$, δ): 1.57 (9H, s), 1.7-1.9 (4H, m), 2.0-2.2 (2H, m), 2.6-2.7 (2H, m), 3.3-3.5 (1H, m), 3.52 (2H, s), 3.80 (3H, s), 5.48 (1H, s), 6.00 (1H, d, J=3.9 Hz), 6.75 (1H, d, J=3.9 Hz), 7.2-7.4 (10H, m)

MS (m/z): 505 (M$^+$+1), 57 (base peak)

Example 35

5-(4-Benzhydryloxypiperidin-1-ylmethyl)-1H-pyrrole-2-carboxylic acid

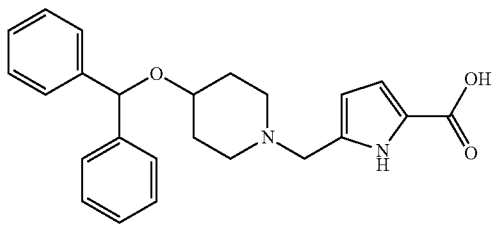 [SMILES: O=C(O)c1ccc(CN2CCC(OC(c3ccccc3)c3ccccc3)CC2)[nH]1]

Into a 50-mL recovery flask (eggplant flask), 790 mg (1.5 mmol) of 5-(4-benzhydryloxypiperidin-1-ylmethyl)pyrrole-1,2-dicarboxylic acid1-tert-butyl ester 2-methyl ester synthesized in Production Example 49 and 20 mL of methanol were fed, and the mixture was stirred under a room temperature. Then, 6.0 mL (6.0 mmol, 4.0 eq.) of a 1-N sodium hydroxide aqueous solution was dropped thereinto, and the mixture was stirred all night at an internal temperature of 60° C.

After the completion of the reaction was confirmed, the solvent was distilled off, and the reaction mixture was diluted with water. The diluted mixture was neutralized with 1-N hydrochloric acid, and the resulting white crystal was separated by suction filtration. The separated product was dried under a reduced pressure to give the title compound (340 mg (83%)).

$^1$H-NMR (CDCl$_3$, δ): 1.8-2.0 (2H, m), 2.3-2.6 (2H, m), 3.0-3.2 (4H, m), 3.7-3.9 (1H, m), 4.02 (2H, s), 5.41 (1H, s), 6.15 (1H, s), 6.70 (1H, s), 7.2-7.4 (10H, m), 11.78 (1H, brs)

MS (m/z): 391 (M$^+$+1), 167 (base peak)

Production Example 51

Methyl 6-[(4-benzhydryloxypiperidin-1-yl)difluoromethyl]pyridine-2-carboxylate

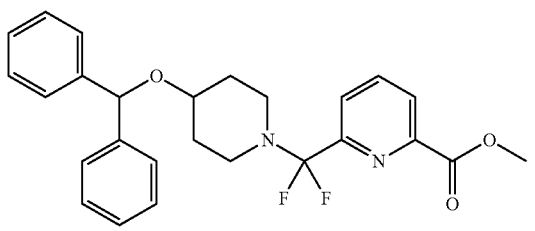 [SMILES: COC(=O)c1cccc(C(F)(F)N2CCC(OC(c3ccccc3)c3ccccc3)CC2)n1]

Into a 100-mL three-neck flask, 640 mg (1.5 mmol) of methyl 6-(4-benzhydryloxypiperidine-1-carbonyl)pyridine-2-carboxylate synthesized in Production Example 42 and 30 mL of cyclopentyl methyl ether were fed, and the atmosphere of the system was replaced with argon gas. Then, 190 mg (1.5 mmol) of oxalyl chloride was dropped thereinto under a room temperature, and the mixture was stirred for one hour. Thereafter, the mixture was stirred under heat reflux all night. After the completion of the reaction was confirmed, the mixture was cooled, and the solvent was distilled off. To the resulting residue were added 20 mL of dimethylimidazolidinone and 250 mg (6.0 mmol) of sodium fluoride successively, and the resulting mixture was stirred under a room temperature all night. After the completion of the reaction was confirmed, the precipitate was removed by filtration, and the filtrate was concentrated and then purified by column chromatography (chloroform/ethyl acetate (volume ratio)=10:1) to give the title compound (380 mg (56%)).

$^1$H-NMR (CDCl$_3$, δ): 1.4-1.8 (4H, m), 3.3-3.9 (5H, m), 3.94 (3H, s), 5.50 (1H, s), 7.2-7.5 (10H, m), 7.73 (1H, d, J=7.7 Hz), 7.80 (1H, t, J=7.7 Hz), 7.96 (1H, d, J=7.7 Hz)

MS (m/z): 453 (M$^+$+1), 167 (base peak)

Example 37

6-[(4-Benzhydryloxypiperidin-1-yl)difluoromethyl]pyridine-2-carboxylic acid

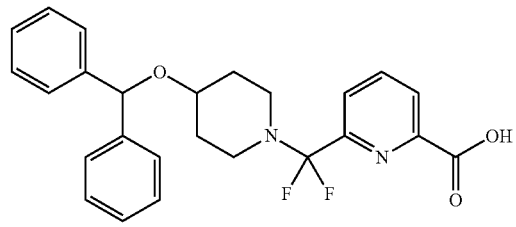 [SMILES: O=C(O)c1cccc(C(F)(F)N2CCC(OC(c3ccccc3)c3ccccc3)CC2)n1]

Into a 50-mL recovery flask (eggplant flask), 380 mg (0.84 mmol) of methyl 6-[(4-benzhydryloxypiperidin-1-yl)difluoromethyl]pyridine-2-carboxylate synthesized in Production Example 51 was fed and dissolved in 10 mL of ethanol. Thereto, 1.7 mL of a 1-N sodium hydroxide aqueous solution was added, and the reaction was conducted at a room temperature. After the completion of the reaction was confirmed, the contents in the system were concentrated, and the residue was diluted with water. The diluted residue was neutralized with 1-N hydrochloric acid and then extracted with chloroform. The organic layer was washed with water and a saturated saline solution in order and then dried over sodium sulfate. After the solvent was concentrated, the resulting brown oily substance was purified by column chromatography (chloroform/methanol (volume ratio)=3:1) to give the title compound (306 mg (83%)).

$^1$H-NMR (d$_6$-DMSO, δ): 1.25 (2H, t, J=7.1 Hz), 1.41 (2H, t, J=7.1 Hz), 3.3-3.8 (5H, m), 5.58 (1H, s), 7.2-7.5 (10H, m), 7.71 (1H, d, J=7.7 Hz), 7.78 (1H, t, J=7.7 Hz), 7.94 (1H, d, J=7.7 Hz)

MS (m/z): 439 (M$^+$+1), 167 (base peak)

Production Example 71

Diethyl 2,5-thiophenedicarboxylate

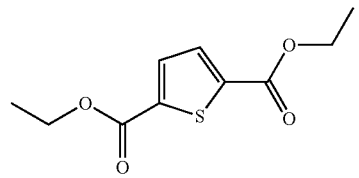

In ethanol (10 mL), 2,5-thiophenedicarboxylic acid (861 mg, 5 mmol) was suspended, and concentrated sulfuric acid (1.6 mL, 30 mmol) was added to the suspension. The mixture was heated under reflux overnight. After the completion of the reaction was confirmed by HPLC, the reaction mixture was allowed to cool down to a room temperature, and ethanol was distilled off under a reduced pressure. Then, water and ethyl acetate were added to the residue, and the extraction with ethyl acetate was performed 3 times. The organic layer was washed with a saturated sodium chloride aqueous solution and then dried over anhydrous magnesium sulfate, and solvent was distilled off. Thus the title compound (1.14 g, 100%) was obtained as a crystal.

$^1$H-NMR (CDCl$_3$, δ): 1.39 (6H, t, J=7.3 Hz), 4.38 (4H, q, J=7.3 Hz), 7.73 (2H, s)

Production Example 72

Ethyl 5-hydroxymethylthiophene-2-carboxylate

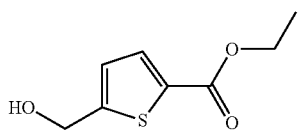

Diethyl 2,5-thiophenedicarboxylate (1.14 g, 5 mmol) synthesized in Production Example 71 was dissolved in ethanol, and sodium tetrahydroborate (113 mg, 3 mmol) was added thereto. The mixture was stirred for 3 days at a room temperature. After the completion of the reaction was confirmed by HPLC, water was added to the mixture, and the resulting mixture was concentrated under a reduced pressure. The residue was dissolved in ethyl acetate, washed with water and a saturated sodium chloride aqueous solution, and then dried over anhydrous magnesium sulfate, and the solvent was distilled off. The resulting residue was purified by flash column chromatography (Yamazen Hi-Flash column, silica gel, hexane/ethyl acetate (volume ratio)=3:2) to give the title compound (491 mg, 52.7%) as an oily substance.

$^1$H-NMR (CDCl$_3$, δ): 1.37 (3H, t, J=7.3 Hz), 4.34 (2H, q, J=7.0 Hz), 4.86 (2H, s), 6.99 (1H, d, J=3.5 Hz), 7.67 (1H, d, J=3.8 Hz)

Production Example 73

Ethyl 5-chloromethylthiophene-2-carboxylate

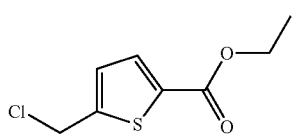

To a suspension of ethyl 5-hydroxymethylthiophene-2-carboxylate synthesized in Production Example 72 in toluene, 212 μL of thionyl chloride was dropwise added, and the mixture was refluxed for 30 minutes. The mixture was allowed to cool down to a room temperature and stirred for one hour. After the completion of the reaction was confirmed by TLC, the solvent was distilled off. The resulting residue was used for the next reaction without purification.

Production Example 75

Ethyl 4-(4-benzhydryloxypiperidin-1-ylmethyl)-1H-pyrazole-3-carboxylate

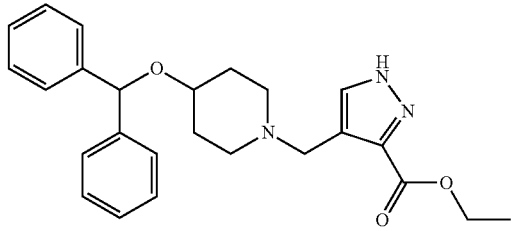 [SMILES: CCOC(=O)c1n[nH]cc1CN1CCC(OC(c2ccccc2)c2ccccc2)CC1]

The title compound was obtained according to the same procedure as in Production Example 49 except that ethyl 4-formyl-1H-pyrazole-carboxylate was used instead of methyl N-tert-butoxycarbonyl-5-formylpyrrole-2-carboxylate.

$^1$H-NMR (CDCl$_3$, δ): 1.38 (3H, t, J=7.1 Hz) 1.6-2.0 (4H, m), 2.1-2.3 (2H, m), 2.7-2.9 (2H, m), 3.3-3.6 (1H, m), 3.73 (2H, s), 4.37 (2H, q, J=7.3 Hz), 5.50 (1H, s), 7.2-7.5 (11H, m), 7.61 (1H, s)

MS (m/z): 419 (M$^+$), 167 (base peak)

Example 55

4-(4-Benzhydryloxypiperidin-1-ylmethyl)-1H-pyrazole-3-carboxylic acid

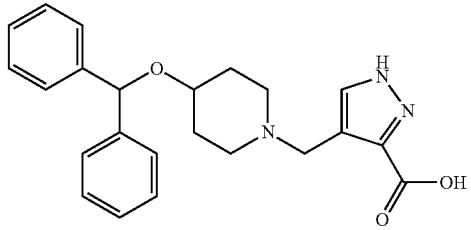 [SMILES: O=C(O)c1n[nH]cc1CN1CCC(OC(c2ccccc2)c2ccccc2)CC1]

The title compound was obtained according to the same procedure as in Example 1 except that ethyl 4-(4-benzhydryloxypiperidin-1-ylmethyl)-1H-pyrazole-3-carboxylate synthesized in Production Example 75 was used instead of the compound synthesized in Production Example 2.

$^1$H-NMR (CDCl$_3$, δ): 1.8-2.2 (4H, m), 2.9-3.3 (4H, m), 3.8-4.0 (3H, m), 5.42 (1H, s), 7.2-7.4 (10H, m), 7.54 (1H, s)

MS (m/z): 390 (M$^+$–1), 167 (base peak)

Production Example 80

(±)-4-[(2,4-Difluorophenyl)phenylmethoxy]piperidine

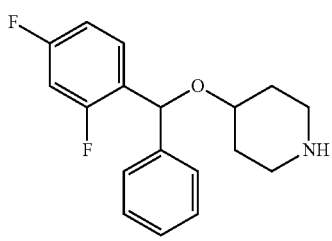 [SMILES: Fc1ccc(C(OC2CCNCC2)c2ccccc2)c(F)c1]

Molecular sieves, (2,4-difluorophenyl)phenylmethanol (3.69 g, 16.8 mmol), and p-toluenesulfonic acid monohydrate (3.84 g, 20.2 mmol) were added to a suspension of 4-hydroxypiperidine (1.7 g, 16.8 mmol) in toluene, and the mixture was refluxed for 3 hours while removing water using a Dean-Stark condenser. After the completion of the reaction was confirmed by HPLC, the reaction mixture was allowed to cool down to a room temperature. From the reaction mixture, the insoluble matter was removed, and then the solvent was distilled off. The resulting residue was dissolved in ethyl acetate and washed with a 2-N sodium hydroxide solution 3 times. The organic layer was dried over magnesium sulfate, and then the solvent was distilled off. Thus the title compound (2.8 g, 54.9%) was obtained as an oily substance.

$^1$H-NMR (CDCl$_3$, δ): 1.4-1.7 (3H, m), 1.9-2.0 (2H, m), 2.5-2.7 (2H, m), 3.0-3.6 (3H, m), 5.86 (1H, s), 6.7-6.9 (2H, m), 7.2-7.5 (6H, m)

Example 63

2-(4-Benzhydryloxypiperidin-1-ylmethyl)-6-methylpyridine

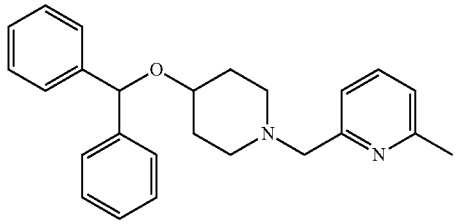 [SMILES: Cc1cccc(CN2CCC(OC(c3ccccc3)c3ccccc3)CC2)n1]

The title compound was obtained according to the same procedure as in Production Example 2 except that 2-bromomethyl-6-methylpyridine was used instead of methyl 5-chloromethylfuran-2-carboxylate.

$^1$H-NMR (CDCl$_3$, δ): 1.6-2.0 (4H, m), 2.1-2.4 (2H, m), 2.52 (3H, s), 2.7-2.9 (2H, m), 3.3-3.5 (1H, m), 3.60 (1H, s), 5.51 (1H, s), 7.00 (1H, d, J=7.7 Hz), 7.1-7.5 (11H, m), 7.52 (1H, t, J=7.7 Hz)

MS (m/z): 373 (M$^+$+1), 107 (base peak)

Example 64

1-[Bis(4-fluorophenyl)methyl]-4-(6-methylpyridin-2-ylmethyl)piperazine

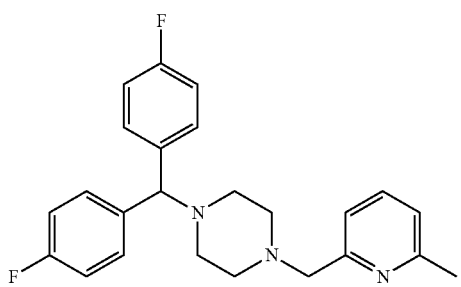 [SMILES: Cc1cccc(CN2CCN(C(c3ccc(F)cc3)c3ccc(F)cc3)CC2)n1]

The title compound was obtained according to the same procedure as in Production Example 2 except that a known compound 1-[bis(4-fluorophenyl)methyl]piperazine and 2-bromomethyl-6-methylpyridine were used instead of 4-benzhydryloxypiperidine and methyl 5-chloromethylfuran-2-carboxylate, respectively.

$^1$H-NMR (CDCl$_3$, δ): 2.2-2.7 (11H, m), 3.63 (2H, s), 4.21 (1H, s), 6.8-7.1 (5H, m), 7.18 (1H, d, J=7.7 Hz), 7.2-7.4 (4H, m), 7.49 (1H, t, J=7.7 Hz)

MS (m/z): 393 (M$^+$), 107 (base peak)

Production Example 84

4-(tert-Butyldimethylsilyloxymethyl)pyridine

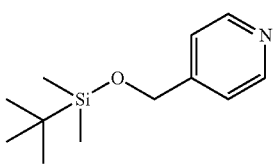

Pyridin-4-ylmethanol (2.2 g, 20 mmol) was dissolved in N,N-dimethylformamide, and tert-butyldimethylsilyl chloride (3.3 g, 22 mmol) and imidazole (2.0 g, 30 mmol were added thereto. The mixture was stirred at a room temperature overnight. After the completion of the reaction was confirmed by HPLC, water was added to the mixture, and the extraction with diethyl ether was performed 3 times. The combined organic layer was washed with a saturated saline solution and dried over magnesium sulfate, and the solvent was distilled off. Thus the title compound (4.5 g, 100%) was obtained as an oily substance.

$^1$H-NMR (CDCl$_3$, δ): 0.12 (6H, s), 0.96 (9H, s), 4.75 (2H, s), 7.2-7.3 (2H, m), 8.55 (2H, dd, J=1.6, 4.6 Hz)

Production Example 85

4-(tert-Butyldimethylsilyloxymethyl)pyridine-1-oxide

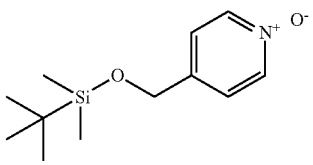

Under a nitrogen atmosphere, 4-(tert-butyldimethylsilyloxymethyl)pyridine (1.1 g, 5 mmol) synthesized in Production Example 84 was dissolved in dichloromethane, and m-chloroperbenzoic acid (1.9 g, 14.5 mmol) was added slowly thereto under an ice cooling. The mixture was heated slowly to a room temperature and then stirred overnight. After the completion of the reaction was confirmed by HPLC, an excess of m-chloroperbenzoic acid was removed by a sodium thiosulfate solution. The remaining mixture was washed with 2-N sodium hydroxide 3 times. The organic layer was dried over magnesium sulfate, and the solvent was distilled off. Thus the title compound (1.2 g, 100%) was obtained as an oily substance.

¹H-NMR (CDCl₃, δ): 0.12 (6H, s), 0.95 (9H, s), 4.70 (2H, s), 7.25 (2H, d, J=7.3 Hz), 8.2 (2H, d, J=7.0 Hz)

Production Example 86

4-(tert-Butyldimethylsilyloxymethyl)pyridine-2-carbonitrile

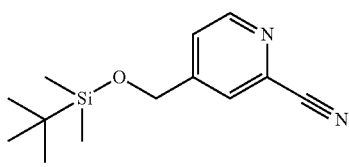 [SMILES: CC(C)(C)[Si](C)(C)OCc1ccnc(C#N)c1]

Under a nitrogen atmosphere, 4-(tert-butyldimethylsilyloxymethyl)pyridine-1-oxide (1.2 g, 5 mmol) synthesized in Production Example 85 was dissolved in triethylamine, and trimethylsilylcyanide (744 μL, 6 mmol) was added thereto. The mixture was stirred at 90° C. for 3 hours. After the completion of the reaction was confirmed by HPLC, the reaction mixture was allowed to cool down to a room temperature. The solvent was distilled off. The resulting residue was dissolved in ethyl acetate and washed with water 3 times and with a saturated saline solution once. Thereafter, the organic layer was dried over magnesium sulfate. The solvent was distilled off, and thus the title compound (260 mg, 20.9%) was obtained as an oily substance.

¹H-NMR (CDCl₃, δ): 0.13 (6H, s), 0.96 (9H, s), 4.78 (2H, s), 7.4-7.5 (1H, m), 7.68 (1H, s), 8.65 (1H, d, J=4.6 Hz)

Production Example 87

4-Hydroxymethylpyridine-2-carbonitrile

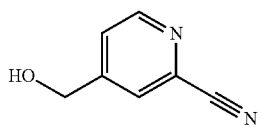

In ethanol, 4-(tert-butyldimethylsilyloxymethyl)pyridine-2-carbonitrile (260 mg, 1.1 mmol) synthesized in Production Example 86 was dissolved, and concentrated sulfuric acid (123 μL, 2.3 mmol) was added thereto. The mixture was refluxed overnight. After the completion of the reaction was confirmed by HPLC, the reaction mixture was allowed to cool down to a room temperature, and the solvent was distilled off. The resulting residue was dissolved in ethyl acetate and washed with water and a saturated saline solution in order. Thereafter, the organic layer was dried over magnesium sulfate, and the solvent was distilled off. Thus the title compound (111 mg, 78.8%) was obtained as a yellowish white solid.

¹H-NMR (CDCl₃, δ): 4.83 (2H, s), 7.5-7.6 (1H, m), 7.74 (1H, s), 8.68 (1H, d, J=5.4 Hz)

Production Example 88

4-Chloromethylpyridine-2-carbonitrile

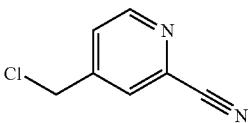

In toluene, 4-hydroxymethylpyridine-2-carbonitrile (111 mg, 0.83 mmol) synthesized in Production Example 87 was dissolved, and thionyl chloride (73 μL) was added thereto. The mixture was refluxed for 30 minutes. Thereafter, the mixture was allowed to cool down to a room temperature and stirred for one hour. After the completion of the reaction was confirmed by HPLC, the solvent was distilled off. The resulting residue was used for the next reaction without purification.

Production Example 89

(±)-4-{4-[(4-Fluorophenyl)phenylmethoxy]piperidino-1-ylmethyl}pyridine-2-carbonitrile

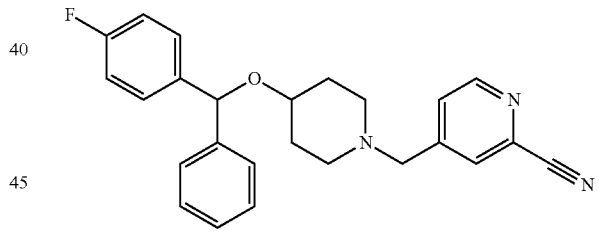

A known compound (±)-4-[(4-fluorophenyl)phenylmethoxy]piperidine (237 mg, 0.83 mmol) was dissolved in N,N-dimethylformamide, and 4-chloromethylpyridine-2-carbonitrile (127 mg, 0.83 mmol) synthesized in Production Example 88 and potassium carbonate (138 mg, 1 mmol) were added thereto. The mixture was stirred at 70° C. overnight. After the completion of the reaction was confirmed by HPLC, the reaction mixture was allowed to cool down to a room temperature, and water and diethyl ether were added thereto. The organic layer was washed with water 3 times and with a saturated saline solution once, and dried over magnesium sulfate. Thereafter, the solvent was distilled off, and the resulting residue was purified by flash column chromatography (Yamazen Hi-Flash column, silica gel, hexane/acetic acid (volume ratio)=2:1) to give the title compound (156 mg, 46.8%) as an oily substance.

$^1$H-NMR (CDCl$_3$, δ): 1.7-1.9 (4H, m), 2.2-2.3 (2H, m), 2.6-2.8 (2H, m), 3.4-3.6 (3H, m), 5.49 (1H, s), 7.00 (2H, t, J=8.6 Hz), 7.2-7.4 (7H, m), 7.48 (1H, d, J=4.9 Hz), 7.72 (1H, s), 8.62 (1H, d, J=4.9 Hz)

Example 65

(±)-4-{4-[(4-Fluorophenyl)phenylmethoxy]piperidin-1-ylmethyl}pyridine-2-carboxylic acid

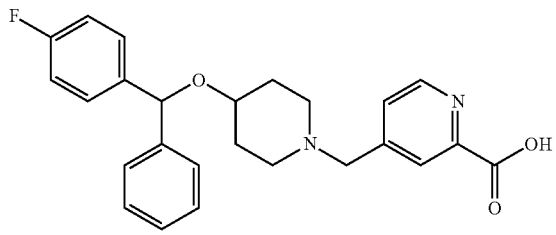 [SMILES: O=C(O)c1cc(CN2CCC(OC(c3ccccc3)c3ccc(F)cc3)CC2)ccn1]

In ethanol, (±)-4-{4-[(4-fluorophenyl)phenylmethoxy]piperidino-1-ylmethyl}pyridine-2-carbonitrile (156 mg, 0.39 mmol) synthesized in Production Example 89 was dissolved, and a 50% sodium hydroxide solution (5 mL) was added thereto. The mixture was refluxed for 8 hours. After the completion of the reaction was confirmed by HPLC, the reaction mixture was allowed to cool down to a room temperature, and the solvent was distilled off. The residue was dissolved in a small quantity of water, and 6-N hydrochloric acid was added thereto for neutralization. Thereafter, the precipitated solid was collected and washed with warm ethanol to give the title compound (90 mg, 54.9%) as a white solid.

$^1$H-NMR (d$_5$-DMSO, δ): 1.8-2.2 (4H, m), 2.9-3.3 (4H, m), 3.67 (1H, br), 4.41 (2H, s), 5.67 (1H, s), 7.1-7.5 (8H, m), 7.9-8.1 (1H, m), 8.2-8.4 (1H, m), 8.77 (1H, d, J=4.3 Hz)

EIMS: m/e 421.3 (M$^+$)

Production Example 90

Methyl 5-bromomethyl-2-methoxybenzoate

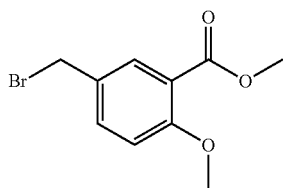

Under a nitrogen atmosphere, methyl 2-methoxy-5-methylbenzoate (901 mg, 5 mmol) was dissolved in acetonitrile, and N-bromosuccinimide (890 mg, 5 mmol) and benzoyl peroxide (24 mg, 0.1 mmol) were added thereto. The mixture was refluxed for one hour. After the completion of the reaction was confirmed by HPLC, the reaction mixture was allowed to cool down to a room temperature, and the solvent was distilled off. Thereafter, the residue was dissolved in ethyl acetate. The organic layer was washed with water 3 times and then with a saturated saline solution, and dried over magnesium sulfate. The solvent was distilled off, and then the resulting residue was purified by flash column chromatography (Yamazen, Hi-Flash column, silica gel, hexane/ethyl acetate (volume ratio)=10:1) to give the title compound (570 mg, 44.0%) as an oily substance.

$^1$H-NMR (CDCl$_3$, δ): 1.56 (3H, s), 3.90 (3H, s), 4.49 (2H, s), 6.96 (1H, d, J=8.6 Hz), 7.51 (1H, dd, J=2.7, 8.6 Hz), 7.84 (1H, d, J=2.7 Hz)

Production Example 92

8-Chloro-11-piperidin-4-ylidene-6,11-dihydro-5H-benzo[5,6]cyclohepta[1,2-b]pyridine

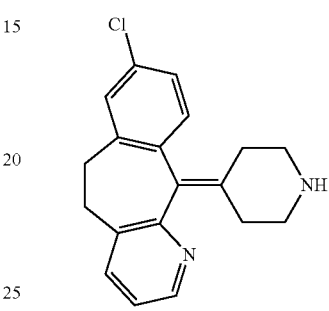

To a solution of ethyl 4-(8-chloro-5,6-dihydro-11H-benzo[5,6]cyclohepta[1,2-b]pyridin-11-ylidene)-1-piperidinecarboxylate (383 mg, 1 mmol) in ethanol, a 30% sodium hydroxide aqueous solution was added. The mixture was refluxed overnight. The solvent was distilled off, and the resulting residue was dissolved in water and neutralized with concentrated hydrochloric acid. The extraction with ethyl acetate was performed 3 times, and the combined organic layer was dried over magnesium sulfate. The solvent was distilled off, and thus the title compound (290 mg, 93.3%) was obtained as a yellowish white solid.

$^1$H-NMR (CDCl$_3$, δ): 2.3-2.4 (4H, m), 2.6-2.9 (4H, m) 3.0-3.1 (2H, m), 3.2-3.5 (2H, m), 7.1-7.2 (4H, m), 7.43 (1H, dd, J=1.4 Hz, 7.6 Hz), 8.40 (1H, dd, J=1.6 Hz, 4.9 Hz)

Production Example 93

Methyl 3-[4-(8-chloro-5,6-dihydrobenzo[5,6]cyclohepta[1,2-b]pyridin-11-ylidene)piperidin-1-ylmethyl]benzoate

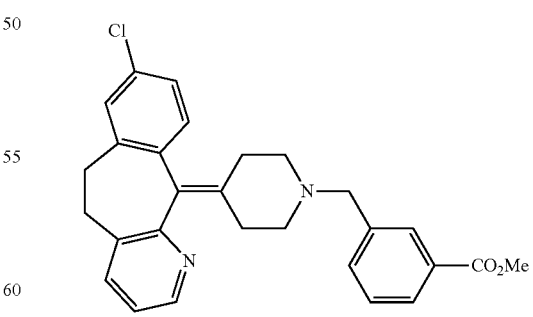

The compound (120 mg, 0.39 mmol) obtained in Production Example 92 was dissolved in N,N-dimethylformamide, and methyl 3-bromomethylbenzoate (99 mg, 0.43 mmol) and potassium carbonate (59 mg, 0.43 mmol) were added thereto. The mixture was stirred at 70° C. overnight. After the solvent was distilled off, ethyl acetate was added to the residue. The organic layer was washed with water 3 times and then with a saturated saline solution, and dried over magnesium sulfate. The solvent was distilled off, and then the resulting residue was purified by flash column chromatography (Yamazen, Hi-Flash column, silica gel, hexane/ethyl acetate 5:1) to give the title compound (170 mg, 95.0%) as an oily substance.

$^1$H-NMR (CDCl$_3$, δ): 2.1-2.5 (6H, m), 2.7-2.9 (4H, m), 3.3-3.5 (2H, m), 3.54 (2H, s), 3.91 (3H, s), 7.1-7.2 (4H, m), 7.3-7.4 (2H, m) 7.5-7.6 (1H, m), 7.9-8.0 (2H, m), 8.39 (1H, dd, J=1.9 Hz, 4.9 Hz)

Example 67

3-[4-(8-Chloro-5,6-dihydrobenzo[5,6]cyclohepta[1,2-b]pyridin-11-ylidene)piperidin-1-ylmethyl]benzoic acid

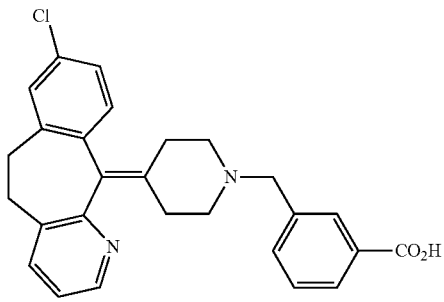 [SMILES: O=C(O)c1cccc(CN2CCC(=C3c4ccc(Cl)cc4CCc4cccnc43)CC2)c1]

The compound (170 mg, 0.37 mmol) obtained in Production Example 93 was dissolved in methanol, and a mixture of the solution and 370 μL of a 2-N sodium hydroxide aqueous solution was heated under reflux for 2 hours. After the mixture was cooled, 3 mL of water and 740 μL of 1-N hydrochloric acid were added thereto, and the resulting mixture was stirred. The precipitated crystal was separated by filtration, washed with water, and dried to give the title compound (104 mg, 63.2%) as a white solid.

$^1$H-NMR (d$_6$-DMSO, δ): 2.7-2.9 (4H, m), 3.3-3.4 (8H, m), 4.36 (2H, s), 7.1-7.4 (4H, m), 7.6-7.7 (1H, m), 7.8-8.2 (4H, m), 8.43 (1H, s), 10.74 (1H, br)

MS (m/z): 445.1 (M$^+$)

Production Examples 94, 95, 97 to 100, 102 to 107, 109 to 111, and Examples 68 to 82

Ester compounds (compound (14)) shown in Table 58 to 65 were obtained in the same manner as in Production Example 93 except that anyone of the compounds synthesized in Production Examples 96, 101 and 108 was used instead of the compound synthesized in Production Example 92 as the compound (12) and/or that another known compound was used instead of methyl 3-bromomethylbenzoate as the compound (13). Moreover, carboxylic acids shown in Tables 58 to 65 were obtained in the same manner as in Example 67 except that any one of these ester compounds was used.

TABLE 58

| | | Ester compound/Caboxylic acid | | |
|---|---|---|---|---|
| Compound (12) | Compound (13) | Chemical formula | $^1$H-NMR | MS (m/z) |
| Production Example 92 | | Production Example 94 | (CDCl$_3$, δ): 2.2-2.6 (6H, m), 2.8-2.9 (4H, m), 3.3-3.4 (2H, m), 3.78 (2H, s), 3.99 (3H, s), 7.1-7.2 (4H, m) 7.4-7.5 (1H, m), 7.8-7.9 (2H, m), 8.00 (1H, dd, J = 1.6 Hz, 7.0 Hz), 8.39 (1H, dd, J = 1.9 Hz, 4.6 Hz) | — |
| | | Example 68 | (d$_6$-DMSO, δ): 2.3-2.4 (4H, m), 2.8-2.9 (2H, m), 3.3-3.4 (2H, m), 4.02 (2H, s), 7.1-7.3 (4H, m), 7.5-7.6 (1H, m), 7.7-7.8 (1H, m), 8.0-8.1 (2H, m), 8.35 (1H, dd, J = 1.4 Hz, 4.6 Hz) | 446.1 (M$^+$) |

TABLE 58-continued

Ester compound/Caboxylic acid

| Compound (12) | Compound (13) | Chemical formula | ¹H-NMR | MS (m/z) |
|---|---|---|---|---|
| Production Example 92 | | Production Example 95 | (CDCl₃, δ): 1.42 (3H, t, J = 6.8 Hz), 2.3-2.6 (6H, m), 2.7-2.8 (4H, m), 3.3-3.4 (2H, m), 3.72 (2H, s), 4.41 (2H, q, J = 7.3 Hz), 7.1-7.2 (4H, m), 7.43 (1H, dd, J = 1.6 Hz, 7.6 Hz), 7.71 (1H, dd, J = 1.6 Hz, 4.9 Hz), 7.95 (1H, s), 8.02 (1H, s), 8.39 (1H, dd, J = 1.6 Hz, 5.1 Hz), 8.69 (1H, d, J = 5.1 Hz) | — |

TABLE 59

Ester compound/Caboxylic acid

| Compound (12) | Compound (13) | Chemical formula | ¹H-NMR | MS (m/z) |
|---|---|---|---|---|
| | | Example 69 | (CDCl₃, δ): 2.7-3.4 (12H, m), 4.16 (2H, s), 7.1-7.2 (4H, m), 7.45 (1H, dd, J = 1.6 Hz, 7.8 Hz), 7.86 (1H, dd, J = 1.4 Hz, 4.9 Hz), 8.0-8.1 (2H, m), 8.3-8.4 (2H, m), 8.62 (1H, d, J = 4.9 Hz) | 446.2 (M⁺) |
| Production Example 96 | | Production Example 97 | (d₆-DMSO, δ): 2.0-2.3 (8H, m), 3.50 (2H, s), 3.84 (3H, s), 6.96 (2H, s), 7.2-7.5 (10H, m), 7.5-7.6 (1H, m), 7.8-7.9 (1H, m) | — |
| | | Example 70 | (d₆-DMSO, δ): 1.9-2.0 (2H, m), 2.2-2.3 (4H, m), 2.4-2.5 (2H, m), 3.53 (2H, s), 6.96 (2H, s), 7.2-7.5 (10H, m), 7.8-7.9 (2H, m) | 408.0 (M⁺) |

TABLE 59-continued

| | | Ester compound/Caboxylic acid | | |
|---|---|---|---|---|
| Compound (12) | Compound (13) | Chemical formula | $^1$H-NMR | MS (m/z) |
| Production Example 96 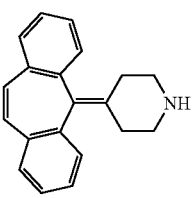 [SMILES: C1=Cc2ccccc2C(=C2CCNCC2)c2ccccc21] | 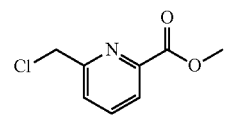 | Production Example 98 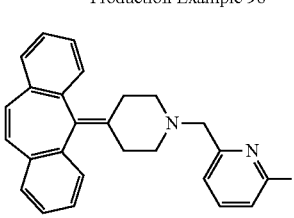 | (d$_6$-DMSO, δ): 1.9-2.0 (2H, m), 2.2-2.3 (4H, m), 2.4-2.5 (2H, m), 3.62 (2H, s), 3.86 (3H, s), 6.97 (2H, s), 7.2-7.4 (8H, m), 7.69 (1H, dd, J = 1.9 Hz, 7.0 Hz), 7.9-8.0 (2H, m) | — |

TABLE 60

| | | Ester compound/Caboxylic acid | | |
|---|---|---|---|---|
| Compound (12) | Compound (13) | Chemical formula | $^1$H-NMR | MS (m/z) |
| | | Example 71 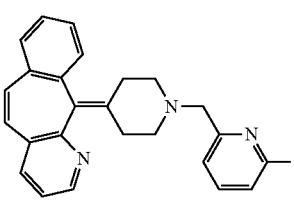 | (d$_6$-DMSO, δ): 2.1-2.2 (2H, m), 2.4-2.5 (2H, m), 2.6-2.8 (2H, m), 3.5-3.6 (2H, m), 4.05 (2H, s), 6.98 (2H, s), 7.2-7.4 (8H, m), 7.7-7.8 (1H, m), 7.9-8.0 (2H, m) | 409.1 (M$^+$) |
| Production Example 96 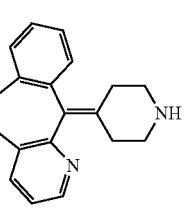 | 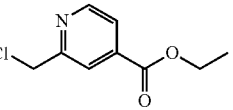 | Production Example 99 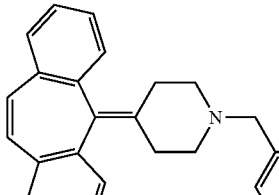 | (d$_6$-DMSO, δ): 1.41 (3H, t, J = 7.3 Hz), 2.1-2.4 (6H, m), 2.5-2.6 (2H, m), 3.68 (2H, s), 4.40 (2H, q, J = 6.8 Hz), 6.91 (2H, s), 6.9-7.4 (8H, m), 7.6-7.7 (1H, m), 7.92 (1H, s), 8.6-8.7 (1H, m) | — |
| | | Example 72 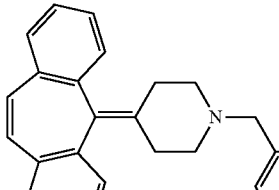 | (d$_6$-DMSO, δ): 2.0-2.1 (2H, m), 2.2-2.4 (4H, m), 2.5-2.6 (2H, m), 3.69 (2H, s), 6.97 (2H, s), 7.2-7.4 (8H, m), 7.67 (1H, dd, J = 1.4 Hz, 5.1 Hz), 7.87 (1H, s), 8.65 (1H, d, J = 4.9 Hz) | 409.2 (M$^+$) |

TABLE 60-continued

| | | Ester compound/Caboxylic acid | | |
|---|---|---|---|---|
| Compound (12) | Compound (13) | Chemical formula | $^1$H-NMR | MS (m/z) |
| Production Example 96 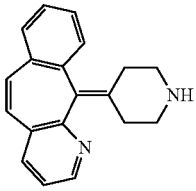 [SMILES: C1=Cc2cccnc2C(=C2CCNCC2)c2ccccc21] | 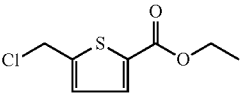 | Production Example 100 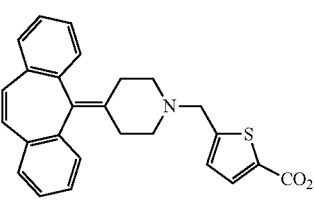 | (CDCl$_3$, δ): 1.36 (3H, t, J = 7.0 Hz), 2.1-2.2 (4H, m), 2.3-2.4 (2H, m), 2.5-2.6 (2H, m), 3.67 (2H, s), 4.32 (2H, q, J = 7.3 Hz), 6.84 (1H, d, J = 3.8 Hz), 6.91 (2H, s), 7.2-7.3 (8H, m) 7.62 (1H, d, J = 3.5 Hz) | — |

TABLE 61

| | | Ester compound/Caboxylic acid | | |
|---|---|---|---|---|
| Compound (12) | Compound (13) | Chemical formula | $^1$H-NMR | MS (m/z) |
| | | Example 73 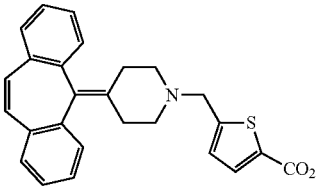 | (d$_6$-DMSO, δ): 1.9-2.0 (2H, m), 2.2-2.3 (2H, m), 2.5-2.8 (4H, m), 3.72 (2H, s), 6.97 (2H, s), 7.0-7.1 (1H, m), 7.2-7.4 (8H, m), 7.57 (1H, d, J = 3.5 Hz) | 414.1 (M$^+$) |
| Production Example 101 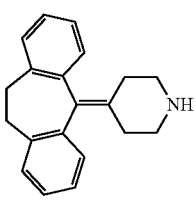 [SMILES: c1ccc2c(c1)CCc1ccccc1C2=C1CCNCC1] | 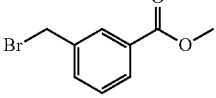 | Production Example 102 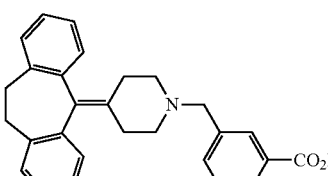 | (CDCl$_3$, δ): 2.2-2.3 (2H, m), 2.3-2.5 (4H, m), 2.6-2.7 (2H, m), 2.7-2.9 (2H, m), 3.3-3.5 (2H, m), 3.54 (2H, s), 3.91 (3H, s), 7.0-7.1 (8H, m), 7.38 (1H, t, J = 7.6 Hz), 7.5-7.6 (1H, m), 7.9-8.0 (2H, m) | — |
| | | Example 74 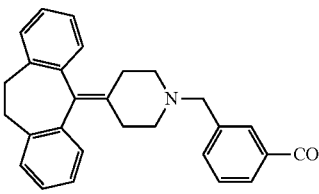 | (d$_6$-DMSO, δ): 2.2-2.4 (4H, m), 2.5-2.6 (2H, m), 2.7-2.8 (2H, m), 3.3-3.4 (4H, m), 3.53 (2H, s), 7.0-7.2 (8H, m), 7.44 (1H, d, J = 7.6 Hz), 7.54 (1H, d, J = 7.6 Hz), 7.82 (1H, d, J = 7.8 Hz), 7.89 (1H, s), 12.95 (1H, br) | 410.2 (M$^+$) |

TABLE 61-continued

| | | Ester compound/Caboxylic acid | | |
|---|---|---|---|---|
| Compound (12) | Compound (13) | Chemical formula | $^1$H-NMR | MS (m/z) |
| Production Example 101 | | Production Example 103 | (CDCl$_3$, δ): 1.42 (3H, t, J = 7.0 Hz), 2.3-2.6 (6H, m), 2.7-2.9 (4H, m), 3.3-3.7 (2H, m), 3.79 (2H, s), 4.46 (2H, q, J = 7.0 Hz), 7.0-7.1 (8H, m), 7.7-7.8 (2H, m), 7.98 (1H, dd, J = 1.6 Hz, 7.3 Hz) | — |

TABLE 62

| | | Ester compound/Caboxylic acid | | |
|---|---|---|---|---|
| Compound (12) | Compound (13) | Chemical formula | $^1$H-NMR | MS (m/z) |
| | | Example 75 | (d$_6$-DMSO, δ): 1.7-2.5 (10H, m), 2.7-2.9 (2H, m), 3.33 (2H, s), 6.9-7.2 (8H, m), 7.59 (1H, d, J = 8.4 Hz), 7.8-8.0 (2H, m) | 411.2 (M$^+$) |
| Production Example 101 | | Production Example 104 | (CDCl$_3$, δ): 1.42 (3H, t, J = 7.0 Hz), 2.2-2.5 (6H, m), 2.6-2.9 (4H, m), 3.3-3.6 (2H, m), 3.71 (2H, s), 4.41 (2H, q, J = 7.3 Hz), 7.0-7.2 (8H, m), 7.71 (1H, dd, J = 1.6 Hz, 5.1 Hz), 7.96 (1H, s), 8.70 (1H, d, J = 5.1 Hz) | — |
| | | Example 76 | (d$_6$-DMSO, δ): 2.2-2.5 (5H, m), 2.7-2.8 (3H, m), 3.2-3.5 (4H, m), 3.73 (2H, s), 7.0-7.2 (8H, m), 7.68 (1H, dd, J = 1.4 Hz, 4.9 Hz), 7.91 (1H, s), 8.66 (1H, d, J = 4.9 Hz) | 411.3 (M$^+$) |

TABLE 62-continued

| | | Ester compound/Caboxylic acid | | |
|---|---|---|---|---|
| Compound (12) | Compound (13) | Chemical formula | $^1$H-NMR | MS (m/z) |
| Production Example 101 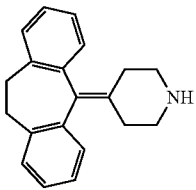 [SMILES: c1ccc2c(c1)CCc1ccccc1C2=C1CCNCC1] | 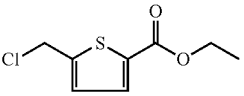 | Production Example 105 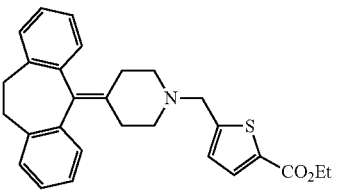 [SMILES: CCOC(=O)c1ccc(CN2CCC(=C3c4ccccc4CCc4ccccc43)CC2)s1] | (CDCl$_3$, δ): 1.36 (3H, t, J = 7.0 Hz), 2.2-2.5 (6H, m), 2.7-2.9 (4H, m), 3.3-3.4 (2H, m), 3.70 (2H, s), 4.33 (2H, q, J = 7.0 Hz), 6.87 (1H, d, J = 3.5 Hz) 7.0-7.1 (8H, m), 7.64 (1H, d, J = 4.0 Hz) | — |

TABLE 63

| | | Ester compound/Caboxylic acid | | |
|---|---|---|---|---|
| Compound (12) | Compound (13) | Chemical formula | $^1$H-NMR | MS (m/z) |
| | | Example 77 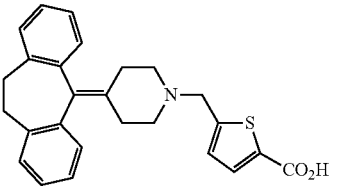 [SMILES: O=C(O)c1ccc(CN2CCC(=C3c4ccccc4CCc4ccccc43)CC2)s1] | (d$_6$-DMSO, δ): 2.2-2.4 (6H, m), 2.6-2.8 (4H, m), 3.2-3.4 (2H, m), 3.71 (2H, s), 6.9-7.1 (9H, m), 7.54 (1H, d, J = 3.8 Hz) | 416.2 (M$^+$) |
| Production Example 101 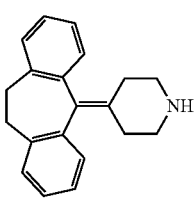 [SMILES: c1ccc2c(c1)CCc1ccccc1C2=C1CCNCC1] | 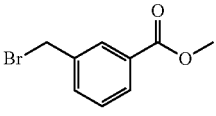 | Production Example 106 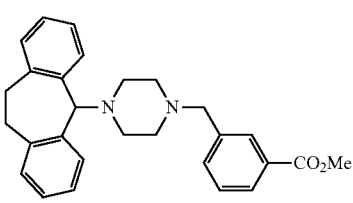 [SMILES: COC(=O)c1cccc(CN2CCN(C3c4ccccc4CCc4ccccc43)CC2)c1] | (CDCl$_3$, δ): 2.2-2.5 (8H, m), 2.7-2.9 (2H, m), 3.50 (2H, s), 3.90 (3H, s), 3.9-4.1 (3H, m), 7.0-7.2 (8H, m), 7.36 (1H, t, J = 7.6 Hz), 7.50 (1H, d, J = 7.6 Hz), 7.8-7.9 (2H, m) | — |
| | | Example 78 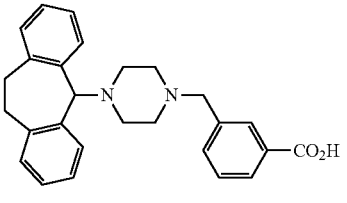 [SMILES: O=C(O)c1cccc(CN2CCN(C3c4ccccc4CCc4ccccc43)CC2)c1] | (d$_6$-DMSO, δ): 2.2-2.4 (6H, m), 2.6-2.8 (2H, m), 3.2-3.4 (2H, m), 3.48 (2H, s), 3.8-4.0 (2H, m), 4.03 (1H, s), 7.0-7.2 (8H, m), 7.3-7.5 (2H, m), 7.80 (1H, d, J = 7.3 Hz), 7.85 (1H, s) | 413.2 (M$^+$) |

TABLE 63-continued

| | | Ester compound/Caboxylic acid | | |
|---|---|---|---|---|
| Compound (12) | Compound (13) | Chemical formula | $^1$H-NMR | MS (m/z) |
| Production Example 101 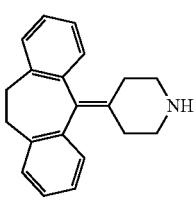 [SMILES: c1ccc2c(c1)CCc1ccccc1C2=C1CCNCC1] | 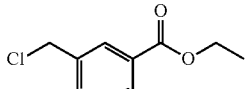 | Production Example 107 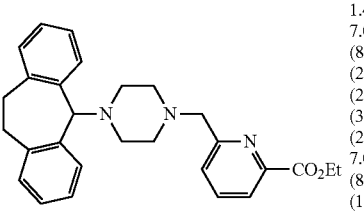 | (CDCl$_3$, δ): 1.42 (3H, t, J = 7.0 Hz), 2.2-2.5 (8H, m), 2.7-2.8 (2H, m), 3.75 (2H, s), 3.9-4.1 (3H, m), 4.45 (2H, q, J = 7.0 Hz), 7.0-7.2 (8H, m), 7.68 (1H, d, J = 8.1 Hz), 7.77 (1H, t, J = 7.6 Hz), 7.96 (1H, d, J = 7.8 Hz) | — |

TABLE 64

| | | Ester compound/Caboxylic acid | | |
|---|---|---|---|---|
| Compound (12) | Compound (13) | Chemical formula | $^1$H-NMR | MS (m/z) |
| | | Example 79 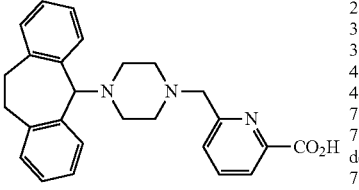 | (d$_6$-DMSO, δ): 2.2-2.4 (6H, m), 2.6-2.8 (2H, m), 3.5-3.7 (2H, m), 3.8-4.0 (4H, m), 4.02 (1H, s), 4.03 (1H, s), 7.0-7.2 (8H, m), 7.44 (1H, app-dd, J = 3.0 Hz), 7.79 (1H, d, J = 3.0 Hz), 7.80 (1H, s) | 414.2 (M$^+$) |
| Production Example 108 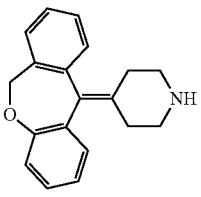 [SMILES: c1ccc2c(c1)COc1ccccc1C2=C1CCNCC1] | 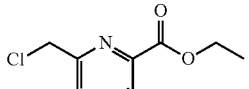 | Production Example 109 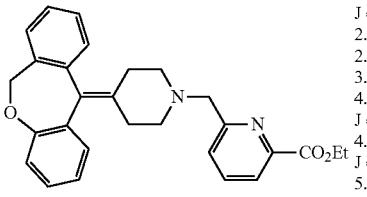 | (CDCl$_3$, δ): 1.43 (3H, t, J = 6.8 Hz), 2.2-2.5 (4H, m), 2.6-2.8 (4H, m), 3.79 (2H, s), 4.46 (2H, q, J = 7.3 Hz), 4.78 (1H, d, J = 12.2 Hz), 5.73 (1H, d, J = 11.9 Hz), 6.7-6.8 (2H, m), 6.9-7.2 (3H, m), 7.2-7.4 (3H, m), 7.7-7.9 (2H, m), 7.98 (1H, d, J = 7.3 Hz) | — |
| | | Example 80 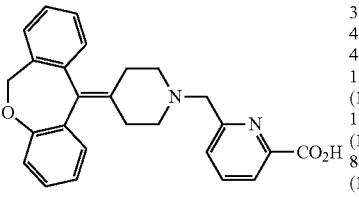 | (d$_6$-DMSO, δ): 2.6-2.9 (4H, m), 3.1-3.5 (4H, m), 4.50 (2H, s), 4.90 (1H, d, J = 12.2 Hz), 5.70 (1H, d, J = 12.2 Hz), 6.75 (1H, d, J = 8.1 Hz), 6.86 (1H, t, J = 7.3 Hz), 7.0-7.5 (6H, m), 7.7-7.8 (1H, m), 8.09 (2H, brs) | 413.2 (M$^+$) |

TABLE 64-continued

| | | Ester compound/Caboxylic acid | | |
|---|---|---|---|---|
| Compound (12) | Compound (13) | Chemical formula | $^1$H-NMR | MS (m/z) |
| Production Example 108 | (2-chloromethyl ethyl isonicotinate structure) | Production Example 110 | (CDCl$_3$, δ): 1.42 (3H, t, J = 7.3 Hz), 2.2-2.5 (4H, m), 2.6-2.8 (4H, m), 3.72 (2H, s), 4.42 (2H, q, J = 7.3 Hz), 4.78 (1H, d, J = 11.9 Hz), 5.73 (1H, d, J = 11.9 Hz), 6.7-6.8 (2H, m), 6.9-7.2 (3H, m), 7.2-7.4 (3H, m), 7.71 (1H, d, J = 5.4 Hz), 7.96 (1H, s), 8.71 (1H, d, J = 5.1 Hz) | — |

TABLE 65

| | | Ester compound/Caboxylic acid | | |
|---|---|---|---|---|
| Compound (12) | Compound (13) | Chemical formula | $^1$H-NMR | MS (m/z) |
| | | Example 81 | (d$_6$-DMSO, δ): 2.2-2.8 (8H, m), 3.74 (2H, s), 4.87 (1H, d, J = 12.4 Hz), 5.60 (1H, d, J = 12.1 Hz), 6.71 (1H, dd, J = 1.4 Hz, 8.4 Hz), 6.82 (1H, dt, J = 1.4 Hz, 7.3 Hz), 6.9-7.2 (3H, m), 7.3-7.4 (2H, m), 7.47 (1H, dd, J = 1.6 Hz, 7.0 Hz), 7.69 (1H, dd, J = 1.6 Hz, 4.9 Hz), 7.92 (1H, s), 8.67 (1H, dd, J = 0.5 Hz, 4.9 Hz) | 413.2 (M$^+$) |
| Production Example 108 | (methyl 3-bromomethylbenzoate structure) | Production Example 111 | (CDCl$_3$, δ): 2.2-2.4 (4H, m), 2.5-2.7 (4H, m), 3.55 (2H, s), 3.91 (3H, s), 4.77 (1H, d, J = 12.4 Hz), 5.72 (1H, d, J = 11.9 Hz), 6.7-6.8 (2H, m), 6.9-7.1 (3H, m), 7.2-7.4 (4H, m), 7.54 (1H, d, J = 7.8 Hz), 7.92 (1H, d, J = 7.8 Hz), 7.98 (1H, s) | — |

TABLE 65-continued

| | | Ester compound/Caboxylic acid | | |
|---|---|---|---|---|
| Compound (12) | Compound (13) | Chemical formula | $^1$H-NMR | MS (m/z) |
| | | Example 82 | ($d_6$-DMSO, δ): 2.0-2.7 (8H, m), 3.55 (2H, s), 4.86 (1H, d, J = 12.2 Hz), 5.59 (1H, d, J = 12.2 Hz), 6.70 (1H, d, J = 8.1 Hz), 6.81 (1H, t, J = 7.6 Hz), 6.9-7.2 (3H, m), 7.2-7.5 (4H, m), 7.55 (1H, d, J = 7.6 Hz), 7.82 (1H, d, J = 7.6 Hz), 7.90 (1H, s) | 412.3 ($M^+$) |

Production Examples 96, 101, 108, 157, 160

Piperidine compounds (compound (12)) shown in Table 66 were obtained according to the same procedure as in Production Example 92 except that another known compound was used instead of ethyl 4-(8-chloro-5,6-dihydro-11H-benzo[5,6]cyclohepta[1,2-b]pyridin-11-ylidene)-1-piperidinecarboxylate as the piperidinyl ester compound.

TABLE 66

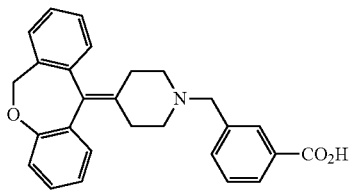 [SMILES: O=C(O)c1cccc(CN2CCC(=C3c4ccccc4COc4ccccc43)CC2)c1]

| | Compound (12) | |
|---|---|---|
| Piperidinyl ester compound | Chemical formula | $^1$H-NMR (CDCl$_3$, δ) |
| | Production Example 96 | 2.1-2.2 (2H, m), 2.4-2.5 (2H, m), 2.8-2.9 (2H, m), 3.1-3.2 (2H, m), 7.00 (2H, s), 7.3-7.4 (8H, m) |
| | Production Example 101 | 2.3-2.4 (4H, m), 2.7-3.1 (6H, m), 3.4-3.5 (2H, m), 7.1-7.2 (8H, m) |

TABLE 66-continued

| | Compound (12) | |
|---|---|---|
| Piperidinyl ester compound | Chemical formula | $^1$H-NMR (CDCl$_3$, δ) |

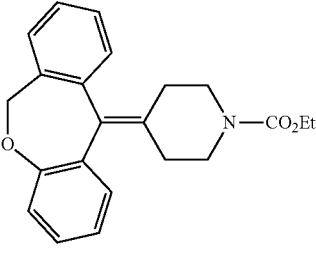 [SMILES: CCOC(=O)N1CCC(=C2c3ccccc3COc3ccccc32)CC1]

Production Example 108

2.6-3.1 (6H, m), 3.3-3.5 (2H, m), 4.82 (1H, d, J = 12.2 Hz), 5.61 (1H, d, J = 12.2 Hz), 6.7-7.0 (2H, m), 6.94 (1H, dd, J = 1.6 Hz, 7.6 Hz), 7.0-7.2 (2H, m), 7.2-7.4 (3H, m), 9.84 (1H, br)

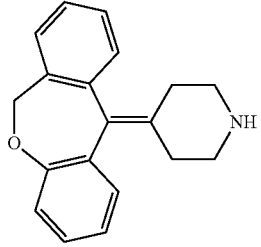 [SMILES: c1ccc2c(c1)COc1ccccc1C2=C1CCNCC1]

Production Example 157

2.2-2.3 (2H, m), 2.4-3.1 (6H, m), 4.78 (1H, d, J = 11.9 Hz), 5.73 (1H, d, J = 12.2 Hz), 6.5-6.6 (2H, m), 6.95 (1H, app-dd, J = 1.6 Hz, 8.6 Hz), 7.14 (1H, dd, J = 1.6 Hz, 7.6 Hz), 7.2-7.4 (3H, m)

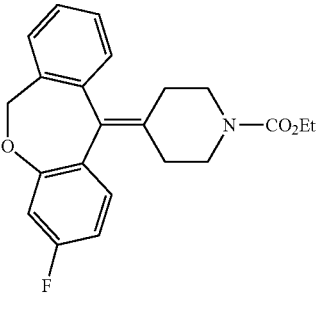 [SMILES: CCOC(=O)N1CCC(=C2c3ccccc3COc3cc(F)ccc32)CC1]

Production Example 160

2.2-2.4 (2H, m), 2.4-3.1 (6H, m), 4.78 (1H, d, J = 11.9 Hz), 5.71 (1H, d, J = 11.9 Hz), 6.7-6.8 (2H, m), 6.9-7.0 (1H, m), 7.13 (1H, dd, J = 1.6 Hz, 7.0 Hz), 7.2-7.4 (3H, m)

Production Examples 114, 125, 126, 129, 130, 136, and Examples 85, 94, 95, 98, 99, 104

Cyano compounds shown in Tables 67 to 70 were obtained in the same manner as in Production Example 89 except that the compound synthesized in Production Example 132 or a known compound was used instead of (±)-4-[(4-fluorophenyl)phenylmethoxy]piperidine as the compound (12) and/or that the compound synthesized in Production Example 88 or a known compound was used instead of 4-chloromethylpyridine-2-carbonitrile as the carbonitrile compound. Moreover, carboxylic acids shown in Tables 67 to 70 were obtained in the same manner as in Example 65 except that any one of these cyano compounds was used.

TABLE 67

| Compound (12) | Carbonitrile compound | Cyano compound/Caboxylic acid | | |
|---|---|---|---|---|
| | | Chemical formula | ¹H-NMR | MS (m/z) |
| (4-fluorophenyl)(phenyl)methoxy piperidine | 5-(bromomethyl)-2-cyanopyridine | Production Example 144 | (CDCl$_3$, δ): 1.7-1.9 (4H, m), 2.1-2.2 (2H, m), 2.6-2.7 (2H, m), 3.4-3.5 (1H, m), 3.54 (2H, s), 5.48 (1H, s), 6.9-7.0 (2H, m), 7.2-7.3 (7H, m), 7.81 (1H, dd, J = 1.9 Hz, 7.8 Hz), 8.64 (1H, d, J = 1.6 Hz) | — |
| | | Example 85 | (d$_6$-DMSO, δ): 1.4-2.2 (4H, m), 2.6-3.6 (7H, m), 5.63 (1H, s), 7.1-7.4 (11H, m), 7.7-8.0 (1H, m) | 421.3 (M⁺) |
| bis(4-fluorophenyl)methyl piperazine | 5-(bromomethyl)-2-cyanopyridine | Production Example 125 | (CDCl$_3$, δ): 2.3-2.5 (8H, m), 3.58 (2H, s), 4.22 (1H, s), 6.9-7.0 (4H, m), 7.3-7.4 (4H, m), 7.63 (1H, d, J = 7.8 Hz), 7.80 (1H, dd, J = 1.6 Hz, 7.8 Hz), 8.64 (1H, d, J = 1.9 Hz) | — |
| | | Example 94 | (d$_6$-DMSO, δ): 2.2-2.4 (8H, m), 3.48 (2H, s), 4.35 (1H, s), 7.11 (4H, t, J = 8.9 Hz), 7.3-7.4 (4H, m), 7.62 (1H, d, J = 8.1 Hz), 7.88 (1H, d, J = 7.9 Hz), 8.3-8.4 (1H, m) | 424.3 (M⁺) |

TABLE 68

| Compound (12) | Carbonitrile compound | Cyano compound/Caboxylic acid | | |
|---|---|---|---|---|
| | | Chemical formula | ¹H-NMR | MS (m/z) |
| (structure: bis(4-fluorophenyl)methyl-piperazine NH) | Production Example 88 | Production Example 126 (structure with 2-cyanopyridin-4-ylmethyl) | (CDCl₃, δ): 2.4-2.5 (8H, m), 3.55 (2H, s), 4.24 (1H, s), 6.9-7.0 (4H, m), 7.3-7.4 (4H, m), 7.46 (1H, d, J = 4.9 Hz), 7.72 (1H, s), 8.61 (1H, d, J = 4.9 Hz) | — |
| | | Example 95 (structure with 2-carboxypyridin-4-ylmethyl) | (d₆-DMSO, δ): 2.2-2.4 (6H, m), 3.3-3.6 (4H, m), 4.36 (1H, s), 7.11 (4H, t, J = 8.6 Hz), 7.4-7.5 (4H, m), 7.8-8.0 (2H, m), 8.3-8.4 (1H, m) | 424.2 (M⁺) |
| (structure: bis(4-fluorophenyl)methyl-piperazine NH) | (4-bromomethyl-3-cyanopyridine) | Production Example 129 (structure with 3-cyanopyridin-4-ylmethyl) | (CDCl₃, δ): 2.4-2.6 (8H, m), 3.71 (2H, s), 4.23 (1H, s), 6.9-7.0 (4H, m), 7.3-7.4 (4H, m), 7.52 (1H, d, J = 5.1 Hz), 8.70 (1H, t, J = 5.4 Hz), 8.82 (1H, s) | — |

TABLE 69

| Compound (12) | Carbonitrile compound | Cyano compound/Caboxylic acid | | |
|---|---|---|---|---|
| | | Chemical formula | ¹H-NMR | MS (m/z) |
| | | Example 98 (structure with 3-carboxypyridin-4-ylmethyl) | (CDCl₃, δ): 1.9-2.1 (6H, m), 3.1-3.2 (2H, m), 4.10 (2H, s), 4.60 (1H, s), 7.05 (4H, t, J = 8.9 Hz), 7.34 (1H, d, J = 5.4 Hz), 7.5-7.6 (4H, m), 8.73 (1H, d, J = 4.9 Hz), 9.29 (1H, s) | 424.1 (M⁺) |

TABLE 69-continued

| | | Cyano compound/Caboxylic acid | | |
|---|---|---|---|---|
| Compound (12) | Carbonitrile compound | Chemical formula | ¹H-NMR | MS (m/z) |
| 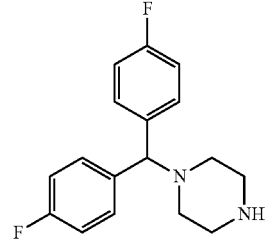 [SMILES: Fc1ccc(C(c2ccc(F)cc2)N2CCNCC2)cc1] | 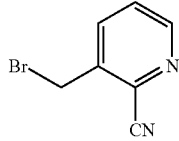 | Production Example 130<br>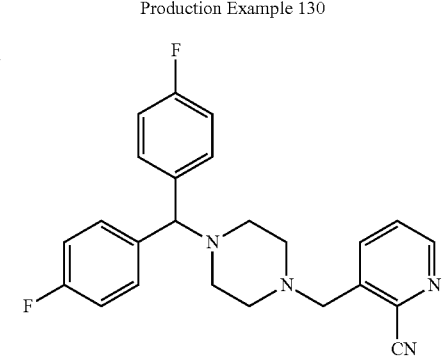 | (CDCl₃, δ): 2.3-2.5 (8H, m), 3.73 (2H, s), 4.22 (1H, s), 6.97 (4H, t, J = 8.4 Hz), 7.3-7.4 (4H, m), 7.47 (1H, dd, J = 4.6 Hz, 7.8 Hz), 7.90 (1H, d, J = 7.6 Hz), 8.59 (1H, d, J = 4.6 Hz) | — |
| | | Example 99<br>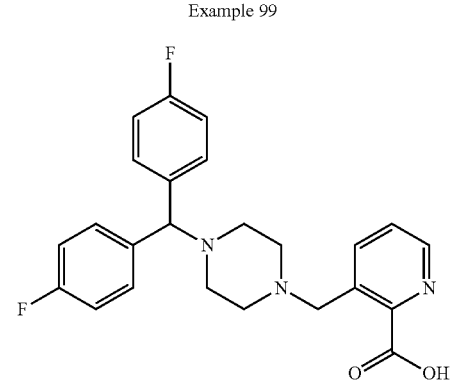 | (CDCl₃, δ): 2.50 (4H, brs), 2.75 (4H, brs), 3.88 (2H, s), 4.25 (1H, s), 6.9-7.0 (4H, m), 7.3-7.4 (5H, m), 7.66 (1H, dd, J = 1.4 Hz, 7.6 Hz), 8.74 (1H, dd, J = 1.6 Hz, 4.6 Hz) | 424.1 (M⁺) |

TABLE 70

| | | Cyano compound/Caboxylic acid | | |
|---|---|---|---|---|
| Compound (12) | Carbonitrile compound | Chemical formula | ¹H-NMR | MS (m/z) |
| Production Example 132<br>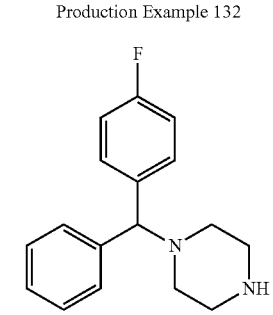 | 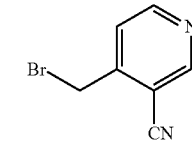 | Production Example 136<br>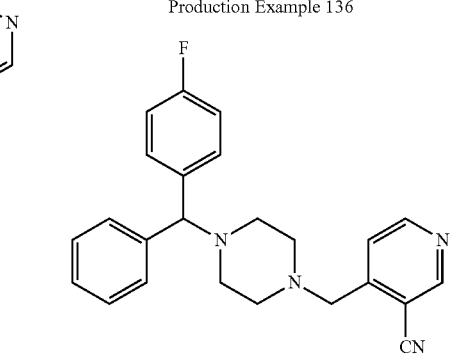 | (CDCl₃, δ): 2.4-2.6 (8H, m), 3.71 (2H, s), 4.23 (1H, s), 6.96 (2H, t, J = 8.9 Hz), 7.1-7.4 (7H, m), 7.53 (1H, d, J = 5.1 Hz), 8.70 (1H, t, J = 4.9 Hz), 8.82 (1H, s) | — |

TABLE 70-continued

| | | Cyano compound/Caboxylic acid | | |
|---|---|---|---|---|
| Compound (12) | Carbonitrile compound | Chemical formula | $^1$H-NMR | MS (m/z) |
| | | Example 104 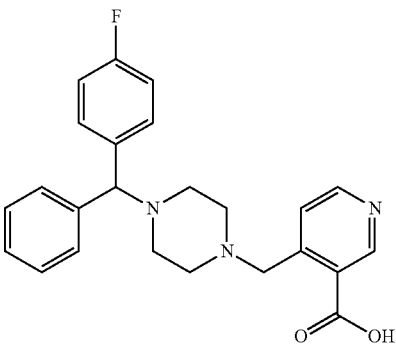 [SMILES: O=C(O)c1cnccc1CN1CCN(C(c2ccccc2)c2ccc(F)cc2)CC1] | (d$_6$-DMSO, δ): 2.39 (4H, brs), 2.74 (4H, brs), 4.02 (2H, s), 4.43 (1H, s), 7.13 (2H, t, J = 8.9 Hz), 7.21 (1H, d, J = 7.6 Hz), 7.30 (2H, d, J = 7.3 Hz), 7.4-7.5 (5H, m), 8.60 (1H, d, J = 4.9 Hz), 8.90 (1H, s) | 406.4 (M$^+$) |

Production Example 132

(±)-1-[(4-Fluorophenyl)phenylmethyl]piperazine

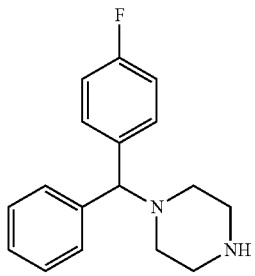 [SMILES: Fc1ccc(C(c2ccccc2)N2CCNCC2)cc1]

Thionyl chloride was added to (±)-(4-fluorophenyl)phenylmethanol, and the mixture was stirred at a room temperature overnight. After the completion of the reaction was confirmed by HPLC, ethyl acetate was added thereto, and water was added to the mixture. The resulting mixture was neutralized with sodium hydrogen carbonate, and then washed water twice and dried over magnesium sulfate. After the solvent was distilled off, the residue was dissolved in acetonitrile, and piperazine (1.7 g, 20 mmol), potassium iodide (3.3 g, 20 mmol), and potassium carbonate (3.3 g, 24 mmol) were added thereto. The mixture was refluxed overnight. After the completion of the reaction was confirmed by HPLC, the insoluble matter was removed, and the solvent was distilled off. The resulting residue was dissolved in ethyl acetate and washed with water 3 times. The organic layer was dried over magnesium sulfate, and then the solvent was distilled off. Thus the title compound (3.9 g, 72.7%) was obtained as a yellowish white solid.

$^1$H-NMR (CDCl$_3$, δ): 2.33 (4H, brs), 2.88 (4H, t, J=4.9 Hz), 4.2-4.3 (2H, m), 6.95 (2H, t, J=8.9 Hz), 7.1-7.4 (7H, m)

Production Examples 137, 140, 143, 146, 149, 152, 203

Piperazine compounds (compound (12)) shown in Table 71 were obtained according to the same procedure as in Production Example 132 except that another known compound was used instead of (±)-(4-fluorophenyl)phenylmethanol as the compound (12a).

TABLE 71

| | Compound (12) | |
|---|---|---|
| Compound (12a) | Chemical formula | $^1$H-NMR (CDCl$_3$, δ) |
| (3-chlorophenyl)(phenyl)methanol structure | Production Example 137 (3-chlorophenyl piperazine structure) | 2.35 (4H, brs), 2.90 (4H, t, J = 4.9 Hz), 4.19 (1H, s), 7.1-7.4 (9H, m) |

TABLE 71-continued
| Compound (12a) | Compound (12) | |
|---|---|---|
| | Chemical formula | ¹H-NMR (CDCl₃, δ) |
| 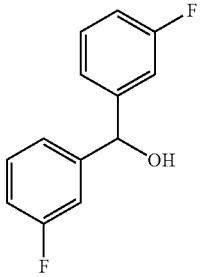 [SMILES: OC(c1cccc(F)c1)c1cccc(F)c1] | Production Example 140 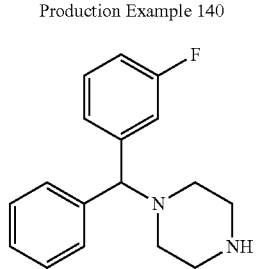 | 2.35 (4H, brs), 2.89 (4H, t, J = 4.9 Hz), 4.21 (1H, s), 6.8-6.9 (2H, m), 7.1-7.3 (6H, m) |
| 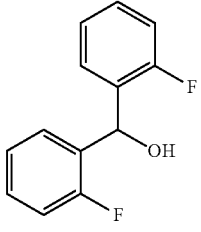 [SMILES: OC(c1ccccc1F)c1ccccc1F] | Production Example 143 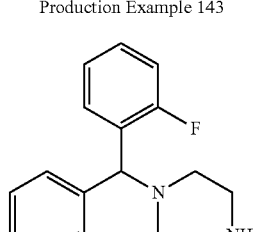 | 2.4-2.5 (4H, m), 2.92 (4H, t, J = 4.9 Hz), 5.06 (1H, s), 6.9-7.2 (6H, m), 7.5-7.6 (2H, m) |
| 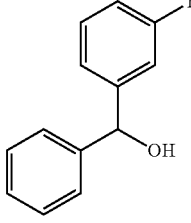 | Production Example 146 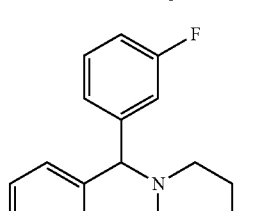 | 2.35 (4H, brs), 2.89 (4H, t, J = 4.9 Hz), 4.21 (1H, s), 6.8-6.9 (1H, m), 7.2-7.3 (6H, m), 7.37 (1H, s), 7.40 (1H, d, J = 1.6 Hz) |
| 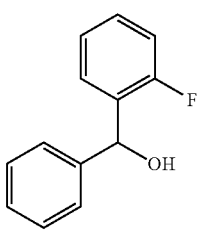 [SMILES: OC(c1ccccc1)c1ccccc1F] | Production Example 149 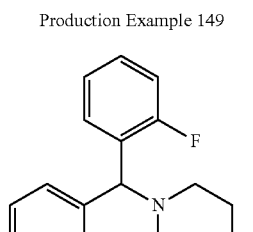 | 2.39 (4H, brs), 2.89 (4H, t, J = 4.9 Hz), 4.67 (1H, s), 6.9-7.0 (1H, m), 7.1-7.3 (5H, m), 7.43 (2H, d, J = 7.3 Hz), 7.63 (1H, dt, J = 1.9 Hz, 7.6 Hz) |
| 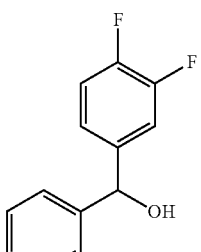 | Production Example 152 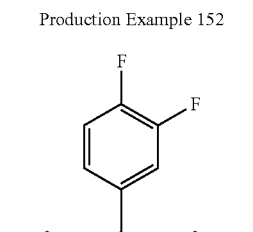 | 2.37 (4H, brs), 2.91 (4H, t, J = 4.9 Hz), 4.19 (1H, s), 7.0-7.4 (8H, m) |

TABLE 71-continued

| Compound (12) | | |
|---|---|---|
| Compound (12a) | Chemical formula | $^1$H-NMR (CDCl$_3$, δ) |
| 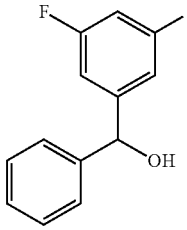 | Production Example 203 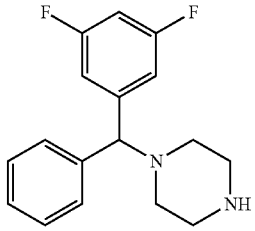 [SMILES: Fc1cc(F)cc(C(c2ccccc2)N2CCNCC2)c1] | 2.35 (4H, brs), 2.89 (4H, t, J = 4.9 Hz), 4.19 (1H, s), 6.6-6.7 (1H, m), 6.9-7.0 (2H, m), 7.2-7.4 (5H, m) |

Example 122

(±)-{4-[(4-Fluorophenyl)phenylmethoxy]piperidin-1-yl}(4-methylpyridin-2-yl)methanone

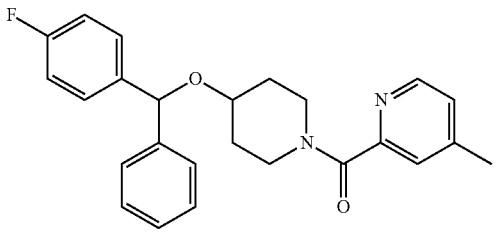 [SMILES: Cc1ccnc(C(=O)N2CCC(OC(c3ccccc3)c3ccc(F)cc3)CC2)c1]

A mixture of 2.431 g of a known compound (±)-4-[(4-fluorophenyl)phenylmethoxy]piperidine, 974 mg of 4-methylpyridine-2-carboxylic acid, 2.922 g of 1-ethyl-3-(3-dimethylaminopropyl)carbodiimide hydrochloride, 1.956 g of 1-hydroxybenzotriazole monohydrate, 29 mL of pyridine, and 208 mg of 4-dimethylaminopyridine was stirred for 1.8 hours. The mixture was poured into salt water and extracted with ethyl acetate twice. The extract was washed with a saturated saline solution and dried over magnesium sulfate. The solvent was distilled off, and then the residue was purified by silica gel column chromatography (chloroform/methanol (volume ratio)=20:1 to 15:1) to give the title compound (1.661 g (58%)).
$^1$H-NMR (CDCl$_3$, δ): 1.6-2.0 (4H, m), 2.38 (3H, s), 3.2-3.4 (1H, s), 3.5-4.1 (4H, m), 5.49 (1H, s), 6.9-7.1 (2H, m), 7.13 (1H, d, J=4.2 Hz), 7.1-7.4 (7H, m), 7.40 (1H, s), 8.41 (1H, d, J=5.0 Hz)
MS (m/z): 404 (M$^+$)

Production Example 163

Ethyl (±)-2-{4-[(4-methoxyphenyl)phenylmethoxy]piperidin-1-ylmethyl}isonicotinate

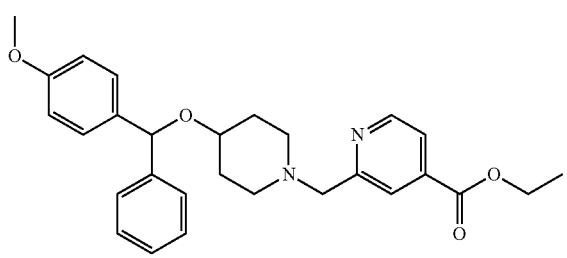 [SMILES: CCOC(=O)c1ccnc(CN2CCC(OC(c3ccccc3)c3ccc(OC)cc3)CC2)c1]

A mixture of 297 mg of a known compound (±)-4-[(4-methoxyphenyl)phenylmethoxy]piperidine, 240 mg of a known compound ethyl 2-chloromethylisonicotinate, 2.3 mL of acetonitrile, and 0.28 mL of triethylamine was stirred overnight. The mixture was poured into salt water and extracted with ethyl acetate. The extract was washed with a saturated saline solution and dried over sodium sulfate. The solvent was distilled off, and then the residue was purified by p-TLC to give the title compound (309 mg (67%)).
$^1$H-NMR (CDCl$_3$, δ): 1.41 (3H, t, J=7.1 Hz), 1.6-2.0 (4H, m), 2.1-2.4 (2H, m), 2.7-2.9 (2H, m), 3.3-3.6 (1H, m), 3.68 (2H, s), 3.77 (3H, s), 4.40 (2H, q, J=7.2 Hz), 5.47 (1H, s), 6.7-6.9 (2H, m), 7.1-7.4 (7H, m), 7.70 (1H, dd, J=1.5 Hz, 5.0 Hz), 7.93 (1H, s), 8.68 (1H, dd, J=0.8 Hz, 5.0 Hz)
MS (m/z): 461 (M$^+$+1)

Example 123

(±)-2-{4-[(4-Methoxyphenyl)phenylmethoxy]piperidin-1-ylmethyl}isonicotinic acid

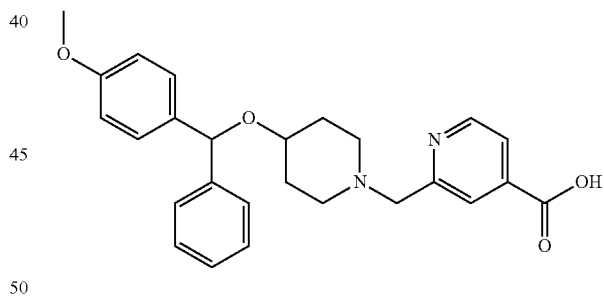

The title compound was obtained according to the same procedure as in Example 1 except that ethyl (±)-2-{4-[(4-methoxyphenyl)phenylmethoxy]piperidin-1-ylmethyl}isonicotinate synthesized in Production Example 163 was used instead of the compound synthesized in Production Example 2.
$^1$H-NMR (d$_6$-DMSO, δ): 1.5-2.0 (4H, m), 2.1-2.4 (2H, m) 2.7-2.9 (2H, m), 3.3-3.5 (1H, m), 3.72 (3H, s), 3.74 (2H, s), 5.57 (1H, s), 6.8-7.0 (2H, m), 7.1-7.4 (7H, m), 7.68 (1H, dd, J=1.5 Hz, 5.0 Hz), 7.88 (1H, s), 8.65 (1H, d, J=4.6 Hz)
MS (m/z): 431 (M$^+$−1)

Production Examples 164 to 167, 176, 177, 180, 183 to 186, 209, 210, 212, 213, 215, 216, 218, 219, and Examples 124 to 127, 132 to 138, 150 to 157

Ester compounds (compound (14)) shown in Tables 72 to 81 were obtained in the same manner as in Production Example 163 except that any one of the compounds synthesized in Production Examples 175, 179, 182, 208, 211, 214 and 217 or a known compound was used instead of (±)-4-[(4-methoxyphenyl)phenylmethoxy]piperidine as the compound (12) and/or that another known compound was used instead of ethyl 2-chloromethylisonicotinate as the compound (13). Moreover, carboxylic acids shown in Tables 72 to 81 were obtained in the same manner as in Example 1 except that any one of these ester compounds was used.

TABLE 72

| Compound (12) | Compound (13) | Ester compound/Caboxylic acid | | |
|---|---|---|---|---|
| | | Chemical formula | ¹H-NMR | MS (m/z) |
| | | Production Example 164 | (CDCl₃, δ): 1.41 (3H, t, J = 7.1 Hz), 1.6-2.0 (4H, m), 2.1-2.4 (2H, m) 2.6-2.9 (2H, m), 3.3-3.5 (1H, m), 3.68 (2H, s), 4.41 (2H, q, J = 7.2 Hz), 5.46 (1H, s), 6.9-7.4 (8H, m), 7.70 (1H, dd, J = 1.5 Hz, 5.0 Hz), 7.93 (1H, s), 8.6-8.8 (1H, m) | 467 (M⁺ + 1) |
| | | Example 124 | (d₆-DMSO, δ): 1.5-1.7 (2H, m), 1.8-2.0 (2H, m), 2.2-2.4 (2H, m), 2.7-2.9 (2H, m), 3.3-3.5 (1H, m), 3.73 (2H, s), 5.67 (1H, s), 7.0-7.5 (8H, m), 7.67 (1H, dd, J = 1.5 Hz, 5.0 Hz), 7.88 (1H, s), 8.65 (1H, d, J = 5.0 Hz) | 439 (M⁺ + 1) |

TABLE 72-continued

| Compound (12) | Compound (13) | Ester compound/Caboxylic acid | | MS (m/z) |
|---|---|---|---|---|
| | | Chemical formula | ¹H-NMR | |
| (structure: 1-[(4-chlorophenyl)(phenyl)methyl]piperazine) | (structure: ethyl 2-(chloromethyl)pyridine-4-carboxylate) | Production Example 165 (ethyl ester structure) | (CDCl₃, δ): 1.40 (3H, t, J = 7.3 Hz), 2.2-2.8 (8H, m), 3.72 (2H, s) 4.22 (1H, s), 4.40 (2H, q, J = 7.2 Hz), 7.1-7.5 (9H, m), 7.69 (1H, dd, J = 1.2 Hz, 5.0 Hz), 7.90 (1H, s), 8.68 (1H, d, J = 5.0 Hz) | 449 (M⁺) |
| | | Example 125 (carboxylic acid structure) | (d₆-DMSO, δ): 2.1-3.0 (8H, m), 3.98 (2H, brs), 4.42 (1H, s), 7.1-7.6 (9H, m), 7.74 (1H, d, J = 3.9 Hz), 7.91 (1H, s), 8.72 (1H, d, J = 5.0 Hz) | 421 (M⁺) |

TABLE 73

| Compound (12) | Compound (13) | Ester compound/Carboxylic acid | | |
|---|---|---|---|---|
| | | Chemical formula | ¹H-NMR | MS (m/z) |
| [N-benzhydryl-1,4-diazocane] | [ethyl 2-(chloromethyl)isonicotinate] | Production Example 166 | (CDCl₃, δ): 1.41 (3H, t, J = 7.1 Hz), 1.6-1.9 (2H, m), 2.6-3.0 (8H, m), 3.88 (2H, s), 4.41 (2H, q, J = 7.2 Hz), 4.63 (1H, s), 7.0-7.6 (10H, m), 7.69 (1H, dd, J = 1.6 Hz, 5.4 Hz), 8.02 (1H, s), 8.67 (1H, dd, J = 0.8 Hz, 5.0 Hz) | 429 (M⁺) |
| | | Example 126 | (d₆-DMSO, δ): 1.6-1.8 (2H, m), 2.5-2.9 (8H, m), 3.92 (2H, s), 4.74 (1H, s), 7.16 (2H, t, J = 7.3 Hz), 7.2-7.5 (4H, m), 7.45 (4H, d, J = 6.9 Hz), 7.67 (1H, dd, J = 1.5 Hz, 5.0 Hz), 7.98 (1H, s), 8.63 (1H, d, J = 5.0 Hz) | 401 (M⁺) |
| [N-benzhydryl-1,4-diazocane] | [ethyl 2-(chloromethyl)isonicotinate] | Production Example 167 | (CDCl₃, δ): 1.42 (3H, t, J = 7.1 Hz), 1.6-1.9 (2H, m), 2.6-3.0 (8H, m), 3.93 (2H, s), 4.46 (2H, q, J = 7.1 Hz), 4.61 (1H, s), 7.1-7.6 (10H, m), 7.7-8.1 (3H, m) | 429 (M⁺) |
| | | Example 127 | (d₆-DMSO, δ): 1.5-1.9 (2H, m), 2.4-2.9 (8H, m), 3.7-4.0 (2H, m), 4.67 (1H, s), 7.1-8.0 (13H, m) | 401 (M⁺) |

TABLE 74

| Compound (12) | Compound (13) | Ester compound/Caboxylic acid | | |
|---|---|---|---|---|
| | | Chemical formula | ¹H-NMR | MS (m/z) |
| Production Example 175 | | Production Example 176 | (CDCl₃, δ): 1.3-1.5 (3H, m), 1.5-2.0 (4H, m), 2.1-2.4 (2H, m), 2.6-2.9 (2H, m), 3.4-3.6 (1H, m), 3.73 (3H, s), 3.75 (2H, s), 4.4-4.6 (2H, m), 5.61 (1H, s), 6.00 (1H, d, J = 1.9 Hz), 7.1-7.5 (5H, m), 7.68 (1H, d, J = 7.7 Hz), 7.79 (1H, t, J = 7.7 Hz) 7.9-8.1 (1H, m) | 469 (M⁺ + 1) |
| | | Example 132 | (d₆-DMSO, δ): 1.4-2.3 (6H, m), 2.7-2.9 (2H, m), 3.3-3.5 (1H, m), 3.63 (2H, brs), 3.73 (3H, s), 5.87 (1H, s), 5.90 (1H, d, J = 1.5 Hz), 7.29 (1H, d, J = 1.9 Hz), 7.3-7.5 (4H, m), 7.63 (1H, d, J = 7.3 Hz), 7.8-8.0 (2H, m) | 441 (M⁺ + 1) |
| Production Example 175 | | Production Example 177 | (CDCl₃, δ): 1.41 (3H, t, J = 7.1 Hz), 1.6-2.0 (4H, m), 2.1-2.3 (2H, m), 2.6-2.9 (2H, m), 3.3-3.6 (1H, m), 3.69 (2H, s), 3.73 (3H, s), 4.41 (2H, q, J = 7.2 Hz), 5.60 (1H, s), 5.99 (1H, d, J = 1.9 Hz), 7.1-7.5 (5H, m), 7.70 (1H, dd, J = 1.5 Hz, 5.0 Hz), 7.92 (1H, s) 8.69 (1H, d, J = 5.0 Hz) | 469 (M⁺ + 1) |
| | | Example 133 | (d₆-DMSO, δ): 1.4-2.4 (6H, m), 2.7-2.9 (2H, m), 3.3-3.5 (1H, m), 3.71 (2H, s), 3.73 (3H, s), 5.87 (1H, s), 5.90 (1H, d, J = 1.9 Hz), 7.29 (1H, d, J = 1.9 Hz), 7.38 (2H, d, J = 8.5 Hz), 7.45 (2H, dd, J = 1.9 Hz, 6.6 Hz), 7.67 (1H, dd, J = 1.5 Hz, 5.0 Hz), 7.87 (1H, s), 8.65 (1H, d, J = 5.0 Hz) | 441 (M⁺ + 1) |

TALBE 75

| Compound (12) | Compound (13) | Ester compound/Caboxylic acid | | |
|---|---|---|---|---|
| | | Chemical formula | ¹H-NMR | MS (m/z) |
| Production Example 179 | Production Example 180 | | (CDCl₃, δ): 1.41 (3H, t, J = 7.1 Hz), 1.7-2.0 (4H, m), 2.1-2.4 (2H, m), 2.6-2.9 (2H, m), 3.5-3.7 (1H, m), 3.70 (2H, s), 4.41 (2H, q, J = 7.1 Hz), 5.78 (1H, s), 7.2-7.5 (5H, m), 7.7-7.8 (2H, m), 7.93 (1H, s), 8.69 (1H, dd, J = 0.8 Hz, 5.0 Hz) | 472 (M⁺) |
| | Example 134 | | (d₆-DMSO, δ): 1.5-2.0 (4H, m), 2.1-2.4 (2H, m), 2.6-2.8 (2H, m), 3.4-3.7 (1H, m), 3.67 (2H, s), 5.97 (1H, s), 7.3-7.5 (4H, m), 7.65 (1H, dd, J = 1.2 Hz, 5.0 Hz), 7.68 (1H, d, J = 3.5 Hz), 7.73 (1H, d, J = 3.5 Hz), 7.85 (1H, s), 8.61 (1H, d, J = 5.0 Hz) | 444 (M⁺ + 1) |
| Production Example 182 | Production Example 183 | | (CDCl₃, δ): 1.40 (3H, t, J = 7.1 Hz), 1.6-2.0 (4H, m), 2.1-2.4 (2H, m), 2.39 (3H, s), 2.6-2.9 (2H, m), 3.4-3.7 (1H, m), 3.69 (2H, s), 4.41 (2H, q, J = 7.1 Hz), 5.74 (1H, s), 6.82 (1H, d, J = 0.8 Hz), 7.2-7.5 (4H, m), 7.70 (1H, dd, J = 1.2 Hz, 5.0 Hz), 7.92 (1H, s), 8.68 (1H, d, J = 5.0 Hz) | 486 (M⁺) |
| | Example 135 | | (d₆-DMSO, δ): 1.5- 2.0 (4H, m), 2.2-2.4 (2H, m), 2.29 (3H, s), 2.6-2.9 (2H, m), 3.4-3.7 (1H, m), 3.71 (2H, s), 5.90 (1H, s), 7.21 (1H, d, J = 0.8 Hz), 7.3-7.5 (4H, m), 7.68 (1H, dd, J = 1.5 Hz, 5.0 Hz), 7.87 (1H, s), 8.65 (1H, d, J = 5.0 Hz) | 458 (M⁺ + 1) |

TABLE 76

| Compound (12) | Compound (13) | Ester compound/Caboxylic acid | | MS (m/z) |
|---|---|---|---|---|
| | | Chemical formula | ¹H-NMR | |
| Production Example 179 | Production Example 184 | (CDCl₃, δ): 1.42 (3H, t, J = 7.1 Hz), 1.5-2.0 (4H, m), 2.1-2.4 (2H, m), 2.6-2.9 (2H, m), 3.5-3.7 (1H, m), 3.77 (2H, s), 4.46 (2H, q, J = 7.1 Hz), 5.78 (1H, s), 7.2-7.5 (5H, m), 7.6-7.8 (2H, m), 7.78 (1H, t, J = 7.7 Hz), 7.97 (1H, d, J = 7.3 Hz) | 471 (M⁺ − 1) |
| | | Example 136 | (d₆-DMSO, δ): 1.5-2.0 (4H, m), 2.1-2.4 (2H, m), 2.6-2.9 (2H, m), 3.4-3.7 (1H, m), 3.68 (2H, brs), 5.98 (1H, s), 7.3-7.5 (4H, m), 7.67 (1H, dd, J = 1.5 Hz, 7.3 Hz), 7.69 (1H, d, J = 3.5 Hz), 7.73 (1H, d, J = 3.5 Hz), 7.8-8.0 (2H, m) | 443 (M⁺) |
| Production Example 182 | Production Example 185 | (CDCl₃, δ): 1.41 (3H, t, J = 7.1 Hz), 1.6-2.0 (4H, m), 2.1-2.4 (2H, m), 2.39 (3H, s), 2.6-2.9 (2H, m), 3.5-3.7 (1H, m), 3.76 (2H, s), 4.45 (2H, q, J = 7.2 Hz), 5.74 (1H, s), 6.83 (1H, d, J = 1.2 Hz), 7.2-7.5 (4H, m), 7.69 (1H, d, J = 7.3 Hz), 7.78 (1H, t, J = 7.7 Hz), 7.9-8.1 (1H, m) | 485 (M⁺ − 1) |
| | | Example 137 | (d₆-DMSO, δ): 1.5-2.0 (4H, m), 2.1-2.4 (2H, m), 2.29 (3H, s), 2.6-2.9 (2H, m), 3.4-3.7 (1H, m), 3.69 (2H, brs), 5.90 (1H, s), 7.21 (1H, d, J = 1.0 Hz), 7.3-7.5 (4H, m), 7.65 (1H, d, J = 7.2 Hz), 7.8-8.0 (2H, m) | 458 (M⁺ + 1) |

TABLE 77

| Compound (12) | Compound (13) | Ester compound/Carboxylic acid | | |
|---|---|---|---|---|
| | | Chemical formula | ¹H-NMR | MS (m/z) |
| 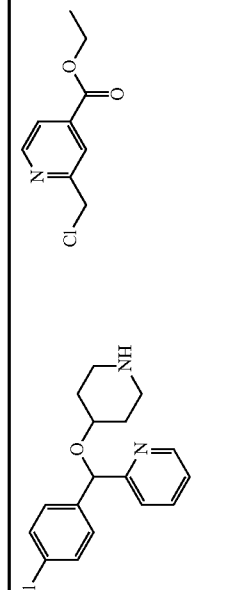 | 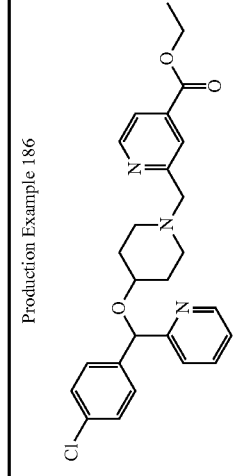 | Production Example 186<br>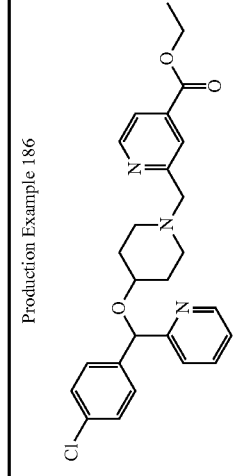 | (CDCl₃, δ): 1.40 (3H, t, J = 7.1 Hz), 1.6-2.0 (4H, m), 2.1-2.4 (2H, m), 2.6-2.9 (2H, m), 3.4-3.6 (1H, m), 3.68 (2H, s), 4.40 (2H, q, J = 7.2 Hz), 5.59 (1H, s), 7.1-7.4 (3H, m), 7.35 (2H, d, J = 8.5 Hz), 7.53 (1H, d, J = 8.1 Hz), 7.5-7.8 (2H, m), 7.92 (1H, s), 8.49 (1H, d, J = 4.6 Hz), 8.68 (1H, d, J = 5.0 Hz) | 466 (M⁺ + 1) |
| | | Example 138<br>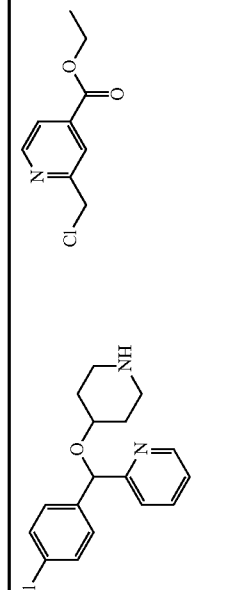 | (d₆-DMSO, δ): 1.5-1.7 (2H, m), 1.8-2.0 (2H, m), 2.1-2.5 (2H, m), 2.6-2.9 (2H, m), 3.3-3.5 (1H, m), 3.70 (2H, s), 5.65 (1H, s), 7.2-7.5 (5H, m), 7.55 (1H, d, J = 7.7 Hz), 7.66 (1H, dd, J = 1.5 Hz, 5.0 Hz), 7.80 (1H, dt, 1.9 Hz, 7.7 Hz), 7.87 (1H, s), 7.5-7.7 (1H, m), 8.63 (1H, d, J = 5.0 Hz) | 438 (M⁺ + 1) |
| Production Example 208<br>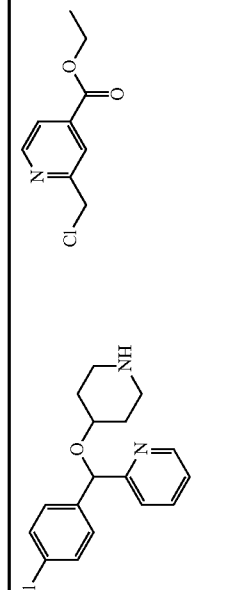 | 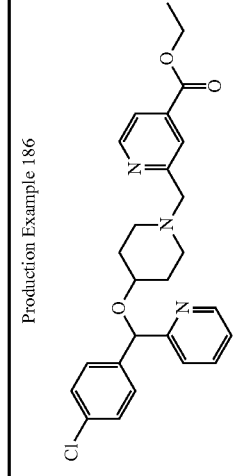 | Production Example 209<br>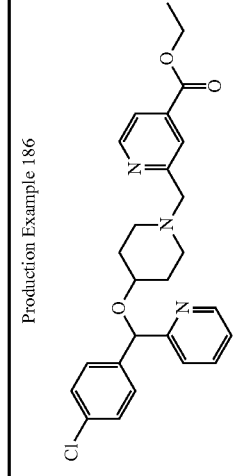 | (CDCl₃, δ): 1.43 (3H, t, J = 7.3 Hz), 1.7-2.1 (4H, m), 2.2-2.3 (2H, m), 2.7-2.8 (2H, m) 3.5-3.6 (1H, m), 3.77 (2H, s), 4.47 (2H, q, J = 7.3 Hz), 5.83 (1H, s), 7.2-7.4 (6H, m), 7.4-7.5 (1H, m), 7.71 (1H, d, J = 3.5 Hz), 7.80 (1H, t, J = 7.3 Hz), 7.98 (1H, d, J = 7.3 Hz) | — |
| | | Example 150<br>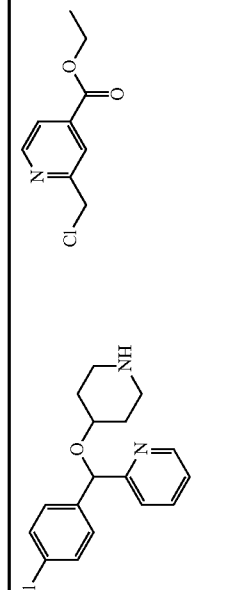 | (CDCl₃, δ): 1.9-2.1 (2H, m), 2.4-2.5 (2H, m), 3.0-3.2 (4H, m), 3.8-3.9 (1H, m), 4.18 (2H, s), 5.80 (1H, s), 7.3-7.5 (7H, m), 7.73 (1H, d, J = 3.2 Hz), 7.96 (1H, t, J = 7.6 Hz), 8.19 (1H, d, J = 7.6 Hz) | 410.2 (M⁺) |

TABLE 78

| Compound (12) | Compound (13) | Ester compound/Carboxylic acid | | |
|---|---|---|---|---|
| | | Chemical formula | ¹H-NMR | MS (m/z) |
| Production Example 208 | | Production Example 210 | (CDCl₃, δ): 1.42 (3H, t, J = 7.0 Hz), 1.7-2.0 (4H, m), 2.2-2.3 (2H, m), 2.7-2.8 (2H, m), 3.5-3.6 (1H, m), 3.70 (2H, s), 4.42 (2H, q, J = 7.0 Hz), 5.82 (1H, s), 7.2-7.4 (4H, m), 7.4-7.5 (2H, m), 7.7-7.8 (2H, m), 7.94 (1H, s), 8.70 (1H, d, J = 5.4 Hz) | — |
| | | Example 151 | (CDCl₃, δ): 2.0-2.2 (2H, m), 2.4-2.5 (2H, m), 3.2-3.4 (4H, m), 3.9-4.0 (1H, m), 4.26 (2H, s), 5.79 (1H, s), 7.3-7.5 (6H, m), 7.72 (1H, d, J = 3.2 Hz), 7.89 (1H, dd, J = 1.4 Hz, 4.9 Hz) 8.41 (1H, s), 8.66 (1H, d, J = 5.1 Hz) | 410.3 (M⁺) |
| Production Example 211 | | Production Example 212 | (CDCl₃, δ): 1.43 (3H, t, J = 7.0 Hz), 1.7-1.9 (4H, m), 2.2-2.3 (2H, m), 2.7-2.8 (2H, m), 3.5-3.6 (1H, m), 3.77 (2H, s), 4.47 (2H, q, J = 7.0 Hz), 5.80 (1H, s), 7.0-7.1 (2H, m), 7.30 (1H, d, J = 7.3 Hz), 7.4-7.5 (2H, m), 7.6-7.7 (2H, m), 7.80 (1H, t, J = 7.6 Hz), 7.98 (1H, d, J = 8.1 Hz) | — |
| | | Example 152 | (d₆-DMSO, δ): 1.9-2.0 (2H, m), 2.2-2.3 (2H, m), 2.9-3.1 (4H, m), 3.7-3.8 (1H, m), 4.09 (2H, s), 5.79 (1H, s), 7.05 (2H, t, J = 8.6 Hz), 7.32 (1H, d, J = 3.5 Hz), 7.3-7.4 (2H, m), 7.6-7.7 (2H, m), 7.69 (1H, d, J = 3.5 Hz), 7.73 (1H, d, J = 3.5 Hz), 7.93 (1H, t, J = 7.6 Hz), 8.15 (1H, d, J = 7.6 Hz) | 428.2 (M⁺) |

TABLE 79

| Compound (12) | Compound (13) | Ester compound/Caboxylic acid | | MS (m/z) |
|---|---|---|---|---|
| | | Chemical formula | ¹H-NMR | |
| Production Example 211 | Production Example 213 | | (CDCl₃, δ): 1.42 (3H, t, J = 7.3 Hz), 1.8-2.0 (4H, m), 2.2-2.3 (2H, m), 2.7-2.8 (2H, m), 3.5-3.6 (1H, m), 3.71 (2H, s), 4.43 (2H, q, J = 7.3 Hz), 5.80 (1H, s), 7.0-7.1 (2H, m), 7.2-7.3 (1H, m) 7.4-7.5 (2H, m), 7.7-7.8 (2H, m), 7.94 (1H, s), 8.70 (1H, d, J = 4.9 Hz) | — |
| | Example 153 | | (d₆-DMSO, δ): 1.9-2.2 (2H, m), 2.4-2.6 (2H, m), 3.1-3.3 (4H, m), 3.9-4.0 (1H, m), 4.18 (2H, s,), 5.78 (1H, s), 7.07 (2H, t, J = 8.6 Hz), 7.34 (1H, d, J = 3.2 Hz), 7.4-7.5 (2H, m), 7.73 (1H, d, J = 3.5 Hz), 7.88 (1H, dd, J = 1.4 Hz, 5.1 Hz), 8.44 (1H, s), 8.63 (1H, d, J = 5.4 Hz) | 428.1 (M⁺) |

TABLE 79-continued

| Compound (12) | Compound (13) | Ester compound/Carboxylic acid | | |
|---|---|---|---|---|
| | | Chemical formula | ¹H-NMR | MS (m/z) |
| Production Example 214 | Production Example 215 | Production Example 215 | (CDCl$_3$, δ): 1.39 (3H, t, J = 7.1 Hz), 1.8-2.2 (2H, m), 2.5-3.0 (4H, m), 3.7-4.2 (3H, m), 4.40 (2H, q, J = 7.1 Hz), 5.31 (1H, s), 6.8-7.4 (8H, m), 7.70 (1H, dd, J = 1.5 Hz, 5.0 Hz), 7.91 (1H, s), 8.68 (1H, dd, J = 0.8 Hz, 5.0 Hz) | 453 (M⁺ + 1) |
| | | Example 154 | (d$_6$-DMSO, δ): 1.7-2.2 (2H, m), 2.5-2.9 (4H, m), 3.7-4.1 (3H, m), 5.53 (1H, s), 7.0-7.5 (8H, m), 7.67 (1H, dd, J = 1.5 Hz, 5.0 Hz), 7.87 (1H, s), 8.5-8.7 (1H, m) | 425 (M⁺ + 1) |

TABLE 80

| | | Ester compound/Caboxylic acid | | |
|---|---|---|---|---|
| Compound (12) | Compound (13) | Chemical formula | ¹H-NMR | MS (m/z) |
| Production Example 214 | | Production Example 216 | (CDCl₃, δ): 1.42 (3H, t, J = 7.1 Hz), 1.8-2.2 (2H, m), 2.5-2.9 (4H, m), 3.8-4.2 (3H, m), 4.46 (2H, q, J = 7.2 Hz), 5.31 (1H, s), 6.9-7.4 (8H, m), 7.64 (1H, d, J = 7.7 Hz), 7.76 (1H, t, J = 7.7 Hz), 7.97 (1H, d, J = 7.7 Hz) | 453 (M⁺ + 1) |
| | | Example 155 | (d₆-DMSO, δ): 1.7-2.2 (2H, m), 2.3-2.9 (4H, m), 3.6-4.2 (3H, m), 5.52 (1H, s), 7.0-7.7 (9H, m), 7.8-8.0 (2H, m) | 425 (M⁺ + 1) |
| Production Example 217 | | Production Example 218 | (CDCl₃, δ): 1.39 (3H, t, J = 7.1 Hz), 1.8-2.2 (2H, m), 2.5-3.0 (4H, m), 3.7-4.2 (3H, m), 4.40 (2H, q, J = 7.1 Hz), 5.31 (1H, s), 6.8-7.4 (8H, m), 7.70 (1H, dd, J = 1.5 Hz, 5.0 Hz), 7.91 (1H, s), 8.68 (1H, d, J = 5.0 Hz) | 453 (M⁺ + 1) |

TABLE 81

| | | Ester compound/Caboxylic acid | | |
|---|---|---|---|---|
| Compound (12) | Compound (13) | Chemical formula | ¹H-NMR | MS (m/z) |
| | | Example 156 | (d₆-DMSO, δ): 1.7-2.2 (2H, m), 2.4-2.9 (4H, m), 3.7-4.1 (3H, m), 5.53 (1H, s), 7.0-7.5 (8H, m), 7.68 (1H, dd, J = 1.5 Hz, 5.0 Hz), 7.86 (1H, s), 8.64 (1H, d, J = 5.0 Hz) | 425 (M⁺ + 1) |

TABLE 81-continued

| | | Ester compound/Caboxylic acid | | |
|---|---|---|---|---|
| Compound (12) | Compound (13) | Chemical formula | $^1$H-NMR | MS (m/z) |
| Production Example 217 | | Production Example 219 | (CDCl$_3$, δ): 1.42 (3H, t, J = 7.1 Hz), 1.8-2.2 (2H, m), 2.5-2.9 (4H, m),, 3.8-4.2 (3H, m), 4.46 (2H, q, J = 7.1 Hz), 5.31 (1H, s), 6.9-7.4 (8H, m), 7.63 (1H, d, 7.7 Hz), 7.76 (1H, t, J = 7.9 Hz), 7.97 (1H, d, J = 7.3 Hz) | 453 (M$^+$ + 1) |
| | | Example 157 | (d$_6$-DMSO, δ): 1.7-2.2 (2H, m), 2.4-2.9 (4H, m), 3.6-4.2 (3H, m), 5.53 (1H, s), 7.0-7.7 (9H, m), 7.8-8.0 (2H, m) | 425 (M$^+$ + 1) |

Production Example 169

Ethyl 6-((R)-3-benzhydryloxypyrrolidin-1-ylmethyl)pyridine-2-carboxylate

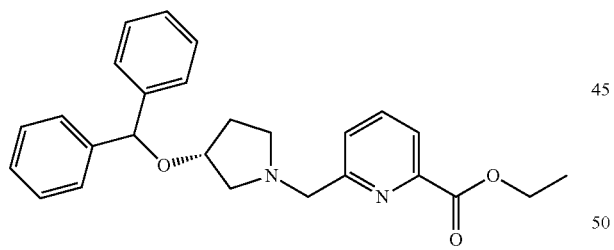

A mixture of 8.144 g of (R)-3-benzhydryloxypyrrolidine synthesized in Production Example 168, 7.701 g of a known compound ethyl 6-chloromethylpyridine-2-carboxylate, 69 mL of acetonitrile, and 9.0 mL of triethylamine was heated under reflux for 3 hours. After being allowed to cool down, the mixture was diluted with ethyl acetate. The diluted mixture was poured into a saturated saline solution, and the organic layer was collected by separation. The organic layer was washed with a saturated saline solution and dried over magnesium sulfate. The solvent was distilled off, and then the residue was purified by silica gel column chromatography (chloroform/acetone (volume ratio)=15:1 to 10:1) to give the title compound (7.22 g (54%)).

$^1$H-NMR (CDCl$_3$, δ): 1.42 (3H, t, J=7.1 Hz), 1.8-2.2 (2H, m), 2.5-2.9 (4H, m), 3.8-4.0 (2H, m), 4.1-4.2 (1H, m), 4.46 (2H, q, J=7.2 Hz), 5.36 (1H, s), 7.1-7.4 (10H, m), 7.65 (1H, d, J=7.7 Hz), 7.76 (1H, t, J=7.7 Hz), 7.96 (1H, d, J=7.7 Hz)

MS (m/z): 416 (M$^+$)

Example 128

6-((R)-3-Benzhydryloxypyrrolidin-1-ylmethyl)pyridine-2-carboxylic acid

The title compound was obtained according to the same procedure as in Example 1 except that ethyl 6-((R)-3-benzhydryloxypyrrolidin-1-ylmethyl)pyridine-2-carboxylate synthesized in Production Example 169 was used instead of the compound synthesized in Production Example 2

$^1$H-NMR (d$_6$-DMSO, δ): 1.7-2.2 (2H, m), 2.4-2.9 (4H, m), 3.7-4.2 (3H, m), 5.49 (1H, s), 7.1-7.7 (11H, m), 7.8-8.0 (2H, m)

MS (m/z): 387 (M$^+$−1)

Production Example 171

Ethyl 6-((S)-3-benzhydryloxypyrrolidin-1-ylmethyl)pyridine-2-carboxylate

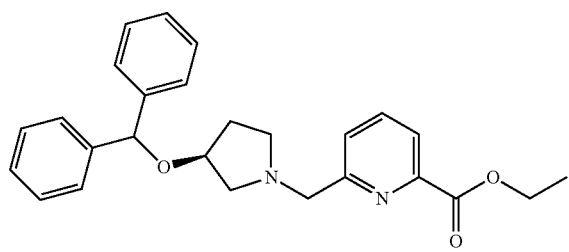 [SMILES: CCOC(=O)c1cccc(CN2CC[C@H](OC(c3ccccc3)c3ccccc3)C2)n1]

The title compound was obtained according to the same procedure as in Production Example 169 except that (S)-3-benzhydryloxypyrrolidine synthesized in Production Example 170 was used instead of (R)-3-benzhydryloxypyrrolidine.

$^1$H-NMR (CDCl$_3$, δ): 1.42 (3H, t, J=7.1 Hz), 1.8-2.2 (2H, m), 2.5-2.9 (4H, m), 3.8-4.0 (2H, m), 4.1-4.2 (1H, m), 4.46 (2H, q, J=7.1 Hz), 5.36 (1H, s), 7.1-7.4 (10H, m), 7.65 (1H, d, J=7.7 Hz), 7.76 (1H, t, J=7.9 Hz), 7.96 (1H, d, J=7.7 Hz)

MS (m/z): 416 (M$^+$)

Example 129

6-((S)-3-Benzhydryloxypyrrolidin-1-ylmethyl)pyridine-2-carboxylic acid

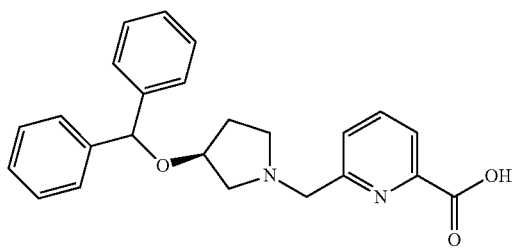 [SMILES: O=C(O)c1cccc(CN2CC[C@H](OC(c3ccccc3)c3ccccc3)C2)n1]

The title compound was obtained according to the same procedure as in Example 1 except that ethyl 6-((S)-3-benzhydryloxypyrrolidin-1-ylmethyl)pyridine-2-carboxylate synthesized in Production Example 171 was used instead of the compound synthesized in Production Example 2.

$^1$H-NMR (d$_6$-DMSO, δ): 1.7-2.2 (2H, m), 2.4-2.9 (4H, m), 3.7-3.9 (2H, m), 4.0-4.2 (1H, m), 5.48 (1H, s), 7.1-7.7 (11H, m), 7.8-8.0 (2H, m)

MS (m/z): 387 (M$^+$−1)

Production Example 172

Ethyl 2-((R)-3-benzhydryloxypyrrolidin-1-ylmethyl)isonicotinate

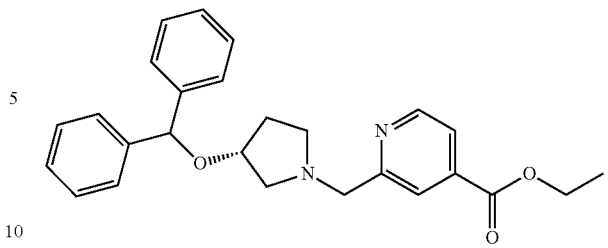

The title compound was obtained according to the same procedure as in Production Example 169 except that a known compound ethyl 2-chloromethylisonicotinate was used instead of ethyl 6-chloromethylpyridine-2-carboxylate.

$^1$H-NMR (CDCl$_3$, δ): 1.39 (3H, t, J=7.1 Hz), 1.8-2.2 (2H, m), 2.5-3.0 (4H, m), 3.7-4.0 (2H, m), 4.0-4.3 (1H, m), 4.40 (2H, q, J=6.9 Hz), 5.36 (1H, s), 7.1-7.4 (10H, m), 7.70 (1H, d, J=5.0 Hz), 7.91 (1H, s), 8.68 (1H, d, J=5.4 Hz)

MS (m/z): 416 (M$^+$)

Example 130

2-((R)-3-Benzhydryloxypyrrolidin-1-ylmethyl)isonicotinic acid

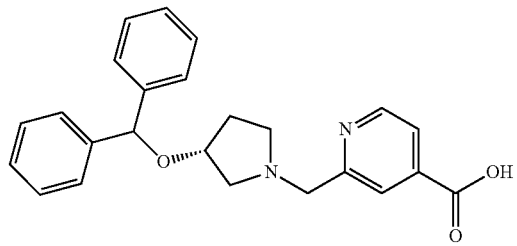 [SMILES: O=C(O)c1ccnc(CN2CC[C@@H](OC(c3ccccc3)c3ccccc3)C2)c1]

The title compound was obtained according to the same procedure as in Example 1 except that ethyl 2-((R)-3-benzhydryloxypyrrolidin-1-ylmethyl)isonicotinate synthesized in Production Example 172 was used instead of the compound synthesized in Production Example 2.

$^1$H-NMR (d$_6$-DMSO, δ): 1.7-2.1 (2H, m), 2.4-2.9 (4H, m), 3.7-3.9 (2H, m), 4.0-4.2 (1H, m), 5.49 (1H, s), 7.1-7.4 (10H, m), 7.65 (1H, dd, J=1.5 Hz, 5.0 Hz), 7.84 (1H, s), 8.5-8.7 (1H, m)

MS (m/z): 387 (M$^+$−1)

Production Example 173

Ethyl 2-((S)-3-benzhydryloxypyrrolidin-1-ylmethyl)isonicotinate

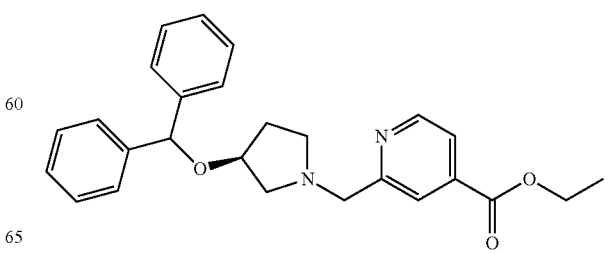

The title compound was obtained according to the same procedure as in Production Example 169 except that a known compound ethyl 2-chloromethylisonicotinate and (S)-3-benzhydryloxypyrrolidine synthesized in Production Example 170 were used instead of ethyl 6-chloromethylpyridine-2-carboxylate and (R)-3-benzhydryloxypyrrolidine, respectively.

$^1$H-NMR (CDCl$_3$, δ): 1.39 (3H, t, J=7.1 Hz), 1.8-2.2 (2H, m), 2.5-3.0 (4H, m), 3.7-4.0 (2H, m), 4.0-4.3 (1H, m), 4.40 (2H, q, J=7.1 Hz), 5.36 (1H, s), 7.1-7.4 (10H, m), 7.70 (1H, dd, J=1.5 Hz, 5.0 Hz), 7.91 (1H, s), 8.68 (1H, d, J=5.0 Hz)

MS (m/z): 417 (M$^+$+1)

Example 131

2-((S)-3-Benzhydryloxypyrrolidin-1-ylmethyl)isonicotinic acid

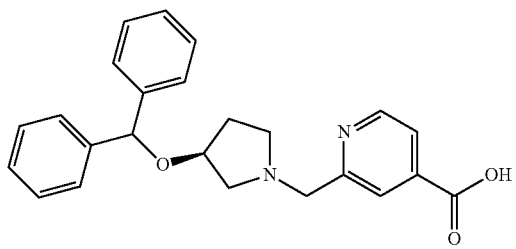 [SMILES: O=C(O)c1ccnc(CN2CC[C@H](OC(c3ccccc3)c3ccccc3)C2)c1]

The title compound was obtained according to the same procedure as in Example 1 except that ethyl 2-((S)-3-benzhydryloxypyrrolidin-1-ylmethyl)isonicotinate synthesized in Production Example 173 was used instead of the compound synthesized in Production Example 2.

$^1$H-NMR (d$_6$-DMSO, δ): 1.7-2.1 (2H, m), 2.4-2.9 (4H, m), 3.7-3.9 (2H, m), 4.0-4.2 (1H, m), 5.49 (1H, s), 7.1-7.4 (10H, m), 7.65 (1H, dd, J=1.5 Hz, 5.0 Hz), 7.84 (1H, s), 8.60 (1H, d, J=5.0 Hz)

MS (m/z): 387 (M$^+$−1)

Production Example 174

(±)-(4-Chlorophenyl)(2-methyl-2H-pyrazol-3-yl)methanol

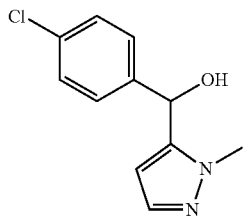

A solution of 6.60 g of 1-methylpyrazole in 150 mL of tetrahydrofuran was cooled to −60° C., and 60 mL of a 1.6-M n-butyllithium/n-hexane solution was added dropwise to the solution under a nitrogen atmosphere. After the mixture was stirred for one hour, a solution of 11.288 g of 4-chlorobenzaldehyde in 50 mL of tetrahydrofuran was added dropwise to the mixture. It took 7 hours to bring back a temperature of the mixture to a room temperature, and then to the mixture, 125 mL of a 1-N ammonium chloride aqueous solution was added. The extraction with ethyl acetate was performed twice, and the extract was washed with a saturated saline solution. After the washed solution was dried over sodium sulfate, the solvent was distilled off. The raw product was purified by silica gel column chromatography (hexane/ethyl acetate (volume ratio)=1:2 to 1:3) to give the title compound (7.898 g (44%)).

$^1$H-NMR (CDCl$_3$, δ): 2.53 (1H, d, J=4.6 Hz), 3.77 (3H, s), 5.90 (1H, d, J=4.2 Hz), 6.02 (1H, d, J=1.9 Hz), 7.2-7.5 (5H, m)

MS (m/z): 222 (M$^+$)

Production Example 175

(±)-4-[(4-Chlorophenyl)(2-methyl-2H-pyrazol-3-yl)methoxy]piperidine

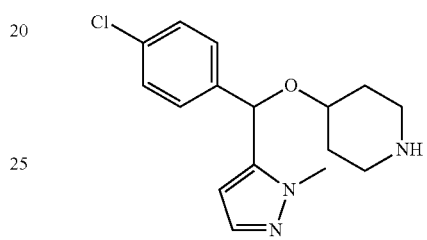

A mixture of 2.074 g of (±)-(4-chlorophenyl)(2-methyl-2H-pyrazol-3-yl)methanol synthesized in Production Example 174, 942 mg of 4-hydroxypiperidine, 1.949 g of p-toluenesulfonic acid monohydrate, and 100 mL of toluene was heated under reflux for 40 minutes while removing water using a Dean-Stark. To the mixture, 1.949 g of p-toluenesulfonic acid monohydrate was added, and the resulting mixture was further heated under reflux for 4.3 hours while removing water. After the mixture was allowed to cool down, toluene and 22 mL of a 1-N sodium hydroxide aqueous solution were added thereto, and the organic layer was collected by separation. The organic layer was washed with 22 mL of a 1-N sodium hydroxide aqueous solution and with a saturated saline solution in this order. The organic layer was dried over sodium sulfate, and then the solvent was distilled off. Thus, the title compound (2.487 g (87%)) was obtained.

$^1$H-NMR (CDCl$_3$, δ): 1.4-1.6 (2H, m), 1.8-2.0 (2H, m), 2.4-2.7 (2H, m), 2.9-3.2 (2H, m), 3.3-3.6 (1H, m), 3.74 (3H, s), 5.64 (1H, s), 6.00 (1H, d, J=1.9 Hz), 7.1-7.5 (5H, m)

MS (m/z): 305 (M$^+$)

Production Example 178

(±)-(4-Chlorophenyl)(thiazol-2-yl)methanol

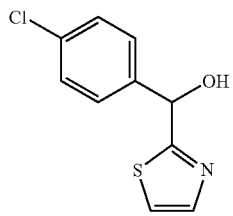 [SMILES: OC(c1ccc(Cl)cc1)c1nccs1]

A solution of 5.003 g of 2-bromothiazole in 20 mL of diethyl ether was added dropwise to 23 mL of a 1.6-M n-butyllithium/n-hexane solution in 20 mL of diethyl ether under cooling at −30° C. After the mixture was stirred for 1.1 hours, a solution of 5.538 g of 4-chlorobenzaldehyde in 20 mL of diethyl ether was added dropwise thereto. It took 1.2 hours to bring back to a room temperature, and then the reaction solution was poured into a mixture of 72 mL of 1-N hydrochloric acid and ice. The insoluble matter was removed by filtration, and then the organic layer was collected by separation. The organic layer was washed with a saturated sodium bicarbonate water and with saturated saline solution in this order. The organic layer was dried over magnesium sulfate, and then the solvent was distilled off. The raw product was purified by silica gel column chromatography (hexane/ethyl acetate (volume ratio)=2:1 to 3:2) to give the title compound (4.425 g (64%)).

$^1$H-NMR (CDCl$_3$, δ): 3.55 (1H, d, J=3.9 Hz), 6.04 (1H, d, J=3.5 Hz), 7.2-7.5 (5H, m), 7.73 (1H, d, J=3.1 Hz)

MS (m/z): 225 (M$^+$)

Production Examples 179, 182, 208, 211

Compounds (12) shown in Table 82 were obtained according to the same procedure as in Production Example 175 any one of the compounds synthesized in Production Examples 178 and 181 or a known compound was used instead of (±)-(4-chlorophenyl)(2-methyl-2H-pyrazol-3-yl)methanol.

TABLE 82

| | Compound (12) | | |
|---|---|---|---|
| Compound (12a) | | Chemical formula | $^1$H-NMR (CDCl$_3$, δ) |
| Production Example 178 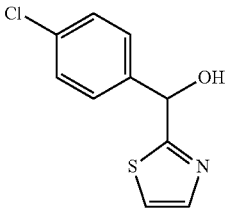 [SMILES: OC(c1ccc(Cl)cc1)c1nccs1] | | Production Example 179 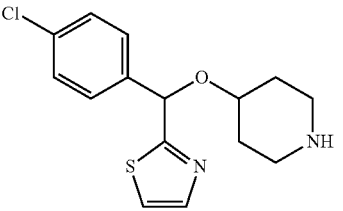 [SMILES: Clc1ccc(C(OC2CCNCC2)c2nccs2)cc1] | — |
| Production Example 181 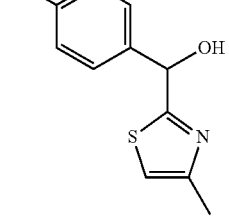 | | Production Example 182 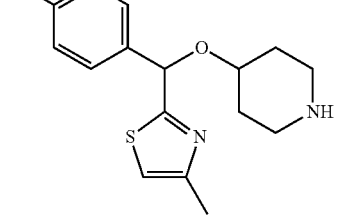 | — |
| 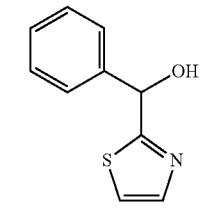 [SMILES: OC(c1ccccc1)c1nccs1] | | Production Example 208 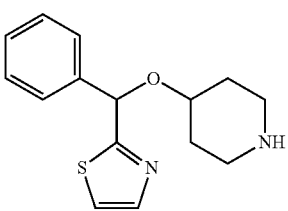 [SMILES: c1ccc(C(OC2CCNCC2)c2nccs2)cc1] | 1.6-1.8 (2H, m), 1.9-2.0 (2H, m), 2.6-2.7 (2H, m), 3.1-3.2 (2H, m), 3.6-3.7 (1H, m), 5.01 (1H, brs), 5.84 (1H, s), 7.2-7.4 (4H, m), 7.4-7.5 (2H, m), 7.70 (1H, d, J = 3.2 Hz) |
| 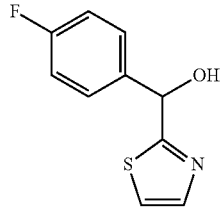 | | Production Example 211 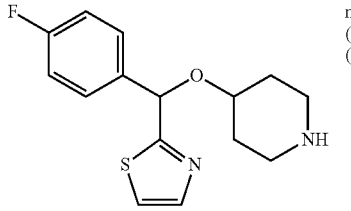 | 1.5-1.7 (3H, m), 1.8-2.0 (2H, m), 2.5-2.7 (2H, m), 3.0-3.2 (2H, m), 3.5-3.7 (1H, m), 5.83 (1H, s), 7.0-7.2 (3H, m), 7.30 (1H, d, J = 3.0 Hz), 7.4-7.5 (1H, m), 7.71 (1H, d, J = 3.0 Hz) |

Production Example 181

(±)-(4-Chlorophenyl)(4-methylthiazol-2-yl)methanol

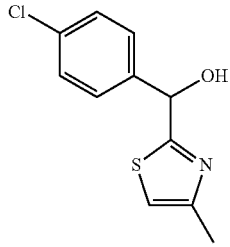

A solution of 5.949 g of 4-methyithiazole in 5 mL of tetrahydrofuran was added dropwise to 38 mL of a 1.6-M n-butyllithium/n-hexane solution in 6 mL of tetrahydrofuran under cooling at −60° C. After the mixture was stirred for 1.5 hours, a solution of 8.434 g of 4-chlorobenzaldehyde in 20 mL of tetrahydrofuran was added dropwise thereto. After the mixture was stirred at the same temperature for 1.8 hours, it took 2 hours to bring back to a room temperature, and then 15 mL of 50% ethanol aqueous solution was added to the mixture. The reaction solution was poured into water, and diethyl ether was added thereto, and the resulting mixture was subjected to extraction. The extract was washed with a saturated saline solution and then dried over magnesium sulfate. The solvent was distilled off, and then the raw product was purified by silica gel column chromatography (hexane/ethyl acetate (volume ratio)=2:1 to 1:1) to give the title compound (10.602 g (74%)).

$^1$H-NMR (CDCl$_3$, δ): 2.40 (3H, s), 3.68 (1H, d, J=3.9 Hz), 5.98 (1H, d, J=3.5 Hz), 6.83 (1H, d, J=0.8 Hz), 7.2-7.5 (4H, m)

MS (m/z): 239 (M$^+$)

Production Example 187

Ethyl 4-(4-benzhydryloxypiperidin-1-ylmethyl)-1H-pyrazole-3-carboxylate

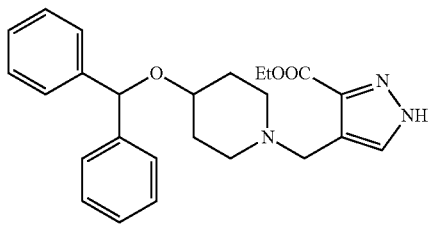 [SMILES: O=C(O)c1n[nH]cc1CN1CCC(OC(c2ccccc2)c2ccccc2)CC1]

4-Benzhydryloxypiperidine (1.0 g, 3.7 mmol) synthesized in Production Example 1, ethyl 4-formylpyrazole-3-carboxylate (630 mg, 3.7 mmol), and dichloromethane (30 mL) were fed to the system, and the atmosphere of the system was replaced with argon gas, and the system was cooled by ice. At 0° C., sodium triacetoxyborohydride (1.2 g, 5.6 mmol) was added thereto, and the mixture was heated to a room temperature. After the disappearance of the raw material was confirmed by TLC, the reaction mixture was quenched with a saturated sodium hydrogen carbonate solution. The reaction mixture was separated into a water layer and an organic layer, and the water layer was extracted with dichloromethane again. The extract was combined to the organic layer. The combined organic layer was dried over sodium sulfate, and the solvent was distilled off. The resulting residue was purified by silica gel column chromatography (hexane:ethyl acetate=1:1) to give the title compound (1.3 g, 83%).

$^1$H-NMR (CDCl$_3$, δ): 1.38 (3H, t, J=7.0 Hz), 1.6-1.8 (2H, m), 1.8-2.0 (2H, m), 2.1-2.3 (2H, m), 2.7-2.9 (2H, m), 3.3-3.5 (1H, m), 3.6-3.8 (2H, m), 4.37 (3H, q, J=7.0 Hz), 5.50 (1H, s), 7.2-7.4 (10H, m), 7.60 (1H, brs)

MS (m/z): 419 (M$^+$)

Example 139

4-(4-Benzhydryloxypiperidin-1-ylmethyl)-1H-pyrazole-3-carboxylic acid

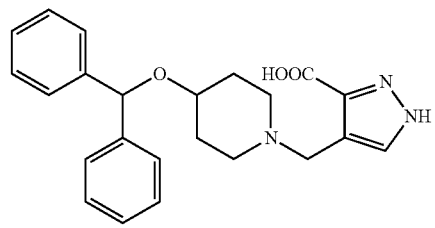

The title compound was obtained according to the same procedure as in Example 1 except that ethyl 4-(4-benzhydryloxypiperidin-1-ylmethyl)-1H-pyrazole-3-carboxylate synthesized in Production Example 187 was used instead of the compound synthesized in Production Example 2.

$^1$H-NMR (CDCl$_3$, δ): 1.7-2.2 (6H, m), 2.9-3.3 (4H, m), 3.7-4.0 (3H, m), 5.42 (1H, s), 7.2-7.4 (10H, m), 7.54 (1H, brs)

MS (m/z): 390 (M$^+$−1)

Production Example 191

1-Benzhydrylazetidin-3-ol

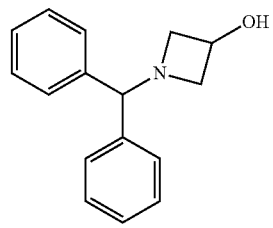 [SMILES: OC1CN(C(c2ccccc2)c2ccccc2)C1]

Benzhydrylamine (12 g, 64 mmol), epichlorohydrin (5.9 g, 64 mmol), and 30 mL of methanol were stored under argon in a light-shielded state for 3 days. Next, the mixture was heated under reflux for 3 days in an oil bath. After the completion of the reaction was confirmed by TLC, the solvent was distilled off. To the resulting residue was added acetone, and the mixture was filtrated. The matter separated by filtration was dissolved in ether and washed with a 6-N sodium hydroxide aqueous solution. The organic layer was dried over sodium sulfate, the solvent was distilled off. Thus the title compound (1.3 g, 83%) was obtained.

$^1$H-NMR (CDCl$_3$, δ): 2.38 (1H, brs), 2.8-3.0 (2H, m), 3.4-3.7 (2H, m), 4.34 (1H, s), 4.3-4.5 (1H, m), 7.1-7.5 (10H, m)

MS (m/z): 238 (M$^+$−1)

Production Example 192

1-Benzhydryl-3-benzhydryloxyazetidine

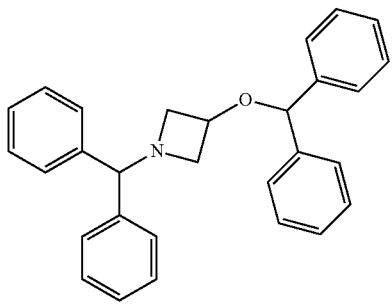 [SMILES: c1ccc(C(OC2CN(C(c3ccccc3)c3ccccc3)C2)c2ccccc2)cc1]

The title compound was obtained according to the same procedure as in Production Example 1 except that 1-benzhydrylazetidin-3-ol synthesized in Production Example 191 was used instead of 4-hydroxypiperidine.

$^1$H-NMR (CDCl$_3$, δ): 2.8-3.0 (2H, m), 3.3-3.5 (2H, m), 4.1-4.3 (1H, m), 4.34 (1H, s), 5.29 (1H, s), 7.1-7.5 (20H, m)

MS (m/z): 483 (M$^+$)

Production Example 193

3-Benzhydryloxyazetidine

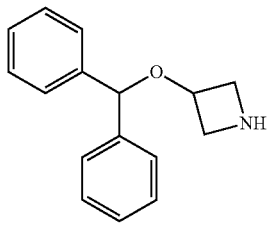 [SMILES: c1ccc(C(OC2CNC2)c2ccccc2)cc1]

In 30 mL of dichloromethane, 1-benzhydryl-3-benzhydryloxyazetidine (1.8 g, 4.5 mmol) obtained in Production Example 192 was dissolved, and the mixture was cooled by ice. Then, a solution of 1-chloroethyl 1-chloroformate (1.6 g, 11 mmol) in dichloromethane was added dropwise thereto at 0° C. After the completion of the dropping, the mixture was stirred at a room temperature overnight. After the completion of the reaction was confirmed by TLC, the reaction solution was concentrated, and methanol was added to the resulting residue. The resulting mixture was stirred at a room temperature. After the completion of the reaction was confirmed by TLC, the reaction solution was concentrated, and the residue was purified by silica gel column chromatography (chloroform:methanol (volume ratio)=10:1) to give the title compound (0.79 g, 74%).

$^1$H-NMR (CDCl$_3$, δ): 3.8-4.0 (4H, m), 4.5-4.7 (1H, m), 5.32 (1H, s), 7.1-7.4 (10H, m)

MS (m/z): 240 (M$^+$+1)

Production Example 195

(±)-(4-Fluorophenyl)phenylmethanol

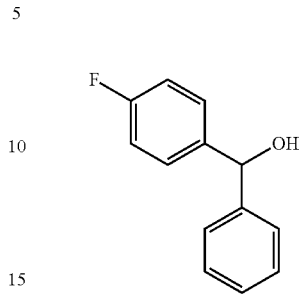

Benzaldehyde (8.5 g, 80 mmol) was dissolved in 100 mL of tetrahydrofuran and cooled in an ice bath. Then, a 1.0-M solution (88 mL, 88 mmol) of 4-fluorophenylmagnesium bromide in tetrahydrofuran was added dropwise thereto at 0° C. After the dropping was completed, the mixture was heated to a room temperature, and the completion of the reaction was confirmed by TLC. After the completion of the reaction, the reaction mixture was poured into 5% hydrochloric acid and extracted with ethyl acetate. The organic layer was washed with water and dried over sodium sulfate, and the solvent was distilled off. The resulting residue was purified by silica gel column chromatography (chloroform/ethanol (volume ratio) =10:1) to give the title compound (13 g, 81%).

$^1$H-NMR (CDCl$_3$, δ): 2.27 (1H, s), 5.81 (1H, s), 7.01 (2H, t, J=9.0 Hz), 7.2-7.5 (7H, m)

MS (m/z): 202 (M$^+$)

Production Example 196

(±)-1-(Chlorophenylmethyl)-4-fluorobenzene

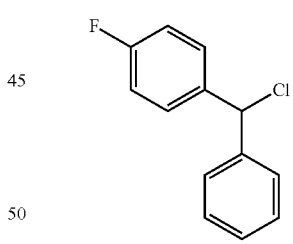

In dichloromethane (30 mL), (±)-(4-fluorophenyl)phenylmethanol (2.1 g, 10 mmol) synthesized in Production Example 195 was dissolved, and thionyl chloride (5.1 g, 42 mmol) was added dropwise thereto at a room temperature. After the completion of the dropping, the mixture was heated under reflux, and the completion of the reaction was confirmed by TLC. After the completion of the reaction, the reaction mixture was concentrated, diluted with ethyl acetate, and washed with water. The organic layer was dried over magnesium sulfate, and the solvent was distilled off. Thus the title compound (2.1 g, 94%) was obtained.

$^1$H-NMR (CDCl$_3$, δ): 6.13 (1H, s), 6.9-7.1 (2H, m), 7.2-7.5 (7H, m)

MS (m/z): 220 (M$^+$)

Production Example 199

Ethyl (±)-4-(cyclohexylphenylmethoxy)piperidine-1-carboxylate

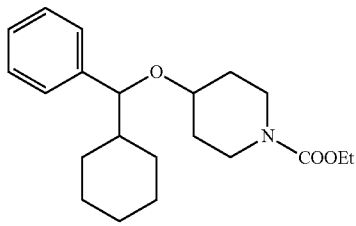 [SMILES: CCOC(=O)N1CCC(OC(c2ccccc2)C2CCCCC2)CC1]

Cyclohexyl phenyl ketone (5.0 g, 27 mmol) was dissolved in ethanol (50 mL) and cooled by ice. Sodium borohydride (510 mg, 13.5 mmol) was added thereto at 0° C. The completion of the addition, the mixture was heated to a room temperature, and the disappearance of the raw material was confirmed by TLC. The reaction solution was concentrated and then diluted with water, and the diluted solution was neutralized with a 1-N hydrochloric acid aqueous solution. Ethyl acetate was added thereto, the mixture was subjected to extraction. Then the extract was dried over sodium sulfate. The solvent was distilled off, and the residue was used for the next step without purification. The resulting viscous oil was dissolved in dichloromethane (10 mL), and thionyl chloride (10 mL, 140 mmol) was added dropwise thereto at a room temperature. After the dropping was completed, the completion of the reaction was confirmed by TLC. After the completion of the reaction, toluene was added to the reaction mixture, and unreacted thionyl chloride was distilled off. The resulting light-yellow oil and 1-carboethoxy-4-hydroxypiperidine (2.1 g, 12 mmol) were mixed, and the mixture was stirred at an oil bath temperature of 130° C. overnight. After the completion of the reaction was confirmed by TLC, the reaction mixture was allowed to cool down. Ethyl acetate was added to the resulting residue, and then the resulting mixture was washed with water. The organic layer was dried over sodium sulfate, and then the solvent was distilled off. Thus a brown oil was obtained. The resulting oil was purified by silica gel column chromatography (hexane/ethyl acetate (volume ratio)=10:1) to give the title compound (5.1 g, 510).

$^1$H-NMR (CDCl$_3$, δ): 0.8-1.4 (3H, m), 1.4-2.2 (14H, m), 3.0-3.3 (3H, m), 3.3-3.4 (1H, m), 3.5-3.8 (2H, m), 3.99 (1H, d, J=8 Hz), 4.10 (2H, q, J=7.0 Hz), 7.1-7.4 (5H, m)

MS (m/z): 345 (M$^+$)

Production Example 200

(±)-4-(Cyclohexylphenylmethoxy)piperidine

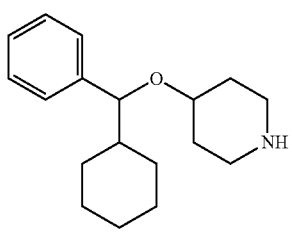

Ethyl (±)-4-(cyclohexylphenylmethoxy)piperidine-1-carboxylate (1.2 g, 3.5 mmol) obtained in Production Example 199 was dissolved in ethanol (10 mL), and a 30% sodium hydroxide aqueous solution (2.0 mL) was added thereto. The mixture was heated under reflux. After the completion of the reaction was confirmed by TLC, the reaction mixture was allowed to cool down. The reaction solution was concentrated and then diluted with water, and the diluted solution was neutralized with 1-N hydrochloric acid. Ethyl acetate was added to the resulting residue, and the resulting mixture was subjected to extraction. The organic layer was washed with water, and then the organic layer was dried over magnesium sulfate. The solvent was distilled off. The resulting compound was used for the next reaction without purification.

$^1$H-NMR (CDCl$_3$, δ): 0.8-2.0 (14H, m), 2.0-2.2 (1H, m), 2.4-2.6 (1H, m), 2.9-3.1 (2H, m), 3.1-3.3 (1H, m), 3.1-3.3 (1H, m), 3.9-4.2 (2H, m), 7.1-7.4 (5H, m)

MS (m/z): 273 (M$^+$)

Pharmacological Test Procedure and Test Results

Hereinafter, the pharmacological test procedure for the validity and safety of the heterocyclic compound or the salt thereof of the present invention and the results thereof will be explained.

Test Example 1

Rat H$_1$ Receptor Affinity Test

An H$_1$ receptor membrane preparation was prepared from rat cerebrum. To 100 μL of the rat H$_1$ receptor membrane preparation, 50 μL of an incubation buffer, 50 μL of a 800 μmol/L promethazine solution (manufactured by SIGMA-ALDRICH), or 50 μL of a solution of each test compound in an incubation buffer was added; the incubation buffer (pH 7.4) had a composition composed of disodium monohydrogen phosphate (50 mmol/L; manufactured by Wako Pure Chemical Industries, Ltd.) and potassium dihydrogen phosphate (50 mmol/L; manufactured by Wako Pure Chemical Industries, Ltd.). To the resulting each sample, 50 μL of 8 nmol/L [$^3$H]-pyrilamine (manufactured by PerkinElmer) (final concentration: 2 nmol/L) was added and mixed. After the mixture was incubated at a room temperature for 30 minutes, the reaction solution was collected on a glass filter by a cell harvester (manufactured by Molecular Devices), and then the filter was washed with the incubation buffer. The glass filter was cut off and transferred in a vial. To the vial was added 5 mL of a scintillator (manufactured by National Diagnostics), and the mixture was shaken for not less than one hour. Thereafter, the radioactive concentration was measured by a liquid scintillation counter. The histamine H$_1$ receptor binding inhibition rate (%) of each test compound relative to the control was calculated, and the value of the 50% inhibition concentration (IC$_{50}$) was determined. The results are shown in Table A and Table B.

Test Example 2

Human H$_1$ Receptor Affinity Test

Chinese hamster ovarian cells (CHO cells) having human H$_1$ receptor forcibly express were purchased and used as an H$_1$ receptor membrane preparation. To 100 μL of the human H$_1$ receptor membrane preparation, 50 μL of an incubation buffer, 50 μL of a 800 μmol/L promethazine solution, or 50 μL of a solution of each test compound in an incubation buffer was added; the incubation buffer (pH 7.4) had a composition compose of Tris-hydrochloric acid (50 mmol/L; manufactured by Wako Pure Chemical Industries, Ltd.) and magnesium chloride (5 mmol/L; manufactured by Wako Pure Chemical Industries, Ltd.). To the resulting each sample, 50 µL of 8 nmol/L [$^3$H]-pyrilamine (final concentration: 2 nmol/L) was added and mixed. After the mixture was incubated at a room temperature for 3 hours, the reaction solution was collected on a glass filter treated with 0.3% polyethyleneimine by a cell harvester, and then the filter was washed with a washing buffer; the washing buffer (pH 7.4) had a composition composed of Tris-hydrochloric acid (50 mmol/L). The glass filter was cut off and transferred in a vial. To the vial was added 5 mL of a scintillator (manufactured by National Diagnostics), and the mixture was shaken for not less than one hour. Thereafter, the radioactive concentration was measured by a liquid scintillation counter. The histamine $H_1$ receptor binding inhibition rate (%) of each test compound relative to the control was calculated, and the value of the 50% inhibition concentration ($IC_{50}$) was determined. The results are shown in Table A and Table B.

TABLE A

| Example No. | Rat $H_1$ receptor $IC_{50}$ (nmol/L) | Human $H_1$ receptor $IC_{50}$ (nmol/L) |
|---|---|---|
| 1 | 81 | 14 |
| 2 | 25 | 10 |
| 3 | 55 | — |
| 4 | 39 | — |
| 5 | 7 | 10 |
| 6 | 38 | 11 |
| 11 | 280 | 22 |
| 17 | 110 | — |
| 18 | 89 | — |
| 20 | 69 | 29 |
| 22 | 5.7 | 13 |
| 23 | 36 | 30 |
| 24 | 8.2 | 9.2 |
| 25 | 12 | 22 |
| 26 | 83 | — |
| 27 | 31 | 8.9 |
| 29 | 63 | — |
| 30 | 42 | 15 |
| 35 | 61 | 15 |
| 36 | 99 | — |
| 37 | 75 | 12 |
| 39 | 72 | 6.8 |
| 40 | 1.2 | 26 |
| 41 | 19 | 18 |
| 42 | 24 | 19 |
| 43 | 18 | 12 |
| 44 | 20 | — |
| 46 | 68 | — |
| 48 | 53 | 25 |

TABLE B

| Example No. | Rat $H_1$ receptor $IC_{50}$ (nmol/L) | Human $H_1$ receptor $IC_{50}$ (nmol/L) |
|---|---|---|
| 49 | 89 | 17 |
| 51 | — | 4.9 |
| 52 | — | 6.7 |
| 53 | — | 14 |
| 68 | 40 | — |
| 70 | 28 | 14 |
| 71 | 16 | 14 |
| 72 | — | 8.9 |
| 75 | 67 | 23 |
| 80 | — | 17 |
| 84 | — | 17 |
| 85 | — | 22 |
| 86 | — | 16 |
| 87 | — | 21 |
| 88 | — | 21 |

TABLE B-continued

| Example No. | Rat $H_1$ receptor $IC_{50}$ (nmol/L) | Human $H_1$ receptor $IC_{50}$ (nmol/L) |
|---|---|---|
| 89 | — | 7.5 |
| 116 | — | 17 |
| 117 | — | 24 |
| 124 | — | 8.4 |
| 128 | — | 6.1 |
| 129 | — | 5.1 |
| 131 | — | 15 |
| 143 | — | 24 |
| 154 | — | 13 |
| 155 | — | 10 |
| Olopatadine | 50 | 5.7 |
| Cetirizine | 88 | 16 |
| Bepotastine | 170 | 20 |
| Loratadine | NT | 88 |
| Fexofenadine | 480 | 120 |

As apparent from Table A and Table B, the compounds of the present invention showed excellent binding inhibitory effect on rat histamine $H_1$ receptor and human histamine $H_1$ receptor.

Test Example 3

Histamine-Induced Skin Reaction Test in Rat

Each rat was sheared the day before test and fasted overnight. each test compound suspended in a 0.5% (W/V) CMC—Na aqueous solution was orally administered to the rat in a dose of 3 mg/kg. One hour after the administration, a 1% Evans Blue physiological saline solution (Tokyo Chemical Industry Co., Ltd.) was administered into the caudal vein in a dose of 5 mL/kg, and immediately histamine 10 µg/0.1 mL/site (manufactured by Wako Pure Chemical Industries, Ltd.) was intradermally administered into the dorsum. Thirty minutes after the administration, the rat was anesthetized with diethyl ether and then euthanized by cervical dislocation. The skin was ablated, and the major axis and minor axis of a spot of the pigment exuded into the skin were measured to calculate the area of the pigment. For each of test compounds that showed the inhibitory effect of about 40% or more by the oral administration in dose of 3 mg/kg, low, middle and high doses were further set, and the 50% inhibition dose ($ID_{50}$ value) was determined. The results are shown in Table C.

Test Example 4

Skin Reaction Test in Mouse

Each mouse was sheared the day before test and fasted overnight. A low, middle or high dose of each test compound suspended in a 0.5% (W/V) CMC-Na aqueous solution was orally administered to the mouse. One hour after the administration, a 1% Evans Blue physiological saline solution (Tokyo Chemical Industry Co., Ltd.) was administered into the caudal vein in a dose of 10 mL/kg, and immediately histamine 3 µg/50 µL/site was intradermally administered into the dorsum. Thirty minutes after the administration, the mouse was anesthetized with diethyl ether and then euthanized by cervical dislocation. The skin was ablated, and the major axis and minor axis of a spot of the pigment exuded into the skin were measured to calculate the area of the pigment. Based on the pigment area, the 50% inhibition dose ($ID_{50}$ value) was determined. The results are shown in Table C.

TABLE C

| Example No. | Skin reaction test in rat $ID_{50}$ (mg/kg) | Skin reaction test in mouse $ID_{50}$ (mg/kg) |
|---|---|---|
| 2 | 3.4 | 0.1 |
| 5 | 1.8 | 0.11 |
| 6 | 0.6 | — |
| 11 | 0.3 | 0.01 |
| 18 | 0.2 | — |
| 22 | 0.5 | 0.01 |
| 23 | 1.8 | — |
| 27 | — | 0.03 |
| 37 | 3.2 | 0.06 |
| 39 | 1.3 | 0.04 |
| 42 | 1.8 | — |
| 48 | 2.9 | 0.05 |
| 49 | 1.5 | — |
| 51 | — | 0.07 |
| 52 | — | 0.1 |
| 67 | 1.2 | 0.09 |
| 70 | 1.6 | 0.12 |
| 71 | 0.6 | 0.07 |
| 72 | — | 0.06 |
| 74 | 2.1 | — |
| 75 | 1.2 | — |
| 87 | — | 0.06 |
| 129 | — | 0.04 |
| Bepotastine | 0.5 | 0.02 |
| Loratadine | 1.1 | 0.07 |
| Fexofenadine | 20 | 0.54 |

As apparent from Table C, it proved that the compounds of the present invention showed the inhibitory effect of histamine-induced vascular hypermeability in rat and mouse. Therefore, it is clear that the compounds of the present invention have excellent antihistaminic effect.

Test Example 5

Inhibitory Effects on Mouse IgE-Dependent Ear Edema Model

To each mouse, 0.25 mL of an anti-DNP-IgE antibody (manufactured by SIGMA-ALDRICH) was intravenously administered for passive sensitization. On the day following the administration, an antigen (DNFB solution; manufactured by Wako Pure Chemical Industries, Ltd.) was applied on the right ear to induce dermatitis (ear swelling). One hour, 24 hours and 7 days after the application of the antigen, the thickness of the right ear was measured by a thickness measuring apparatus (dial thickness gauge). The dose of each test compound was one-third as large as each $ID_{50}$ value obtained in the histamine skin reaction test in rat mouse; the test compound was orally administered twice a day, that is, one hour before and 6 hours after the application of the antigen. The thickness of the right ear before the sensitization was measured beforehand; the inhibition rates of the swelling in immediate phase, late phase, and very late phase were calculated. The results are shown in Table D.

TABLE D

| Example No. | Dose (mg/kg × twice) | Inhibitory effects in each allergic reaction phase | | |
|---|---|---|---|---|
| | | Immediate phase | Late phase | Very late phase |
| 2 | 1 | ++ | ++ | + |
| 11 | 0.1 | ++ | ++ | ++ |

TABLE D-continued

| Example No. | Dose (mg/kg × twice) | Inhibitory effects in each allergic reaction phase | | |
|---|---|---|---|---|
| | | Immediate phase | Late phase | Very late phase |
| 39 | 0.4 | ++ | ++ | ++ |
| Olopatadine | 0.01 | ++ | — | + |

++ Inhibitory rate 45 to 25%,
+ Inhibitory rate 24 to 10%,
− Inhibitory rate less than 10%

As apparent from Table D, the compounds of the present invention showed the inhibitory effect on the ear edema observed in immediate phase, late phase, and very late phase. Therefore, it is clear that the compounds of the present invention show excellent antiinflammatory effect.

Test Example 6

Effects on Mouse Antigen-Induced Pulmonary Eosinophilic Infiltration Model

To each mouse, 0.5 mL of a physiological saline solution containing 8 μg of ovalbumin (OVA) (manufactured by SIGMA-ALDLICH) and 2 mg of aluminum hydroxide gel was intraabdominally administered twice (administered on Day 0 (the first day) and Day 5 (the sixth day)). One week after the final sensitization, a 0.5% OVA physiological saline solution was inhaled to the mouse by a nebulizer in the morning and afternoon for one hour each time. The dose of each test compound was 5 times as large as each $ID_{50}$ value obtained in the skin reaction test in rat; the test compound was orally administered twice a day that is, 30 minutes before the antigen challenge in the morning and 30 minutes before the antigen challenge in the afternoon. About 48 hours after the antigen challenge, the mouse was euthanized by pentobarbital deep anesthesia, and the bronchoalveolar lavage fluid (BALF) was collected. The total number of cells in the BALF was counted. Then, a smear sample was produced and subjected to May-Grunwald-Giemsa staining to measure the composition rate of monocyte, eosinophil and neutrophil in the smear sample. Based on the data, the count of eosinophil in mouse was calculated. The results are shown in FIGS. 1 to 3.

Figure 2:
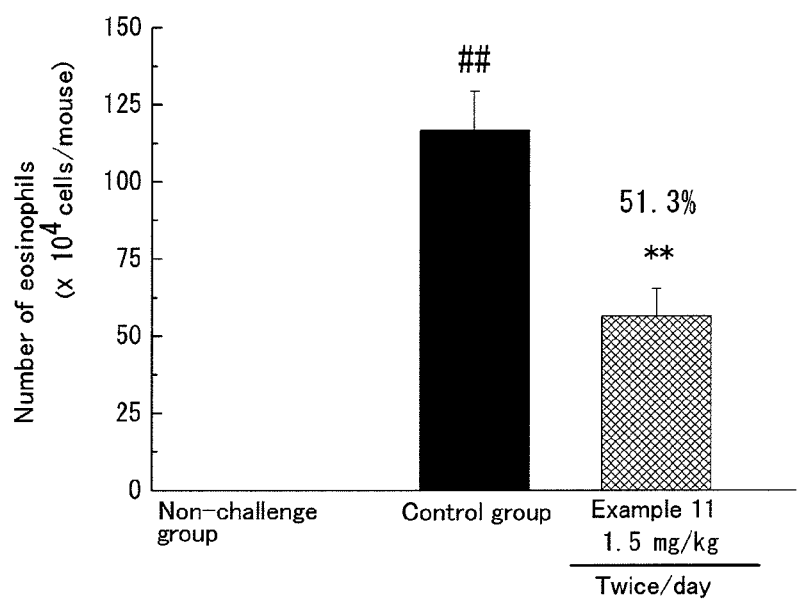
FIG. 2 is a graph showing results of the compound of Example 11 in Test Example 6.
Figure 3:
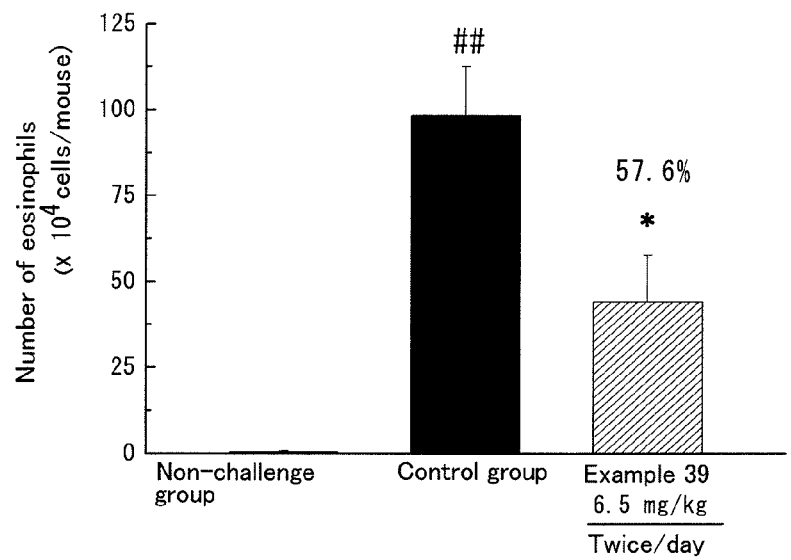
FIG. 3 is a graph showing results of the compound of Example 39 in Test Example 6.

As apparent from FIGS. 1 to 3, the compounds of the present invention showed the inhibitory effect on the antigen-induced pulmonary eosinophilic infiltration. Therefore, it is clear that the compounds of the present invention show excellent antiinflammatory effect. In FIGS. 1 to 3, the non-challenge group indicates a group to which the 0.5% OVA physiological saline solution was not inhaled (a group in which the antigen challenge was not performed); the control group indicates a group to which a 0.5% CMC sodium solution was administered as a test compound. The count of eosinophil in the non-challenge group is almost zero.

Test Example 7

Effects on Locomotor Activity in Mouse

To each mouse fasted overnight, each test compound suspended in a 0.5% (W/V) CMC—Na aqueous solution was orally administered. Immediately, each group (3 mice per group) was accommodated in a separate polycarbonate cage. The cumulative locomotor activity was measured every 5 minutes from immediately after the administration up to 2 hour after the administration by a locomotor activity measuring apparatus. The dose of each test compound was 50 times as large as each $ID_{50}$ value obtained in the histamine skin reaction test in rat mouse. The results are shown in FIGS. 4 to 6.

Figure 4:
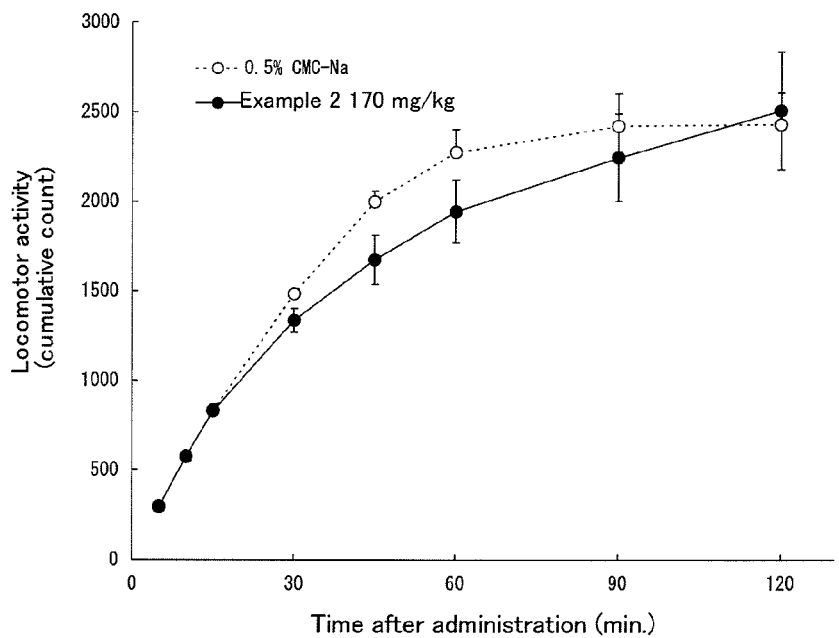
FIG. 4 is a graph showing results of the compound of Example 2 in Test Example 7.
Figure 5:
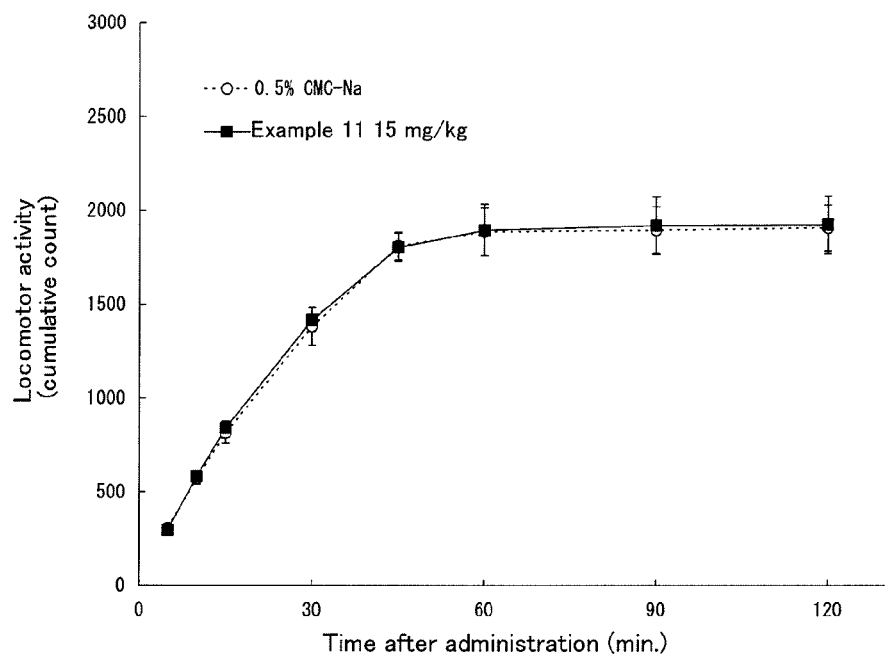
FIG. 5 is a graph showing results of the compound of Example 11 in Test Example 7.
Figure 6:
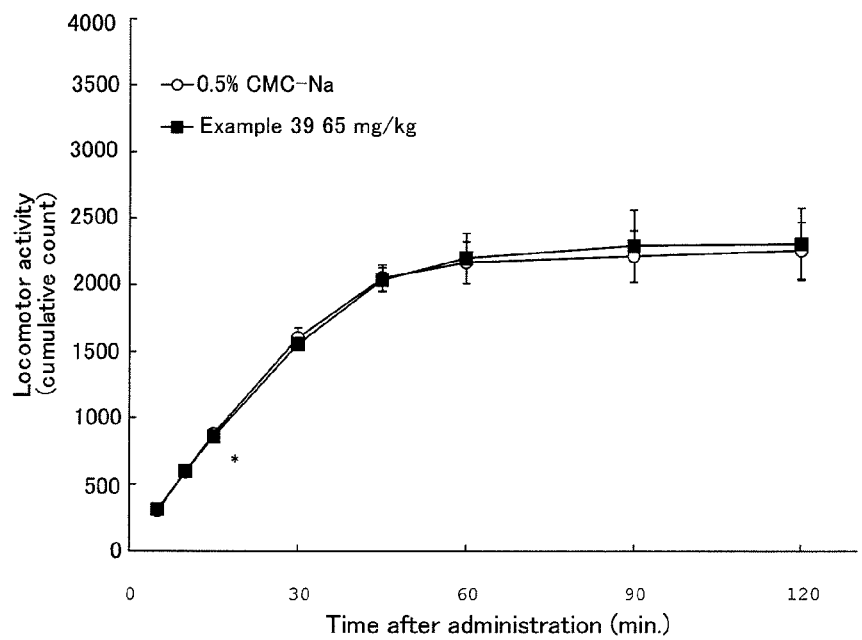
FIG. 6 is a graph showing results of the compound of Example 39 in Test Example 7.

As apparent from FIGS. 4 to 6, the compounds of the present invention did not affect the locomotor activity in mouse even when each compound was administered in a dose of 50 times as large as each $ID_{50}$ value obtained in the histamine skin reaction test in mouse. Therefore, the compounds of the present invention have apparently reduced central nervous system effects and are highly safe without side effects such as sleepiness.

Test Example 8

Inhibitory Effects on Mouse IgE-Dependent Ear Edema Model

To each mouse, 0.25 mL of an anti-DNP-IgE antibody (manufactured by SIGMA-ALDRICH) was intravenously administered for passive sensitization. On the day following the administration, an antigen (DNFB solution; manufactured by Wako Pure Chemical Industries, Ltd.) was applied on the right ear to induce dermatitis (ear swelling). One hour, 24 hours and 7 days after the application of the antigen, the thickness of the right ear was measured by a thickness measuring apparatus (dial thickness gauge). The dose of each test compound was 5 or 10 times as large as each $ID_{50}$ value obtained in the histamine skin reaction test in mouse; the test compound was orally administered twice a day, that is, one hour before and 6 hours after the application of the antigen. The thickness of the right ear before the sensitization was measured beforehand; the inhibition rates of the swelling in immediate phase, late phase, and very late phase were calculated. The results are shown in Table E.

TABLE E

| Example No. | Dose (mg/kg × twice) | Inhibitory effects in each allergic reaction phase | | |
|---|---|---|---|---|
| | | Immediate phase | Late phase | Very late phase |
| 2 | 1 (10 times) | ++ | ++ | + |
| 11 | 0.05 (5 times) | ++ | ++ | ++ |
| 27 | 0.15 (5 times) | ++ | ++ | ++ |
| 39 | 0.4 (10 times) | ++ | ++ | ++ |
| 87 | 0.3 (5 times) | ++ | ++ | + |
| 129 | 0.4 (10 times) | ++ | ++ | ++ |
| Olopatadine | 1 (250 times) | ++ | − | − |

++ Inhibitory rate 45 to 20%,
+ Inhibitory rate 19 to 10%,
− Inhibitory rate less than 10%

As apparent from Table E, the compounds of the present invention showed the inhibitory effect on the ear edema observed in each of immediate phase, late phase, and very late phase at a lower dose. Therefore, it is clear that the compounds of the present invention show excellent antiinflammatory effect.

Test Example 9

Effects on Mouse Antigen-Induced Pulmonary Eosinophilic Infiltration Model

To each mouse, 0.5 mL of a physiological saline solution containing 8 μg of ovalbumin (OVA) (manufactured by SIGMA-ALDICH) and 2 mg of aluminum hydroxide gel was intraabdominally administered twice (administered on Day 0 (the first day) and Day 5 (the sixth day)). One week after the final sensitization, a 0.5%; OVA physiological saline solution was inhaled to the mouse by a nebulizer in the morning and afternoon for one hour each time. The dose of each test compound was 30 to 170 times as large as each $ID_{50}$ value obtained in the skin reaction test in mouse; the test compound was orally administered twice a day that is, 30 minutes before the antigen challenge in the morning and 30 minutes before the antigen challenge in the afternoon. About 48 hours after the antigen challenge, the mouse was euthanized by pentobarbital deep anesthesia, and the bronchoalveolar lavage fluid (BALF) was collected. The total number of cells in the BALF was counted. Then, a smear sample was produced and subjected to May-Grunwald-Giemsa staining to measure the composition rate of monocyte, eosinophil and neutrophil in the smear sample. Based on the data, the count of eosinophil in mouse was calculated. The results are shown in FIGS. 7 to 9.

Figure 7:
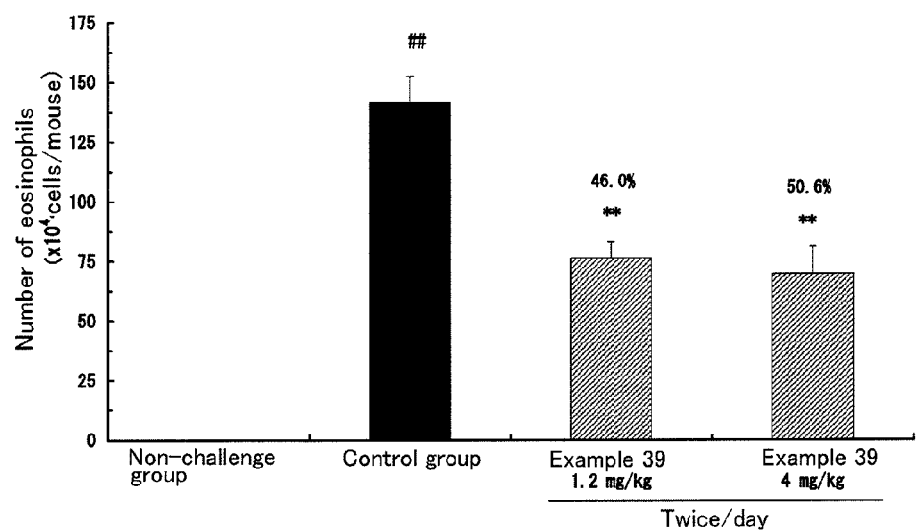
FIG. 7 is a graph showing results of the compound of Example 2 in Test Example 9.
Figure 8:
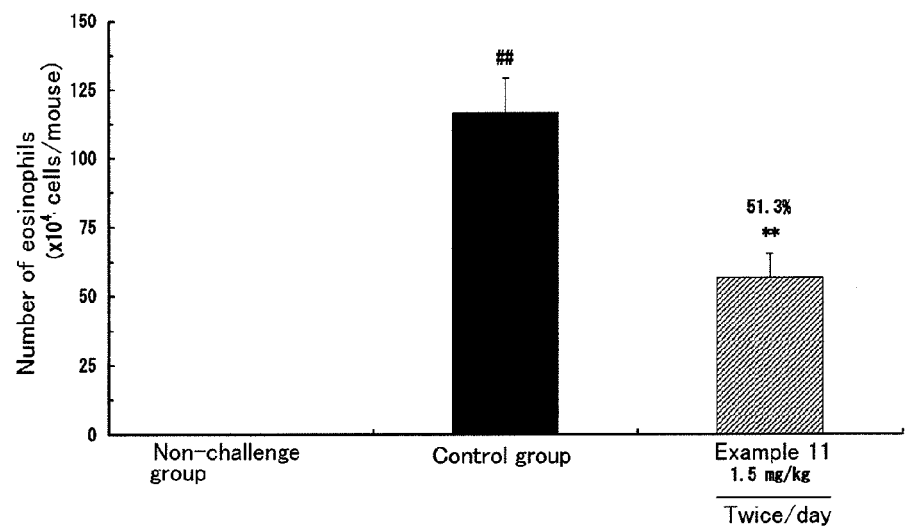
FIG. 8 is a graph showing results of the compound of Example 11 in Test Example 9.
Figure 9:
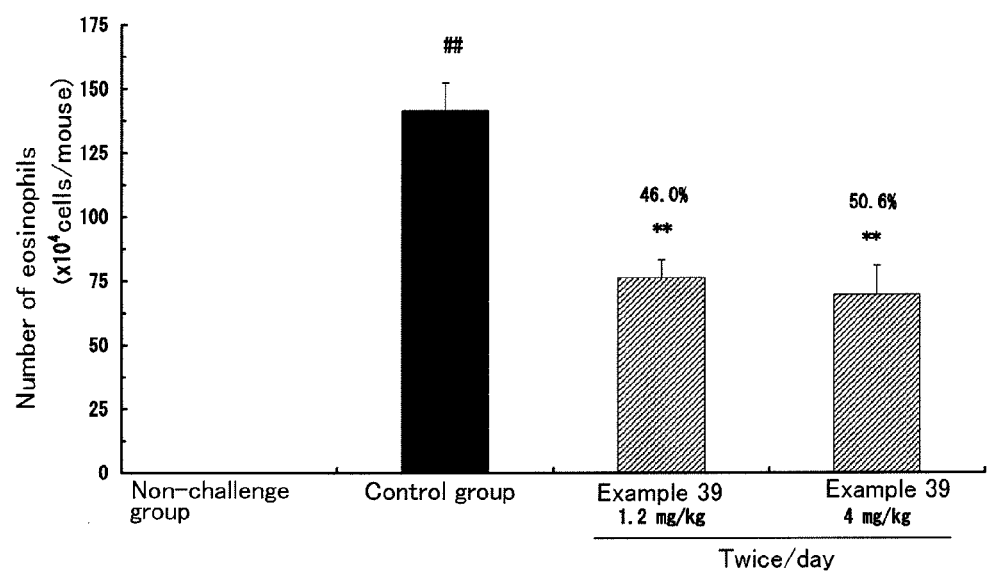
FIG. 9 is a graph showing results of the compound of Example 39 in Test Example 9.

As apparent from FIGS. 7 to 9, the compounds of the present invention showed the inhibitory effect on the antigen-induced pulmonary eosinophilic infiltration. Therefore, it is clear that the compounds of the present invention show excellent antiinflammatory effect. In FIGS. 7 to 9, the non-challenge group indicates a group to which the 0.5% OVA physiological saline solution was not inhaled (a group in which the antigen challenge was not performed); the control group indicates a group to which a 0.5% CMC sodium solution was administered as a test compound. The count of eosinophil in the non-challenge group is zero.

Test Example 10

Effects on Locomotor Activity in Mouse

To each mouse fasted overnight, each test compound (Examples 1, 2, 10, 11, 22, 30, 39, 40, 41, 43, 52, 87, 124, 131, 134, 135, and 136) suspended in a 0.5% (W/V) CMC-Na aqueous solution was orally administered. Immediately, each group (3 mice per group) was accommodated in a separate polycarbonate cage. The cumulative locomotor activity was measured every 5 minutes from immediately after the administration up to 2 hour after the administration by a locomotor activity measuring apparatus. The dose of each test compound was 300 to 2500 times as large as each $ID_{50}$ value obtained in the histamine skin reaction test in mouse.

As with Test Example 7, the compounds of the present invention did not affect the locomotor activity in mouse even when each compound was administered in a dose of 300 or more times as large as each $ID_{50}$ value obtained in the histamine skin reaction test in mouse. Therefore, the compounds of the present invention have apparently reduced central nervous system effects and are highly safe without side effects such as sleepiness.

Preparation Example 1

Using the following formulation, a tablet was obtained in accordance with a known manner described in General Rules for Preparations of Japanese Pharmacopoeia XIV.

Formulation example per tablet (total amount 150 mg):

| | |
|---|---|
| Compound of Example 2 | 30 mg |
| Lactose | 67 mg |
| Corn starch | 28 mg |
| Crystalline cellulose | 15 mg |
| Hydroxypropyl cellulose | 8 mg |
| Magnesium stearate | 2 mg |

Preparation Example 2

Using the following formulation, a capsule was obtained in accordance with a known manner described in General Rules for Preparations of Japanese Pharmacopoeia XIV.

Formulation example per capsule (total amount 180 mg):

| | |
|---|---|
| Compound of Example 2 | 50 mg |
| Lactose | 100 mg |
| Corn starch | 28 mg |
| Magnesium stearate | 2 mg |

Preparation Example 3

The compound of Example 2 (10 mg) was dissolved in 3 mL of a physiological saline, and the solution was adjusted to pH 7 with a 0.1-N sodium hydroxide aqueous solution. Then, a physiological saline was further added thereto so that the total volume of the solution was 5 mL. The resulting solution was divided in ampoules, and the ampoules were heat-sterilized to give injectable solutions.

INDUSTRIAL APPLICABILITY

The pharmaceutical composition of the present invention is useful as a prophylactic and/or therapeutic agent for an allergic disease (for example, bronchial asthma, rhinitis, nasal blockage, and dermatitis).

The invention claimed is:
1. A heterocyclic compound represented by the following formula (1b):

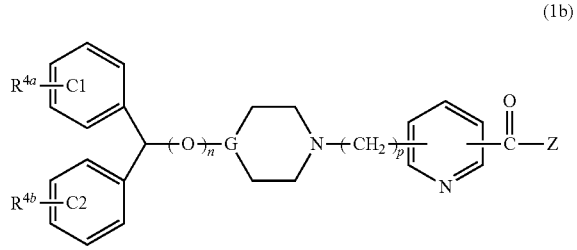

(1b)

the ring C1 and the ring C2 are the same or different and each represent a $C_{6-10}$ arene ring or an aromatic 5- or 6-membered heterocyclic ring; and
$R^{4a}$ and $R^{4b}$ are the same or different and each represent a substituent selected from the group consisting of a hydrogen atom, a halogen atom, a straight chain or branched chain $C_{1-4}$ alkyl group, a straight chain or branched chain haloC$_{1-4}$ alkyl group, a straight chain or branched chain $C_{1-4}$ alkoxy group, and a straight chain or branched chain haloC$_{1-4}$ alkoxy group;

in the ring C1 and the ring C2, $R^{4a}$ and $R^{4b}$ may be the same or different in species from each other;
$R^{4a}$ and $R^{4b}$ may bond together to form the ring C3, wherein the ring C3 may have a substituent such as the above-mentioned halogen atom;
Z represents a hydroxyl group, an alkoxy group, a cycloalkyloxy group, an aryloxy group, an aralkyloxy group, an amino group, or an N-substituted amino group;
the position of the group —C(O)—Z is a 2- or 4-position of the pyridine ring relative to a nitrogen atom N constituting the ring A in a counterclockwise direction; and
wherein p is 1 or 2;
n is 1 when G is CH; n is 0 when G is N;
or
a salt thereof.

2. A heterocyclic compound or a salt thereof according to claim 1, wherein
Z is a hydroxyl group; a $C_{1-6}$ alkoxy group; an amino group; or an N-substituted amino group in which the nitrogen atom has at least one substituent selected from the group consisting of a $C_{1-6}$ alkyl group and a $C_{1-6}$ alkyl-carbonyl group.

3. A heterocyclic compound or a salt thereof according to claim 1, wherein
Z is a hydroxyl group; a $C_{1-4}$ alkoxy group; an amino group; or an N-substituted amino group in which the nitrogen atom has at least one substituent selected from the group consisting of a $C_{1-4}$ alkyl group and a $C_{1-4}$ alkyl-carbonyl group.

4. A heterocyclic compound or a salt thereof according to claim 1, wherein
Z is a hydroxyl group; a $C_{1-3}$ alkoxy group; an amino group; or an N-substituted amino group in which the nitrogen atom has at least one substituent selected from the group consisting of a $C_{1-3}$ alkyl group and a $C_{1-3}$ alkyl-carbonyl group.

5. A heterocyclic compound or a salt thereof according to claim 1, wherein
Z is a hydroxyl group; a $C_{1-2}$ alkoxy group; an amino group; or an N-substituted amino group in which the nitrogen atom has at least one substituent selected from the group consisting of a $C_{1-2}$ alkyl group and a $C_{1-2}$ alkyl-carbonyl group.

6. A heterocyclic compound or a salt thereof according to claim 1, selected from the group consisting of
a (4-benzhydryloxypiperidin-1-ylmethyl)pyridinecarboxylic acid,
a {4-[(halophenyl)phenylmethoxy]piperidin-1-ylmethyl} pyridinecarboxylic acid,
a {4-[(C$_{1-4}$alkylphenyl)phenylmethoxy]piperidin-1-ylmethyl}pyridinecarboxylic acid,
a {4-[(fluoroC$_{1-4}$alkylphenyl)phenylmethoxy]piperidin-1-ylmethyl}pyridinecarboxylic acid,
a {4-[(C$_{1-4}$alkoxyphenyl)phenylmethoxy]piperidin-1-ylmethyl}pyridinecarboxylic acid,
a {4-[(fluoroC$_{1-4}$alkoxyphenyl)phenylmethoxy]piperidin-1-ylmethyl}pyridinecarboxylic acid,
a {4-[bis(halophenyl)methoxy]piperidin-1-ylmethyl} pyridinecarboxylic acid,
a {4-[bis(halophenyl)methyl]piperazin-1-ylmethyl} pyridinecarboxylic acid,
or
a salt thereof.

7. A process for producing a heterocyclic compound represented by the formula (1b) recited in claim 1, which comprises:

(I) a step for allowing a compound represented by the following formula (12):

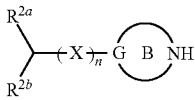 (12)

the ring B represents a heterocyclic ring which contains G and nitrogen atom N as constituent atoms thereof and which may have a substituent, wherein G represents CH or N and which is selected from the group consisting of a piperidine ring and a piperazine ring;
both $R^{2a}$ and $R^{2b}$ are a benzene ring, or one of $R^{2a}$ and $R^{2b}$ is a benzene ring and the other is a thiazole ring, wherein each ring may have a substituent;
X represents an oxygen atom or a sulfur atom;
n denotes 0 or 1, and the ring B is the piperazine ring when n is 0, and the ring B the piperidine ring when n is 1;
to react with a compound represented by the following formula (13):

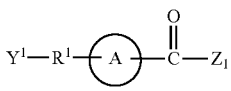 (13)

wherein $Y^1$ represents a halogen atom; $Z_1$ represents an alkoxy group, a cycloalkyloxy group, an aryloxy group, or an aralkyloxy group;
$R^1$ represents an alkylene group which may have a substituent;
wherein ring A is pyridine and the position of the group —C(O)—Z is a 2- or 4-position of the pyridine ring relative to a nitrogen atom N constituting the ring A in a counterclockwise direction; and
or
(II) a step for allowing a compound represented by the following formula (15):

 (15)

wherein $Y^2$ represents a halogen atom; the ring A, the ring B, $R^1$, G, X, n, $R^{2a}$, and
$R^{2b}$ have the same meanings as defined above,
to react with a compound represented by the following formula (16):

HO—$R^5$  (15)

wherein $R^5$ represents an alkyl group, a cycloalkyl group, an aryl group, or an aralkyl group,
and carbon monoxide,
for obtaining a heterocyclic compound represented by the formula (1b) wherein Z is an alkoxy group, a cycloalkyloxy group, an aryloxy group, or an aralkyloxy group;
the process may further comprise a step for subjecting the heterocyclic compound represented by the formula (1) wherein Z is an alkoxy group, a cycloalkyloxy group, an aryloxy group, or an aralkyloxy group to hydrolysis or amide bond formation reaction for obtaining a heterocyclic compound represented by the formula (1b) wherein Z is a hydroxyl group, an amino group, or an N-substituted amino group; or
the process may furthermore comprise a step for subjecting the heterocyclic compound represented by the formula (1b) wherein Z is an amino group to alkylation or acylation reaction for obtaining a heterocyclic compound represented by the formula (1b) wherein Z is an N-alkylamino group or an N-acylamino group.

8. A pharmaceutical composition comprising an effective amount of a compound recited in claim 1 or a pharmaceutically acceptable salt thereof and an inert carrier.

9. A pharmaceutical composition according to claim 8, which comprises and effective amount of a compound recited in claim 1 or a pharmaceutically acceptable salt thereof with an antiallergic, an antihistamic or anti-inflammatory efficacy, and an inert carrier.

10. A method for treating an allergic disease, which comprises administering an effective amount of a compound recited in claim 1 or a pharmaceutically acceptable salt thereof to a subject with the allergic disease.

11. A heterocyclic compound or a salt thereof selected from the group consisting of
6-((R)-3-benzhydryloxypyrrolidin-1-ylmethyl)pyridine-2-carboxylic acid;
6-((S)-3-benzhydryloxypyrrolidin-1-ylmethyl)pyridine-2-carboxylic acid; and
2-((S)-3-benzhydryloxypyrrolidin-1-ylmethyl)isonicotinic acid.

* * * * *